US012408672B2

(12) United States Patent
Santiago-Ortiz et al.

(10) Patent No.: US 12,408,672 B2
(45) Date of Patent: Sep. 9, 2025

(54) AGRICULTURALLY BENEFICIAL MICROBES, MICROBIAL COMPOSITIONS, AND CONSORTIA

(71) Applicant: BIOCONSORTIA, INC., Davis, CA (US)

(72) Inventors: Jorge Santiago-Ortiz, Davis, CA (US); Thomas Williams, Woodland, CA (US); Debora Wilk, Davis, CA (US); Hong Zhu, West Sacramento, CA (US); Abhishek Patri, Davis, CA (US); Graham Hymus, Davis, CA (US)

(73) Assignee: BIOCONSORTIA, INC., Davis, CA (US)

( * ) Notice: Subject to any disclaimer, the term of this patent is extended or adjusted under 35 U.S.C. 154(b) by 0 days.

(21) Appl. No.: 17/659,903

(22) Filed: Apr. 20, 2022

(65) Prior Publication Data
US 2022/0264892 A1    Aug. 25, 2022

Related U.S. Application Data

(63) Continuation of application No. PCT/US2021/037653, filed on Jun. 16, 2021.

(60) Provisional application No. 62/705,239, filed on Jun. 17, 2020.

(51) Int. Cl.
| | |
|---|---|
| A01N 63/22 | (2020.01) |
| A01N 63/20 | (2020.01) |
| A01N 63/25 | (2020.01) |
| A01N 63/30 | (2020.01) |
| A01P 3/00 | (2006.01) |
| A01P 5/00 | (2006.01) |
| A01P 21/00 | (2006.01) |
| C12N 1/14 | (2006.01) |
| C12N 1/20 | (2006.01) |

(52) U.S. Cl.
CPC ............ *A01N 63/20* (2020.01); *A01N 63/22* (2020.01); *A01N 63/25* (2020.01); *A01N 63/30* (2020.01); *A01P 3/00* (2021.08); *A01P 5/00* (2021.08); *A01P 21/00* (2021.08); *C12N 1/14* (2013.01); *C12N 1/20* (2013.01)

(58) Field of Classification Search
None
See application file for complete search history.

(56) References Cited

U.S. PATENT DOCUMENTS

| | | |
|---|---|---|
| 555,444 A | 2/1896 | Hartwell |
| 591,841 A | 10/1897 | Heaven |
| 4,245,432 A | 1/1981 | Dannelly |
| 4,339,456 A | 7/1982 | Rushing |
| 4,372,080 A | 2/1983 | Rushing |
| 4,452,008 A | 6/1984 | Sandhu et al. |
| 4,465,017 A | 8/1984 | Simmons |
| 4,634,587 A | 1/1987 | Hsiao |
| 4,735,015 A | 4/1988 | Schmolka |
| 4,759,945 A | 7/1988 | Nemecek et al. |
| 5,328,942 A | 7/1994 | Akhtar et al. |
| 5,389,399 A | 2/1995 | Bazin et al. |
| 5,554,445 A | 9/1996 | Struszczyk et al. |
| 5,580,544 A | 12/1996 | Dao et al. |
| 5,605,793 A | 2/1997 | Stemmer |
| 5,661,103 A | 8/1997 | Harms et al. |
| 5,791,084 A | 8/1998 | Kohno et al. |
| 5,837,458 A | 11/1998 | Minshull |
| 5,849,320 A | 12/1998 | Turnblad |
| 5,876,739 A | 3/1999 | Turnblad et al. |
| 5,916,029 A | 6/1999 | Smith et al. |
| 5,918,413 A | 7/1999 | Otani et al. |
| 5,939,356 A | 8/1999 | Wellinghoff |
| 7,097,830 B2 | 8/2006 | Nautiyal et al. |
| 7,118,739 B2 | 10/2006 | da Luz |
| 7,213,367 B2 | 5/2007 | Wertz et al. |
| 8,383,097 B2 | 2/2013 | Frodyma |
| 8,652,490 B2 | 2/2014 | Hewlitt |
| 9,113,636 B2 | 8/2015 | von Maltzahn et al. |
| 9,150,851 B2 | 10/2015 | Wigley et al. |
| 9,288,995 B2 | 3/2016 | von Maltzahn et al. |
| 9,315,874 B2 | 4/2016 | Liu et al. |
| 9,532,573 B2 | 1/2017 | von Maltzahn et al. |

(Continued)

FOREIGN PATENT DOCUMENTS

| | | |
|---|---|---|
| BR | 112022025288 | 2/2023 |
| CN | 104403962 | * 3/2015 |

(Continued)

OTHER PUBLICATIONS

Damodaran, T. et al., "Identification of rhizosphere bacterial diversity with promosing salt tolerance, PGP traits and their explitation for seed germination enhancement in sodic soil," Agricultural Research, vol. 8(1), pp. 36-43 (2019).*

(Continued)

*Primary Examiner* — John Pak

(57) ABSTRACT

The disclosure relates to isolated microorganisms—including novel strains of the microorganisms, microbial consortia, and agricultural compositions comprising the same. Furthermore, the disclosure teaches methods of utilizing the described microorganisms, microbial consortia, and agricultural compositions comprising the same, in methods for imparting beneficial properties to target plant species. In particular aspects, the disclosure provides methods of increasing desirable plant traits in agronomically important crop species.

9 Claims, 16 Drawing Sheets

Specification includes a Sequence Listing.

(56) References Cited

U.S. PATENT DOCUMENTS

| | | |
|---|---|---|
| 9,615,584 B2 | 4/2017 | Reddy et al. |
| 9,622,485 B2 | 4/2017 | von Maltzahn et al. |
| 9,809,812 B2 | 11/2017 | Wigley et al. |
| 9,862,955 B2 | 1/2018 | Chung et al. |
| 10,058,101 B2 | 8/2018 | von Maltzahn et al. |
| 10,405,554 B2 | 9/2019 | Grandlic et al. |
| 10,412,971 B2 | 9/2019 | Grandlic et al. |
| 10,428,394 B2 | 10/2019 | Inai et al. |
| 10,499,652 B2 | 12/2019 | von Maltzahn et al. |
| 10,602,744 B2 | 3/2020 | Wigley |
| 10,954,173 B2 | 3/2021 | Venkatramesh et al. |
| 11,066,341 B2 | 7/2021 | Yoon et al. |
| 11,166,465 B2 | 11/2021 | von Maltzahn et al. |
| 11,528,911 B2 | 12/2022 | Grandlic et al. |
| 11,793,202 B2 | 10/2023 | von Maltzahn et al. |
| 2010/0143316 A1 | 6/2010 | Hsieh et al. |
| 2010/0179060 A1* | 7/2010 | Fernandez Martinez ................... C12N 1/205 504/117 |
| 2010/0189693 A1 | 7/2010 | Hewlett |
| 2012/0015806 A1 | 1/2012 | Paikray et al. |
| 2012/0129794 A1 | 5/2012 | Dowd et al. |
| 2013/0031673 A1 | 1/2013 | Grandlic |
| 2014/0082770 A1 | 3/2014 | Wigley et al. |
| 2015/0147303 A1 | 5/2015 | Hsieh |
| 2015/0156982 A1 | 6/2015 | Spangenberg et al. |
| 2015/0373993 A1 | 12/2015 | von Maltzahn et al. |
| 2016/0237512 A1 | 8/2016 | Inai et al. |
| 2017/0094978 A1 | 4/2017 | Grandlic et al. |
| 2017/0191072 A1 | 7/2017 | Chung et al. |
| 2018/0020676 A1* | 1/2018 | Taghavi ................ C05F 11/08 504/117 |
| 2018/0258502 A1 | 9/2018 | Lewis et al. |
| 2019/0183131 A1 | 6/2019 | Kendirgi et al. |
| 2019/0261633 A1* | 8/2019 | Lu .......................... C12N 1/205 |
| 2019/0382714 A1 | 12/2019 | Wigley et al. |
| 2020/0138038 A1 | 5/2020 | Ashby et al. |
| 2020/0178540 A1* | 6/2020 | Dagher .................. A01N 63/27 |
| 2020/0179060 A1 | 6/2020 | Kopel et al. |
| 2020/0255355 A1 | 8/2020 | Venkatramesh et al. |
| 2020/0283484 A1 | 9/2020 | Rotem et al. |
| 2020/0359634 A1* | 11/2020 | Lu ........................... A01N 63/10 |
| 2020/0405781 A1 | 12/2020 | Holzapfel et al. |
| 2020/0407807 A1 | 12/2020 | Holzapfel et al. |
| 2020/0407808 A1 | 12/2020 | Holzapfel et al. |
| 2020/0407809 A1 | 12/2020 | Holzapfel et al. |
| 2021/0123043 A1 | 4/2021 | Wigley et al. |
| 2021/0310017 A1 | 10/2021 | White, Jr. et al. |
| 2021/0321621 A1 | 10/2021 | Gordon et al. |
| 2022/0022461 A1 | 1/2022 | Wigley et al. |
| 2022/0211046 A1* | 7/2022 | Malang .................. A01N 63/22 |
| 2022/0232833 A1 | 7/2022 | von Maltzahn |
| 2022/0372432 A1* | 11/2022 | Yang ........................ B09C 1/10 |

FOREIGN PATENT DOCUMENTS

| | | |
|---|---|---|
| CN | 104630094 A | 5/2015 |
| CN | 105695368 * | 6/2016 |
| CN | 106635903 A | 5/2017 |
| CN | 107964514 * | 4/2018 |
| CN | 109072168 A | 12/2018 |
| CN | 109097302 * | 12/2018 |
| CN | 110982764 A | 4/2020 |
| CN | 111172084 * | 5/2020 |
| CN | 116075222 | 5/2023 |
| JP | 2015517807 | 6/2015 |
| JP | 2015517807 A | 6/2015 |
| JP | 2019532956 A | 11/2019 |
| WO | 2012125050 | 9/2012 |
| WO | 2014046553 | 3/2014 |
| WO | 2014162919 | 10/2014 |
| WO | 2014201044 | 12/2014 |
| WO | 2014210372 | 12/2014 |
| WO | 2015200902 | 12/2015 |
| WO | 2016108976 A1 | 7/2016 |
| WO | 2016118850 | 7/2016 |
| WO | 2016130586 | 8/2016 |
| WO | 2017019633 | 2/2017 |
| WO | 2017127535 | 7/2017 |
| WO | 2018045004 | 3/2018 |
| WO | 2019028355 | 2/2019 |
| WO | 2019058377 | 3/2019 |
| WO | 2019175777 | 9/2019 |
| WO | 2019175780 | 9/2019 |
| WO | 2019175782 | 9/2019 |
| WO | 2019175783 | 9/2019 |
| WO | 2019236672 | 12/2019 |
| WO | WO 2020/214843 * | 10/2020 |
| WO | 2021028911 | 2/2021 |
| WO | 2021144172 | 7/2021 |
| WO | 2022195585 | 9/2022 |

OTHER PUBLICATIONS

Machine translation of CN 109097302 (Dec. 2018), description and claims.*

Machine translation of CN 111172084 (May 2020), description and claims.*

Machine translation of CN 105695368 (Jun. 2016), description and claims.*

Machine translation of CN 104403962 (May 2015), description and claims.*

Simione, F.P., "Key issues relating to the genetic stability and preservation of cells and cell banks," Journal of Parenteral Science and Technology, vol. 46(6), pp. 226-232 (1992).*

Reva, O.N. et al., "Genetic, epigenetic and phenotypic diversity of four *Bacillus velezensis* strains used for plant protection or as probiotics," Frontiers in Microbiology, vol. 10, Article 2610, Nov. 2019, pp. 1-25.*

Database N-Geneseq, sequence search printout for WO 2020/214843 (Oct. 22, 2020), Seq Id No. 270.*

Page-Mann, P., "How long do seeds last?" Small Farms Quarterly, Cornell College of Agriculture and Life Sciences, Jan. 13, 2020, retrieved from the internet: <https://smallfarms.cornell.edu/2020/01/how-long-do-seeds-last/>.*

Database N-Geneseq, sequence search printout for CN 107964514 (Apr. 27, 2018), Seq Id No. 1.*

Machine translation of CN 107964514 (Apr. 27, 2018).*

Aislabie et al. FEMS Micrbiology Ecology 52:279-286. 2005 (published online Dec. 8, 2004).

Ali et al. British Microbiology Research Journal. 2015. 6(1): 32-40. Published Dec. 15, 2014. (Year: 2014).

Bacillus velezensis FZB42, complete sequence—Nucleotide—NCBI; original deposit date Feb. 1, 2007.

European search report for Application No. 21216698.7 (2022).

IPRP for PCT/US2021/037653, mail date Dec. 29, 2022, 16 pages.

ISR and WO for PCT/US2016/017204, mailed Aug. 10, 2016, 13 pages.

ISR and WO for PCT/US2016/043933, mailed Jan. 26, 2017, 14 pages.

ISR and WO for PCT/US2021/037653, mail date Dec. 13, 2021.

Li et al. "*Frigidibacter albus* gen. nov., sp. nov., a novel member of the family Rhodobacgeraceae isolated from lake water"; International Journal of Systematic and Evolutionary Microbiology. 2015. 65: 1199-1206. Epub. Jan. 21, 2015. (Year: 2015).

Pereira et al. Ecological Engineering 73:526-535. 2014.

Ramirez-Bahena et al. International Journal of Systematic and Evolutionary Microbiology. 2014. 64: 2338-2345. Published Jul. 1, 2014. (Year: 2014).

Shruthi, Studies on zinc solubilizing bacteria and their effect on growth and yield of maize (*Zea mays* L.); Thesis submitted to the Univ of Ag Sciences, Dharwad. 2013.

Yu, X., et al., Gen bank Accession FJ455451. Publication [online]. Dec. 10, 2008 [retrieved Mar. 22, 2017] 2 pages.

International Search Report and Written Opinion for PCT/US2021/037653, mail date Dec. 13, 2021.

(56) References Cited

OTHER PUBLICATIONS

"Arthrobacter", MicrobeWiki, available at https://microbewiki.kenyon.edu/index.php/Arthrobacter, Sep. 14, 2015, 3 pages.
Adesemoye et al. "Plant-microbes interactions in enhanced fertilizer-use efficiency", Appl Microbiol Biotechnol 85:1-12. 2009.
Krebs, B., Höding, B., Kübart, S., Workie, M. A., Junge, H., Schmiedeknecht, G., et al. (1998). Use of *Bacillus subtilis* as biocontrol agent. I. Activities and characterization of *Bacillus subtilis* strains. J. Plant Dis. Prot. 105, 181-197.
Simione, "Key issues relating to the genetic stability and preservation of cells and cell banks", J Parenteral Science and Technology vol. 46 No 6 pp. 226-232; 1992.
Damodaran et al., "Identification of rhizosphere bacterial diversity with promising salt tolerance, PGP traits and their exploitation for seed germination enhancement in sodic soil"; Agric Res vol. 8 No 1 pp. 36-43; 2019.
ASCEND® plant growth regulator product sheet EPA Reg. No. 9779-335.
Baek et al., "*Novosphingobium sediminicola* sp. nov. isolated from freshwater sediment" Int Journal Systematic and Evolutionary Microbiology vol. 61 pp. 2464-2468; 2011.
Berger et al., "K. radicincitans, a beneficial bacteria that promotes radish growth under field conditions", Agronomy Sustainable Dev, vol. 35 No 4 pp. 1521-1528; 2015.
Berger et al., "Nitrogen supply influences plant growth and transcriptional responses induced by Enterobacter radicincitans in Solanum lycopersicum", Plant and Soil, vol. 370 pp. 641-652; 2013.
Bergottini, VM et al. "Bio-inoculation of yerba mate seedlings (Ilex paraguariensisSt. Hill.) with native plant growth-promoting rhizobacteria: a sustainable alternative to improve crop yield" Biol. Fertil. Soils. 2015. 51: 749-755. Published online Apr. 9, 2015. ( Year: 2015).
Brock et al., "Impact of the PGPB Enterobacter radicincitans DSM 16656 on Growth, Glucosinolate Profile, and Immune Responses of *Arabidopsis thaliana*" Microb Ecol vol. 65 No. 3 pp. 661-670; 2013.
Calvo et al, "Agricultural uses of plant biostimulants", Plant and Soil vol. 383 No 1 pp. 3-41; 2014.
Choi, Jung-Hye, et al. "*Acidovorax soli* sp. nov., isolated from landfill soil." International Journal of Systematic and Evolutionary Microbiology (2010); 60.12: 2715-2718.
Colby, R.S., "Calculating Synergistic and Antagonistic Responses of Herbicide Combinations", Weeds, 15( 1 ):20-22 ( 1967).
Crameri et al., "DNA shuffling of a family of genes from diverse species accelerates directed evolution", Nature vol. 391 pp. 288-291; 1988.
Crameri et al., "Molecular evolotuion of an arsenate detoxification pathway by DNA shuffling", Nature Biotech vol. 15 pp. 436-438; 1997.
De Almeida et al., Transgenic expression of two marker genes under the control of an *Arabidopsis* rbcS promoter: Sequences encoding the Rubisco transit peptide increase expression levels, Mol. Gen. Genetics 218:78-86. 1989.
Eckford, R. et al., "Free-living heterotrophic bacteria isolated from fuel-contaminated Antarctic soils", Applied and Environmental Microbiology, 68(10):5181-5185 (2002).
Fahraeus, (1957) The infection of clover root hairs by nodule bacteria studied by a simple glass slide technique J . Gen Microbial. 16:374-381.
Idriss et al., "Extracellular phytase activity of *Bacillus amyloliquefaciens* FZB45 contributes to its plant-growth-promoting effect", Microbiology 148:2097-2109; 2002.
James et al, Invection of sugar cane by the nitrogen-fixing bacterium Acetobacter diazotrophicus, J Expt Botany vol. 45 No 275 pp. 757-766; 1994.
Jones et al., High level expression of introduced chimaeric genes in regenerated transformed plants, EMBO J. 4:2411-2418. 1985.
Kim et al., "Rahnella aquatilis, a bacterium isolated from soybean rhizosphere, can solubilize hydrozyapatite", FEMS Microbiology Letters vol. 153, pp. 273-277; 1997.
Li et al, "*Acidovorax radicis* sp. Nov., a wheat root colonizing bacterium", In J Syst Evol Micro vol. 61 No. 11 pp. 2589-2594; 2011.
Li, Dan. "Phenotypic variation and molecular signaling in the interaction of the rhizosphere bacteria *Acidovorax* sp. N35 and Rhizobium radiobacter F4 with roots", Dissertation 2011; LMU Munchen: Faculty of Biology.
Miche et al., "Effects of rice seed surface sterilisation with hypochlorite on inoculated Burkholderia vietamiensis" (2001) Appl Environ Microbiol. 67(7): 3046-3052.
Moore et al. Strategies for the in vitro evolution of protein function: enzyme evolution by random recombination of improved sequences. J. Mol. Biol. 272:336-347. 1997.
Muangthong et al., "Isolation and Characterisation of Endophytic Nitrogen Fixing Bacteria in Sugarcane" Tropical Life Sciences Research vol. 26 No. 1 pp. 41-51.
N-Large™ plant growth regulator product sheet EPA Reg. No. 57538-18.
ProGibb® plant growth regulator product sheet EPA Reg. No. 73049-1 (alternative name RyzUp SmartGrass®).
Release® plant growth regulator product sheet EPA Reg. No. 73049-6.
Remus et al, "Colonization behaviour of two enterobacterial strains on cereals", Biol Fert Soils vol. 30 pp. 559-557; 2000.
Ruppel Silke et al, "Quantification and Localization of Bacteria in Plant Tissues Using Quantitative Real-Time PCR and Online Emission Fingerprinting", Plant and Soil vol. 286 No. 1-2 pp. 21-35; 2006.
Schneider et al, "Endophytes for Plant Protection: The State of the Art", DPG Spectrum Phytomedizin, Proceedings of the 5th International Symposium on Plant Protection and Plant Health in Europe , 2013, 347 pages.
Shamsinah et al, "Genome sequence of Kosakonia radicincitans UMEnt01/12, a bacterium associated with bacterial wilt diseased banana plant" FEMS Micro Letters vol. 358 No. 1 pp. 11-13; 2014.
Stemmer W.P. Dna shuffling by random fragmentation and reassembly: in vitro recombination for molecular evolution. PNAS 91:10747-10751. 1994.
Stemmer W.P.C. Rapid evolution of a protein in vitro by DNA shuffling. Nature 370:389-391. 1994.
Strobel et al., "Bioprospecting for Microbial endophytes and their Natural Products" (2003) Microbiology and Molecular Biology Reviews 67(4):491-502.
Vandamme et al. Polyphasic taxonomy, a consensus approach to bacterial systematics. Microbiol Rev, 60:407-438. 1996.
Witzel et al., Plant and Soil vol. 419 pp. 557-573; 2017.
X-CYTE™ plant growth regulator product sheet EPA Reg. No. 57538-15.
Yemm, E.W. and Willis, A.J., "The estimation of carbohydrates in plant extracts by anthrone" Biochem. J., 57:508-514 (1954).
Zhang et al, "*Arthrobacter cupressi* sp. nov., an actinomycete isolated from the rhizosphere soil of Cupressus sempervirens" Int J System Evol Micro vol. 62 Pt 11 pp. 2731-2736; 2012.
Zhang et al. Directed evolution of a fucosidase from a galactosidase by DNA shuffling and screening. PNAS 94:4504-4509. 1997.
Zhang, et al., Mol Plant Microbe Interact. (2008); 21(6): 737-744.
Zinniel et al., (2002) Applied and Environmental Microbiology 68(5):2198-2208.
Kilian et al., ""FZB24® *Bacillus subtilis*—mode of action of a microbial agentenhancing plant vitality"", Pflanzenschutz-Nachrichten Bayer vol. 1 pp. 72-93. 2000.
Chen et al., ""Comparative analysis of the complete genome sequenceof the plant growth-promoting bacterium Bacillusamyloliquefaciens FZB42"", Nature Biotechnology vol. 25 No. 9 pp. 1007-1014; 2007.
Fan et al., "Bacillus velezensis FZB42 in 2018: The Gram-Positive Model Strain for Plant Growth Promotion andBiocontrol", Frontiers in Microbiology vol. 9 Article 2491; 2018.
International Preliminary Report of Patentability WO2021257718 PCT/US2021/037653 15 pages dated Dec. 29, 2022.
Zhou, "Diversity of antimicrobial pepetides of Bacillus isolated from fecces of giant panda", abstract, Database EMBL-EBI Accession No. KF860131; Feb. 4, 2014.

(56) References Cited

OTHER PUBLICATIONS

Wen, "Study of microorganisms bioderadable bagasse in the deep sea", abstract, Database EMBL-EBI Accession No. KF857355; May 1, 2014.
Huang, "Effects of microflora on citrus soil microorganisms", abstract, Database EMBL-EBI Accession No. MK736121; Apr. 10, 2019.
Leon-Palmero, "Diversity and antimicrobial potential in sea anemone and holothurian microbiomes", abstract, Database EMBL-EBI Accession No. KX369291; Apr. 13, 2018.
Akoijam, "Microbial diversity of Loktak Lake, Manipur, India", abstract, Database EMBL-EBI Accession No. MH910168; Jul. 21, 2015.
Jung, "Screening and characterization of Bacillus strains as potential started cultures for the fermentation of doenjang, a Korean fermented soybean paste", abstract, Database EMBL-EBI Accession No. KR262841; Jul. 21, 2015.
Diniz, "Selection and identification of microorganisms isolated from corn stigma with antifungal activity against Fusarium verticilliodes", abstract, Database EMBL-EBI Accession No. MK461843; Mar. 20, 2019.
Lee, "Paenibacillus alba J20-6", abstract, Database EMBL-EBI Accession No. JQ966212; Jun. 18, 2012.
Han, "*Paenibacillus* sp. HWE-109", abstract, Database EMBL-EBI Accession No. KC355353; Mar. 27, 2013.
Arhipova, "Decay, yield loss and associated fungi in stands of grey alder (Alnus incana) in Latvia", abstract, Database EMBL-EBI Accession No. GU062287; Oct. 25, 2014.
Shen, "*Bacillus* sp. C141", abstract, Database EMBL-EBI Accession No. MF511824; Jul. 28, 2017.
Kumar, "Uranium (U)-tolerant bacterial diversity from U ore deosit of Domiasiat in North-East India and its prospective utilisation in bioremediation", abstract, Database EMBL-EBI Accession No. JF768726; Jun. 6, 2013.
Chen, "Penifupyrone, an Unusual Cytotoxic Funicone Derivative from the Endophytic Fungus Penicillium sp. HSZ-43", abstract, Database EMBL-EBI Accession No. KJ681497; Jul. 1, 2014.
Cao, "*Paenibacillus ferrarius* sp. nov., isolated from iron mineral soil", abstract, Database EMBL-EBI Accession No. KF925453; Jan. 7, 2016.
Keerthana, "Phylogenetic diversity analysis of bacterial sp. Isolated from various effluent contaminated sites around Erode district", abstract, Database EMBL-EBI Accession No. KF751677; Dec. 12, 2013.
Meerak, "Phylogeny of gamma-polyglutamic acid-producing Bacillus strains isoalted from fermented soybean foods manufatured in Asian countries", abstract, Database EMBL-EBI Accession No. AB300805; Mar. 5, 2009.
Kumar, "Fipronil degrading microbial consortium", abstract, Database EMBL-EBI Accession No. MH244337; May 9, 2018.
Kim, "Paenibacillus illinoisensis strain 18JY14-35", abstract, Database EMBL-EBI Accession No. MH497643.
Ntougias, "Diversity and efficiency of anthracene-degrading bacteria isolated from a denitrifying activated sludge system treating municipal wastewater", abstract, Database EMBL-EBI Accession No. KM210238; May 22, 2015.
Zhang, "Microbacterium esteraromaticum TJ-1-56", abstract, Database EMBL-EBI Accession No. MF196241; Jun. 14, 2017.
Kim et al., "Plant growth promoting effects of Bacillus amyloliquefaciens H-2-5 on crop plants and influence on physiological changes in soybean under soil saliniity", Physiology and Molecular Biology of Plants, Society of Green World, Bareilly, In, vol. 23 No. 3, pp. 571-580; Jun. 14, 2017.
Shao et al., "Contribution of indole-3-acetic acid in the plant growth promotion by the rhizospheric strain Bacillus amyloliquefaciens SQR9", Biology and Fertility of Soils, Springer Berlin Heidelberg, vol. 51 No. 3, pp. 321-330; Nov. 22, 2014.
Kang et al., "Phosphate solubilizing Bacillus megaterium mj1212 regulates endogenous plant carbohydrates and amino acids contents to promote mustard plant growth", Indian Journal of Microbiology, Hisar, In., vol. 54 No. 4, pp. 427-433; Jun. 4, 2014.
Khan et al., "The endophytic bacteria Bacillus velzensis Lle-9, isolated from Lilium leucanthum, harbors antifungal activity and plant growth-promoting effects", Journal of Micrbiology and Biotechnology, vol. 30 No. 5, pp. 668-680; May 28, 2020.
Mehta et al., "Tricalcium phosphate solubilisation bynew endophyte Bacillus methylotrophicus CKAM isolated from apple root endosphere and its plant growth-promoting activities", Acta Physiologiae Plantarum, Springer Berlin Heidelberg, vol. 36 No. 8, pp. 2033-2045; Jun. 1, 2014.
Jinal et al., "Phytoextraction of iron from contaminated soils by inoculation of iron-tolerant plant growth-promoting bacteria in L. Czern", Environmental Science and Pollution Research, Springer Berlin Heidelberg, vol. 26 No. 32, pp. 32815-32823; Sep. 9, 2019.
Ghosh et al., "A comparativeanalysis of exopolysaccharide and phytohormone secretions by four drought-tolerant rhizobacterial strains and their impact on osmotic-stress mitigation in *Arabidopsis thaliana*", World Journal of Microbiology and Biotechnology, Spring Netherlands, Dordrect, vol. 35 No. 6, pp. 1-15; May 30, 2019.
Singh, "Arthrobotrys oligospora-mediated biological control of diseases of tomato (Lycopersicon esculentum Mill.) caused by Meloidogyne incongnita and Rhizoctonia solani", Journal of Applied Microbiology, vol. 114 No. 1, pp. 196-208; Oct. 31, 2012.
European Search Report EP Application No. 21826051.1 mailing date May 31, 2024, 27 pages.
Written Opinion WO2021257718 PCT/US2021/037653 14 pages dated Dec. 28, 2021.
International Search Report WO2021257718 PCT/US2021/037653 6 pages dated Dec. 28, 2021.
International Preliminary Report on Patentability WO2021257718 PCT/US2021/037653 15 pages dated Dec. 28, 2021.
GARDENER 2004, Ecology of *Bacillus and Paenibacillus* spp. in Agricultural Systems, Phytopathology, pp. 1252-1258.
GenBank Deposit No. AY055221.1 Bacillus amyloliquefaciens strain FZB42 16S ribosomal RNA gene, partial sequence; 2002.
GenBank Deposit No. JX645713.1 Bacillus amyloliquefaciens strain B6 16S ribosomal RNA gene, partial sequence; 2012.
GenBank Deposit No. KJ482881.1 *Bacillus* sp. TV53May 16S ribosomal RNA gene, partial sequence; 2014.
GenBank Deposit No. KM117174.1 Bacillus amyloliquefaciens strain M Rh 131 16S ribosomal RNA gene, partial sequence; 2014.
GenBank Deposit No. MH910168.1 Bacillus velezensis strain 64 16S ribosomal RNA gene, partial sequence; 2018.
GenBank Deposit No. MT107118.1 Bacillus amyloliquefaciens strain MPRN2 16S ribosomal RNA gene, partial sequence; 2020.
GenBank Deposit No. MT626036.1 Bacillus amyloliquefaciens strain SRCM 112835 16S ribosomal RNA gene, partial sequence; 2020.
GenBank Deposit No. MZ723401.1 Bacillus amyloliquefaciens strain B3 16S ribosomal RNA gene, partial sequence; 2021.
GenBank Deposit No. NC_009725.2 Bacillus velezensis FZB42, complete sequence; 2007.
Rabbee et al., ""Bacillus velezensis: A Beneficial Biocontrol Agent or FacultativePhytopathogen for Sustainable Agriculture""; Agronomy vol. 13 No. 840; 14 pages; 2023.
Wockenfuss et al., "A Bacillus velezensis strain shows antimicrobial activity against soilborne and foliar fungi and oomycetes"; Front. Fungal Biol., Feb. 22, 2024, Sec. Fungi-Plant Interactions, vol. 5; 2024.
De Jesus Silva et al., "Complete Genome Sequence of the Biocontrol Agent Bacillus velezensis UFLA258 and Its Comparisonwith Related Species: Diversity within the Commons"; Genome Biol Evol vol. 11 No. 10, pp. 2818-2823; 2019.
Akoijam, C.; et al.: "Microbial diversity of Loktak Lake, Manipur, India", abstract, Database EMBL-EBI Accession No. MH910168; Jul. 21, 2015.
Arhipova, N.; et al.: "Decay, yield loss and associated fungi in stands of grey alder (Alnus incana) in Latvia", abstract, Database EMBL-EBI Accession No. GU062287; Oct. 25, 2014.
Cao, Y.; et al.: "*Paenibacillus ferrarius* sp. nov., isolated from iron mineral soil", abstract, Database EMBL-EBI Accession No. KF925453; Jan. 7, 2016.

(56) References Cited

OTHER PUBLICATIONS

Chen, M. -J.: "Penifupyrone, an Unusual Cytotoxic Funicone Derivative from the Endophytic Fungus *Penicillium* sp. HSZ-43", abstract, Database EMBL-EBI Accession No. KJ681497; Jul. 1, 2014.
De Jesus Silva, Fabiola; et al.: "Complete Genome Sequence of the Biocontrol Agent Bacillus velezensis UFLA258 and Its Comparison with Related Species: Diversity within the Commons", Genome Biol. Evol., Oct. 3, 2019 (Oct. 3, 2019), vol. 11 No. 10, pp. 2818-2823.
Diniz, "Selection and identification of microorganisms isolated from corn stigma with antifungal activity against Fusarium verticillioides", abstract, Database EMBL-EBI Accession No. MK461843; Mar. 20, 2019.
European Search Report EP Application No. 21826051.1, mailed May 31, 2024.
GenBank Accession No. KF925453.1, 2016, "*Paenibacillus ferrarius* strain CY1 16S ribosomal RNA gene, partial sequence".
GenBank Deposit No. HM535371, 2010, "*Penicillium* sp. E-18 18S ribosomal RNA gene, partial sequence; internal transcribed spacer 1, 5.8S ribosomal RNA gene, and internal transcribed spacer 2, complete sequence; and 28S ribosomal RNA gene, partial sequence".
GenBank Deposit No. MH142465, 2019, "Talaromyces stipitatus strain Y.H. Yeh V0511 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence."
Ghosh, Daipayan; et al.: "A comparative analysis of exopolysaccharide and phytohormone secretions by four drought-tolerant rhizobacterial strains and their impact on osmotic-stress mitigation in *Arabidopsis thaliana*", World Journal of Microbiology and Biotechnology, Spring Netherlands, Dordrect, May 30, 2019 (May 30, 2019), vol. 35, No. 6, pp. 1-15.
Han, J. -H.; et al.: "*Paenibacillus* sp. HWE-109", abstract, Database EMBL-EBI Accession No. KC355353; Mar. 27, 2013.
Huang, J.: "Effects of microflora on citrus soil microorganisms", abstract, Database EMBL-EBI Accession No. MK736121; Apr. 10, 2019.
Jinal, Hardik Naik; et al.: "Phytoextraction of iron from contaminated soils by inoculation of iron-tolerant plant growth-promoting bacteria in L. Czern", Environmental Science and Pollution Research, Springer Berlin Heidelberg, Sep. 9, 2019 (Sep. 9, 2019), vol. 26, No. 32, pp. 32815-32823.
Jung, J. Y.; et al.: "Screening and characterization of Bacillus strains as potential started cultures for the fermentation of doenjang, a Korean fermented soybean paste", abstract, Database EMBL-EBI Accession No. KR262841; Jul. 21, 2015.
Kang, Sang-Mo; et al.: "Phosphate solubilizing Bacillus megaterium mj1212 regulates endogenous plant carbohydrates and amino acids contents to promote mustard plant growth", Indian Journal of Microbiology, Hisar, In., Jun. 4, 2014 (Jun. 4, 2014), vol. 54, No. 4, pp. 427-433.
Keerthana, R.; et al.: "Phylogenetic diversity analysis of bacterial sp. Isolated from various effluent contaminated sites around Erode district", abstract, Database EMBL-EBI Accession No. KF751677; Dec. 12, 2013.
Khan, Mohammad Sayyar; et al.: "The endophytic bacteria Bacillus velzensis Lle-9, isolated from Lilium leucanthum, harbors antifungal activity and plant growth-promoting effects", Journal of Micrbiology and Biotechnology, May 28, 2020 (May 28, 2020), vol. 30, No. 5, pp. 668-680.

Kim, M .: "Paenibacillus illinoisensis strain 18JY14-35", abstract, Database EMBL-EBI Accession No. MH497643.
Kim, Min-Ji; et al.: "Plant growth promoting effects of Bacillus amyloliquefaciens H-2-5 on crop plants and influence on physiological changes in soybean under soil salinity", Physiology and Molecular Biology of Plants, Society of Green World, Bareilly, In, Jun. 14, 2017 (Jun. 14, 2017), vol. 23, No. 3, pp. 571-580.
Kumar, D.; et al.: "Fipronil degrading microbial consortium", abstract, Database EMBL-EBI Accession No. MH244337; May 9, 2018.
Kumar, R.; et al.: "Uranium (U)-tolerant bacterial diversity from U ore deposit of Domiasiat in North-East India and its prospective utilisation in bioremediation", abstract, Database EMBL-EBI Accession No. JF768726; Jun. 6, 2013.
Lee, S.: "Paenibacillus alba J20-6", abstract, Database EMBL-EBI Accession No. JQ966212; Jun. 18, 2012.
Leon-Palmero, E.; et al.: "Diversity and antimicrobial potential in sea anemone and holothurian microbiomes", abstract, Database EMBL-EBI Accession No. KX369291; Apr. 13, 2018.
Li et al., "Isolation and evaluation of endophytic Bacillus tequilensis GYLH001 with potential application for biological control of Magnaporthe oryzae"; PLoS ONE 13(10:e0203505; 2018.
Meerak, J.; et al.: "Phylogeny of gamma-polyglutamic acid-producing Bacillus strains isolated from fermented soybean foods manufactured in Asian countries", abstract, Database EMBL-EBI Accession No. AB300805; Mar. 5, 2009.
Mehta, Preeti; et al.: "Tricalcium phosphate solubilisation bynew endophyte Bacillus methylotrophicus CKAM isolated from apple root endosphere and its plant growth-promoting activities", Acta Physiologiae Plantarum, Springer Berlin Heidelberg, Jun. 1, 2014 (Jun. 1, 2014), vol. 36, No. 8, pp. 2033-2045.
Ntougias, S.; et al.: "Diversity and efficiency of anthracene-degrading bacteria isolated from a denitrifying activated sludge system treating municipal wastewater", abstract, Database EMBL-EBI Accession No. KM210238; May 22, 2015.
Rabbee, Muhammad Fazle; et al.: "Bacillus velezensis: A Beneficial Biocontrol Agent or Facultative Phytopathogen for Sustainable Agriculture", Agronomy, 2023, vol. 13, No. 840, 14 pages.
Shao, Jiahui; et al.: "Contribution of indole-3-acetic acid in the plant growth promotion by the rhizospheric strain Bacillus amyloliquefaciens SQR9", Biology and Fertility of Soils, Springer Berlin Heidelberg, Nov. 22, 2014 (Nov. 22, 2014), vol. 51, No. 3, pp. 321-330.
Shen, S.: "*Bacillus* sp. C141", abstract, Database EMBL-EBI Accession No. MF511824; Jul. 28, 2017.
Singh, U.B.; et al.: "Arthrobotrys oligospora-mediated biological control of diseases of tomato (Lycopersicon esculentum Mill.) caused by Meloidogyne incongnita and Rhizoctonia solani", Journal of Applied Microbiology, Oct. 31, 2012 (Oct. 31, 2012), vol. 114, No. 1, pp. 196-208.
Wen, J.: "Study of microorganisms biodegradable bagasse in the deep sea", abstract, Database EMBL-EBI Accession No. KF857355; May 1, 2014.
Wockenfuss, Anna; et al.: "A Bacillus velezensis strain shows antimicrobial activity against soilborne and foliar fungi and oomycetes", Frontiers in Fungal Biology, Feb. 23, 2024 (Feb. 23, 2024), vol. 5.
Zhang, Y.: "Microbacterium esteraromaticum TJ-1-56", abstract, Database EMBL-EBI Accession No. MF196241; Jun. 14, 2017.
Zhou, Z. et al.: "Diversity of antimicrobial peptides of Bacillus isolated from feces of giant panda", abstract, Database EMBL-EBI Accession No. KF860131; Feb. 4, 2014.

\* cited by examiner

Inoculated control    Not-inoculated control    Inoculated, and treated with BEC60

Cauliflower leaf

Cauliflower lateral root

AGRICULTURALLY BENEFICIAL MICROBES, MICROBIAL COMPOSITIONS, AND CONSORTIA

CROSS-REFERENCE TO RELATED APPLICATIONS

This application is a Continuation of PCT Application No. PCT/US2021/037653 filed on 16 Jun. 2021, which claims the benefit under 35 U.S.C. 119(e) of U.S. Provisional Patent Application Ser. No. 62/705,239 filed 17 Jun. 2020, each of which is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named 20041USCON_SequenceListing_ST25.txt created on 12 Apr. 2022 and having a size of 42,273 bytes and is filed concurrently with the specification. The sequence listing comprised in this ASCII formatted document is part of the specification and is herein incorporated by reference in its entirety.

FIELD

The instant disclosure relates generally to the field of biology, specifically microbes and microbial compositions for the improvement of plants.

BACKGROUND

According to the United Nations World Food Program, there are close to 900 million malnourished people in the world. The malnourishment epidemic is particularly striking in the developing nations of the world, where one in six children is underweight. The paucity of available food can be attributed to many socioeconomic factors; however, regardless of ultimate cause, the fact remains that there is a shortage of food available to feed a growing world population, which is expected to reach 9 billion people by 2050. The United Nations estimates that agricultural yields must increase by 70-100% to feed the projected global population in 2050.

These startling world population and malnutrition figures highlight the importance of agricultural efficiency and productivity, in sustaining the world's growing population. The technological advancements achieved by modern row crop agriculture, which has led to never before seen crop yields, are impressive. However, despite the advancements made by technological innovations such as genetically engineered crops and new novel pesticidal and herbicidal compounds, there is a need for improved crop performance, in order to meet the demands of an exponentially increasing global population.

Scientists have estimated that if the global agricultural "yield gap" (which is the difference between the best observed yield and results elsewhere) could be closed, then worldwide crop production would rise by 45-70%. That is, if all farmers, regardless of worldwide location, could achieve the highest attainable yield expected for their respective regions, then a great majority of the deficiencies in worldwide food production could be addressed. However, solving the problem of how to achieve higher yields across a heterogenous worldwide landscape are difficult.

Often, yield gaps can be explained by inadequate water, substandard farming practices, inadequate fertilizers, and the non-availability of herbicides and pesticides. However, to vastly increase the worldwide use of water, fertilizers, herbicides, and pesticides, would not only be economically infeasible for most of the world, but would have negative environmental consequences.

Thus, meeting global agricultural yield expectations, by simply scaling up current high-input agricultural systems—utilized in most of the developed world—is simply not feasible.

There is therefore an urgent need in the art for improved methods of increasing crop performance and imparting beneficial traits to desired plant species.

SUMMARY

Included are isolated and biologically pure microorganisms that have application, inter alia, in agriculture. The disclosed microorganisms can be utilized in their isolated and biologically pure states, as well as being formulated into agriculturally acceptable compositions. Further provided are agriculturally beneficial microbial consortia, comprising at least two members of the disclosed microorganisms, as well as methods of utilizing said consortia in agricultural applications. In some aspects, genomic modification of the microbes (individual, consortia, and/or communities) are contemplated, for the improvement of microbial traits and the improvement of microbe-associated plants.

The present disclosure addresses this important issue of how to improve crop performance, thereby closing the worldwide yield gap, along with providing ways of imparting other beneficial traits to plant species.

The solution to increasing crop performance and increasing yield proffered by the present disclosure is not detrimental to the earth's resources, as it does not rely upon increased water consumption or increased input of synthetic chemicals into a system. Rather, the present disclosure utilizes microbes to impart beneficial properties, including increased yields, to desirable plants.

The disclosure therefore offers an environmentally sustainable solution that allows farmers to increase yields of important crops, which is not reliant upon increased utilization of synthetic herbicides and pesticides.

In embodiments, the disclosure provides for an efficient and broadly applicable agricultural platform utilizing microbes and microbial consortia (a plurality of microbes, in some aspects a plurality that improves the health or desired phenotype of the plant, such as an agronomic trait, with which it is associated) that promote one or more desirable plant properties.

The microbes disclosed herein improve the performance of plants, such as crop plants, by both direct and indirect mechanisms. In some aspects, the microbe becomes symbiotic with the plant. In some aspects, the microbe produces a compound (e.g., a metabolite) that confers a benefit to the plant or that the plant can use for improved characteristics. In some aspects, the microbe improves the solubility of one or more compositions, such as a nutrient, thereby benefitting the plant. In some aspects, the microbe imparts a tolerance to the plant to an exogenous substance such as an herbicide or a pesticide. In some aspects, the microbe produces a composition that is detrimental to a plant pest, such as an insect. In some aspects, the microbe fixes Nitrogen, thereby improving the nutritional status of the plant. Other aspects beyond the exemplary non-limiting aspects listed above are contemplated.

In some embodiments, a single microbe is utilized. In some aspects, the single microbe is isolated and purified. In some aspects, the single microbe is a taxonomic species of bacteria. In some aspects, the single microbe is an identifiable strain of a taxonomic species of bacteria. In some aspects, the single microbe is a novel, newly discovered strain of a taxonomic species of bacteria.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about $10^2$ CFU/mL in a liquid formulation, or at least about $10^2$ CFU/gram in a non-liquid formulation.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about $10^2$ CFU/mL in a liquid formulation, or at least about $10^2$ CFU/gram in a non-liquid formulation; further comprising at least one additional microbe.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about $10^2$ CFU/mL in a liquid formulation, or at least about $10^2$ CFU/gram in a non-liquid formulation; further comprising at least one additional microbe; wherein the at least one additional microbe is selected from Table 2.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about $10^2$ CFU/mL in a liquid formulation, or at least about $10^2$ CFU/gram in a non-liquid formulation, wherein the plant element is a seed.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about $10^2$ CFU/mL in a liquid formulation, or at least about $10^2$ CFU/gram in a non-liquid formulation, wherein the plant element is a seed; wherein the seed comprises a transgene.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumi-*

*lus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about $10^2$ CFU/mL in a liquid formulation, or at least about $10^2$ CFU/gram in a non-liquid formulation; wherein the plant element is a leaf.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about $10^2$ CFU/mL in a liquid formulation, or at least about $10^2$ CFU/gram in a non-liquid formulation; wherein the plant element is a root.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about $10^2$ CFU/mL in a liquid formulation, or at least about $10^2$ CFU/gram in a non-liquid formulation; wherein the plant element is a whole plant.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about $10^2$ CFU/mL in a liquid formulation, or at least about $10^2$ CFU/gram in a non-liquid formulation; wherein the formulation component is selected from the group consisting of: a compound that improves the stability of the microbe, a preservative, a carrier, a surfactant, an anticomplex agent, and any combination thereof.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about $10^2$ CFU/mL in a liquid formulation, or at least about $10^2$ CFU/gram in a non-liquid formulation; wherein the agricultural composition comprises a fungicide, a nematicide, a bactericide, an insecticide, a herbicide, or any combination thereof.

In some aspects, it is provided a plurality of synthetic compositions, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about $10^2$ CFU/mL in a liquid formulation, or at least about $10^2$ CFU/gram in a non-liquid formulation; wherein said synthetic compositions are substantially confined within an object selected from the group consisting of: a tube, a bottle, a jar, an ampule, a package, a vessel, a bag, a box, a bin, an envelope, a carton, a container, a silo, a shipping container, a truck bed, and a case.

In some aspects, it is provided a plurality of synthetic compositions, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about 10^2 CFU/mL in a liquid formulation, or at least about 10^2 CFU/gram in a non-liquid formulation; wherein the synthetic compositions are at a temperature below zero degrees Celsius.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about 10^2 CFU/mL in a liquid formulation, or at least about 10^2 CFU/gram in a non-liquid formulation; wherein the plant element is obtained from a plant selected from the group consisting of: maize, soybean, wheat, cotton, cucumber, tomato, pepper, potato, strawberry, orange, lemon, lime, apple, snap beans, zucchini, pea, lettuce, broccoli, celery, cauliflower, sorghum, and canola.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about 10^2 CFU/mL in a liquid formulation, or at least about 10^2 CFU/gram in a non-liquid formulation; wherein the agricultural composition comprises a growth medium.

In some aspects, it is provided a synthetic composition, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about 10^2 CFU/mL in a liquid formulation, or at least about 10^2 CFU/gram in a non-liquid formulation; wherein the agricultural composition comprises a growth medium; wherein the growth medium comprises soil.

In some aspects, it is provided a plurality of synthetic compositions, comprising: (a) a microbial cell, exudate therefrom, or culture broth therefrom, wherein the microbial cell is selected from the group consisting of: i. a microbial cell comprising a 16S or ITS sequence sharing at least 97% identity with a sequence selected from SEQ ID NOs: 1-21; ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding; wherein the microbe is present at a concentration of at least about 10^2 CFU/mL in a liquid formulation, or at least about 10^2 CFU/gram in a non-liquid formulation; wherein the agricultural composition comprises a growth medium; wherein the growth medium comprises soil; wherein the plurality of synthetic compositions are placed in the soil in a regular pattern with substantially equal spacing between each of the synthetic compositions.

In some aspects, it is provided a synthetic composition comprising: (a) an exudate or culture broth of a plurality of cells, wherein the cells comprise at least one microbial cell selected from the group consisting of: i. a microbial cell comprising a 16S or ITS sequence sharing at least 97% identity with a sequence selected from SEQ ID NOs: 1-21;

ii. a microbial cell obtained or derived from a microbe of Table 1 or Table 1A; and iii. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and (b) at least one heterologous composition selected from the group consisting of: a plant element, a formulation component, an agricultural composition, and any combination of the preceding.

In some aspects, it is provided a method of modulating a trait of agronomic importance in a plant obtained or derived from a plant element, comprising treating said plant element with a formulation comprising a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*.

In some aspects, it is provided a method of modulating a trait of agronomic importance in a plant obtained or derived from a plant element, comprising treating said plant element with a formulation comprising a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; wherein the trait of agronomic importance is selected from the group consisting of: disease resistance, drought tolerance, heat tolerance, cold tolerance, salinity tolerance, metal tolerance, herbicide tolerance, chemical tolerance, improved water use efficiency, improved nitrogen utilization, improved nitrogen fixation, pest resistance, herbivore resistance, pathogen resistance, increase in yield, increase in yield under water-limited conditions, health enhancement, vigor improvement, growth improvement, photosynthetic capability improvement, nutrition enhancement, altered protein content, altered oil content, increase in biomass, increase in shoot length, increase in root length, improved root architecture, increase in seed weight, altered seed carbohydrate composition, altered seed oil composition, increase in radical length, number of pods, delayed senescence, stay-green, altered seed protein composition, increase in dry weight of mature plant reproductive elements, increase in fresh weight of mature plant reproductive elements, increase in number of mature plant reproductive elements per plant, increase in chlorophyll content, increase in number of pods per plant, increase in length of pods per plant, increase in number of seeds per plant, increase in seed weight per plant, reduced number of wilted leaves per plant, reduced number of severely wilted leaves per plant, increase in number of non-wilted leaves per plant, or improved plant visual appearance.

In some aspects, it is provided a method of modulating a trait of agronomic importance in a plant obtained or derived from a plant element, comprising treating said plant element with a formulation comprising a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; wherein the microbial cell, exudate therefrom, or culture broth therefrom, is present in an amount capable of providing a benefit to a plant derived from the plant element, as compared to a plant derived from a plant element not treated with said microbial cell or exudate therefrom.

In some aspects, it is provided a method of cultivating a plant, comprising introducing to a plant element of said plant a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and wherein said microbial cell is heterologously disposed to the plant element.

In some aspects, it is provided a method of cultivating a plant, comprising introducing to a plant element of said plant a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and wherein said microbial cell is heterologously disposed to the plant element; wherein said introducing to the plant element is accomplished by an indirect method selected from the group consisting of: in-furrow application, soil drench application, and side-dress application.

In some aspects, it is provided a method of cultivating a plant, comprising introducing to a plant element of said plant a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and wherein said microbial cell is heterologously disposed to the plant element; wherein said introducing to the plant element is accomplished by coating said plant element with a liquid formulation of the microbe or exudate therefrom.

In some aspects, it is provided a method of cultivating a plant, comprising introducing to a plant element of said plant a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and wherein said microbial cell is heterologously disposed to the plant element; wherein said introducing to the plant element is accomplished by coating said plant element with a substantially non-liquid formulation of the microbe or exudate therefrom.

In some aspects, it is provided a method of cultivating a plant, comprising introducing to a plant element of said plant a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and wherein said microbial cell is heterologously disposed to the plant element; wherein said plant element is a seed.

In some aspects, it is provided a method of cultivating a plant, comprising introducing to a plant element of said plant a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and wherein said microbial cell is heterologously disposed to the plant element; wherein said plant element is a leaf.

In some aspects, it is provided a method of cultivating a plant, comprising introducing to a plant element of said plant a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and wherein said microbial cell is heterologously disposed to the plant element; wherein said plant element is a root.

In some aspects, it is provided a method of cultivating a plant, comprising introducing to a plant element of said plant a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; and wherein said microbial cell is heterologously disposed to the plant element; wherein said plant element is a whole plant.

In some aspects, it is provided a method of modulating a trait of agronomic importance in a harvested product, comprising introducing to the organism from which the harvested product was obtained a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacil-* lus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus.

In some aspects, it is provided a method of modulating a trait of agronomic importance in a harvested product, comprising introducing to the harvested product a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus.*

In some aspects, it is provided a method of modulating a trait of agronomic importance in a harvested product, comprising introducing to the organism from which the harvested product was obtained a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; wherein the harvested product is a fruit.

In some aspects, it is provided a method of modulating a trait of agronomic importance in a harvested product, comprising introducing to the harvested product a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; wherein the harvested product is a fruit.

In some aspects, it is provided a method of modulating a trait of agronomic importance in a harvested product, comprising introducing to the organism from which the harvested product was obtained a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; wherein the harvested product is a vegetable.

In some aspects, it is provided a method of modulating a trait of agronomic importance in a harvested product, comprising introducing to the harvested product a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; wherein the harvested product is a vegetable.

In some aspects, it is provided a method of modulating a trait of agronomic importance in a harvested product, comprising introducing to the organism from which the harvested product was obtained a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; wherein the harvested product is a seed.

In some aspects, it is provided a method of modulating a trait of agronomic importance in a harvested product, comprising introducing to the harvested product a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; wherein the harvested product is a seed.

In some aspects, it is provided a method of modulating a trait of agronomic importance in a harvested product, comprising introducing to the organism from which the harvested product was obtained a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; wherein the harvested product is a fiber.

In some aspects, it is provided a method of modulating a trait of agronomic importance in a harvested product, comprising introducing to the harvested product a microbial cell, exudate therefrom, or culture broth therefrom, wherein the microbial cell is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*; wherein the harvested product is a fiber.

In some aspects, it is provided A substantially cell-free preparation obtained or derived from a culture of a microbe, wherein the microbe is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*.

In some aspects, it is provided a purified composition prepared from a substantially cell-free preparation obtained or derived from a culture of a microbe, wherein the microbe is selected from the group consisting of: a. a microbial cell comprising a 16S or ITS sequence sharing at least 97% identity with a sequence selected from SEQ ID NOs: 1-21; b. a microbial cell obtained or derived from a microbe of Table 1 or Table 1A; and c. a microbial cell obtained or derived from a microbe of any of the following taxa: *Arthrobotrys oligospora, Bacillus amyloliquefaciens, Bacillus megaterium, Bacillus methylotrophicus, Bacillus pumilus, Bacillus tequilensis, Bacillus velezensis, Lysinibacillus fusiformis, Microbacterium arabinogalactanolyticum, Orbilia auricolor, Paenibacillus alginolyticus, Paenibacillus ehimensis, Paenibacillus illinoisensis, Paenibacillus taichungensis, Talaromyces pinophilus*.

In some aspects, it is provided an isolated bacterial strain selected from Table 1 or Table 1A, or an isolated bacterial strain having substantially similar morphological and physiological characteristics, substantially similar genetic characteristics, progeny, mutants, or genetically edited, altered, or modified variants thereof.

In some aspects, it is provided an isolated bacterial strain comprising a polynucleotide sequence sharing at least 97% sequence identity with any one of SEQ ID NOs: 1-21.

In some aspects, it is provided an agricultural composition, comprising: a) an isolated bacterial strain comprising a polynucleotide sequence sharing at least 97% sequence identity with any one of SEQ ID NOs: 1-21; and b) an agriculturally acceptable carrier; wherein the bacterial strain is present in the agricultural composition in an amount effective for producing an improved phenotype in a plant with which it is associated.

In some aspects, it is provided an agricultural composition, comprising: a) an isolated bacterial strain comprising a polynucleotide sequence sharing at least 97% sequence identity with any one of SEQ ID NOs: 1-21; and b) an agriculturally acceptable carrier; wherein the bacterial strain is present in the agricultural composition in an amount effective for producing an improved phenotype in a plant with which it is associated; wherein the agricultural composition is formulated as a seed coating, a foliar spray, a soil drench, a dip treatment, an in-furrow treatment, a soil amendment, granules, a broadcast treatment, or a post-harvest disease control treatment.

In some aspects, it is provided a microbial cell comprising a 16S or ITS sequence sharing at least 97% identity with a sequence selected from SEQ ID NOs: 1-21 and a plant element, wherein the microbial cell is heterologously disposed to the plant element.

In some embodiments, a single microbe from Table 1 or Table 1A is utilized.

In some embodiments, a microbe from the genus *Bacillus* is utilized. In some embodiments, a combination of one or more microbes from the genus *Bacillus* is utilized. In some embodiments, a microbe from the genus *Paenibacillus* is utilized. In some embodiments, a combination of one or more microbes from the genus *Paenibacillus* is utilized. In some embodiments, a microbe from the genus *Arthrobotrys* (teleomorph *Orbilia*) is utilized. In some embodiments, a microbe from the genus *Lysinibacillus* is utilized. In some embodiments, a microbe from the genus *Microbacterium* is utilized. In some embodiments, a microbe from the genus *Talaromyces* is utilized.

In some aspects, the single microbe—whether a taxonomically identifiable species or strain—is combined with one or more other microbes of a different species or strain. In certain aspects, the combination of two or more microbes forms a consortia or consortium. The terms consortia and consortium are utilized interchangeably.

In certain aspects, the disclosure provides for the development of highly functional microbial consortia that help promote the development and expression of a desired phenotypic or genotypic plant trait. In some embodiments, the consortia of the present disclosure possess functional attributes that are not found in nature, when the individual microbes are living alone. That is, in various embodiments, the combination of particular microbial species into consortia, leads to the microbial combination possessing functional attributes that are not possessed by any one individual member of the consortia when considered alone.

In some embodiments, this functional attribute possessed by the microbial consortia is the ability to impart one or more beneficial properties to a plant species, for example: increased growth, increased yield, increased nutrient utilization (e.g., nitrogen, phosphate, and the like), increased nitrogen utilization efficiency, increased stress tolerance, increased drought tolerance, increased photosynthetic rate, enhanced water use efficiency, increased pathogen resistance, modifications to plant architecture that don't necessarily impact plant yield, but rather address plant functionality, etc.

The ability to impart these beneficial properties upon a plant is not possessed, in some embodiments, by the individual microbes as they would occur in nature. Rather, in some embodiments, it is by the hand of man combining these microbes into consortia that a functional composition is developed, said functional composition possessing attributes and functional properties that do not exist in nature. In some embodiments, the consortia may include microbes that have been genetically edited, altered, or modified through the modification of genetic material including DNA, RNA, proteins and/or combinations of the same via techniques known to those of ordinary skill in the art.

However, in other embodiments, the disclosure provides for individual isolated and biologically pure microbes that are able to impart beneficial properties upon a desired plant species, without the need to combine said microbes into consortia.

In some embodiments, the microbial consortia can be any combination of one or more individual microbes from Table 1 or Table 1A. In other embodiments, a single microbe from Table 1 or Table 1A is used in combination with one or more microbes selected from Table 2. In other embodiments, one or more microbes from Tables 1 and/or 1A are utilized in combination with another microbe from said tables, or with one or more microbes from Table 2. In certain embodiments, the microbial consortia comprise two microbes, or three microbes, or four microbes, or five microbes, or six microbes, or seven microbes, or eight microbes, or nine microbes, or 10 microbes, or more than 10 microbes.

Another object of the disclosure relates to the use of the isolated microbes and microbial consortia as plant growth promoters. In other aspects, the isolated microbes and microbial consortia function as growth modifiers, which can, e.g., subvert normal senescence that leads to increased biomass.

Yet another object of the disclosure relates to the use of the isolated microbes and microbial consortia as soil health enhancers and plant health enhancers. In other aspects, the isolated microbes and microbial consortia function as biostimulants.

An additional object of the disclosure relates to the use of the isolated microbes and microbial consortia as pesticides. In other aspects, the isolated microbes and microbial consortia function as biofungicides. In other aspects, the isolated microbes and microbial consortia function as bionematicides.

Another object of the disclosure is to design a microbial consortium, which is able to perform multidimensional activities in common. In certain aspects, the microbes comprising the consortium act synergistically. In aspects, the effect that the microbial consortium has on a certain plant characteristic is greater than the effect that would be observed had any one individual microbial member of the consortium been utilized singularly. That is, in some aspects, the consortium exhibit a greater than additive effect upon a desired plant characteristic, as compared to the effect that would be found if any individual member of the consortium had been utilized by itself.

In some aspects, the consortia lead to the establishment of other plant-microbe interactions, e.g., by acting as primary colonizers or founding populations that set the trajectory for the future microbiome development.

In embodiments, the disclosure is directed to synergistic combinations (or mixtures) of microbial isolates.

In some aspects, the consortia taught herein provide a wide range of agricultural applications, including: improvements in yield of grain, fruit, and flowers; improvements in growth of plant parts; improved ability to utilize nutrients (e.g., nitrogen, phosphate, and the like), improved resistance to disease; biopesticidal effects including improved resistance to fungi, insects and nematodes; improved survivability in extreme climate; and improvements in other desired plant phenotypic characteristics. Significantly, these benefits to plants can be obtained without any hazardous side effects to the environment.

In some aspects, the individual microbes of the disclosure, or consortia comprising same, can be combined into an agriculturally acceptable composition.

In some embodiments, the agricultural compositions of the present disclosure include, but are not limited to: wetters, compatibilizing agents, antifoam agents, cleaning agents, sequestering agents, drift reduction agents, neutralizing agents, buffers, corrosion inhibitors, dyes, odorants, spreading agents, penetration aids, sticking agents, binders, dispersing agents, thickening agents, stabilizers, emulsifiers, freezing point depressants, antimicrobial agents, fertilizers, pesticides, herbicides, inert carriers, polymers, and the like.

In one embodiment of the present disclosure, the microbes (including isolated single species, or strains, consortia, or compositions thereof, such as metabolites), are supplied in the form of seed coatings or other applications to the seed. In embodiments, the seed coating may be applied to a naked and untreated seed. In other embodiments, the seed coating may be applied to a previously treated seed. Thus, in some embodiments, the present disclosure teaches a method of treating a seed comprising applying an isolated bacterial strain or a microbial consortium to a seed. In certain embodiments, the isolated bacterial strain or microbial consortium is applied as an agricultural composition including an agriculturally acceptable carrier. In some embodiments, the agricultural compositions may be formulated as: a soil drench, a foliar spray, a dip treatment, an in furrow treatment, a soil amendment, granules, a broadcast treatment, a post-harvest disease control treatment, or a seed treatment. In some embodiments, the agricultural compositions may be applied alone in or in rotation spray programs with other agricultural products. In some embodiments, the agricultural compositions may be compatible with tank mixing. In some embodiments, the agricultural compositions may be compatible with tank mixing with other agricultural products. In some embodiments, the agricultural compositions may be compatible with equipment used for ground, aerial, and irrigation applications.

In some embodiments, the applied microbes may become endophytic and consequently may be present in the growing plant that was treated and its subsequent offspring. In other embodiments the microbes might be applied at the same time as a co-treatment with seed treatments.

In one embodiment of the present disclosure, the microbes are supplied in the form of granules, or plug, or soil drench that is applied to the plant growth media. In other embodiments, the microbes are supplied in the form of a foliar application, such as a foliar spray or liquid composition. The foliar spray or liquid application may be applied to a growing plant or to a growth media, e.g., soil.

In other embodiments, the microbes (including isolated single species, or strains, or consortia, or compositions thereof, such as metabolites) are supplied as fertilizers, pesticides, or other amendments that may be applied to soil. In some embodiments, the microbes are supplied as fertilizers, pesticides, or other amendments that are applied to soil prior to planting. In some embodiments, the microbes are supplied as fertilizers, pesticides, or other amendments that are applied to soil concurrent with planting. In some embodiments, the microbes are supplied as fertilizers, pesticides, or other amendments that are applied to soil after planting.

In other embodiments of the present disclosure, the microbes (including isolated single species or strains, or consortia) and/or compositions thereof (e.g., metabolites) are supplied in the form of a post-harvest disease control application.

In embodiments, the agricultural compositions of the disclosure can be formulated as: (1) solutions; (2) wettable powders; (3) dusting powders; (4) soluble powders; (5) emulsions or suspension concentrates; (6) seed dressings, (7) tablets; (8) water-dispersible granules; (9) water soluble granules (slow or fast release); (10) microencapsulated granules or suspensions; (11) as irrigation components, and (12) a component of fertilizers, pesticides, and other compatible amendments, among others. In certain aspects, the compositions may be diluted in an aqueous medium prior to conventional spray application. The compositions of the present disclosure can be applied to the soil, plant, seed, rhizosphere, rhizosheath, or other area to which it would be beneficial to apply the microbial compositions.

Still another object of the disclosure relates to the agricultural compositions being formulated to provide a high colony forming units (CFU) bacterial population or consortia. In some aspects, the agricultural compositions have adjuvants that provide for a pertinent shelf life. In embodiments, the CFU concentration of the taught agricultural compositions is higher than the concentration at which the microbes would exist naturally, outside of the disclosed methods. In another embodiment, the agricultural composition contains the microbial cells in a concentration of $10^2$-$10^{12}$ CFU per gram of the carrier or $10^5$-$10^9$ CFU per gram of the carrier. In an aspect, the microbial cells are applied as a seed coat directly to a seed at a concentration of $10^5$-$10^9$ CFU. In other aspects, the microbial cells are applied as a seed overcoat on top of another seed coat at a concentration of $10^5$-$10^9$ CFU. In other aspects, the microbial cells are applied as a co-treatment together with another seed treatment at a rate of $10^5$-$10^9$ CFU.

In aspects, the disclosure is directed to agricultural microbial formulations that promote plant growth. In aspects, the disclosure provides for the taught isolated microbes, and consortia comprising same, to be formulated as an agricultural bioinoculant. The taught bioinoculants can be applied to plants, seeds, or soil, or combined with fertilizers, pesticides, and other compatible amendments. Suitable examples of formulating bioinoculants comprising isolated microbes can be found in U.S. Pat. No. 7,097,830, which is herein incorporated by reference.

The disclosed microbial formulations can: lower the need for nitrogen containing fertilizers, solubilize minerals, provide biopesticidal protection of the plants, protect plants against pathogens (e.g., fungi, insects, and nematodes), and make available to the plant valuable nutrients, such as nitrogen and/or phosphate, thus reducing and eliminating the need for using chemical pesticides and chemical fertilizers.

In some embodiments, the isolated and biologically pure microbes of the present disclosure can be utilized, in a method of imparting one or more beneficial properties or traits to a desired plant species.

In some embodiments, the agriculturally acceptable composition containing isolated and biologically pure microbes of the present disclosure can be utilized, in a method of imparting one or more beneficial properties or traits to a desired plant species.

In some embodiments, the consortia of the present disclosure can be utilized, in a method of imparting one or more beneficial properties or traits to a desired plant species.

In some embodiments, the agriculturally acceptable composition containing consortia of the present disclosure can be utilized, in a method of imparting one or more beneficial properties or traits to a desired plant species.

In some aspects, the isolated and biologically pure microbes of the present disclosure, and/or the consortia of the present disclosure, are derived from an accelerated microbial selection process ("AMS" process). The AMS process utilized in some aspects of the present disclosure is described, for example, in: (1) International Patent Application NO PCT/NZ2012/000041, published on Sep. 20, 2012, as International Publication NO WO 2012125050 A1, and (2) International Patent Application NO PCT/NZ2013/000171, published on Mar. 27, 2014, as International Publication NO WO 2014046553 A1, each of these PCT Applications is herein incorporated by reference in their entirety for all purposes. The AMS process is described in the present disclosure, for example, in FIGS. 1-4.

However, in other embodiments, the microbes of the present disclosure are not derived from an accelerated microbial selection process. In some aspects, the microbes utilized in embodiments of the disclosure are chosen from amongst members of microbes present in a database. In particular aspects, the microbes utilized in embodiments of the disclosure are chosen from microbes present in a database based upon particular characteristics of said microbes.

The present disclosure provides that a plant element or plant part can be effectively augmented, by coating said plant element or plant part with an isolated microbe or microbial consortia, in an amount that is not normally found on the plant element or plant part.

Some embodiments described herein are methods for preparing an agricultural seed composition, or seed coating, comprising: contacting the surface of a seed with a formulation comprising a purified microbial population that comprises at least one isolated microbe that is heterologous to, or rarely present on the seed. Further embodiments entail preparing an agricultural plant composition, comprising: contacting the surface of a plant with a formulation comprising a purified microbial population that comprises at least one isolated microbe that is heterologous to the plant. In other aspects, the formulation or microbe(s) is(are) introduced into the interior of the seed, for example into the cotyledon or the embryo other seed tissue.

In some aspects, applying an isolated microbe, microbial consortia, exudate, metabolite, and/or agricultural composition of the disclosure to a seed or plant modulates a trait of agronomic importance. The trait of agronomic importance can be, e.g., disease resistance, drought tolerance, heat tolerance, cold tolerance, salinity tolerance, metal tolerance, herbicide tolerance, chemical tolerance, improved water use efficiency, improved nitrogen utilization, improved resistance to nitrogen stress, improved nitrogen fixation, improved nutrient utilization (e.g., phosphate, potassium, and the like), pest resistance, herbivore resistance, pathogen resistance, reduced pathogen levels (e.g., via the excretion of metabolites that impair pathogen survival), increased yield, increased yield under water limited conditions, health enhancement, vigor improvement, growth improvement, photosynthetic capability improvement, nutrition enhancement, altered protein content, altered oil content, increased biomass, increased shoot length, increased root length, improved root architecture, increased seed weight, faster seed germination, altered seed carbohydrate composition, altered seed oil composition, number of pods, delayed senescence, stay-green, and altered seed protein composition. In some aspects, at least 2, 3, 4, or more traits of agronomic importance are modulated. In some aspects, the modulation is a positive effect on one of the aforementioned agronomic traits.

In some aspects, the isolated microbes, consortia, and/or agricultural compositions of the disclosure can be applied to a plant, in order to modulate or alter a plant characteristic such as altered oil content, altered protein content, altered seed carbohydrate composition, altered seed oil composition, altered seed protein composition, chemical tolerance, cold tolerance, delayed senescence, disease resistance, drought tolerance, ear weight, growth improvement, health enhancement, heat tolerance, herbicide tolerance, herbivore resistance, improved nitrogen fixation, improved nitrogen utilization, improved root architecture, improved water use efficiency, increased biomass, decreased biomass, increased root length, decreased root length, increased seed weight, increased shoot length, decreased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome relative to a reference plant.

In some embodiments, the agricultural formulations taught herein comprise at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient.

The methods described herein can include contacting a seed or plant with at least 100 CFU or spores, at least 300 CFU or spores, at least 1,000 CFU or spores, at least 3,000 CFU or spores, at least 10,000 CFU or spores, at least 30,000 CFU or spores, at least 100,000 CFU or spores, at least 300,000 CFU or spores, at least 1,000,000 CFU or spores or more, of the microbes taught herein.

The methods described herein can include contacting a seed or plant with a composition that includes metabolites produced by a single microbe or microbial consortium disclosed herein. In some aspects, the methods include contacting a seed or plant with a composition that includes at least 1 mg of metabolites produced by a single microbe or microbial consortium disclosed herein. In some aspects, the methods include contacting a seed or plant with a composition that includes at least 10 mg of metabolites produced by a single microbe or microbial consortium disclosed herein. In some aspects, the methods include contacting a seed or plant with a composition that includes at least 100 mg of metabolites produced by a single microbe or microbial consortium disclosed herein. In some aspects, the methods include contacting a seed or plant with a composition that includes at least 1 g of metabolites produced by a single microbe or microbial consortium disclosed herein. In some aspects, the methods include contacting a seed or plant with a composition that includes at least 10 g of metabolites produced by a single microbe or microbial consortium disclosed herein. In some aspects, the methods include contacting a seed or plant with a composition that includes at least 100 g of metabolites produced by a single microbe or microbial consortium disclosed herein. In some aspects, the methods include contacting a seed or plant with a composition that includes at least 1 kg of metabolites produced by a single microbe or microbial consortium disclosed herein. In some aspects, the methods include contacting a seed or plant with a composition that includes greater than 1 kg of metabolites produced by a single microbe or microbial consortium disclosed herein.

In some embodiments of the methods described herein, an isolated microbe of the disclosure is present in a formulation in an amount effective to be detectable within and/or on a target tissue of an agricultural plant. For example, the microbe is detected in an amount of at least 100 CFU or spores, at least 300 CFU or spores, at least 1,000 CFU or spores, at least 3,000 CFU or spores, at least 10,000 CFU or spores, at least 30,000 CFU or spores, at least 100,000 CFU or spores, at least 300,000 CFU or spores, at least 1,000,000 CFU or spores, or more, in and/or on a target tissue of a plant. Alternatively or in addition, the microbes of the disclosure may be present in a formulation in an amount effective to increase the biomass and/or yield of a plant that has had such a formulation applied thereto, by at least 1%, at least 2%, at least 3%, at least 5%, at least 10%, at least 15%, at least 20%, at least 30%, at least 40%, at least 50%, at least 60%, at least 70%, at least 80%, at least 90%, at least 100%, or more, when compared with a reference agricultural plant that has not had the formulations of the disclosure applied. Alternatively or in addition, the microbes of the disclosure may be present in a formulation in an amount effective to detectably modulate an agronomic trait of interest of a plant that has had such a formulation applied thereto, by at least 1%, at least 2%, at least 3%, at least 5%, at least 10%, at least 15%, at least 20%, at least 30%, at least 40%, at least 50%, at least 60%, at least 70%, at least 80%, at least 90%, at least 100%, or more, when compared with a reference agricultural plant that has not had the formulations of the disclosure applied.

In some embodiments of the methods described herein, one or more metabolites isolated from the microbes or consortia of the disclosure are present in a formulation in an amount effective to be detectable within and/or on a target tissue of an agricultural plant. For example, the metabolites are detected in an amount of at least 1 mg, at least 10 mg, at least 50 mg, at least 100 mg, at least 200 mg, at least 400 mg, at least 600 mg, at least 800 mg, at least 1 g, or more, in and/or on a target tissue of a plant. Alternatively or in addition, the metabolites isolated from the microbes and consortia of the disclosure may be present in a formulation in an amount effective to increase the biomass and/or yield of a plant that has had such a formulation applied thereto, by at least 1%, at least 2%, at least 3%, at least 5%, at least 10%, at least 15%, at least 20%, at least 30%, at least 40%, at least 50%, at least 60%, at least 70%, at least 80%, at least 90%, at least 100%, or more, when compared with a reference agricultural plant that has not had the formulations of the disclosure applied. Alternatively or in addition, the metabolites isolated from the microbes and consortia of the disclosure may be present in a formulation in an amount effective to detectably modulate an agronomic trait of interest of a plant that has had such a formulation applied thereto, by at least 1%, at least 2%, at least 3%, at least 5%, at least 10%, at least 15%, at least 20%, at least 30%, at least 40%, at least 50%, at least 60%, at least 70%, at least 80%, at least 90%, at least 100%, or more, when compared with a reference agricultural plant that has not had the formulations of the disclosure applied.

In some embodiments, the agricultural compositions taught herein are shelf-stable. In some aspects, the microbes taught herein are freeze-dried. In some aspects, the microbes taught herein are spray-dried. In some aspects, the microbes taught herein are placed in a liquid formulation. In some aspects, the microbes taught herein are present on granules, Also described herein are a plurality of isolated microbes confined within an object selected from the group consisting of: bottle, jar, ampule, package, vessel, bag, box, bin, envelope, carton, container, silo, shipping container, truck bed, and case.

In some aspects, combining a selected plant species with a disclosed microbe—operational taxonomic unit (OTU), strain, or composition comprising any of the aforementioned—leads to improved yield from crops and generation of products thereof. Therefore, in one aspect, the present disclosure provides a synthetic combination of a seed of a first plant and a preparation of a microbe(s) that is coated onto the surface of the seed of the first plant, such that the microbe is present at a higher level on the surface of the seed, than is present on the surface of an uncoated reference seed. In another aspect, the present disclosure provides a synthetic combination of a part of a first plant and a preparation of a microbe(s) that is coated onto the surface of the part of the first plant, such that the microbe is present at a higher level on the surface of the part of the first plant, than is present on the surface of an uncoated reference plant part. The aforementioned methods can be used alone, or in parallel with plant breeding and transgenic technologies.

In some embodiments, an isolated bacterial strain may be selected from the group consisting of *Bacillus velezensis* deposited as NRRL Accession No. B-67810, *Bacillus methylotrophicus* deposited as NRRL Accession No. B-67812 *Bacillus amyloliquefaciens* deposited as NRRL Accession No. B-67815, B-67947, or B-67947, *Paenibacillus alginolyticus* deposited as NRRL Accession No. B-67813, or B-67811, *Orbilia auricolor/Arthrobotrys oligospora* deposited as NRRL Accession No. 67879 (teleomorph and anamorph, respectively, of the same species of microorganism), *Bacillus pumilus* deposited as NRRL Accession No. B-67878, and *Lysinibacillus fusiformis* deposited as NRRL Accession No. B-67871.

In some embodiments, a biological consortium may include isolated bacterial strains of *Paenibacillus alginolyticus* deposited as NRRL Accession No. B-67813, and B-67811. In some embodiments, a biological consortium may include isolated bacterial strains of *Bacillus amyloliquefaciens* deposited as NRRL Accession No. B-67947 and B-67813. In some embodiments, a biological consortium may include isolated bacterial strains of *Bacillus velezensis* deposited as NRRL Accession No. B-50614 and *Bacillus pumilus* deposited as NRRL Accession No. B-67878.

In some embodiments, the isolated bacterial strain has substantially similar morphological and physiological characteristics as an isolated bacterial strain of the present disclosure. In some embodiments, the isolated bacterial strain has substantially similar genetic characteristics as an isolated bacterial strain of the present disclosure. In some embodiments, the isolated bacterial strain is a mutant, naturally occurring or man-made, of an isolated bacterial strain of the present disclosure. In some embodiments, the isolated bacterial strain is a genetically edited, altered, or modified bacterial strain. In some embodiments, an isolated bacterial strain of the present disclosure is in substantially pure culture. In some embodiments, an isolated bacterial strain of the present disclosure is in pure culture. In some embodiments, an isolated bacterial strain of the present disclosure is in a cell fraction, extract or supernatant.

In some embodiments, progeny and/or mutants of an isolated bacterial strain of the present disclosure are contemplated. In some embodiments, progeny, mutants, and/or genetically modified versions of an isolated bacterial strain of the present disclosure are contemplated. In some embodiments, an isolated bacterial strain of the present disclosure comprises a polynucleotide sequence sharing at least 97% sequence identity with any one of SEQ ID Nos: 1-12.

In some embodiments, a cell-free or inactivated preparation of an isolated bacterial strain of the present disclosure is contemplated, or a mutant of said isolated bacterial strain. In some embodiments, a cell-free or inactivated preparation of an isolated bacterial strain of the present disclosure is contemplated, or a mutant or genetically edited, altered, or modified variant of said isolated bacterial strain. In some embodiments, a metabolite produced by an isolated bacterial strain of the present disclosure is contemplated, or a mutant of said isolated bacterial strain. In some embodiments, a metabolite produced by an isolated bacterial strain of the present disclosure is contemplated, or a mutant or genetically modified variant of said isolated bacterial strain.

In some embodiments, an agricultural composition comprises an isolated bacterial strain and an agriculturally acceptable carrier. The isolated bacterial strain may be present in the composition at $1\times10^2$ to $1\times10^{12}$ CFU per gram. The agricultural composition may be formulated as a seed coating.

In some embodiments, a method of imparting at least one beneficial trait upon a plant species comprises applying an isolated bacterial strain to the plant or to a growth medium in which said plant is located. In some embodiments, a method of imparting at least one beneficial trait upon a plant species comprises applying an agricultural composition of the present disclosure to the plant or to a growth medium in which the plant is located.

In some embodiments, the present disclosure teaches a method of growing a plant having at least one beneficial trait. In some embodiments, the method comprises applying an isolated bacterial strain or microbial consortium to the seed of a plant; sowing or planting the seed; and growing the plant. In certain embodiments, the isolated bacterial strain or microbial consortium is applied as an agricultural composition that further includes an agriculturally acceptable carrier.

In some embodiments a microbial consortium comprises at least two microbes selected from the groups consisting of: A) *Bacillus tequilensis, Bacillus methylotrophicus, Bacillus amyloliquefaciens, Paenibacillus alginolyticus, Orbilia auricolor/Arthrobotrys oligospora* (teleomorph and anamorph, respectively), *Bacillus pumilus*, and *Lysinibacillus fusiformis*; and B) *Arthrobacter cupressi, Arthrobacter* mysorens, *Arthrobacter nicotinovorans, Arthrobacter pascens, Bacillus megaterium, Bacillus subtilis, Bacillus thuringiensis, Bacillus velezensis, Brevibacterium frigoritolerans, Herbaspirillum chlorophenolicum, Kosakonia radicincitans, Lysinibacillus fusiformis, Massilia kyonggiensis, Massilia niastensis, Novosphingobium sediminicola, Paenibacillus amylolyticus, Paenibacillus glycanilyticus, Paenibacillus polymyxa, Pseudomonas fluorescens, Pseudomonas jinjuensis, Pseudomonas oryzihabitans, Pseudomonas putida, Rahnella aquatilis,* and *Tumebacillus permanentifrigoris*; and combinations thereof, wherein at least one microbe from A) is selected.

In some embodiments a microbial consortium comprises at least two isolated bacterial strains selected from the groups consisting of: A) *Bacillus velezensis* deposited as NRRL Accession No. B-67810, *Bacillus methylotrophicus* deposited as NRRL Accession No. B-67812, *Bacillus amyloliquefaciens* deposited as NRRL Accession No. B-67815, *Bacillus amyloliquefaciens* deposited as NRRL Accession No. B-67947, *Bacillus amyloliquefaciens* deposited as NRRL Accession No. B-67949, *Paenibacillus alginolyticus* deposited as NRRL Accession No. B-67813, *Paenibacillus alginolyticus, Paenibacillus alginolyticus, Paenibacillus alginolyticus* deposited as NRRL Accession No. B-67811, *Orbilia auricolor/Arthrobotrys oligospora* deposited as NRRL Accession No. 67879 (teleomorph and anamorph, respectively), *Bacillus pumilus* deposited as NRRL Accession No. B-67878, and *Lysinibacillus fusiformis* deposited as NRRL Accession No. B-67871; and B) *Arthrobacter cupressi* deposited as NRRL Accession No. B-67183, *Arthrobacter cupressi* deposited as NRRL Accession No. B-67184, *Arthrobacter mysorens, Arthrobacter nicotinovorans* deposited as NRRL Accession No. B-67289, *Arthrobacter pascens, Bacillus megaterium* deposited as NRRL Accession No. B-67370, *Bacillus megaterium, Bacillus megaterium, Bacillus subtilis, Bacillus subtilis, Bacillus subtilis, Bacillus thuringiensis, Bacillus velezensis* deposited as NRRL Accession No. B-50614, *Brevibacterium frigoritolerans* deposited as NRRL Accession No. B-67360, *Herbaspirillum chlorophenolicum* deposited as NRRL Accession No. B-67236, *Herbaspirillum chlorophenolicum* deposited as NRRL Accession No. B-67197, *Kosakonia radicincitans* deposited as NRRL Accession No. B-67171, *Kosakonia radicincitans* deposited as NRRL Accession No. B-67946, *Lysinibacillus fusiformis, Massilia kyonggiensis* deposited as NRRL Accession No. B-67198, *Massilia niastensis* deposited as NRRL Accession No. B-67235, *Massilia niastensis* deposited as NRRL Accession No. B-67199, *Massilia niastensis, Novosphingobium sediminicola* deposited as NRRL Accession No. B-67945, *Paenibacillus amylolyticus, Paenibacillus glycanilyticus* deposited as NRRL Accession No. B-67204, *Paenibacillus polymyxa, Pseudomonas fluorescens, Pseudomonas fluorescens, Pseudomonas fluorescens, Pseudomonas fluorescens, Pseudomonas fluorescens, Pseudomonas jinjuensis* deposited as NRRL Accession No. B-67207, *Pseudomonas oryzihabitans* deposited as NRRL Accession No. B-67225, *Pseudomonas oryzihabitans, Pseudomonas oryzihabitans, Pseudomonas oryzihabitans, Pseudomonas putida, Pseudomonas putida, Pseudomonas putida, Pseudomonas putida, Pseudomonas putida, Pseudomonas putida, Pseudomonas putida, Pseudomonas putida, Rahnella aquatilis, Tumebacillus permanentifrigoris* deposited as NRRL Accession No. B-67301, and *Tumebacillus permanentifrigoris* deposited as NRRL Accession No. B-67302; and combinations thereof, wherein at least one microbe from A) is selected.

In some embodiments, the microbial consortium has substantially similar morphological and physiological characteristics as a microbial consortium of the present disclosure. In some embodiments, the microbial consortium has substantially similar genetic characteristics as a microbial consortium of the present disclosure. In some embodiments, the microbial consortium is in substantially pure culture. In some embodiments, a subsequent generation of any microbe of the microbial consortium is contemplated. In some embodiments, a mutant of any microbe of the microbial consortium is contemplated. In some embodiments, a genetically edited, altered, or modified variant of any microbe of the microbial consortium is contemplated. In some embodiments, a cell-free or inactivated preparation of the microbial consortium, or a mutant or genetically edited, altered, or modified variant of any microbe in the microbial consortium, is contemplated. In some embodiments, a metabolite produced by the microbial consortium, or a mutant or genetically edited, altered, or modified variant of any microbe in the microbial consortium, is contemplated.

In some embodiments, an agricultural composition comprises a microbial consortium and an agriculturally acceptable carrier. The microbial consortium of the agricultural composition may be present in the composition at $1 \times 10^3$ to $1 \times 10^{12}$ bacterial cells per gram. In some embodiments, the agricultural composition is formulated as a seed coating. In some embodiments, a method of imparting at least one beneficial trait upon a plant species comprises applying a microbial consortium to said plant, or to a growth medium in which said plant is located. In some embodiments, a method of imparting at least one beneficial trait upon a plant species, comprising applying the agricultural composition to the plant, or to a growth medium in which said plant is located.

In some embodiments, a microbial consortium comprises a microbe selected from the group consisting of *Bacillus velezensis* deposited as NRRL Accession No. B-67810, *Bacillus methylotrophicus* deposited as NRRL Accession No. B-67812, *Bacillus amyloliquefaciens* deposited as NRRL Accession No. B-67815, *Bacillus amyloliquefaciens* deposited as NRRL Accession No. B-67947, *Bacillus amyloliquefaciens* deposited as NRRL Accession No. B-67949, *Paenibacillus alginolyticus* deposited as NRRL Accession No. B-67813, *Paenibacillus alginolyticus, Paenibacillus alginolyticus, Paenibacillus alginolyticus* deposited as NRRL Accession No. B-67811, *Orbilia auricolor/Arthrobotrys oligospora* deposited as NRRL Accession No. 67879 (teleomorph and anamorph, respectively), *Bacillus pumilus* deposited as NRRL Accession No. B-67878, and *Lysinibacillus fusiformis* deposited as NRRL Accession No. B-67871.

In some embodiments, a method of imparting at least one beneficial trait upon a plant species comprises applying at least one isolated bacterial species to the plant, or to a growth medium in which the plant is located, wherein at least one isolated bacterial species is selected from the group consisting of: *Bacillus tequilensis, Bacillus methylotrophicus, Bacillus amyloliquefaciens, Paenibacillus alginolyticus, Orbilia auricolor/Arthrobotrys oligospora* (teleomorph and anamorph, respectively), *Bacillus pumilus, Lysinibacillus fusiformis,* and combinations thereof.

In a further embodiment, at least one isolated bacterial species is a strain selected from the group consisting of: *Bacillus tequilensis Bacillus velezensis* deposited as NRRL Accession No. B-67810, *Bacillus methylotrophicus* deposited as NRRL Accession No. B-67812, *Bacillus amyloliquefaciens* deposited as NRRL Accession No. B-67815,

*Bacillus amyloliquefaciens* deposited as NRRL Accession No. B-67947, *Bacillus amyloliquefaciens* deposited as NRRL Accession No. B-67949, *Paenibacillus alginolyticus* deposited as NRRL Accession No. B-67813, *Paenibacillus alginolyticus, Paenibacillus alginolyticus, Paenibacillus alginolyticus* deposited as NRRL Accession No. B-67811, *Orbilia auricolor/Arthrobotrys oligospora* deposited as NRRL Accession No. 67879 (teleomorph and anamorph, respectively), *Bacillus pumilus* deposited as NRRL Accession No. B-67878, and *Lysinibacillus fusiformis* deposited as NRRL Accession No. B-67871, and combinations thereof.

In some embodiments, an isolated bacterial strain is selected from Table 1 or Table 1A. In some embodiments, an isolated bacterial strain is contemplated having substantially similar morphological and physiological characteristics as an isolated bacterial strain selected from Table 1 or Table 1A. In some embodiments, an isolated bacterial strain is contemplated having substantially similar genetic characteristics as an isolated bacterial strain from Table 1 or Table 1A. In some embodiments, a substantially pure culture is contemplated of an isolated bacterial strain from Table 1 or Table 1A. In some embodiments, a progeny or a mutant of an isolated bacterial strain from Table 1 or Table 1A is contemplated. In some embodiments, a cell-free or inactivated preparation is contemplated from an isolated bacterial strain, or a mutant thereof, from Table 1 or Table 1A. In some embodiments, a metabolite produced by an isolated bacterial strain, or a mutant thereof, from Table 1 or Table 1A.

In some embodiments, an agricultural composition comprises an isolated bacterial strain from Table 1 or Table 1A and an agriculturally acceptable carrier. In some embodiments, the isolated bacterial strain is present in the agricultural composition at $1 \times 10^2$ to $1 \times 10^{12}$ CFU per gram. In some embodiments, the agricultural composition is formulated as a seed coating. In some embodiments, a method of imparting at least one beneficial trait upon a plant species comprises applying an isolated bacterial strain from Table 1 or Table 1A to the plant, or to a growth medium in which said plant is located. In some embodiments, a method of imparting at least one beneficial trait upon a plant species comprises applying an agricultural composition of the present disclosure to the plant, or to a growth medium in which said plant is located.

In some embodiments, a microbial consortium comprises at least two microbes selected from those listed in Table 1 or Table 1A. In some embodiments, a microbial consortium comprises at least two microbes, wherein at least one microbe is selected from Table 1 or Table 1A, and other microbe(s) may be selected from Table 2.

In some embodiments, a plant seed enhanced with a microbial seed coating comprises a plant seed and a seed coating applied onto said plant seed, wherein the seed coating comprises at least two microbes as listed in Tables 1, 1A, and 2, and wherein at least one microbe is selected from Table 1 or Table 1A. In a further embodiment, the seed coating comprises a combination of microbes. In a further embodiment, the seed coating comprises at least one microbe as listed in Table 1 or Table 1A at a concentration of $1 \times 10^2$ to $1 \times 10^9$ CFU per seed. In some embodiments, a microbe selected from Table 1 is used in agriculture. In some embodiments, a synthetic combination of a plant and microbe comprises at least one plant and at least one microbe selected from Table 1 or Table 1A.

In some embodiments, a method of increasing or promoting a desirable phenotypic trait of a plant species comprises applying at least one microbe selected from Table 1 or Table 1A to said plant, or to a growth medium in which said plant is located. In a further embodiment, the method of applying the at least one bacteria occurs by coating a plant seed with said bacteria, coating a plant part with said bacteria, spraying said bacteria onto a plant part, spraying said bacteria into a furrow into which a plant or seed will be placed, drenching said bacteria onto a plant part or into an area into which a plant will be placed, spreading said bacteria onto a plant part or into an area into which a plant will be placed, broadcasting said bacteria onto a plant part or into an area into which a plant will be placed, and combinations thereof.

In any of the methods, the microbe can include a 16S rRNA nucleic acid sequence having at least 97% sequence identity to a 16S rRNA nucleic acid sequence of a bacteria selected from a genus or species provided in Table 1 or Table 1A.

BRIEF DESCRIPTION OF THE DRAWINGS AND THE SEQUENCE LISTING

The disclosure can be more fully understood from the following detailed description and the accompanying drawings and Sequence Listing, which form a part of this application.

FIG. 1 shows a generalized process schematic of a disclosed method of accelerated microbial selection (AMS), also referred to herein as directed microbial selection. When the process is viewed in the context of a microbial consortium, the schematic is illustrative of a process of directed evolution of a microbial consortium. The process is one method by which the beneficial microbes of the present disclosure were obtained.

Figure 1:
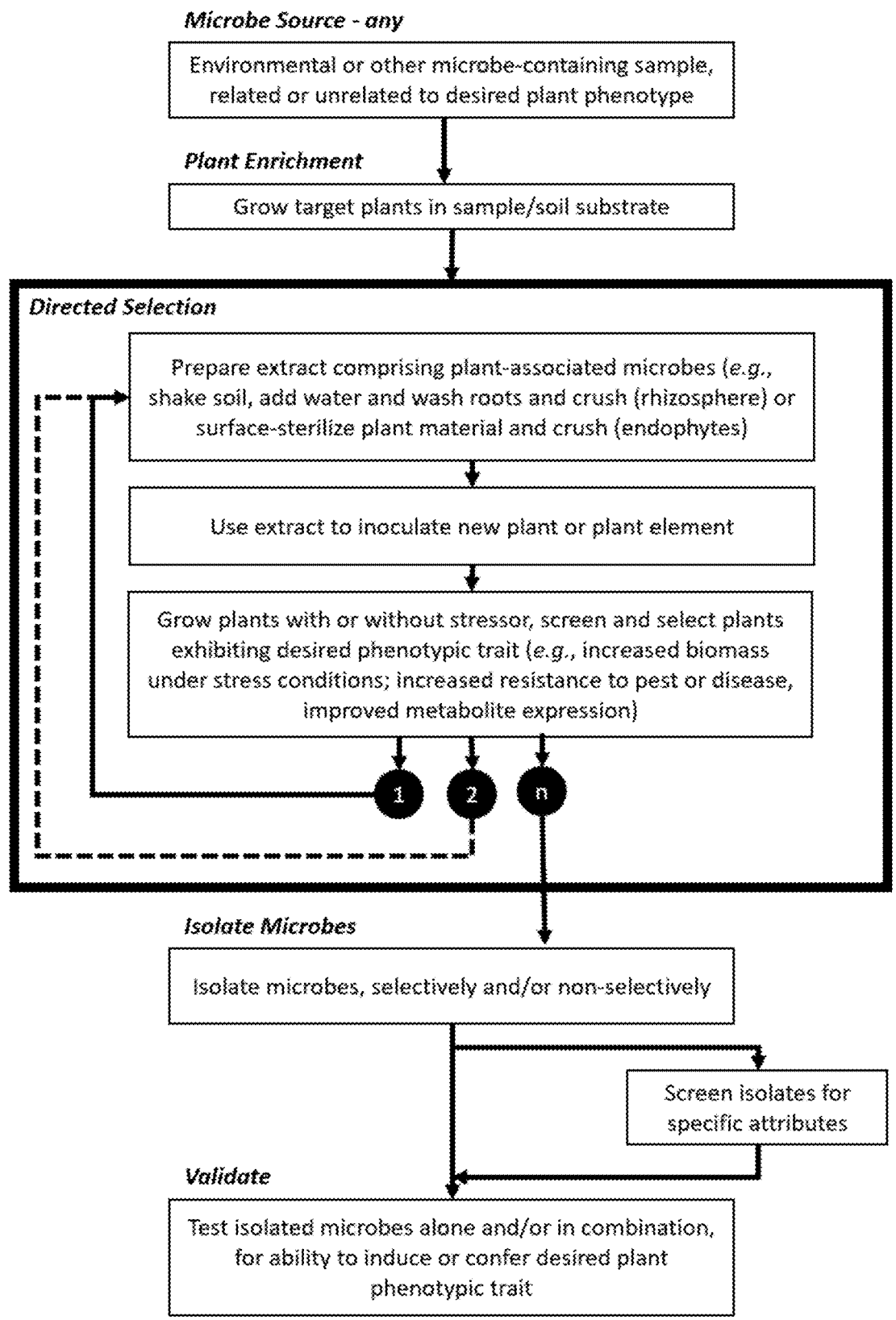
Figure 2:
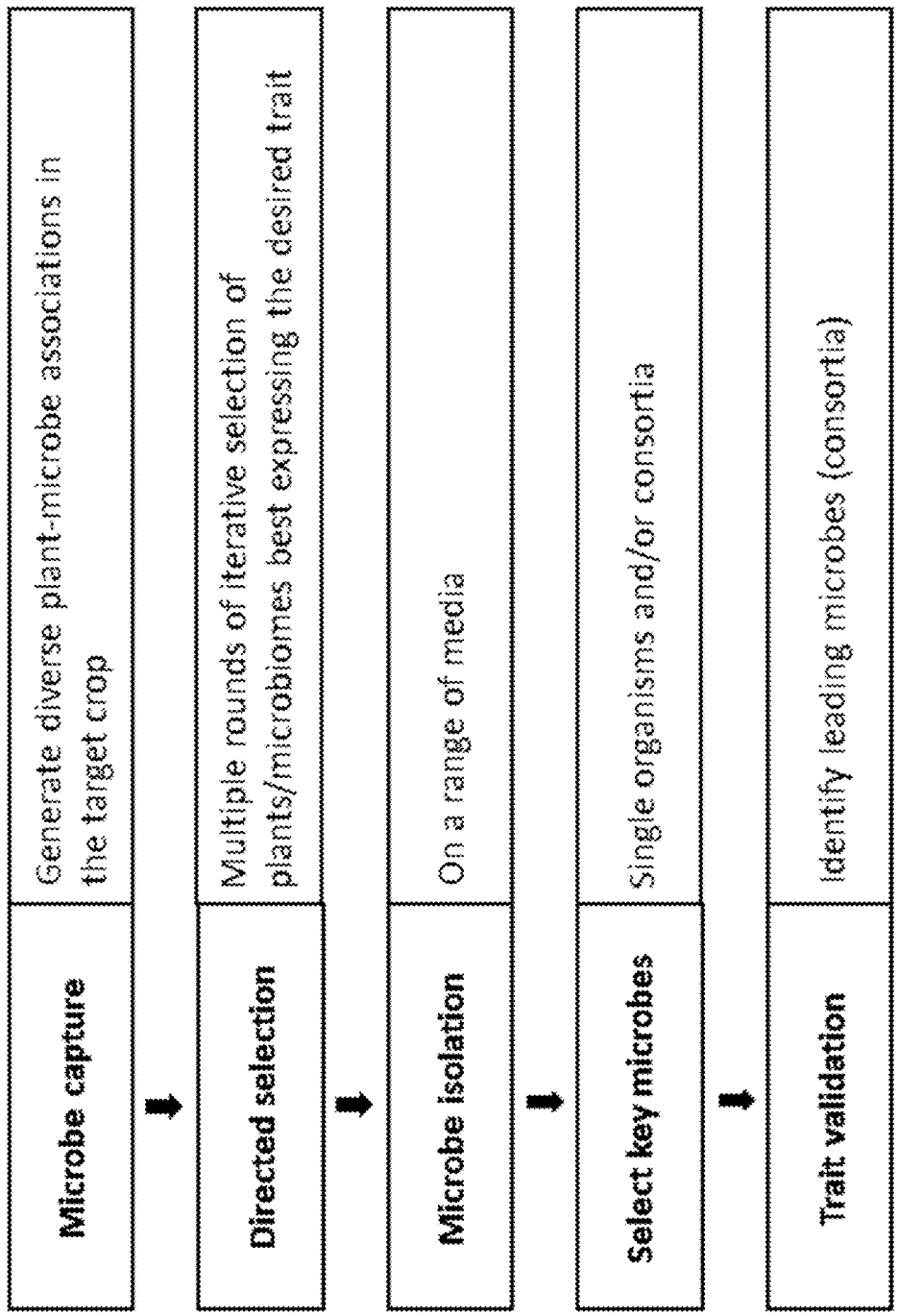
FIG. 2 shows a generalized process flow chart of an embodiment, by which the beneficial microbes of the present disclosure were obtained.
Figure 3:
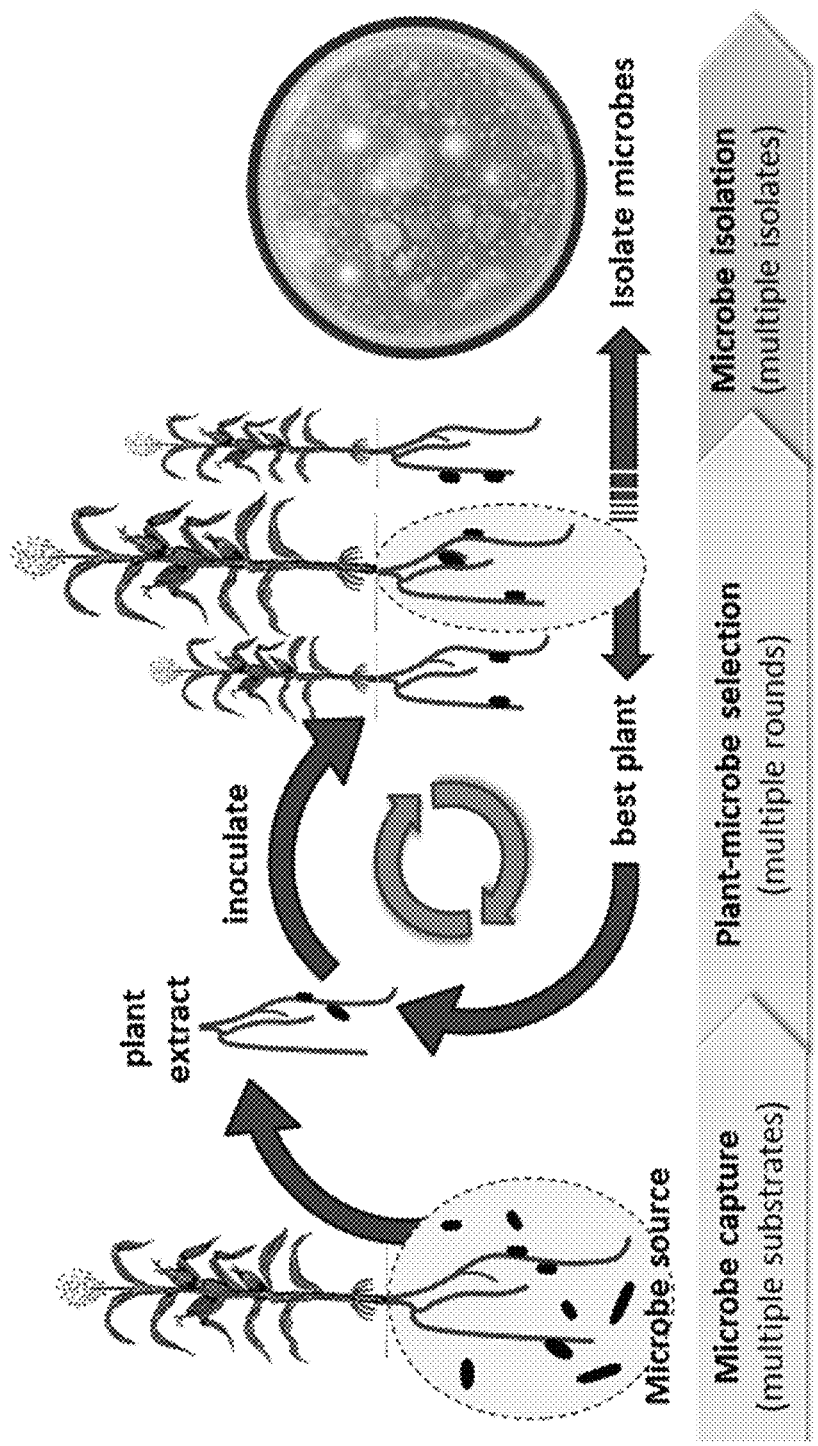
FIG. 3 shows a graphic representation and associated flow chart of an embodiment, by which the beneficial microbes of the present disclosure were obtained.
Figure 4:
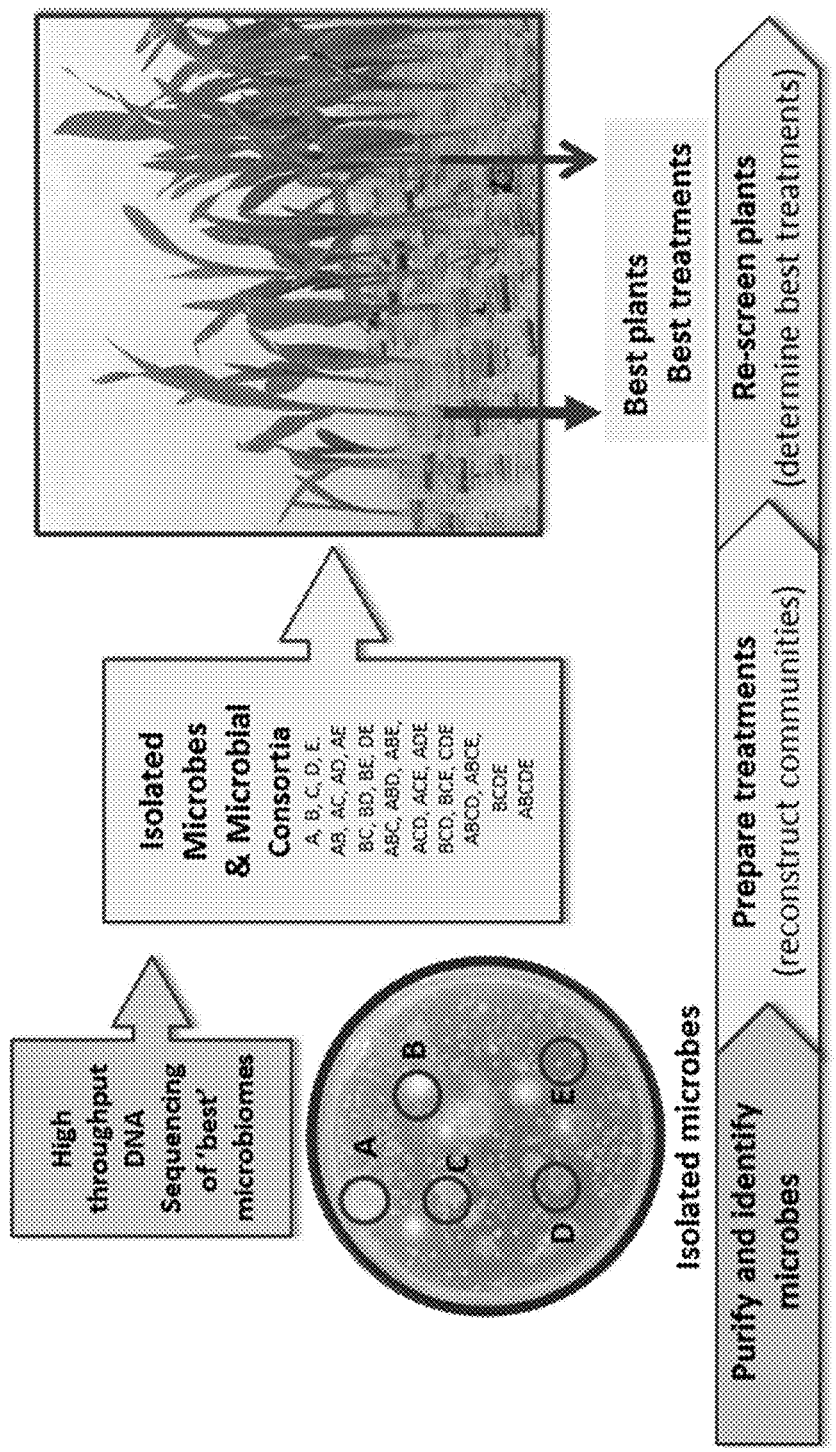
FIG. 4 shows a graphic representation and associated flow chart of an embodiment, by which the beneficial microbes of the present disclosure were obtained.
Figure 5:
FIG. 5 shows that *B. velezensis* BEC80 colonizes roots (GFP-tagged microbe on cauliflower roots).

The sequence descriptions and sequence listing attached hereto comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference.

The microorganisms described in this Application were deposited with the Agricultural Research Service Culture Collection (NRRL), which is an International Depositary Authority, located at 1815 North University Street, Peoria, IL 61604, USA.

The deposits were made under the terms of the Budapest Treaty on the International Recognition of the Deposit of Microorganisms for the Purposes of Patent Procedure.

The deposits were made in accordance with, and to satisfy, the criteria set forth in 37 C.F.R. §§ 1.801-1.809 and the Manual of Patent Examining Procedure §§ 2402-2411.05.

The NRRL accession numbers, dates of deposit, and descriptions for the aforementioned Budapest Treaty deposits are provided in Tables 1 and 2.

TABLE 1

Microbes

| Microbial Species | Strain ID | Origin | Budapest Treaty BTIDA Accession No. & Deposit Date | SEQ ID NO | Sequence Type |
|---|---|---|---|---|---|
| *Bacillus* tequilensis | BEC80 | US | NRRL B-67810 Jul. 3, 2019 | 1 | 16S |
| *Bacillus* methyl otrophicus | BEC60 | US | NRRL B-67812 Jul. 3, 2019 | 2 | 16S |
| *Bacillus* amyloliquefaciens | BEC69 | US | NRRL B-67815 Jul. 3, 2019 | 3 | 16S |
| *Bacillus* amyloliquefaciens | BEC77A | US | NRRL B-67947 Apr. 2, 2020 | 4 | 16S |
| *Bacillus* amyloliquefaciens | BEC77B | US | NRRL B-67949 Apr. 2, 2020 | 5 | 16S |
| *Paenibacillus* alginolyticus | BEC68A | US | NRRL B-67813 Jul. 3, 2019 | 6 | 16S |
| *Paenibacillus* alginolyticus | BEC68B | US | NRRL____ | 7 | 16S |
| *Paenibacillus* alginolyticus | BEC68C | US | NRRL____ | 8 | 16S |
| *Paenibacillus* alginolyticus | BEC68D | US | NRRL B-67811 Jul 3, 2019 | 9 | 16S |
| Orbilia auricolor (teleomorph)/ Arthrobotrys oligospora (anamorph) | BEC93 | US | NRRL B-67879 Oct. 30, 2019 | 10 | ITS |
| *Bacillus pumilus* | BEC89B | US | NRRL B-67878 Oct. 30, 2019 | 11 | 16S |
| Lysinibacillus fusiformis | BEC91 | US | NRRL B-67871 Oct. 30, 2019 | 12 | 16S |

TABLE 1A

Microbes

| Microbial Species | Strain ID | Origin | Budapest Treaty BTIDA Accession No. & Deposit Date | SEQ ID NO | Sequence Type |
|---|---|---|---|---|---|
| *Bacillus* methyl otrophicus | BEC56 | | NRRL____ | 13 | 16S |
| *Bacillus* amyloliquefaciens | BEC118A | | NRRL____ | 14 | 16S |
| *Bacillus* tequilensis | BEC118B | | NRRL____ | 15 | 16S |
| *Bacillus* megaterium | BEC71 | | NRRL____ | 16 | 16S |
| *Paenibacillus* taichungensis | BEC110 | | NRRL____ | 17 | 16S |
| *Paenibacillus* ehimensis | BEC120 | | NRRL____ | 18 | 16S |
| *Paenibacillus* illinoisensis | BEC108 | | NRRL____ | 19 | 16S |
| Microbacterium arabinogalactanolyticum | BEC102 | | NRRL____ | 20 | 16S |
| Talaromyces pinophilus | BEC101 | | NRRL____ | 21 | ITS |

TABLE 2

Microbes

| Microbial Species | Strain | Origin | BTIDA Accession No. & Deposit Date |
|---|---|---|---|
| *Arthrobacter* cupressi | 62 | US | NRRL B-67184 |
| *Arthrobacter* cupressi | 59 | US | NRRL B-67183 |
| *Arthrobacter* mysorens | 700 | US | |
| *Arthrobacter* nicotinovorans | 717 | US | NRRL B-67289 Jul. 14, 2016 |
| *Arthrobacter* pascens | 682 | US | |
| *Bacillus megaterium* | 4473 | US | NRRL B-67370 Jan. 17, 2016 |
| *Bacillus megaterium* | 255 | US | |
| *Bacillus megaterium* | 251 | US | |
| *Bacillus subtilis* | 395 | US | |
| *Bacillus subtilis* | 1089 | US | |
| *Bacillus subtilis* | 989 | US | |
| *Bacillus thuringiensis* | 715 | US | |
| *Bacillus velezensis* | IM20 | US | NRRL B-50614 |
| *Brevibacterium frigoritolerans* | 4468 | US | NRRL B-67360 Jan. 5, 2016 |
| *Herbaspirillum chlorophenolicum* | 58 | US | NRRL B-67236 |
| *Herbaspirillum chlorophenolicum* | 162 | US | NRRL B-67197 |
| *Kosakonia radicincitans* | 44 | US | NRRL B-67171 |
| *Kosakonia radicincitans* | 107 | US | NRRL B-67946 |
| *Lysinibacillus fusiformis* | 63466 | NZ | |
| *Massilia* kyonggiensis | 97 | US | NRRL B-67198 |
| *Massilia* niastensis | 54456 | NZ | |
| *Massilia* niastensis | 55184 | NZ | NRRL B-67235 |
| *Massilia* niastensis | 1217 | US | NRRL B-67199 |
| *Noyosphingobium sediminicola* | 82 | US | NRRL B-67945 |
| *Paenibacillus amylolyticus* | 66316 | NZ | |
| *Paenibacillus glyconilyticus* | 418 | US | NRRL B-67204 |
| *Paenibacillus polymyxa* | 1118 | US | |
| *Pseudomonas fluorescens* | 1352 | US | |
| *Pseudomonas fluorescens* | 56530 | NZ | |
| *Pseudomonas fluorescens* | 54480 | NZ | |
| *Pseudomonas fluorescens* | 57634 | NZ | |
| *Pseudomonas fluorescens* | 56249 | NZ | |
| *Pseudomonas jinjuensis* | 804 | US | NRRL B-67207 |
| *Pseudomonas oryzihabitans* | 55530 | NZ | NRRL B-67225 |
| *Pseudomonas oryzihabitans* | 1195 | US | |
| *Pseudomonas oryzihabitans* | 1199 | US | |
| *Pseudomonas oryzihabitans* | 1184 | US | |
| *Pseudomonas putida* | 1353 | US | |
| *Pseudomonas putida* | 1351 | US | |
| *Pseudomonas putida* | 1333 | US | |
| *Pseudomonas putida* | 178 | US | |
| *Pseudomonas putida* | 467 | US | |
| *Pseudomonas putida* | 370 | US | |
| *Pseudomonas putida* | 369 | US | |
| *Pseudomonas putida* | 360 | US | |
| *Rohnella aquatilis* | 1158 | US | |
| *Tumebacillus permanentifrigoris* | 72287 | NZ | NRRL B-67301 Aug. 4, 2016 |
| *Tumebacillus permanentifrigoris* | 72229 | NZ | NRRL B-67302 Jul. 22, 2016 |

DETAILED DESCRIPTION

While the following terms are believed to be well understood by one of ordinary skill in the art, the following are set forth to facilitate explanation of the presently disclosed subject matter.

The term "a" or "an" refers to one or more of that entity, i.e., can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "microorganism" or "microbe" should be taken broadly. These terms are used interchangeably and include, but are not limited to, the two prokaryotic domains, Bacteria and Archaea, as well as eukaryotic Fungi and Protists. In some embodiments, the disclosure refers to the "microbes" of Tables 1-2, or the "microbes" of various other tables or paragraphs present in the disclosure. This characterization can refer to not only the identified taxonomic bacterial genera of the tables, but also the identified taxonomic species, as well as the various novel and newly identified bacterial strains of said tables.

As used herein, the term "microbe" or "microorganism" refers to any species or taxon of microorganism, including, but not limited to, archaea, bacteria, microalgae, fungi (including mold and yeast species), mycoplasmas, microspores, nanobacteria, oomycetes, and protozoa. In some embodiments, a microbe or microorganism encompasses individual cells (e.g., unicellular microorganisms) or more than one cell (e.g., multi-cellular microorganism). A "population of microorganisms" may thus refer to a multiple cells of a single microorganism, in which the cells share common genetic derivation.

As used herein, the term "bacterium" or "bacteria" refers in general to any prokaryotic organism, and may reference an organism from either Kingdom Eubacteria (Bacteria), Kingdom Archaebacteria (Archae), or both. In some cases, bacterial genera or other taxonomic classifications have been reassigned due to various reasons (such as but not limited to the evolving field of whole genome sequencing), and it is understood that such nomenclature reassignments are within the scope of any claimed taxonomy. For example, certain species of the genus *Erwinia* have been described in the literature as belonging to genus *Pantoea* (Zhang, Y., Qiu, S. Examining phylogenetic relationships of *Erwinia* and *Pantoea* species using whole genome sequence data. Antonie van Leeuwenhoek 108, 1037-1046 (2015).).

The term "16S" refers to the DNA sequence of the 16S ribosomal RNA (rRNA) sequence of a bacterium. 16S rRNA gene sequencing is a well-established method for studying phylogeny and taxonomy of bacteria. [00166] As used herein, the term "fungus" or "fungi" refers in general to any organism from Kingdom Fungi. Historical taxonomic classification of fungi has been according to morphological presentation. Beginning in the mid-1800's, it was recognized that some fungi have a pleomorphic life cycle, and that different nomenclature designations were being used for different forms of the same fungus. In 1981, the Sydney Congress of the International Mycological Association laid out rules for the naming of fungi according to their status as anamorph, teleomorph, or holomorph (Taylor, J. W. One Fungus=One Name: DNA and fungal nomenclature twenty years after PCR. IMA Fungus 2, 113-120 (2011).). With the development of genomic sequencing, it became evident that taxonomic classification based on molecular phylogenetics did not align with morphological-based nomenclature (Shenoy, B. D., Jeewon, R. and Hyde, K. D. (2007). Impact of DNA sequence-data on the taxonomy of anamorphic fungi. Fungal Diversity 26: 1-54.). As a result, in 2011 the International Botanical Congress adopted a resolution approving the International Code of Nomenclature for Algae, Fungi, and Plants (Melbourne Code) (2012), with the stated outcome of designating "One Fungus=One Name" (Hawksworth, D. L. Managing and coping with names of pleomorphic fungi in a period of transition. IMA Fungus 3, 15-24 (2012)).

The term "Internal Transcribed Spacer" ("ITS") refers to the spacer DNA (non-coding DNA) situated between the small-subunit ribosomal RNA (rRNA) and large-subunit (LSU) rRNA genes in the chromosome or the corresponding transcribed region in the polycistronic rRNA precursor transcript. ITS gene sequencing is a well-established method for studying phylogeny and taxonomy of fungi. In some cases, the "Large SubUnit" ("LSU") sequence is used to identify fungi. LSU gene sequencing is a well-established method for studying phylogeny and taxonomy of fungi. Some fungal microbes of the present invention may be described by an ITS sequence and some may be described by an LSU sequence. Both are understood to be equally descriptive and accurate for determining taxonomy.

The term "microbial consortia" or "microbial consortium" refers to a subset of a microbial community of individual microbial species, or strains of a species, which can be described as carrying out a common function, or can be described as participating in, or leading to, or correlating with, a recognizable parameter or plant phenotypic trait. The community may comprise one or more species, or strains of a species, of microbes. In some instances, the microbes coexist within the community symbiotically.

The term "microbial community" means a group of microbes comprising two or more species or strains. Unlike microbial consortia, a microbial community does not have to be carrying out a common function, or does not have to be participating in, or leading to, or correlating with, a recognizable parameter or plant phenotypic trait.

The term "accelerated microbial selection" or "AMS" is used interchangeably with the term "directed microbial selection" or "DMS" and refers to the iterative selection methodology that was utilized, in some embodiments of the disclosure, to derive the claimed microbial species or consortia of said species.

As used herein, "isolate," "isolated," "isolated microbe," and like terms, are intended to mean that the one or more microorganisms has been separated from at least one of the materials with which it is associated in a particular environment (for example soil, water, plant tissue).

Thus, an "isolated microbe" does not exist in its naturally occurring environment; rather, it is through the various techniques described herein that the microbe has been removed from its natural setting and placed into a non-naturally occurring state of existence. Thus, the isolated strain may exist as, for example, a biologically pure culture, or as spores (or other forms of the strain) in association with an agricultural carrier.

In certain aspects of the disclosure, the isolated microbes exist as isolated and biologically pure cultures. It will be appreciated by one of skill in the art, that an isolated and biologically pure culture of a particular microbe, denotes that said culture is substantially free (within scientific reason) of other living organisms and contains only the individual microbe in question. The culture can contain varying concentrations of said microbe. The present disclosure notes that isolated and biologically pure microbes often "necessarily differ from less pure or impure materials." See, e.g., In re Bergstrom, 427 F.2d 1394, (CCPA 1970) (discussing purified prostaglandins), see also, In re Bergy, 596 F.2d 952 (CCPA 1979) (discussing purified microbes), see also, Parke-Davis & Co. v. H. K. Mulford & Co., 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., Merck & Co. v. Olin Mathieson Chemical Corp., 253 F.2d 156 (4th Cir. 1958) (discussing purity limitations for vitamin B12 produced by microbes), incorporated herein by reference.

As used herein, "individual isolates" should be taken to mean a composition, or culture, comprising a predominance of a single genera, species, or strain, of microorganism, following separation from one or more other microorganisms. The phrase should not be taken to indicate the extent to which the microorganism has been isolated or purified. However, "individual isolates" can comprise substantially only one genus, species, or strain, of microorganism.

The term "growth medium" as used herein, is any medium which is suitable to support growth of a plant. By way of example, the media may be natural or artificial including, but not limited to: soil, potting mixes, bark, vermiculite, hydroponic solutions alone and applied to solid plant support systems, and tissue culture gels. It should be appreciated that the media may be used alone or in combination with one or more other media. It may also be used with or without the addition of exogenous nutrients and physical support systems for roots and foliage.

In one embodiment, the growth medium is a naturally occurring medium such as soil, sand, mud, clay, humus, regolith, rock, or water. In another embodiment, the growth medium is artificial. Such an artificial growth medium may be constructed to mimic the conditions of a naturally occurring medium; however, this is not necessary. Artificial growth media can be made from one or more of any number and combination of materials including sand, minerals, glass, rock, water, metals, salts, nutrients, water. In one embodiment, the growth medium is sterile. In another embodiment, the growth medium is not sterile.

The medium may be amended or enriched with additional compounds or components, for example, a component which may assist in the interaction and/or selection of specific groups of microorganisms with the plant and each other. For example, antibiotics (such as penicillin) or sterilants (for example, quaternary ammonium salts and oxidizing agents) could be present and/or the physical conditions (such as salinity, plant nutrients (for example organic and inorganic minerals (such as phosphorus, nitrogenous salts, ammonia, potassium and micronutrients such as cobalt and magnesium), pH, and/or temperature) could be amended.

The term "plant" generically includes whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. A "plant element" is intended to reference either a whole plant or a plant component, which may comprise differentiated and/or undifferentiated tissues, for example but not limited to plant tissues, parts, and cell types. In one embodiment, a plant element is one of the following: whole plant, seedling, meristematic tissue, ground tissue, vascular tissue, dermal tissue, seed, leaf, root, shoot, stem, flower, fruit, stolon, bulb, tuber, corm, keiki, shoot, bud, tumor tissue, and various forms of cells and culture (e.g., single cells, protoplasts, embryos, callus tissue). The term "plant organ" refers to plant tissue or a group of tissues that constitute a morphologically and functionally distinct part of a plant. As used herein, a "plant part" is synonymous to a "portion" of a plant, and refers to any part of the plant, and can include distinct tissues and/or organs, and may be used interchangeably with the term "tissue" throughout.

"Progeny" comprises any subsequent generation of an organism, produced via sexual or asexual reproduction.

As used herein, the term "plant element" refers to plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, as well as the parts themselves. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

Similarly, a "plant reproductive element" is intended to generically reference any part of a plant that is able to initiate other plants via either sexual or asexual reproduction of that plant, for example but not limited to: seed, seedling, root, shoot, cutting, scion, graft, stolon, bulb, tuber, corm, keiki, or bud. The plant element may be in plant or in a plant organ, tissue culture, or cell culture.

The term "monocotyledonous" or "monocot" refers to the subclass of angiosperm plants also known as "monocotyledoneae", whose seeds typically comprise only one embryonic leaf, or cotyledon. The term includes references to whole plants, plant elements, plant organs (e.g., leaves, stems, roots, etc.), seeds, plant cells, and progeny of the same.

The term "dicotyledonous" or "dicot" refers to the subclass of angiosperm plants also knows as "dicotyledoneae", whose seeds typically comprise two embryonic leaves, or cotyledons. The term includes references to whole plants, plant elements, plant organs (e.g., leaves, stems, roots, etc.), seeds, plant cells, and progeny of the same.

As used herein, the term "cultivar" refers to a variety, strain, or race, of plant that has been produced by horticultural or agronomic techniques and is not normally found in wild populations.

As used herein, "improved" should be taken broadly to encompass improvement of a characteristic of a plant, as compared to a control plant, or as compared to a known average quantity associated with the characteristic in question. For example, "improved" plant biomass associated with application of a beneficial microbe, or consortia, of the disclosure can be demonstrated by comparing the biomass of a plant treated by the microbes taught herein to the biomass of a control plant not treated. Alternatively, one could compare the biomass of a plant treated by the microbes taught herein to the average biomass normally attained by the given plant, as represented in scientific or agricultural publications known to those of skill in the art. In the present disclosure, "improved" does not necessarily demand that the data be statistically significant (e.g., $p<0.05$); rather, any quantifiable difference demonstrating that one value (e.g., the average treatment value) is different from another (e.g., the average control value) can rise to the level of "improved."

As used herein, "inhibiting and suppressing" and like terms should not be construed to require complete inhibition or suppression, although this may be desired in some embodiments.

As used herein, the term "genotype" refers to the genetic makeup of an individual cell, cell culture, tissue, organism (e.g., a plant), or group of organisms.

The compositions and methods herein may provide for an improved "agronomic trait" or "trait of agronomic importance" or "trait of agronomic interest" to a plant, which may include, but not be limited to, the following: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered oil content, increased biomass, increased shoot length, increased root length, improved root architecture, modulation of a metabolite, modulation of the proteome, increased seed weight, altered seed carbohydrate composition, altered seed oil composition, altered seed protein composition, altered seed nutrient composition, as compared to an isoline plant not comprising a modification derived from the methods or compositions herein "Agronomic trait potential" is intended to mean a capability of a plant element for exhibiting a phenotype, preferably an improved agronomic trait, at some point during its life cycle, or conveying said phenotype to another plant element with which it is associated in the same plant.

As used herein, the term "molecular marker", "marker", or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed by the average person skilled in molecular-biological techniques.

As used herein, the term "trait" refers to a characteristic or phenotype. For example, in the context of some embodiments of the present disclosure, yield of a crop relates to the amount of marketable biomass produced by a plant (e.g., fruit, fiber, grain). Desirable traits may also include other plant characteristics, including but not limited to: water use efficiency, nutrient use efficiency, production, mechanical harvestability, fruit maturity, shelf life, pest/disease resistance, early plant maturity, tolerance to stresses, etc. A trait may be inherited in a dominant or recessive manner, or in a partial or incomplete-dominant manner. A trait may be monogenic (i.e., determined by a single locus) or polygenic (i.e., determined by more than one locus) or may also result from the interaction of one or more genes with the environment.

As used herein, the term "phenotype" refers to the observable characteristics of an individual cell, cell culture, organism (e.g., a plant), or group of organisms which results from the interaction between that individual's genetic makeup (i.e., genotype) and the environment.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue", "homolog", or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, CA). Another alignment program is Sequencher (Gene Codes, Ann Arbor, Michigan), using default parameters.

As used herein, the term "nucleotide change" refers to, e.g., nucleotide substitution, deletion, insertion, chemical alteration, or any of the preceeding, as is well understood in the art.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g., at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g., 10 to 50 nucleotides) and at least about 60° C. for long probes or primers (e.g., greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g., Ausubel et al., 1998 and Sambrook et al., 2001. In some embodiments, stringent conditions are hybridization in 0.25 M Na2HPO4 buffer (pH 7.2) containing 1 mM Na2EDTA, 0.5-20% sodium dodecyl sulfate at 45° C., such as 0.5%, 1%, 2%, 3%, 4%, 5%, 6%, 7%, 8%, 9%, 10%, 11%, 12%, 13%, 14%, 15%, 16%, 17%, 18%, 19% or 20%, followed by a wash in 5×SSC, containing 0.1% (w/v) sodium dodecyl sulfate, at 55° C. to 65° C.

In some embodiments, the cell or organism has at least one heterologous trait. As used herein, the term "heterologous trait" refers to a phenotype imparted to a cell or organism by an exogenous molecule or other organism (e.g., a microbe), DNA segment, heterologous polynucleotide or heterologous nucleic acid.

Various changes in phenotype are of interest to the present disclosure, including but not limited to modifying the fatty acid composition in a plant, altering the amino acid content of a plant, altering a plant's pathogen defense mechanism, increasing a plant's yield of an economically important trait (e.g., grain yield, forage yield, etc.) and the like. These results can be achieved by providing expression of heterologous products or increased expression of endogenous products in plants using the methods and compositions of the present disclosure A "synthetic combination" can include a combination of a plant and a microbe of the disclosure. The combination may be achieved, for example, by coating the surface of a seed of a plant, such as an agricultural plant, or host plant tissue (root, stem, leaf, etc.), with a microbe of the disclosure. Further, a "synthetic combination" can include a combination of microbes of various strains or species. Synthetic combinations have at least one variable that distinguishes the combination from any combination that occurs in nature. That variable may be, inter alia, a concentration of microbe on a seed or plant tissue that does not occur naturally, or a combination of microbe and plant that does not naturally occur, or a combination of microbes or strains that do not occur naturally together. In each of these instances, the synthetic combination demonstrates the hand of man and possesses structural and/or functional attributes that are not present when the individual elements of the combination are considered in isolation.

In some embodiments, a microbe can be "endogenous" to a seed or plant. As used herein, a microbe is considered "endogenous" to a plant or seed, if the microbe is derived from the plant specimen from which it is sourced. That is, if the microbe is naturally found associated with said plant. In embodiments in which an endogenous microbe is applied to a plant, then the endogenous microbe is applied in an amount that differs from the levels found on the plant in nature. Thus, a microbe that is endogenous to a given plant can still form a synthetic combination with the plant, if the microbe is present on said plant at a level that does not occur naturally.

In some embodiments, a composition (such as a microbe) can be "heterologous" (also termed "exogenous") to another composition (such as a seed or plant), and in some aspects is referred to herein as a "heterologous composition". As used herein, a microbe is considered "heterologous" to a plant or seed, if the microbe is not derived from the plant specimen from which it is sourced. That is, if the microbe is not naturally found associated with said plant. For example, a microbe that is normally associated with leaf tissue of a maize plant is considered exogenous to a leaf tissue of another maize plant that naturally lacks said microbe. In another example, a microbe that is normally associated with a maize plant is considered exogenous to a wheat plant that naturally lacks said microbe.

A composition is "heterologously disposed" when mechanically or manually applied, artificially inoculated, associated with, or disposed onto or into a plant element, seedling, plant or onto or into a plant growth medium or onto or into a treatment formulation so that the treatment exists on or in the plant element, seedling, plant, plant growth medium, or formulation in a manner not found in nature prior to the application of the treatment, e.g., said combination which is not found in nature in that plant variety, at that stage in plant development, in that plant tissue, in that abundance, or in that growth environment (for example, drought). In some embodiments, such a manner is contemplated to be selected from the group consisting of: the presence of the microbe; presence of the microbe in a different number of cells, concentration, or amount; the presence of the microbe in a different plant element, tissue, cell type, or other physical location in or on the plant; the presence of the microbe at different time period, e.g., developmental phase of the plant or plant element, time of day, time of season, and combinations thereof. In some embodiments, "heterologously disposed" means that the microbe being applied to a different tissue or cell type of the plant element than that in which the microbe is naturally found. In some embodiments, "heterologously disposed" means that the microbe is applied to a developmental stage of the plant element, seedling, or plant in which said microbe is not naturally associated, but may be associated at other stages. For example, if a microbe is normally found at the flowering stage of a plant and no other stage, a microbe applied at the seedling stage may be considered to be heterologously disposed. In some embodiments, a microbe is heterologously disposed the microbe is normally found in the root tissue of a plant element but not in the leaf tissue, and the microbe is applied to the leaf. In another non-limiting example, if a microbe is naturally found in the mesophyll layer of leaf tissue but is being applied to the epithelial layer, the microbe would be considered to be heterologously disposed. In some embodiments, "heterologously disposed" means that the native plant element, seedling, or plant does not contain detectable levels of the microbe in that same plant element, seedling, or plant. In some embodiments, "heterologously disposed" means that the microbe being applied is at a greater concentration, number, or amount of the plant element, seedling, or plant, than that which is naturally found in said plant element, seedling, or plant. For example, a microbe is heterologously disposed when present at a concentration that is at least 1.5 times greater, between 1.5 and 2 times greater, 2 times greater, between 2 and 3 times greater, 3 times greater, between 3 and 5 times greater, 5 times greater, between 5 and 7 times greater, 7 times greater, between 7 and 10 times greater, 10 times greater, or even greater than 10 times higher number, amount, or concentration than the concentration that was present prior to the disposition of said microbe. In another non-limiting example, a microbe that is naturally found in a tissue of a cupressaceous tree would be considered heterologous to tissue of a maize, wheat, cotton, soybean plant. In another example, a microbe that is naturally found in leaf tissue of a maize, spring wheat, cotton, soybean plant is considered heterologous to a leaf tissue of another maize, spring wheat, cotton, soybean plant that naturally lacks said microbe, or comprises the microbe in a different quantity.

Microbes can also be "heterologously disposed" on a given plant tissue. This means that the microbe is placed upon a plant tissue that it is not naturally found upon. For instance, if a given microbe only naturally occurs on the roots of a given plant, then that microbe could be exogenously applied to the above-ground tissue of a plant and would thereby be "heterologously disposed" upon said plant tissue. As such, a microbe is deemed heterologously disposed, when applied on a plant that does not naturally have the microbe present or does not naturally have the microbe present in the number that is being applied.

The compositions and methods herein may provide for a "modulated" "agronomic trait" or "trait of agronomic importance" to a host plant, which may include, but not be limited to, the following: altered oil content, altered protein content, altered seed carbohydrate composition, altered seed oil composition, and altered seed protein composition, chemical tolerance, cold tolerance, delayed senescence, disease resistance, drought tolerance, ear weight, growth improvement, health enhancement, heat tolerance, herbicide tolerance, herbivore resistance, improved nitrogen fixation, improved nitrogen utilization, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome, compared to an isoline plant grown from a seed without said seed treatment formulation. By the term "modulated", it is intended to refer to a change in an agronomic trait that is changed by virtue of the presence of the microbe(s), exudate, broth, metabolite, etc. In aspects, the modulation provides for the imparting of a beneficial trait.

Microbes and Microorganisms

As used herein the term "microorganism" should be taken broadly. It includes, but is not limited to, prokaryotic Bacteria and Archaea, as well as eukaryotic Fungi and Protists.

By way of example, the microorganisms may include: Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium, Variovorax* and *Halomonas*), Firmicutes (such as *Bacillus, Paenibacillus, Lactobacillus, Mycoplasma,* and *Acetobacterium*), Actinobacteria (such as *Brevibacterium, Janibacter, Streptomyces, Rhodococcus, Microbacterium, Curtobacterium, Cellulomonas*, and *Nocardioides*), and the fungi Ascomycota (such as *Trichoderma, Ampelomyces, Coniothyrium, Paecoelomyces, Penicillium, Cladosporium, Hypocrea, Beauveria, Metarhizium, Verticullium, Cordyceps, Pichea,* and *Candida*), Basidiomycota (such as *Coprinus, Corticium,* and *Agaricus*) and Oomycota (such as *Pythium*), and Mucoromycota (such as *Mucor,* and *Mortierella*); as well as *Orbilia/Arthrobotrys, Lysinibacillus, Microbacterium, Talaromyces, Arthrobacter, Kosakonia, Masilha, Novosphingobium,* and *Tumebacillus*.

In a particular embodiment, the microorganism is an endophyte, or an epiphyte, or a microorganism inhabiting the plant rhizosphere or rhizosheath. That is, the microorganism may be found present in the soil material adhered to the roots of a plant or in the area immediately adjacent a plant's roots.

In one embodiment, the microorganism is an endophyte. Endophytes may benefit host plants by preventing pathogenic organisms from colonizing them. Extensive colonization of the plant tissue by endophytes creates a "barrier effect," where the local endophytes outcompete and prevent pathogenic organisms from taking hold. Endophytes may also produce chemicals which inhibit the growth of competitors, including pathogenic organisms.

In certain embodiments, the microorganism is unculturable. This should be taken to mean that the microorganism is not known to be culturable or is difficult to culture using methods known to one skilled in the art.

Microorganisms of the present disclosure may be collected or obtained from any source or contained within and/or associated with material collected from any source.

In an embodiment, the microorganisms are obtained from any general terrestrial environment, including its soils, plants, fungi, animals (including invertebrates) and other biota, including the sediments, water and biota of lakes and rivers; from the marine environment, its biota and sediments (for example sea water, marine muds, marine plants, marine invertebrates (for example sponges), marine vertebrates (for example, fish)); the terrestrial and marine geosphere (regolith and rock, for example crushed subterranean rocks, sand and clays); the cryosphere and its meltwater; the atmosphere (for example, filtered aerial dusts, cloud and rain droplets); urban, industrial and other man-made environments (for example, accumulated organic and mineral matter on concrete, roadside gutters, roof surfaces, road surfaces).

In another embodiment the microorganisms are collected from a source likely to favor the selection of appropriate microorganisms. By way of example, the source may be a particular environment in which it is desirable for other plants to grow, or which is thought to be associated with terroir. In another example, the source may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the microorganisms may be collected from commercial crops grown in such environments, or more specifically from individual crop plants best displaying a trait of interest amongst a crop grown in any specific environment, for example the fastest-growing plants amongst a crop grown in saline-limiting soils, or the least damaged plants in crops exposed to severe insect damage or disease epidemic, or plants having desired quantities of certain metabolites and other compounds, including fiber content, oil content, and the like, or plants displaying desirable colors, taste, or smell. The microorganisms may be collected from a plant of interest or any material occurring in the environment of interest, including fungi and other animal and plant biota, soil, water, sediments, and other elements of the environment as referred to previously. In certain embodiments, the microorganisms are individual isolates separated from different environments.

In one embodiment, a microorganism or a combination of microorganisms, of use in the methods of the disclosure may be selected from a pre-existing collection of individual microbial species or strains based on some knowledge of their likely or predicted benefit to a plant. For example, the microorganism may be predicted to: improve nitrogen fixation; release phosphate from the soil organic matter; release phosphate from the inorganic forms of phosphate (e.g., rock phosphate); "fix carbon" in the root microsphere; live in the rhizosphere of the plant thereby assisting the plant in absorbing nutrients from the surrounding soil and then providing these more readily to the plant; increase the number of nodules on the plant roots and thereby increase the number of symbiotic nitrogen fixing bacteria (e.g., *Rhizobium* species) per plant and the amount of nitrogen fixed by the plant; elicit plant defensive responses such as ISR (induced systemic resistance) or SAR (systemic acquired resistance) which help the plant resist the invasion and spread of pathogenic microorganisms; compete with microorganisms deleterious to plant growth or health by antagonism, or competitive utilization of resources such as nutrients or space; change the color of one or more part of the plant, or change the chemical profile of the plant, its smell, taste or one or more other quality.

In one embodiment a microorganism or combination of microorganisms is selected from a pre-existing collection of individual microbial species or strains that provides no knowledge of their likely or predicted benefit to a plant. For example, a collection of unidentified microorganisms isolated from plant tissues without any knowledge of their ability to improve plant growth or health, or a collection of microorganisms collected to explore their potential for producing compounds that could lead to the development of pharmaceutical drugs.

In one embodiment, the microorganisms are acquired from the source material (for example, soil, rock, water, air, dust, plant or other organism) in which they naturally reside. The microorganisms may be provided in any appropriate form, having regard to its intended use in the methods of the disclosure. However, by way of example only, the microorganisms may be provided as an aqueous suspension, gel, homogenate, granule, powder, slurry, live organism or dried material.

The microorganisms of the disclosure may be isolated in substantially pure or mixed cultures. They may be concentrated, diluted, or provided in the natural concentrations in which they are found in the source material. For example, microorganisms from saline sediments may be isolated for use in this disclosure by suspending the sediment in fresh water and allowing the sediment to fall to the bottom. The water containing the bulk of the microorganisms may be removed by decantation after a suitable period of settling and either applied directly to the plant growth medium, or concentrated by filtering or centrifugation, diluted to an appropriate concentration and applied to the plant growth medium with the bulk of the salt removed. By way of further example, microorganisms from mineralized or toxic sources may be similarly treated to recover the microbes for application to the plant growth material to minimize the potential for damage to the plant.

In another embodiment, the microorganisms are used in a crude form, in which they are not isolated from the source material in which they naturally reside. For example, the microorganisms are provided in combination with the source material in which they reside; for example, as soil, or the roots, seed or foliage of a plant. In this embodiment, the source material may include one or more species of microorganisms.

In some embodiments, a mixed population of microorganisms is used in the methods of the disclosure.

In embodiments of the disclosure where the microorganisms are isolated from a source material (for example, the material in which they naturally reside), any one or a combination of a number of standard techniques which will be readily known to skilled persons may be used. However, by way of example, these in general employ processes by which a solid or liquid culture of a single microorganism can be obtained in a substantially pure form, usually by physical separation on the surface of a solid microbial growth medium or by volumetric dilutive isolation into a liquid microbial growth medium. These processes may include isolation from dry material, liquid suspension, slurries or homogenates in which the material is spread in a thin layer over an appropriate solid gel growth medium, or serial dilutions of the material made into a sterile medium and inoculated into liquid or solid culture media.

Whilst not essential, in one embodiment, the material containing the microorganisms may be pre-treated prior to the isolation process in order to either multiply all microorganisms in the material, or select portions of the microbial population, either by enriching the material with microbial nutrients (for example, by pasteurizing the sample to select for microorganisms resistant to heat exposure (for example, bacilli), or by exposing the sample to low concentrations of an organic solvent or sterilant (for example, household bleach) to enhance the survival of spore-forming or solvent-resistant microorganisms). Microorganisms can then be isolated from the enriched materials or materials treated for selective survival, as above.

In an embodiment of the disclosure, endophytic or epiphytic microorganisms are isolated from plant material. Any number of standard techniques known in the art may be used and the microorganisms may be isolated from any appropriate tissue in the plant, including for example root, stem and leaves, and plant reproductive tissues. By way of example, conventional methods for isolation from plants typically include the sterile excision of the plant material of interest (e.g., root or stem lengths, leaves), surface sterilization with an appropriate solution (e.g., 2% sodium hypochlorite), after which the plant material is placed on nutrient medium for microbial growth (See, for example, Strobel G and Daisy B (2003) Microbiology and Molecular Biology Reviews 67 (4): 491-502; Zinniel D K et al. (2002) Applied and Environmental Microbiology 68 (5): 2198-2208).

In one embodiment of the disclosure, the microorganisms are isolated from root tissue. Further methodology for isolating microorganisms from plant material are detailed hereinafter.

In one embodiment, the microbial population is exposed (prior to the method or at any stage of the method) to a selective pressure. For example, exposure of the microorganisms to pasteurization before their addition to a plant growth medium (preferably sterile) is likely to enhance the probability that the plants selected for a desired trait will be associated with spore-forming microbes that can more easily survive in adverse conditions, in commercial storage, or if applied to seed as a coating, in an adverse environment.

In certain embodiments, as mentioned herein before, the microorganism(s) may be used in crude form and need not be isolated from a plant or a media. For example, plant material or growth media which includes the microorganisms identified to be of benefit to a selected plant may be obtained and used as a crude source of microorganisms for the next round of the method or as a crude source of microorganisms at the conclusion of the method. For example, whole plant material could be obtained and optionally processed, such as mulched or crushed. Alternatively, individual tissues or parts of selected plants (such as leaves, stems, roots, and seeds) may be separated from the plant and optionally processed, such as mulched or crushed. In certain embodiments, one or more part of a plant which is associated with the second set of one or more microorganisms may be removed from one or more selected plants and, where any successive repeat of the method is to be conducted, grafted on to one or more plant used in any step of the plant breeding methods.

Exemplary Microbes

In aspects, the present disclosure provides isolated microbes, including novel strains of identified microbial species, presented in Table 1 or Table 1A.

In other aspects, the present disclosure provides isolated whole microbial cultures of the species and strains identified in Table 1 or Table 1A. These cultures may comprise microbes at various concentrations.

In aspects, the disclosure provides for utilizing a microbe selected from Table 1 or Table 1A in agriculture.

In some embodiments, the disclosure provides isolated microbial species belonging to genera of: *Bacillus, Paenibacillus, Orbilia, Arthrobotrys, Lysinibacillus, Microbacterium*, and/or *Talaromyces*.

In some embodiments, a microbe from the genus *Bacillus* is utilized in agriculture to impart one or more beneficial properties to a plant species.

In some embodiments, a microbe from the genus *Paenibacillus* is utilized in agriculture to impart one or more beneficial properties to a plant species.

In some embodiments, a microbe from the genus *Orbilia* is utilized in agriculture to impart one or more beneficial properties to a plant species.

In some embodiments, a microbe from the genus *Arthrobotrys* is utilized in agriculture to impart one or more beneficial properties to a plant species.

In some embodiments, a microbe from the genus *Lysinibacillus* is utilized in agriculture to impart one or more beneficial properties to a plant species.

In some embodiments, a microbe from the genus *Microbacterium* is utilized in agriculture to impart one or more beneficial properties to a plant species.

In some embodiments, a microbe from the genus *Talaromyces* is utilized in agriculture to impart one or more beneficial properties to a plant species.

In some embodiments, the disclosure provides isolated microbes belonging to microbial species selected from the group consisting of: *Bacillus tequilensis, Bacillus methylotrophicus, Bacillus amyloliquefaciens, Paenibacillus alginolyticus, Orbilia auricolor Arthrobotrys oligospora* (teleomorph and anamorph, respectively), *Bacillus pumilus, Lysinibacillus fusiformis, Bacillus megaterium, Paenibacillus taichungensis, Paenibacillus ehimensis, Paenibacillus illinoisensis, Microbacterium arabinogalactanolyticum*, and *Talaromyces pinophilus*.

In some embodiments, the disclosure provides isolated microbes belonging to microbial species selected from the group consisting of: *Bacillus tequilensis, Bacillus methylotrophicus, Bacillus amyloliquefaciens, Paenibacillus alginolyticus, Orbilia auricolor/Arthrobotrys oligospora* (teleomorph and anamorph, respectively), *Bacillus pumilus, Lysinibacillus fusiformis, Bacillus megaterium, Paenibacillus taichungensis, Paenibacillus ehimensis, Paenibacillus illinoisensis, Microbacterium arabinogalactanolyticum*, and *Talaromyces pinophilus*. Particular novel strains of these aforementioned species can be found in Table 1 or Table 1A.

Furthermore, the disclosure relates to microbes having characteristics substantially similar to that of a microbe identified in Table 1 or Table 1A.

The isolated microbial species, and novel strains of said species, identified in the present disclosure, are able to impart beneficial properties or traits, such as a trait of agronomic importance, to target plant species.

For instance, the isolated microbes described in Table 1 or Table 1A, or consortia of said microbes, are able to improve plant health and vitality. The improved plant health and vitality can be quantitatively measured, for example, by measuring the effect that said microbial application has upon a plant phenotypic or genotypic trait.

Sourcing of Microbes

The microbes of the present disclosure were obtained, among other places, at various locales in New Zealand and the United States Isolation and Culturing of Microbes The microbes of Table 1 and Table 1A were identified by utilizing standard microscopic techniques to characterize the microbes' phenotype, which was then utilized to identify the microbe to a taxonomically recognized species.

The isolation, identification, and culturing of the microbes of the present disclosure can be effected using standard microbiological techniques. Examples of such techniques may be found in Gerhardt, P. (ed.) Methods for General and Molecular Microbiology. American Society for Microbiology, Washington, D.C. (1994) and Lennette, E. H. (ed.) Manual of Clinical Microbiology, Third Edition. American Society for Microbiology, Washington, D.C. (1980), each of which is incorporated by reference.

Isolation can be effected by streaking the specimen on a solid medium (e.g., nutrient agar plates) to obtain a single colony, which is characterized by the phenotypic traits described hereinabove (e.g., Gram positive/negative, capable of forming spores aerobically/anaerobically, cellular morphology, carbon source metabolism, acid/base production, enzyme secretion, metabolic secretions, etc.) and to reduce the likelihood of working with a culture which has become contaminated.

For example, for isolated bacteria of the disclosure, biologically pure isolates can be obtained through repeated subculture of biological samples, each subculture followed by streaking onto solid media to obtain individual colonies. Methods of preparing, thawing, and growing lyophilized bacteria are commonly known, for example, Gherna, R. L. and C. A. Reddy. 2007. Culture Preservation, p 1019-1033. In C. A. Reddy, T. J. Beveridge, J. A. Breznak, G. A. Marzluf, T. M. Schmidt, and L. R. Snyder, eds. American Society for Microbiology, Washington, D.C., 1033 pages; herein incorporated by reference. Thus freeze-dried liquid formulations and cultures stored long term at −70° C. in solutions containing glycerol are contemplated for use in providing formulations of the present inventions.

The bacteria of the disclosure can be propagated in a liquid medium under aerobic conditions. Medium for growing the bacterial strains of the present disclosure includes a carbon source, a nitrogen source, and inorganic salts, as well as specially required substances such as vitamins, amino acids, nucleic acids and the like. Examples of suitable carbon sources which can be used for growing the bacterial strains include, but are not limited to, starch, peptone, yeast extract, amino acids, sugars such as glucose, arabinose, mannose, glucosamine, maltose, and the like; salts of organic acids such as acetic acid, fumaric acid, adipic acid, propionic acid, citric acid, gluconic acid, malic acid, pyruvic acid, malonic acid and the like; alcohols such as ethanol and glycerol and the like; oil or fat such as soybean oil, rice bran oil, olive oil, corn oil, sesame oil. The amount of the carbon source added varies according to the kind of carbon source and is typically between 1 to 100 gram(s) per liter of medium. Preferably, glucose, starch, and/or peptone is contained in the medium as a major carbon source, at a concentration of 0.1-5% (W/V). Examples of suitable nitrogen sources which can be used for growing the bacterial strains of the present invention include, but are not limited to, amino acids, yeast extract, tryptone, beef extract, peptone, potassium nitrate, ammonium nitrate, ammonium chloride, ammonium sulfate, ammonium phosphate, ammonia or combinations thereof. The amount of nitrogen source varies according to the type of nitrogen source, typically between 0.1 to 30 gram per liter of medium. The inorganic salts, potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc chloride, cupric sulfate, calcium chloride, sodium chloride, calcium carbonate, sodium carbonate can be used alone or in combination. The amount of inorganic acid varies according to the kind of the inorganic salt, typically between 0.001 to 10 gram per liter of medium. Examples of specially required substances include, but are not limited to, vitamins, nucleic acids, yeast extract, peptone, meat extract, malt extract, dried yeast and combinations thereof. Cultivation can be effected at a temperature, which allows the growth of the bacterial strains, essentially, between 20° C. and 46° C. In some aspects, a temperature range is 30° C.-37° C. For optimal growth, in some embodiments, the medium can be adjusted to pH 7.0-7.4. It will be appreciated that commercially available media may also be used to culture the bacterial strains, such as Nutrient Broth or Nutrient Agar available from Difco, Detroit, MI It will be appreciated that cultivation time may differ depending on the type of culture medium used and the concentration of sugar as a major carbon source.

In aspects, cultivation lasts between 24-96 hours. Bacterial cells thus obtained are isolated using methods, which are well known in the art. Examples include, but are not limited to, membrane filtration and centrifugal separation. The pH may be adjusted using sodium hydroxide and the like and the culture may be dried using a freeze dryer, until the water content becomes equal to 4% or less. Microbial co-cultures may be obtained by propagating each strain as described hereinabove. It will be appreciated that the microbial strains may be cultured together when compatible culture conditions can be employed.

Identification of Microbes

Microbes can be distinguished into a genus based on polyphasic taxonomy, which incorporates all available phenotypic and genotypic data into a consensus classification (Vandamme et al. 1996. Polyphasic taxonomy, a consensus approach to bacterial systematics. Microbiol Rev 1996, 60:407-438). One accepted genotypic method for defining species is based on overall genomic relatedness, such that strains which share approximately 70% or more relatedness using DNA-DNA hybridization, with 5° C. or less ΔTm (the difference in the melting temperature between homologous and heterologous hybrids), under standard conditions, are considered to be members of the same species. Thus, populations that share greater than the aforementioned 70% threshold can be considered to be variants of the same species.

For bacterial microbes, the 16S rRNA sequences are often used for determining taxonomy and making distinctions between species, in that if a 16S rRNA sequence shares less than a specified % sequence identity from a reference sequence, then the two organisms from which the sequences were obtained are said to be of different species.

Thus, one could consider microbes to be of the same species, if they share at least 80%, 85%, 90%, 95%, 97%, 98%, or 99% sequence identity across the 16S or 16S rRNA or rDNA sequence. In some aspects, a microbe could be considered to be the same species only if it shares at least 95% identity.

Further, one could define microbial strains of a species, as those that share at least 80%, 85%, 90%, 95%, 97%, 98%, or 99% sequence identity across the 16S rRNA sequence. Comparisons may also be made with 23 S rRNA sequences against reference sequences. In some aspects, a microbe could be considered to be the same strain only if it shares at least 95% identity. In some embodiments, "substantially similar genetic characteristics" means a microbe sharing at least 95% identity.

For fungal microbes, the ITS (Internal Transcriber Sequence) is often used for identification of taxonomy. Among the regions of the ribosomal cistron, the internal transcribed spacer (ITS) region has the highest probability of successful identification for the broadest range of fungi, with the most clearly defined barcode gap between inter- and intraspecific variation, and has been proposed as the formal fungal identification sequence (Schoch et al., PNAS Apr. 17, 2012 109 (16) 6241-6246).

In one embodiment, microbial strains of the present disclosure include those that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs: 1-21.

In one embodiment, microbes of the present disclosure include those that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs: 1-21.

In one embodiment, microbial consortia of the present disclosure include two or more microbes that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs: 1-21.

In one embodiment, microbial consortia of the present disclosure include two or more microbial strains, wherein at least one of those comprises a polynucleotide sequences that shares at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs: 1-21.

In one embodiment, microbial consortia of the present disclosure include two or more microbial strains, wherein at least one of those comprises a polynucleotide sequences that shares at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs: 1-21, and wherein at least one of the microbes is optionally selected from Table 2.

Unculturable microbes often cannot be assigned to a definite species in the absence of a phenotype determination, the microbes can be given a candidatus designation within a genus provided their 16S rRNA sequences subscribes to the principles of identity with known species.

One approach is to observe the distribution of a large number of strains of closely related species in sequence space and to identify clusters of strains that are well resolved from other clusters. This approach has been developed by using the concatenated sequences of multiple core (housekeeping) genes to assess clustering patterns, and has been called multilocus sequence analysis (MLSA) or multilocus sequence phylogenetic analysis. MLSA has been used successfully to explore clustering patterns among large numbers of strains assigned to very closely related species by current taxonomic methods, to look at the relationships between small numbers of strains within a genus, or within a broader taxonomic grouping, and to address specific taxonomic questions. More generally, the method can be used to ask whether bacterial species exist—that is, to observe whether large populations of similar strains invariably fall into well-resolved clusters, or whether in some cases there is a genetic continuum in which clear separation into clusters is not observed.

In order to more accurately make a determination of genera, a determination of phenotypic traits, such as morphological, biochemical, and physiological characteristics are made for comparison with a reference genus archetype. The colony morphology can include color, shape, pigmentation, production of slime, etc. Features of the cell are described as to shape, size, Gram reaction, extracellular material, presence of endospores, flagella presence and location, motility, and inclusion bodies. Biochemical and physiological features describe growth of the organism at different ranges of temperature, pH, salinity and atmospheric conditions, growth in presence of different sole carbon and nitrogen sources. One of ordinary skill in the art would be reasonably apprised as to the phenotypic traits that define the genera of the present disclosure. For instance, colony color, form, and texture on a particular agar (e.g., YMA) was used to identify species of *Rhizobium*.

In one embodiment, bacterial microbes taught herein were identified utilizing 16S rRNA gene sequences. It is known in the art that 16S rRNA contains hypervariable regions that can provide species/strain-specific signature sequences useful for bacterial identification. In the present disclosure, many of the microbes were identified via partial (500-1200 bp) 16S rRNA sequence signatures. In aspects, each strain represents a pure colony isolate that was selected from an agar plate. Selections were made to represent the diversity of organisms present based on any defining morphological characteristics of colonies on agar medium. The medium used, in embodiments, was R2A, PDA, Nitrogen-free semi-solid medium, or MRS agar. Colony descriptions of each of the 'picked' isolates were made after 24-hour growth and then entered into our database. Sequence data was subsequently obtained for each of the isolates.

Phylogenetic analysis using the 16S rRNA gene was used to define "substantially similar" species belonging to common genera and also to define "substantially similar" strains of a given taxonomic species. Further, we recorded physiological and/or biochemical properties of the isolates that can be utilized to highlight both minor and significant differences between strains that could lead to advantageous behavior on plants.

Microbial Consortia

In aspects, the disclosure provides microbial consortia comprising a combination of at least any two microbes selected from amongst the microbes identified in Table 1 and/or Table 1A.

In other aspects, the disclosure provides microbial consortia comprising a combination of at least two microbes, wherein at least one microbe is selected from amongst the microbes identified in Table 1 or Table 1A and additional microbes may optionally be selected from amongst the microbes identified in Table 2.

In certain embodiments, the consortia of the present disclosure comprise two microbes, or three microbes, or four microbes, or five microbes, or six microbes, or seven microbes, or eight microbes, or nine microbes, or ten or more microbes. Said microbes of the consortia are different microbial species, or different strains of a microbial species.

In some embodiments, the disclosure provides consortia, comprising: at least one isolated microbial species belonging to genera of: *Bacillus, Paenibacillus, Orbilia, Arthrobotrys, Lysinibacillus, Microbacterium*, or *Talaromyces*.

In some embodiments, the disclosure provides consortia, comprising: at least one isolated microbial species belonging to genera of: *Bacillus, Paenibacillus, Orbilia, Arthrobotrys, Lysinibacillus, Microbacterium*, or *Talaromyces* and which may optionally further comprise at least one isolated microbial species belonging to the genera of: *Arthrobacter, Bacillus, Brevibacterium, Herbaspirillum, Kosakonia, Lysinibacillus, Massilia, Novosphingobium, Paenibacillus, Pseudomonas, Rahnella*, or *Tumebacillus*.

In some embodiments, the disclosure provides consortia, comprising: at least one isolated microbial species belonging to genera of: *Bacillus, Paenibacillus, Orbilia, Arthrobotrys, Lysinibacillus, Microbacterium*, or *Talaromyces* and which further comprise at least one isolated microbial species belonging to the genera of: *Arthrobacter, Bacillus, Brevibacterium, Herbaspirillum, Kosakonia, Lysinibacillus, Massilia, Novosphingobium, Paenibacillus, Pseudomonas, Rahnella*, and *Tumebacillus*.

In some embodiments, the disclosure provides consortia, comprising: at least one isolated microbial species selected from the group consisting of: *Bacillus tequilensis, Bacillus methylotrophicus, Bacillus amyloliquefaciens, Paenibacillus alginolyticus, Orbilia auricolor/Arthrobotrys oligospora* (teleomorph and anamorph, respectively), *Bacillus pumilus, Lysinibacillus fusiformis, Bacillus megaterium, Paenibacillus taichungensis, Paenibacillus ehimensis, Paenibacillus illinoisensis, Microbacterium arabinogalactanolyticum*, and *Talaromyces pinophilus*.

In some embodiments, the disclosure provides consortia, comprising: at least one novel isolated microbial strain of a species selected from the group consisting of: *Bacillus tequilensis, Bacillus methylotrophicus, Bacillus amyloliquefaciens, Paenibacillus alginolyticus, Orbilia auricolor/Arthrobotrys oligospora* (teleomorph and anamorph, respectively), *Bacillus pumilus, Lysinibacillus fusiformis, Bacillus megaterium, Paenibacillus taichungensis, Paenibacillus ehimensis, Paenibacillus illinoisensis, Microbacterium arabinogalactanolyticum*, and *Talaromyces pinophilus*, and which may optionally further comprise at least one isolated microbial strain of a species selected from the group consisting of: *Arthrobacter cupressi, Arthrobacter mysorens, Arthrobacter nicotinovorans, Arthrobacter pascens, Bacillus megaterium, Bacillus subtilis, Bacillus thuringiensis, Brevibacterium frigoritolerans, Herbaspirillum chlorophenolicum, Kosakonia radicincitans, Lysinibacillus fusiformis, Massilia kyonggiensis, Massilia niastensis, Novosphingobium sediminicola, Paenibacillus amylolyticus, Paenibacillus glycanilyticus, Paenibacillus polymyxa, Pseudomonas fluorescens, Pseudomonas jinjuensis, Pseudomonas oryzihabitans, Pseudomonas putida, Rahnella aquatilis*, and *Tumebacillus permanentifrigoris*.

In some embodiments, the disclosure provides consortia, comprising: at least one novel isolated microbial strain of a species selected from the group consisting of: *Bacillus tequilensis, Bacillus methylotrophicus, Bacillus amyloliquefaciens, Paenibacillus alginolyticus, Orbilia auricolor/Arthrobotrys oligospora* (teleomorph and anamorph, respectively), *Bacillus pumilus, Lysinibacillus fusiformis, Bacillus megaterium, Paenibacillus taichungensis, Paenibacillus ehimensis, Paenibacillus illinoisensis, Microbacterium arabinogalactanolyticum*, and *Talaromyces pinophilus*, and which further comprises at least one isolated microbial strain of species selected from the group consisting of: *Arthrobacter cupressi, Arthrobacter mysorens, Arthrobacter nicotinovorans, Arthrobacter pascens, Bacillus megaterium, Bacillus subtilis, Bacillus thuringiensis, Brevibacterium frigoritolerans, Herbaspirillum chlorophenolicum, Kosakonia radicincitans, Lysinibacillus fusiformis, Massilia kyonggiensis, Massilia niastensis, Novosphingobium sediminicola, Paenibacillus amylolyticus, Paenibacillus glycanilyticus, Paenibacillus polymyxa, Pseudomonas fluorescens, Pseudomonas jinjuensis, Pseudomonas oryzihabitans, Pseudomonas putida, Rahnella aquatilis*, and *Tumebacillus permanentifrigoris*.

In some embodiments, the disclosure provides consortia comprising an isolated microbial strain of *Bacillus pumilus* and an isolated microbial strain of *Bacillus velezensis*.

Particular novel strains of these aforementioned species can be found in Tables 1, 1A, and 2.

The microbe components of a consortium could be selected from any of the microbes identified in Tables 1, 1A, and 2, provided that at least one microbe in any of the consortia includes at least one microbe selected from Table 1 or Table 1A.

Microbial-Produced Compositions

In some cases, the microbes of the present disclosure may produce one or more compounds and/or have one or more activities, e.g., one or more of the following: production of a metabolite, production of a phytohormone such as auxin, production of acetoin, production of an antimicrobial compound, production of a siderophore, production of a polyketide, production of a phenazine, production of a cellulase, production of a pectinase, production of a chitinase, production of a glucanase, production of a xylanase, nitrogen fixation, or mineral phosphate solubilization.

For example, a microbe of the disclosure may produce a phytohormone selected from the group consisting of an auxin, a cytokinin, a gibberellin, ethylene, a brassinosteroid, and abscisic acid.

Thus, a "metabolite produced by" a microbe of the disclosure, is intended to capture any molecule (small molecule, vitamin, mineral, protein, nucleic acid, lipid, fat, carbohydrate, etc.) produced by the microbe. Often, the exact mechanism of action, whereby a microbe of the disclosure imparts a beneficial trait upon a given plant species is not known. It is hypothesized, that in some instances, the microbe is producing a metabolite that is beneficial to the plant. Thus, in some aspects, a cell-free or inactivated preparation of microbes is beneficial to a plant, as the microbe does not have to be alive to impart a beneficial trait upon the given plant species, so long as the preparation includes a metabolite that was produced by said microbe and which is beneficial to a plant.

In one embodiment, the microbes of the disclosure may produce auxin (e.g., indole-3-acetic acid (IAA)). Production of auxin can be assayed. Many of the microbes described herein may be capable of producing the plant hormone auxin indole-3-acetic acid (IAA) when grown in culture. Auxin plays a key role in altering the physiology of the plant, including the extent of root growth.

Therefore, in an embodiment, the microbes of the disclosure are present as a population disposed on the surface or within a tissue of a given plant species. The microbes may produce a composition, such as a metabolite, in an amount effective to cause a detectable increase in the amount of composition that is found on or within the plant, when compared to a reference plant not treated with the microbes or cell-free or inactive preparations of the disclosure. The composition produced by said microbial population may be beneficial to the plant species.

Such microbial-produced compositions may be present in the cell culture broth or medium/a in which the microbes are grown, or may encompass an exudate produced by the microbes. As used herein, "exudate" refers to one or more compositions excreted by or extracted from one or more microbial cell(s). As used herein, "broth" refers to the collective composition of a cell culture medium after microbial cells are placed in the medium. The composition of the broth may change over time, during different phases of microbial growth and/or development. Broth and/or exudate may improve the traits of plants with which they become associated.

Microbial-Induced Traits in Plants

The present disclosure utilizes microbes to impart beneficial properties (or beneficial traits) to desirable plant species, such as agronomic species of interest. In the current disclosure, the terminology "beneficial property" or "beneficial trait" is used interchangeably and denotes that a desirable plant phenotypic or genetic property of interest is modulated, by the application of a microbe or microbial consortia as described herein. As aforementioned, in some aspects, it may very well be that a metabolite produced by a given microbe is ultimately responsible for modulating or imparting a beneficial trait to a given plant.

There are a vast number of beneficial traits that can be modulated by the application of microbes of the disclosure. For instance, the microbes may have the ability to impart one or more beneficial properties to a plant species, for example: increased growth, increased yield, increased nitrogen utilization efficiency, increased stress tolerance, increased drought tolerance, increased photosynthetic rate, enhanced water use efficiency, increased pathogen resistance, modifications to plant architecture that don't necessarily impact plant yield, but rather address plant functionality, causing the plant to increase production of a metabolite of interest, etc.

In aspects, the microbes taught herein provide a wide range of agricultural applications, including: improvements in yield of grain, fruit, and flowers, improvements in growth of plant parts, improved ability to utilize nutrients (e.g., nitrogen, phosphate, and the like), improved resistance to disease, biopesticidal effects including improved resistance to fungi and nematodes; improved survivability in extreme climate, and improvements in other desired plant phenotypic characteristics.

In some aspects, the isolated microbes, consortia, and/or agricultural compositions of the disclosure can be applied to a plant, in order to modulate or alter a plant characteristic such as altered oil content, altered protein content, altered seed carbohydrate composition, altered seed oil composition, altered seed protein composition, chemical tolerance, cold tolerance, delayed senescence, disease resistance, drought tolerance, ear weight, growth improvement, health enhancement, heat tolerance, herbicide tolerance, herbivore resistance, improved nitrogen fixation, improved nitrogen utilization, improved nutrient utilization (e.g., phosphate, potassium, and the like), improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, reduced pathogen levels (e.g., via the excretion of metabolites that impair pathogen survival), pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome relative to a reference plant.

In some aspects, the isolated microbes, consortia, and/or agricultural compositions of the disclosure can be applied to a plant, in order to modulate in a negative way, a particular plant characteristic. For example, in some aspects, the microbes of the disclosure are able to decrease a phenotypic trait of interest, as this functionality can be desirable in some applications. For instance, the microbes of the disclosure may possess the ability to decrease root growth or decrease root length. Or the microbes may possess the ability to decrease shoot growth or decrease the speed at which a plant grows, as these modulations of a plant trait could be desirable in certain applications.

In some embodiments, the isolated microbes, consortia, and/or agricultural compositions of the disclosure can be applied to a plant, in order to impart nematode stress tolerance to plants. Suitably, in such embodiments, the microbes may be selected from the group consisting of *Orbilia auricolor/Arthrobotrys oligospora, Lysinibacillus fusiformis*, and *Bacillus velenzensis*, or the consortia may comprise or consist of *Bacillus velenzensis* and *Bacillus pumilus*. Suitably, the microbes may be selected from the group consisting of *Orbilia auricolor/Arthrobotrys oligospora* BEC93, *Lysinibacillus fusiformis* BEC91, and *Bacillus velenzensis* BEC89A, or the consortia may comprise or consist of *Bacillus velenzensis* BEC89A and *Bacillus pumilus* BEC89B.

In some embodiments, the isolated microbes, consortia, and/or agricultural compositions of the disclosure can be applied to a plant, in order to provide biostimulation (biostimulant effects) to plants. Suitably, in such embodiments, the microbes may be selected from the group consisting of *Bacillus amyloliquefaciens, Bacillus megaterium, Bacillus tequilensis, Microbacterium arabinogalactanolyticum, Paenibacillus alginolyticus, Paenibacillus ehimensis, Paenibacillus illinoisensis, Paenibacillus taichungensis*, and *Talaromyces pinophilus*. Suitably, the microbes may be selected from the group consisting of *Bacillus amyloliquefaciens* BEC69, *Paenibacillus alginolyticus* BEC68A, *Paenibacillus alginolyticus* BEC68B, *Paenibacillus alginolyticus* BEC68C, *Paenibacillus alginolyticus* BEC68D, *Bacillus amyloliquefaciens* BEC77A, *Bacillus amyloliquefaciens* BEC77B, *Bacillus amyloliquefaciens* BEC69, *Bacillus tequilensis* BEC78, *Bacillus megaterium* BEC71, *Paenibacillus taichungensis* BEC110, *Paenibacillus ehimensis* BEC120, *Paenibacillus illinoisensis* BEC108, *Microbacterium arabinogalactanolyticum* BEC102, and *Talaromyces pinophilus* BEC101.

In some embodiments, the isolated microbes, consortia, and/or agricultural compositions of the disclosure can be applied to a plant, in order to provide disease tolerance to plants. Suitably, in such embodiments, the microbes may be selected from the group consisting of *Bacillus velezensis* and *Bacillus methylotrophicus*. Suitably, the microbes may be selected from the group consisting of *Bacillus velezensis* BEC80 and *Bacillus methylotrophicus* BEC60 and *Bacillus methylotrophicus* BEC56.

Agricultural Compositions

In some embodiments, the microbes of the disclosure are combined with agricultural compositions. Agricultural compositions generally refer to organic and inorganic compounds that can include compositions that promote the cultivation of the microbe and/or the plant element; compositions involved in formulation of microbes for application to plant elements (for example, but not limited to:

wetters, compatibilizing agents (also referred to as "compatibility agents"), antifoam agents, cleaning agents, sequestering agents, drift reduction agents, neutralizing agents and buffers, corrosion inhibitors, dyes, odorants, spreading agents (also referred to as "spreaders"), penetration aids (also referred to as "penetrants"), sticking agents (also referred to as "stickers" or "binders"), dispersing agents, thickening agents (also referred to as "thickeners"), stabilizers, emulsifiers, freezing point depressants, antimicrobial agents, and the like); compositions involved in conferring protection to the plant element or plant (for example, but not limited to: pesticides, nematicides, fungicides, bactericides, herbicides, and the like); as well as other compositions that may be of interest for the particular application.

In some embodiments, the agricultural compositions of the present disclosure are solid. Where solid compositions are used, it may be desired to include one or more carrier materials with the active isolated microbe or consortia. In some embodiments, the present disclosure teaches the use of carriers including, but not limited to: mineral earths such as silicas, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or compositions of these.

Growth Compositions

In some embodiments, a composition is provided to the microbe and/or the plant element that promotes the growth and development. Exemplary compositions include liquid (such as broth, media) and/or solid (such as soil, nutrients). Various organic or inorganic compounds may be added to the growth composition to facilitate the health of the microbe, alone or in combination with the plant element, for example but not limited to: amino acids, vitamins, minerals, carbohydrates, simple sugars, lipids.

Formulation Compositions

One or more compositions, in addition to the microbe(s) or microbial-produced composition, may be combined for various application, stability, activity, and/or storage reasons. The additional compositions may be referred to as "formulation components".

In some embodiments, the agricultural compositions of the present disclosure are liquid. Thus in some embodiments, the present disclosure teaches that the agricultural compositions disclosed herein can include compounds or salts such as monoethanolamine salt, sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate.

In some embodiments, the present disclosure teaches that agricultural compositions can include binders such as: polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or compositions of these; lubricants such as magnesium stearate, sodium stearate, talc or polyethylene glycol, or compositions of these; antifoams such as silicone emulsions, long-chain alcohols, phosphoric esters, acetylene diols, fatty acids or organofluorine compounds, and complexing agents such as: salts of ethylenediaminetetraacetic acid (EDTA), salts of trinitrilotriacetic acid or salts of polyphosphoric acids, or compositions of these.

In some embodiments, the agricultural compositions comprise surface-active agents. In some embodiments, the surface-active agents are added to liquid agricultural compositions. In other embodiments, the surface-active agents are added to solid formulations, especially those designed to be diluted with a carrier before application. Thus, in some embodiments, the agricultural compositions comprise surfactants. Surfactants are sometimes used, either alone or with other additives, such as mineral or vegetable oils as adjuvants to spray-tank mixes to improve the biological performance of the microbes on the target. The types of surfactants used for bioenhancement depend generally on the nature and mode of action of the microbes. The surface-active agents can be anionic, cationic, or nonionic in character, and can be employed as emulsifying agents, wetting agents, suspending agents, or for other purposes. In some embodiments, the surfactants are non-ionics such as: alky ethoxylates, linear aliphatic alcohol ethoxylates, and aliphatic amine ethoxylates. Surfactants conventionally used in the art of formulation and which may also be used in the present formulations are described, in McCutcheon's Detergents and Emulsifiers Annual, MC Publishing Corp., Ridgewood, N.J., 1998, and in Encyclopedia of Surfactants, Vol. I-III, Chemical Publishing Co., New York, 1980-81. In some embodiments, the present disclosure teaches the use of surfactants including alkali metal, alkaline earth metal or ammonium salts of aromatic sulfonic acids, for example, ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or compositions of these.

In some embodiments, the present disclosure teaches other suitable surface-active agents, including salts of alkyl sulfates, such as diethanolammonium lauryl sulfate; alkylarylsulfonate salts, such as calcium dodecylbenzenesulfonate; alkylphenol-alkylene oxide addition products, such as nonylphenol-C18 ethoxylate; alcohol-alkylene oxide addition products, such as tridecyl alcohol-C16 ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

In some embodiments, the agricultural compositions comprise wetting agents. A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank or other vessel to reduce the wetting time of wettable powders and to improve the penetration of water into water-dispersible granules. In some embodiments, examples of wetting agents used in the agricultural compositions of the present disclosure, including wettable powders, suspension concentrates, and water-dispersible granule formulations are: sodium lauryl sulphate; sodium dioctyl sulphosuccinate; alkyl phenol ethoxylates; and aliphatic alcohol ethoxylates.

In some embodiments, the agricultural compositions of the present disclosure comprise dispersing agents. A dispersing agent is a substance which adsorbs onto the surface of particles and helps to preserve the state of dispersion of the particles and prevents them from re-aggregating. In some embodiments, dispersing agents are added to agricultural compositions of the present disclosure to facilitate dispersion and suspension during manufacture, and to ensure the particles redisperse into water in a spray tank. In some embodiments, dispersing agents are used in wettable powders, suspension concentrates, and water-dispersible granules. Surfactants that are used as dispersing agents have the ability to adsorb strongly onto a particle surface and provide a charged or steric barrier to re-aggregation of particles. In some embodiments, the most commonly used surfactants are anionic, non-ionic, or mixtures of the two types.

In some embodiments, for wettable powder formulations, the most common dispersing agents are sodium lignosulphonates. In some embodiments, suspension concentrates provide very good adsorption and stabilization using polyelectrolytes, such as sodium naphthalene sulphonate formaldehyde condensates. In some embodiments, tristyrylphenol ethoxylate phosphate esters are also used. In some embodiments, such as alkylarylethylene oxide condensates and EO-PO block copolymers are sometimes combined with anionics as dispersing agents for suspension concentrates.

In some embodiments, the agricultural compositions of the present disclosure comprise polymeric surfactants. In some embodiments, the polymeric surfactants have very long hydrophobic 'backbones' and a large number of ethylene oxide chains forming the 'teeth' of a 'comb' surfactant. In some embodiments, these high molecular weight polymers can give very good long-term stability to suspension concentrates, because the hydrophobic backbones have many anchoring points onto the particle surfaces. In some embodiments, examples of dispersing agents used in agricultural compositions of the present disclosure are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

In some embodiments, the agricultural compositions of the present disclosure comprise emulsifying agents. An emulsifying agent is a substance, which stabilizes a suspension of droplets of one liquid phase in another liquid phase. Without the emulsifying agent the two liquids would separate into two immiscible liquid phases. In some embodiments, the most commonly used emulsifier blends include alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. In some embodiments, emulsion stability can sometimes be improved by the addition of a small amount of an EO-PO block copolymer surfactant.

In some embodiments, the agricultural compositions of the present disclosure comprise solubilizing agents. A solubilizing agent is a surfactant, which will form micelles in water at concentrations above the critical micelle concentration. The micelles are then able to dissolve or solubilize water-insoluble materials inside the hydrophobic part of the micelle. The types of surfactants usually used for solubilization are non-ionics: sorbitan monooleates; sorbitan monooleate ethoxylates; and methyl oleate esters.

In some embodiments, the agricultural compositions of the present disclosure comprise organic solvents. Organic solvents are used mainly in the formulation of emulsifiable concentrates, ULV formulations, and to a lesser extent granular formulations. Sometimes mixtures of solvents are used. In some embodiments, the present disclosure teaches the use of solvents including aliphatic paraffinic oils such as kerosene or refined paraffins. In other embodiments, the present disclosure teaches the use of aromatic solvents such as xylene and higher molecular weight fractions of C9 and C10 aromatic solvents. In some embodiments, chlorinated hydrocarbons are useful as co-solvents to prevent crystallization of pesticides when the formulation is emulsified into water. Alcohols are sometimes used as co-solvents to increase solvent power.

In some embodiments, the agricultural compositions comprise gelling agents. Thickeners or gelling agents are used mainly in the formulation of suspension concentrates, emulsions, and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. In some embodiments, the agricultural compositions comprise one or more thickeners including, but not limited to: montmorillonite, e.g., bentonite; magnesium aluminum silicate; and attapulgite. In some embodiments, the present disclosure teaches the use of polysaccharides as thickening agents. The types of polysaccharides most commonly used are natural extracts of seeds and seaweeds or synthetic derivatives of cellulose. Some embodiments utilize xanthan and some embodiments utilize cellulose. In some embodiments, the present disclosure teaches the use of thickening agents including, but are not limited to: guar gum; locust bean gum; carrageenam; alginates; methyl cellulose; sodium carboxymethyl cellulose (SCMC); hydroxyethyl cellulose (HEC). In some embodiments, the present disclosure teaches the use of other types of anti-settling agents such as modified starches, polyacrylates, polyvinyl alcohol, and polyethylene oxide. Another good anti-settling agent is xanthan gum.

In some embodiments, the presence of surfactants, which lower interfacial tension, can cause water-based formulations to foam during mixing operations in production and in application through a spray tank. Thus, in some embodiments, in order to reduce the tendency to foam, anti-foam agents are often added either during the production stage or before filling into bottles/spray tanks. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

In some embodiments, the agricultural compositions comprise a preservative.

In some embodiments, the agricultural compositions may be formulated as: a soil drench, a foliar spray, a dip treatment, an in-furrow treatment, a soil amendment, granules, a broadcast treatment, a post-harvest disease control treatment, or a seed treatment. In some embodiments, the agricultural compositions may be applied alone in or in rotation spray programs with other agricultural products.

In some embodiments, the agricultural compositions may be compatible with tank mixing. In some embodiments, the agricultural compositions may be compatible with tank mixing with other agricultural products. In some embodiments, the agricultural compositions may be compatible with equipment used for ground, aerial, and irrigation applications.

In some embodiments, the agricultural compositions may be applied to genetically modified seeds or plants.

Protective Compositions

Further, the individual microbes, or microbial consortia, or microbial communities, developed according to the disclosed methods can be combined with known actives available in the agricultural space, such as: pesticide, herbicide, bactericide, fungicide, insecticide, virucide, miticide, nematicide, acaricide, plant growth regulator, rodenticide, anti-algae agent, biocontrol or beneficial agent. Further, the microbes, microbial consortia, or microbial communities developed according to the disclosed methods can be combined with known fertilizers. Such combinations may exhibit synergistic properties. Further still, the individual microbes, or microbial consortia, or microbial communities, developed according to the disclosed methods can be combined with inert ingredients. Also, in some aspects, the disclosed microbes are combined with biological active agents.

In some embodiments, the individual microbes, or microbial consortia, or microbial communities, developed according to the disclosed methods can be combined with biopesticides that function as an herbicide, bactericide, fungicide, insecticide, virucide, miticide, nematicide, acaricide, rodenticide, and/or anti-algae agent. Such biopesticides may be, but are not limited to, macrobial organisms (e.g., beneficial nematodes and the like), microbial organisms (e.g., Serenade, Bt, and the like), plant extracts (e.g., Timorex Gold and the like), biochemical (e.g., insect pheromones and the like), and/or minerals and oils (e.g., canola oil).

Pesticides and Biopesticides

In some embodiments, the agricultural compositions of the present disclosure comprise pesticides, used in combination with the taught microbes. In some embodiments, the agricultural compositions of the present disclosure comprise biopesticides, used in combination with the taught microbes.

In some embodiments, the individual microbes, or microbial consortia, or microbial communities, developed according to the disclosed methods can be combined with known pesticides in the agricultural space, such as: pesticides that function as an herbicide, bactericide, fungicide, insecticide, virucide, miticide, nematicide, acaricide, rodenticide, and/or anti-algae agent.

In some embodiments, the individual microbes, or microbial consortia, or microbial communities, developed according to the disclosed methods can be combined with known biopesticides in the agricultural space, such as: biopesticides that function as an herbicide, bactericide, fungicide, insecticide, virucide, miticide, nematicide, acaricide, rodenticide, and/or anti-algae agent.

For example, in some embodiments, the present disclosure teaches agricultural compositions comprising one or more of the following active ingredients including: macrobial organisms (e.g., beneficial nematodes and the like), microbial organisms (e.g., Serenade, Bt, and the like), plant extracts (e.g., Timorex Gold and the like), biochemical (e.g., insect pheromones and the like), and/or minerals and oils (e.g., canola oil).

In some embodiments, the individual microbes, or microbial consortia, or microbial communities, developed according to the disclosed methods can be combined with an herbicide selected from the group consisting of: an acetamide selected from the group consisting of acetochlor, alachlor, butachlor, dimethachlor, dimethenamid, flufenacet, mefenacet, metolachlor, metazachlor, napropamide, naproanilide, pethoxamid, pretilachlor, propachlor, and thenylchlor; an amino acid derivative selected from the group consisting of bilanafos, glufosinate, and sulfosate; an aryloxyphenoxypropionate selected from the group consisting of clodinafop, cyhalofop-butyl, fenoxaprop, fluazifop, haloxyfop, metamifop, propaquizafop, quizalofop, and quizalo-fop-P-tefuryl; diquat and paraquat; a (thio)carbamate selected from the group consisting of asulam, butylate, carbetamide, desmedipham, dimepiperate, eptam (EPTC), esprocarb, molinate, orbencarb, phenmedipham, prosulfocarb, pyributicarb, thiobencarb, and triallate; a cyclohexanedione selected from the group consisting of butroxydim, clethodim, cycloxydim, profoxydim, sethoxydim, tepraloxydim, and tralkoxydim; a dinitroaniline selected from the group consisting of benfluralin, ethalfluralin, oryzalin, pendimethalin, prodiamine, and trifluralin; a diphenyl ether selected from the group consisting of acifluorfen, aclonifen, bifenox, diclofop, ethoxyfen, fomesafen, lactofen, and oxyfluorfen; a hydroxybenzonitrile selected from the group consisting of bomoxynil, dichlobenil, and ioxynil; an imidazolinone selected from the group consisting of imazamethabenz, imazamox, imazapic, imazapyr, imazaquin, and imazethapyr; a phenoxy acetic acid selected from the group consisting of clomeprop, 2,4-dichlorophenoxyacetic acid (2,4-D), 2,4-DB, dichlorprop, MCPA, MCPA-thioethyl, MCPB, and Mecoprop; a pyrazine selected from the group consisting of chloridazon, flufenpyr-ethyl, fluthiacet, norflurazon, and pyridate; a pyridine selected from the group consisting of aminopyralid, clopyralid, diflufenican, dithiopyr, fluridone, fluroxypyr, picloram, picolinafen, and thiazopyr; a sulfonyl urea selected from the group consisting of amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, and 14(2-chloro-6-propyl-imidazol[1,2]-blpyridazin-3-yl)sulfonyl)-3-(4,6-dimethoxy-pyrimidin-2-yl)urea; a triazine selected from the group consisting of ametryn, atrazine, cyanazine, a dimethametryn, ethiozin, hexazinone, metamitron, metribuzin, prometryn, simazine, terbuthylazine, terbutryn, and triaziflam; a urea compound selected from the group consisting of chlorotoluron, daimuron, diuron, fluometuron, isoproturon, linuron, methabenzthiazuron, and tebuthiuron; an acetolactate synthase inhibitor selected from the group consisting of bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, and pyroxsulam; and a compound selected from the group consisting of amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethlyl, chlorthal, cinmethylin, clomazone, cumyluron, cyprosulfamide, dicamba, difenzoquat, diflufenzopyr, *Drechslera monoceras*, endothal, ethofumesate, etobenzanid, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, 4-hydroxy-3-[2-(2-methoxy-ethoxymethyl)-6-trifluoromethyl-pyridine-3-carbonyl]-bicyclol[3.2.1]oct-3-en-2-one, (3-[2-chloro-4-fluoro-5-(3-methyl-2,6-dioxo-4-trifluoromethyl-3,6-dihydro-2H-pyrimidin-1-yl)-phenoxyl]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

In some embodiments, the individual microbes, or microbial consortia, or microbial communities, developed according to the disclosed methods can be combined with an insecticide selected from the group consisting of: an organo(thio)phosphate selected from the group consisting of acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, and trichlorfon; a carbamate selected from the group consisting of alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, and triazamate; a pyrethroid selected from the group consisting of allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, taufluvalinate, tefluthrin, tetramethrin, tralomethrin, transfluthrin, profluthrin, and dimefluthrin; an insect growth regulator selected from the group consisting of a) a chitin synthesis inhibitor wherein said chitin synthesis inhibitor is a benzoylurea selected from the group consisting of chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, and clofentazine; b) an ecdysone antagonist selected from the group consisting of halofenozide, methoxyfenozide, tebufenozide, and azadirachtin; c) a juvenoid selected from the group consisting of pyriproxyfen, methoprene, and fenoxycarb; or d) a lipid biosynthesis inhibitor selected from the group consisting of spirodiclofen, spiromesifen, and spirotetramat; a nicotinic receptor agonist/antagonist compound selected from the group consisting of clothianidin, dinotefuran, imidacloprid, thiamethoxam, nitenpyram, acetamiprid, thiacloprid, and 1-(2-chloro-thiazol-5-ylmethyl)-2-nitrimino-3,5-dimethyl-[1,3,5]triazinane; a GABA antagonist compound selected from the group consisting of endosulfan, ethiprole, fipronil, vaniliprole, pyrafluprole, pyriprole, and 5-amino-1-(2,6-dichloro-4-methyl-phenyl)-4-sulfinamoyl-1H-pyrazole-3-carbothioic acid amide; a macrocyclic lactone insecticide selected from the group consisting of abamectin, emamectin, milbemectin, lepimectin, spinosad, and spinetoram; a mitochondrial electron transport inhibitor (METI) I acaricide selected from the group consisting of fenazaquin, pyridaben, tebufenpyrad, tolfenpyrad, and flufenerim; a METI II and III compound selected from the group consisting of acequinocyl, fluacyprim, and hydramethylnon; chlorfenapyr; an oxidative phosphorylation inhibitor selected from the group consisting of cyhexatin, diafenthiuron, fenbutatin oxide, and propargite; cryomazine; piperonyl butoxide; a sodium channel blocker selected from the group consisting of indoxacarb and metaflumizone; and a compound selected from the group consisting of benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, and pyrifluquinazon.

In some embodiments, the present invention teaches a synergistic use of the presently disclosed microbes or microbial consortia with known pesticides in the agricultural space, such as: pesticides that function as an herbicide, bactericide, fungicide, insecticide, virucide, miticide, nematicide, acaricide, rodenticide, and/or anti-algae agent.

In some embodiments, the present invention teaches a synergistic use of the presently disclosed microbes or microbial consortia with known biopesticides in the agricultural space, such as: biopesticides that function as an herbicide, bactericide, fungicide, insecticide, virucide, miticide, nematicide, acaricide, rodenticide, and/or anti-algae agent.

In some embodiments, when the microbe or microbial consortia identified according to the taught methods is combined with a pesticide one witnesses an additive effect on a plant phenotypic trait of interest. In other embodiments, when the microbe or microbial consortia identified according to the taught methods is combined with a pesticide one witness a synergistic effect on a plant phenotypic trait of interest.

In some embodiments, when the microbe or microbial consortia identified according to the taught methods is combined with a biopesticide one witnesses an additive effect on a plant phenotypic trait of interest. In other embodiments, when the microbe or microbial consortia identified according to the taught methods is combined with a biopesticide one witness a synergistic effect on a plant phenotypic trait of interest.

The synergistic effect obtained by the taught methods can be quantified according to Colby's formula (i.e., $(E)=X+Y-(X*Y/100)$). See Colby, R. S., "Calculating Synergistic and Antagonistic Responses of Herbicide Combinations," 1967 Weeds, vol. 15, pp. 20-22, incorporated herein by reference in its entirety. Thus, by "synergistic" is intended a component which, by virtue of its presence, increases the desired effect by more than an additive amount.

The isolated microbes and consortia of the present disclosure can synergistically increase the effectiveness of agriculturally active pesticide compounds and also agricultural auxiliary pesticide compounds.

The isolated microbes and consortia of the present disclosure can synergistically increase the effectiveness of agriculturally active biopesticide compounds and also agricultural auxiliary biopesticide compounds.

Plant Growth Regulators and Biostimulants

In some embodiments, the agricultural compositions of the present disclosure comprise plant growth regulators and/or biostimulants, used in combination with the taught microbes.

In some embodiments, the individual microbes, or microbial consortia, or microbial communities, developed according to the disclosed methods can be combined with known plant growth regulators in the agricultural space, such as: auxins, gibberellins, cytokinins, ethylene generators, growth inhibitors, and growth retardants.

For example, in some embodiments, the present disclosure teaches agricultural compositions comprising one or more of the following active ingredients including: ancymidol, butralin, alcohols, chloromequat chloride, cytokinin, daminozide, ethepohon, flurprimidol, giberrelic acid, gibberellin mixtures, indole-3-butryic acid (IBA), maleic hydrazide, mefludide, mepiquat chloride, mepiquat pentaborate, naphthalene-acetic acid (NAA), 1-napthaleneacetemide, (NAD), n-decanol, placlobutrazol, prohexadione calcium, trinexapac-ethyl, uniconazole, salicylic acid, abscisic acid, ethylene, brassinosteroids, jasmonates, polyamines, nitric oxide, strigolactones, or karrikins among others.

In some embodiments, the individual microbes, or microbial consortia, or microbial communities, developed according to the disclosed methods can be combined with seed inoculants known in the agricultural space, such as: QUICK-ROOTS®, VAULT®, RHIZO-STICK®, NODULATOR®, DORMAL®, SABREX®, among others. In some embodiments, a *Bradyrhizobium* inoculant is utilized in combination with any single microbe or microbial consortia disclosed here. In particular aspects, a synergistic effect is observed when one combines one of the aforementioned inoculants, e.g., QUICKROOTS® or *Bradyrhizobium*, with a microbe or microbial consortia as taught herein.

In some embodiments, the agricultural compositions of the present disclosure comprise a plant growth regulator, which contains: kinetin, gibberellic acid, and indole butyric acid, along with copper, manganese, and zinc.

In some embodiments, the present disclosure teaches agricultural compositions comprising one or more commercially available plant growth regulators, including but not limited to: Abide®, A-Rest®, Butralin®, Fair®, Royaltac M®, Sucker-Plucker®, Off-Shoot®, Contact-85®, Citadel®, Cycocel®, E-Pro®, Conklin®, Culbac®, Cytoplex®, Early Harvest®, Foli-Zyme®, Goldengro®, Happygro®, Incite®, Megagro®, Ascend®, Radiate®, Stimulate®, Suppress®, Validate®, X-Cyte®, B-Nine®, Compress®, Dazide®, Boll Buster®, Boll D®, Cerone®, Cotton Quik®, Ethrel®, Finish®, Flash®, Florel®, Mature®, MFX®, Prep®, Proxy®, Quali-Pro®, SA-50®, Setup®, Super Boll®, Whiteout®, Cutless®, Legacy®, Mastiff®, Topflor®, Ascend®, Cytoplex®, Ascend®, Early Harvest®, Falgro®, Florgib®, Foli-Zyme®, GA3®, GibGro®, Green Sol®, Incite®, N-Large®, PGR IV®, Pro-Gibb®, Release®, Rouse®, Ryzup®, Stimulate®, BVB®, Chrysal®, Fascination®, Procone®, Fair®, Rite-Hite®, Royal®, Sucker Stuff®, Embark®, Sta-Lo®, Pix®, Pentia®, DipN Grow®, Goldengro®, Hi-Yield®, Rootone®, Antac®, FST-7®, Royaltac®, Bonzi®, Cambistat®, Cutdown®, Downsize®, Florazol®, Paclo®, Paczol®, Piccolo®, Profile®, Shortstop®, Trimmit®, Turf Enhancer®, Apogee®, Armor Tech®, Goldwing®, Governor®, Groom®, Legacy®, Primeraone®, Primo®, Provair®, Solace®, T-Nex®, T-Pac®, Concise®, and Sumagic®.

In some embodiments, the present invention teaches a synergistic use of the presently disclosed microbes or microbial consortia with plant growth regulators and/or stimulants such as phytohormones or chemicals that influence the production or disruption of plant growth regulators.

In some embodiments, the present invention teaches that phytohormones can include: Auxins (e.g., Indole acetic acid IAA), Gibberellins, Cytokinins (e.g., Kinetin), Abscisic acid, Ethylene (and its production as regulated by ACC synthase and disrupted by ACC deaminase).

In some embodiments, the individual microbes, or microbial consortia, or microbial communities, developed according to the disclosed methods can be combined with biostimulants. Such biostimulants may be, but are not limited to, microbial organisms, plant extracts, seaweeds, acids, biochar, and the like.

In some embodiments, the individual microbes, or microbial consortia, or microbial communities, developed according to the disclosed methods can be combined with fertilizers, which may be organic (e.g., manure, blood, fish, and the like), nitrogen-based (e.g., nitrate, ammonium, urea, and the like), phosphate, and potassium. Such fertilizers may also contain micronutrients including, but not limited to, sulfur, iron, zinc, and the like.

In some embodiments, the present invention teaches additional plant-growth promoting chemicals that may act in synergy with the microbes and microbial consortia disclosed herein, such as: humic acids, fulvic acids, amino acids, polyphenols and protein hydrolysates.

Thus, in some embodiments, the disclosure provides for the application of the taught microbes in combination with Ascend® upon any crop. Further, the disclosure provides for the application of the taught microbes in combination with Ascend® upon any crop and utilizing any method or application rate.

In some embodiments, the present disclosure teaches agricultural compositions with biostimulants.

As used herein, the term "biostimulant" refers to any substance that acts to stimulate the growth of microorganisms that may be present in soil or other plant growing medium.

The level of microorganisms in the soil or growing medium is directly correlated to plant health. Microorganisms feed on biodegradable carbon sources, and therefore plant health is also correlated with the quantity of organic matter in the soil. While fertilizers provide nutrients to feed and grow plants, in some embodiments, biostimulants provide biodegradable carbon, e.g., molasses, carbohydrates, e.g., sugars, to feed and grow microorganisms. Unless clearly stated otherwise, a biostimulant may comprise a single ingredient, or a combination of several different ingredients, capable of enhancing microbial activity or plant growth and development, due to the effect of one or more of the ingredients, either acting independently or in combination.

In some embodiments, biostimulants are compounds that produce non-nutritional plant growth responses. In some embodiments, many important benefits of biostimulants are based on their ability to influence hormonal activity. Hormones in plants (phytohormones) are chemical messengers regulating normal plant development as well as responses to the environment. Root and shoot growth, as well as other growth responses are regulated by phytohormones. In some embodiments, compounds in biostimulants can alter the hormonal status of a plant and exert large influences over its growth and health. Thus, in some embodiments, the present disclosure teaches sea kelp, humic acids, fulvic acids, and B Vitamins as common components of biostimulants. In some embodiments, the biostimulants of the present disclosure enhance antioxidant activity, which increases the plant's defensive system. In some embodiments, vitamin C, vitamin E, and amino acids such as glycine are antioxidants contained in biostimulants.

In other embodiments, biostimulants may act to stimulate the growth of microorganisms that are present in soil or other plant growing medium. Prior studies have shown that when certain biostimulants comprising specific organic seed extracts (e.g., soybean) were used in combination with a microbial inoculant, the biostimulants were capable of stimulating growth of microbes included in the microbial inoculant. Thus, in some embodiments, the present disclosure teaches one or more biostimulants that, when used with a microbial inoculant, is capable of enhancing the population of both native microbes and inoculant microbes. For a review of some popular uses of biostimulants, please see Calvo et al., 2014, Plant Soil 383:3-41.

Combinations of Plant Elements, Microbes, and Agricultural Compositions

In some embodiments, the present disclosure teaches that the individual microbes, or microbial consortia, or microbial communities, or any combination of the preceding, for example comprising any one or a plurality of microorganisms disclosed in Table 1 or Table 1A, may be applied to a plant element, optionally in combination with any agricultural composition, for the improvement of a plant phenotype.

Isolated microbes or communities or consortia (generally "microbes" or "microbe", interchangeably) may be applied to a heterologous plant element, creating a synthetic combination. Microbes are considered heterologous to a plant element if they are not normally associated with the plant element in nature, or if found, are applied in amounts different than that found in nature. In some embodiments, the microbes may be found naturally in one part of a plant but not another, and introduction of the microbes to another part of the plant is considered a heterologous association.

It is further contemplated that the microbe, either isolated or in combination with a plant or plant element, may be further associated with one or more agricultural compositions, such as those described above.

Synthetic combinations of microbes and plant elements, microbes and agricultural compositions, and microbes and plant elements and agricultural compositions are contemplated (generally "synthetic compositions", compositions that comprise components not typically found associated in nature).

Plant Element Treatments

In some embodiments, the present disclosure also concerns the discovery that treating plant elements before they are sown or planted with a combination of one or more of the microbes or agricultural compositions of the present disclosure can enhance a desired plant trait, e.g., plant growth, plant health, and/or plant resistance to pests.

Thus, in some embodiments, the present disclosure teaches the use of one or more of the microbes or microbial consortia as plant element treatments. The plant element treatment can be a plant element coating applied directly to an untreated and "naked" plant element. However, the plant element treatment can be a plant element overcoat that is applied to a plant element that has already been coated with one or more previous plant element coatings or plant element treatments. The previous plant element treatments may include one or more active compounds, either chemical or biological, and one or more inert ingredients.

The term "plant element treatment" generally refers to application of a material to a plant element prior to or during the time it is planted in soil. Plant element treatment with microbes, and other agricultural compositions of the present disclosure, has the advantages of delivering the treatments to the locus at which the plant elements are planted shortly before germination of the plant element and emergence of a plant element.

In other embodiments, the present disclosure also teaches that the use of plant element treatments minimizes the amount of microbe or agricultural composition that is required to successfully treat the plants, and further limits the amount of contact of workers with the microbes and compositions compared to application techniques such as spraying over soil or over emerging plant element.

Moreover, in some embodiments, the present disclosure teaches that the microbes disclosed herein are important for enhancing the early stages of plant life (e.g., within the first thirty days following emergence of the plant element). Thus, in some embodiments, delivery of the microbes and/or compositions of the present disclosure as a plant element treatment places the microbe at the locus of action at a critical time for its activity.

In some embodiments, the microbial compositions of the present disclosure are formulated as a plant element treatment. In some embodiments, it is contemplated that the plant elements can be substantially uniformly coated with one or more layers of the microbes and/or agricultural compositions disclosed herein, using conventional methods of mixing, spraying, or a combination thereof through the use of treatment application equipment that is specifically designed and manufactured to accurately, safely, and efficiently apply plant element treatment products to plant elements. Such equipment uses various types of coating technology such as rotary coaters, drum coaters, fluidized bed techniques, spouted beds, rotary mists, or a combination thereof. Liquid plant element treatments such as those of the present disclosure can be applied via either a spinning "atomizer" disk or a spray nozzle, which evenly distributes the plant element treatment onto the plant element as it moves though the spray pattern. In aspects, the plant element is then mixed or tumbled for an additional period of time to achieve additional treatment distribution and drying.

The plant elements can be primed or unprimed before coating with the microbial compositions to increase the uniformity of germination and emergence. In an alternative embodiment, a dry powder formulation can be metered onto the moving plant element and allowed to mix until completely distributed.

In some embodiments, the plant elements have at least part of the surface area coated with a microbiological composition, according to the present disclosure. In some embodiments, a plant element coat comprising the microbial composition is applied directly to a naked plant element. In some embodiments, a plant element overcoat comprising the microbial composition is applied to a plant element that already has a plant element coat applied thereon. In some aspects, the plant element may have a plant element coat comprising, e.g., clothianidin and/or *Bacillus firmus*-I-1582, upon which the present composition will be applied on top of, as a plant element overcoat. In some aspects, the taught microbial compositions are applied as a plant element overcoat to plant elements that have already been treated with PONCHO™ VOTiVO™. In some aspects, the plant element may have a plant element coat comprising, e.g., Metalaxyl, and/or clothianidin, and/or *Bacillus firmus*-I-1582, upon which the present composition will be applied on top of, as a plant element overcoat. In some aspects, the taught microbial compositions are applied as a plant element overcoat to plant elements that have already been treated with ACCELERON™.

In some embodiments, the microorganism-treated plant elements have a microbial spore concentration, or microbial cell concentration, from about: $10^2$ to $10^{12}$, $10^2$ to $10^{11}$, $10^2$ to $10^{10}$, $10^2$ to $10^9$, $10^2$ to $10^8$, $10^2$ to $10^7$, $10^2$ to $10^6$, $10^2$ to $10^5$, $10^2$ to $10^4$, or $10^2$ to $10^3$ per plant element.

In some embodiments, the microorganism-treated plant elements have a microbial spore concentration, or microbial cell concentration, from about: $10^3$ to $10^{12}$, $10^3$ to $10^{11}$, $10^3$ to $10^{10}$, $10^3$ to $10^9$, $10^3$ to $10^8$, $10^3$ to $10^7$, $10^3$ to $10^6$, $10^3$ to $10^5$, or $10^3$ to $10^4$ per plant element.

In some embodiments, the microorganism-treated plant elements have a microbial spore concentration, or microbial cell concentration, from about: $10^4$ to $10^{12}$, $10^4$ to $10^{11}$, $10^4$ to $10^{10}$, $10^4$ to $10^9$, $10^4$ to $10^8$, $10^4$ to $10^7$, $10^4$ to $10^6$, or $10^4$ to $10^5$ per plant element.

In some embodiments, the microorganism-treated plant elements have a microbial spore concentration, or microbial cell concentration, from about: $10^5$ to $10^{12}$, $10^5$ to $10^{11}$, $10^5$ to $10^{10}$, $10^5$ to $10^9$, $10^5$ to $10^8$, $10^5$ to $10^7$, or $10^5$ to $10^6$ per plant element.

In some embodiments, the microorganism-treated plant elements have a microbial spore concentration, or microbial cell concentration, from about: 105 to 109 per plant element.

In some embodiments, the microorganism-treated plant elements have a microbial spore concentration, or microbial cell concentration, of at least about: $1\times10^3$, or $1\times10^4$, or $1\times10^5$, or $1\times10^6$, or $1\times10^7$, or $1\times10^8$, or $1\times10^9$ per plant element.

In some embodiments, the amount of one or more of the microbes and/or agricultural compositions applied to the plant element depend on the final formulation, as well as size or type of the plant or plant element utilized. In some embodiments, one or more of the microbes are present in about 2% w/w/to about 80% w/w of the entire formulation. In some embodiments, the one or more of the microbes employed in the compositions is about 5% w/w to about 65% w/w, or 10% w/w to about 60% w/w by weight of the entire formulation.

In some embodiments, the plant elements may also have more spores or microbial cells per plant element, such as, for example about $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, or $10^{17}$ spores or cells per plant element.

In some embodiments, the plant element coats of the present disclosure can be up to 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 310 µm, 320 µm, 330 µm, 340 µm, 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, 510 µm, 520 µm, 530 µm, 540 µm, 550 µm, 560 µm, 570 µm, 580 µm, 590 µm, 600 µm, 610 µm, 620 µm, 630 µm, 640 µm, 650 µm, 660 µm, 670 µm, 680 µm, 690 µm, 700 µm, 710 µm, 720 µm, 730 µm, 740 µm, 750 µm, 760 µm, 770 µm, 780 µm, 790 µm, 800 µm, 810 µm, 820 µm, 830 µm, 840 µm, 850 µm, 860 µm, 870 µm, 880 µm, 890 µm, 900 µm, 910 µm, 920 µm, 930 µm, 940 µm, 950 µm, 960 µm, 970 µm, 980 µm, 990 µm, 1000 µm, 1010 µm, 1020 µm, 1030 µm, 1040 µm, 1050 µm, 1060 µm, 1070 µm, 1080 µm, 1090 µm, 1100 µm, 1110 µm, 1120 µm, 1130 µm, 1140 µm, 1150 µm, 1160 µm, 1170 µm, 1180 µm, 1190 µm, 1200 µm, 1210 µm, 1220 µm, 1230 µm, 1240 µm, 1250 µm, 1260 µm, 1270 µm, 1280 µm, 1290 µm, 1300 µm, 1310 µm, 1320 µm, 1330 µm, 1340 µm, 1350 µm, 1360 µm, 1370 µm, 1380 µm, 1390 µm, 1400 µm, 1410 µm, 1420 µm, 1430 µm, 1440 µm, 1450 µm, 1460 µm, 1470 µm, 1480 µm, 1490 µm, 1500 µm, 1510 µm, 1520 µm, 1530 µm, 1540 µm, 1550 µm, 1560 µm, 1570 µm, 1580 µm, 1590 µm, 1600 µm, 1610 µm, 1620 µm, 1630 µm, 1640 µm, 1650 µm, 1660 µm, 1670 µm, 1680 µm, 1690 µm, 1700 µm, 1710 µm, 1720 µm, 1730 µm, 1740 µm, 1750 µm, 1760 µm, 1770 µm, 1780 µm, 1790 µm, 1800 µm, 1810 µm, 1820 µm, 1830 µm, 1840 µm, 1850 µm, 1860 µm, 1870 µm, 1880 µm, 1890 µm, 1900 µm, 1910 µm, 1920 µm, 1930 µm, 1940 µm, 1950 µm, 1960 µm, 1970 µm, 1980 µm, 1990 µm, 2000 µm, 2010 µm, 2020 µm, 2030 µm, 2040 µm, 2050 µm, 2060 µm, 2070 µm, 2080 µm, 2090 µm, 2100 µm, 2110 µm, 2120 µm, 2130 µm, 2140 µm, 2150 µm, 2160 µm, 2170 µm, 2180 µm, 2190 µm, 2200 µm, 2210 µm, 2220 µm, 2230 µm, 2240 µm, 2250 µm, 2260 µm, 2270 µm, 2280 µm, 2290 µm, 2300 µm, 2310 µm, 2320 µm, 2330 µm, 2340 µm, 2350 µm, 2360 µm, 2370 µm, 2380 µm, 2390 µm, 2400 µm, 2410 µm, 2420 µm, 2430 µm, 2440 µm, 2450 µm, 2460 µm, 2470 µm, 2480 µm, 2490 µm, 2500 µm, 2510 µm, 2520 µm, 2530 µm, 2540 µm, 2550 µm, 2560 µm, 2570 µm, 2580 µm, 2590 µm, 2600 µm, 2610 µm, 2620 µm, 2630 µm, 2640 µm, 2650 µm, 2660 µm, 2670 µm, 2680 µm, 2690 µm, 2700 µm, 2710 µm, 2720 µm, 2730 µm, 2740 µm, 2750 µm, 2760 µm, 2770 µm, 2780 µm, 2790 µm, 2800 µm, 2810 µm, 2820 µm, 2830 µm, 2840 µm, 2850 µm, 2860 µm, 2870 µm, 2880 µm, 2890 µm, 2900 µm, 2910 µm, 2920 µm, 2930 µm, 2940 µm, 2950 µm, 2960 µm, 2970 µm, 2980 µm, 2990 µm, or 3000 µm thick.

In some embodiments, the plant element coats of the present disclosure can be 0.5 mm, 1 mm, 1.5 mm, 2 mm, 2.5 mm, 3 mm, 3.5 mm, 4 mm, 4.5 mm, or 5 mm thick.

In some embodiments, the plant element coats of the present disclosure can be at least 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5%, 48%, 48.5%, 49%, 49.5%, or 50% of the uncoated plant element weight.

In some embodiments, the microbial spores and/or cells can be coated freely onto the plant elements or they can be formulated in a liquid or solid composition before being coated onto the plant elements. For example, a solid composition comprising the microorganisms can be prepared by mixing a solid carrier with a suspension of the spores until the solid carriers are impregnated with the spore or cell suspension. This mixture can then be dried to obtain the desired particles.

In some other embodiments, it is contemplated that the solid or liquid microbial compositions of the present disclosure further contain functional agents e.g., activated carbon, nutrients (fertilizers), and other agents capable of improving the germination and quality of the products or a combination thereof.

Plant element coating methods and compositions that are known in the art can be particularly useful when they are modified by the addition of one of the embodiments of the present disclosure. Such coating methods and apparatus for their application are disclosed in, for example: U.S. Pat. Nos. 5,916,029; 5,918,413; 5,554,445; 5,389,399; 4,759,945; 4,465,017, and U.S. patent application Ser. No. 13/260,310, each of which is incorporated by reference herein.

Plant element coating compositions are disclosed in, for example: U.S. Pat. Nos. 5,939,356; 5,876,739, 5,849,320; 5,791,084, 5,661,103; 5,580,544, 5,328,942; 4,735,015; 4,634,587; 4,372,080, 4,339,456; and 4,245,432, each of which is incorporated by reference herein.

In some embodiments, a variety of additives can be added to the plant element treatment formulations comprising the inventive compositions. Binders can be added and include those composed of an adhesive polymer that can be natural or synthetic without phytotoxic effect on the plant element to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

Any of a variety of colorants may be employed, including organic chromophores classified as nitroso; nitro; azo, including monoazo, bisazo and polyazo; acridine, anthraquinone, azine, diphenylmethane, indamine, indophenol, methine, oxazine, phthalocyanine, thiazine, thiazole, triarylmethane, xanthene. Other additives that can be added include trace nutrients such as salts of iron, manganese, boron, copper, cobalt, molybdenum and zinc.

A polymer or other dust control agent can be applied to retain the treatment on the plant element surface.

In some specific embodiments, in addition to the microbial cells or spores, the coating can further comprise a layer of adherent. The adherent should be non-toxic, biodegradable, and adhesive. Examples of such materials include, but are not limited to, polyvinyl acetates; polyvinyl acetate copolymers; polyvinyl alcohols; polyvinyl alcohol copolymers; celluloses, such as methyl celluloses, hydroxymethyl celluloses, and hydroxymethyl propyl celluloses; dextrins; alginates; sugars; molasses; polyvinyl pyrrolidones; polysaccharides; proteins; fats; oils; gum arabics; gelatins; syrups; and starches. More examples can be found in, for example, U.S. Pat. No. 7,213,367, incorporated herein by reference.

Various additives, such as adherents, dispersants, surfactants, and nutrient and buffer ingredients, can also be included in the plant element treatment formulation. Other conventional plant element treatment additives include, but are not limited to: coating agents, wetting agents, buffering agents, and polysaccharides. At least one agriculturally acceptable carrier can be added to the plant element treatment formulation such as water, solids, or dry powders. The dry powders can be derived from a variety of materials such as calcium carbonate, gypsum, vermiculite, talc, humus, activated charcoal, and various phosphorous compounds.

In some embodiments, the plant element coating composition can comprise at least one filler, which is an organic or inorganic, natural or synthetic component with which the active components are combined to facilitate its application onto the plant element. In aspects, the filler is an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminium or magnesium silicates.

In some embodiments, the plant element treatment formulation may further include one or more of the following ingredients: other pesticides, including compounds that act only below the ground; fungicides, such as captan, thiram, metalaxyl, fludioxonil, oxadixyl, and isomers of each of those materials, and the like; herbicides, including compounds selected from glyphosate, carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; chemical fertilizers; biological fertilizers; and biocontrol agents such as other naturally-occurring or recombinant bacteria and fungi from the genera *Rhizobium, Bacillus, Pseudomonas, Serratia, Trichoderma, Glomus, Gliocladium* and mycorrhizal fungi. These ingredients may be added as a separate layer on the plant element, or alternatively may be added as part of the plant element coating composition of the disclosure.

In some embodiments, the formulation that is used to treat the plant element in the present disclosure can be in the form of a suspension; emulsion; slurry of particles in an aqueous medium (e.g., water); wettable powder; wettable granules (dry flowable); and dry granules. If formulated as a suspension or slurry, the concentration of the active ingredient in the formulation can be about 0.5% to about 99% by weight (w/w), or 5-40%, or as otherwise formulated by those skilled in the art.

As mentioned above, other conventional inactive or inert ingredients can be incorporated into the formulation. Such inert ingredients include, but are not limited to: conventional sticking agents; dispersing agents such as methylcellulose, for example, serve as combined dispersant/sticking agents for use in plant element treatments; polyvinyl alcohol; lecithin, polymeric dispersants (e.g., polyvinylpyrrolidone/vinyl acetate); thickeners (e.g., clay thickeners to improve viscosity and reduce settling of particle suspensions); emulsion stabilizers; surfactants; antifreeze compounds (e.g., urea), dyes, colorants, and the like. Further inert ingredients useful in the present disclosure can be found in McCutcheon's, vol. 1, "Emulsifiers and Detergents," MC Publishing Company, Glen Rock, N.J., U.S.A., 1996, incorporated by reference herein.

The plant element coating formulations of the present disclosure can be applied to plant elements by a variety of methods, including, but not limited to: mixing in a container (e.g., a bottle or bag), mechanical application, tumbling, spraying, and immersion. A variety of active or inert material can be used for contacting plant elements with microbial compositions according to the present disclosure.

In some embodiments, the amount of the microbes or agricultural composition that is used for the treatment of the plant element will vary depending upon the type of plant element and the type of active ingredients, but the treatment will comprise contacting the plant elements with an agriculturally effective amount of the inventive composition.

As discussed above, an effective amount means that amount of the inventive composition that is sufficient to affect beneficial or desired results. An effective amount can be administered in one or more administrations.

In some embodiments, in addition to the coating layer, the plant element may be treated with one or more of the following ingredients: other pesticides including fungicides and herbicides; herbicidal safeners; fertilizers and/or biocontrol agents. These ingredients may be added as a separate layer or alternatively may be added in the coating layer.

In some embodiments, the plant element coating formulations of the present disclosure may be applied to the plant elements using a variety of techniques and machines, such as fluidized bed techniques, the roller mill method, rotostatic plant element treaters, and drum coaters. Other methods, such as spouted beds may also be useful. The plant elements may be pre-sized before coating. After coating, the plant elements are typically dried and then transferred to a sizing machine for sizing. Such procedures are known in the art.

In some embodiments, the microorganism-treated plant elements may also be enveloped with a film overcoating to protect the coating. Such overcoatings are known in the art and may be applied using fluidized bed and drum film coating techniques.

In other embodiments of the present disclosure, compositions according to the present disclosure can be introduced onto a plant element by use of solid matrix priming. For example, a quantity of an inventive composition can be mixed with a solid matrix material and then the plant element can be placed into contact with the solid matrix material for a period to allow the composition to be introduced to the plant element. The plant element can then optionally be separated from the solid matrix material and stored or used, or the mixture of solid matrix material plus plant element can be stored or planted directly. Solid matrix materials which are useful in the present disclosure include polyacrylamide, starch, clay, silica, alumina, soil, sand, polyurea, polyacrylate, or any other material capable of absorbing or adsorbing the inventive composition for a time and releasing that composition into or onto the plant element. It is useful to make sure that the inventive composition and the solid matrix material are compatible with each other. For example, the solid matrix material should be chosen so that it can release the composition at a reasonable rate, for example over a period of minutes, hours, or days.

In some embodiments, the present disclosure teaches that the individual microbes, or microbial consortia, or microbial communities, developed according to the disclosed methods—including any single microorganism or combination of microorganisms disclosed in Table 1 or Table 1A, or any microbe or combination thereof from Table 1 or Table 1A in combination with one or more microbes from Table 2, of the specification—can be combined with any plant biostimulant.

In some embodiments, the present disclosure teaches agricultural compositions comprising one or more commercially available biostimulants, including but not limited to: Vitazyme®, Diehard™ Biorush®, Diehard™ Biorush® Fe, Diehard™ Soluble Kelp, Diehard™ Humate SP, Phocon®, Foliar Plus™, Plant Plus™, Accomplish LM®, Titan®, Soil Builder™ Nutri Life, Soil Solution™, Seed Coat™, PercPlus™, Plant Power®, CropKarb®, Thrust™, Fast2Grow®, Baccarat®, and Potente® among others.

In some embodiments, when the microbe or microbial consortia identified according to the taught methods is combined with an active chemical agent one witnesses an additive effect on a plant phenotypic trait of interest. In other embodiments, when the microbe or microbial consortia identified according to the taught methods is combined with an active chemical agent one witness a synergistic effect on a plant phenotypic trait of interest.

In some embodiments, when the microbe or microbial consortia identified according to the taught methods is combined with a fertilizer one witnesses an additive effect on a plant phenotypic trait of interest. In other embodiments, when the microbe or microbial consortia identified according to the taught methods is combined with a fertilizer one witness a synergistic effect on a plant phenotypic trait of interest.

In some embodiments, when the microbe or microbial consortia identified according to the taught methods is combined with a plant growth regulator, one witnesses an additive effect on a plant phenotypic trait of interest. In some embodiments, when the microbe or microbial consortia identified according to the taught methods is combined with a plant growth regulator, one witnesses a synergistic effect. In some aspects, the microbes of the present disclosure are combined with Ascend® and a synergistic effect is observed for one or more phenotypic traits of interest.

In some embodiments, when the microbe or microbial consortia identified according to the taught methods is combined with a biostimulant, one witnesses an additive effect on a plant phenotypic trait of interest. In some embodiments, when the microbe or microbial consortia identified according to the taught methods is combined with a biostimulant, one witnesses a synergistic effect.

The synergistic effect obtained by the taught methods can be quantified according to Colby's formula (i.e., $(E)=X+Y-(X*Y/100)$). See Colby, R. S., "Calculating Synergistic and Antagonistic Responses of Herbicide Combinations," 1967 Weeds, vol. 15, pp. 20-22, incorporated herein by reference in its entirety. Thus, by "synergistic" is intended a component which, by virtue of its presence, increases the desired effect by more than an additive amount.

The isolated microbes and consortia of the present disclosure can synergistically increase the effectiveness of agricultural active compounds and also agricultural auxiliary compounds.

In other embodiments, when the microbe or microbial consortia identified according to the taught methods is combined with a fertilizer one witnesses a synergistic effect.

Furthermore, in certain embodiments, the disclosure utilizes synergistic interactions to define microbial consortia. That is, in certain aspects, the disclosure combines together certain isolated microbial species, which act synergistically, into consortia that impart a beneficial trait upon a plant, or which are correlated with increasing a beneficial plant trait.

The agricultural compositions developed according to the disclosure can be formulated with certain auxiliaries, in order to improve the activity of a known active agricultural compound. This has the advantage that the amounts of active ingredient in the formulation may be reduced while maintaining the efficacy of the active compound, thus allowing costs to be kept as low as possible and any official regulations to be followed. In individual cases, it may also possible to widen the spectrum of action of the active compound since plants, where the treatment with a particular active ingredient without addition was insufficiently successful, can indeed be treated successfully by the addition of certain auxiliaries along with the disclosed microbial isolates and consortia. Moreover, the performance of the active may be increased in individual cases by a suitable formulation when the environmental conditions are not favorable.

Such auxiliaries that can be used in an agricultural composition can be an adjuvant. Frequently, adjuvants take the form of surface-active or salt-like compounds. Depending on their mode of action, they can roughly be classified as modifiers, activators, fertilizers, pH buffers, and the like. Modifiers affect the wetting, sticking, and spreading properties of a formulation. Activators break up the waxy cuticle of the plant and improve the penetration of the active ingredient into the cuticle, both short-term (over minutes) and long-term (over hours). Fertilizers such as ammonium sulfate, ammonium nitrate or urea improve the absorption and solubility of the active ingredient and may reduce the antagonistic behavior of active ingredients. pH buffers are conventionally used for bringing the formulation to an optimal pH.

For further embodiments of agricultural compositions of the present disclosure, See "Chemistry and Technology of Agrochemical Formulations," edited by D. A. Knowles, copyright 1998 by Kluwer Academic Publishers, hereby incorporated by reference.

Plants and Agronomic Benefits

A wide variety of plants, including those cultivated in agriculture, are capable of receiving benefit from the application of microbes, such as those described herein, including single microbes, consortia, and/or compositions produced therefrom, or comprising any of the preceding. Any number of a variety of different plants, including mosses and lichens and algae, may be used in the methods of the disclosure. In embodiments, the plants have economic, social, or environmental value. For example, the plants may include those used as: food crops, fiber crops, oil crops, in the forestry industry, in the pulp and paper industry, as a feedstock for biofuel production, and as ornamental plants.

In other embodiments, the plants may be economically, socially, or environmentally undesirable, such as weeds. The following is a list of non-limiting examples of the types of plants the methods of the disclosure may be applied to:

Food Crops

Cereals e.g maize, rice, wheat, barley, sorghum, millet, oats, rye, triticale, and buckwheat;

Leafy vegetables e.g., brassicaceous plants such as cabbages, broccoli, bok choy, rocket; salad greens such as spinach, cress, and lettuce;

Fruiting and flowering vegetables e.g., avocado, sweet corn, artichokes; curcubits e.g., squash, cucumbers, melons, courgettes, pumpkins; solanaceous vegetables/fruits e.g., tomatoes, eggplant, and capsicums;

Podded vegetables e.g., groundnuts, peanuts, peas, soybeans, beans, lentils, chickpea, okra;

Bulbed and stem vegetables e.g., asparagus, celery, *Allium* crops e.g garlic, onions, and leeks;

Roots and tuberous vegetables e.g., carrots, beet, bamboo shoots, cassava, yams, ginger, Jerusalem artichoke, parsnips, radishes, potatoes, sweet potatoes, taro, turnip, and wasabi;

Sugar crops including sugar beet (*Beta vulgaris*), sugar cane (*Saccharum officinarum*);

Crops grown for the production of non-alcoholic beverages and stimulants e.g., coffee, black, herbal, and green teas, cocoa, marijuana, and tobacco;

Fruit crops such as true berry fruits (e.g., kiwifruit, grape, currants, gooseberry, guava, feijoa, pomegranate), citrus fruits (e.g., oranges, lemons, limes, grapefruit), epigynous fruits (e.g., bananas, cranberries, blueberries), aggregate fruit (blackberry, raspberry, boysenberry), multiple fruits (e.g., pineapple, fig), stone fruit crops (e.g., apricot, peach, cherry, plum), pip-fruit (e.g., apples, pears) and others such as strawberries, sunflower seeds;

Culinary and medicinal herbs e.g., rosemary, basil, bay laurel, coriander, mint, dill, *Hypericum*, foxglove, alovera, rosehips, and cannabis;

Crop plants producing spices e.g., black pepper, cumin cinnamon, nutmeg, ginger, cloves, saffron, cardamom, mace, paprika, masalas, star anise;

Crops grown for the production of nuts e.g., almonds and walnuts, Brazil nut, cashew nuts, coconuts, chestnut, macadamia nut, pistachio nuts; peanuts, pecan nuts;

Crops grown for production of beers, wines and other alcoholic beverages e.g grapes, and hops;

Oilseed crops e.g., soybean, peanuts, cotton, olives, sunflower, sesame, lupin species and brassicaeous crops (e.g., canola/oilseed rape); and, edible fungi e.g., white mushrooms, Shiitake and oyster mushrooms;

Plants used in Pastoral Agriculture

Legumes: *Trifolium* species, *Medicago* species, and *Lotus* species; White clover (*T. repens*); Red clover (*T. pratense*); Caucasian clover (*T. ambigum*); subterranean clover (*T. subterraneum*); Alfalfa/Lucerne (*Medicago sativum*); annual medics; barrel medic; black medic; Sainfoin (*Onobrychis viciifolia*); Birdsfoot trefoil (*Lotus corniculatus*); Greater Birdsfoot trefoil (*Lotus pedunculatus*);

Seed legumes/pulses including Peas (*Pisum sativum*), Common bean (*Phaseolus vulgaris*), Broad beans (*Vicia faba*), Mung bean (*Vigna radiata*), Cowpea (*Vigna unguiculata*), Chick pea (*Cicer arietum*), Lupins (*Lupinus* species);

Cereals including Maize/corn (*Zea mays*), Sorghum (*Sorghum* spp.), Millet (*Panicum miliaceum, P. sumatrense*), Rice (*Oryza sativa* indica, *Oryza sativa japonica*), Wheat (*Triticum aestivum*), Barley (*Hordeum vulgare*), Rye (*Secale cereale*), Triticale (*Triticum X Secale*), Oats (*Avena sativa*);

Forage and Amenity grasses: Temperate grasses such as *Lolium* species; *Festuca* species; *Agrostis* spp., Perennial ryegrass (*Lolium perenne*); hybrid ryegrass (*Lolium hybridum*); annual ryegrass (*Lolium multiflorum*), tall fescue (*Festuca arundinacea*); meadow fescue (*Festuca pratensis*); red fescue (*Festuca rubra*); *Festuca ovina*; Festuloliums (*Lolium X Festuca* crosses); Cocksfoot (*Dactylis glomerata*); Kentucky bluegrass *Poa pratensis; Poa palustris; Poa nemoralis; Poa trivialis; Poa compresa; Bromus* species; *Phalaris* (*Phleum* species); *Arrhenatherum elatius; Agropyron* species; *Avena strigosa; Setaria italic;*

Tropical grasses such as: *Phalaris* species; *Brachiaria* species; *Eragrostis* species; *Panicum* species; Bahai grass (*Paspalum notatum*); *Brachypodium* species; and, grasses used for biofuel production such as Switchgrass (*Panicum virgatum*) and *Miscanthus* species;

Fiber Crops

Cotton, hemp, jute, coconut, sisal, flax (*Linum* spp.), New Zealand flax (*Phormium* spp.); plantation and natural forest species harvested for paper and engineered wood fiber products such as coniferous and broadleafed forest species;

Tree and Shrub Species Used in Plantation Forestry and Bio-Fuel Crops

Pine (*Pinus* species); Fir (*Pseudotsuga* species); Spruce (*Picea* species); Cypress (*Cupressus* species); Wattle (*Acacia* species); Alder (*Alnus* species); Oak species (*Quercus* species); Redwood (*Sequoiadendron* species); willow (*Salix* species); birch (*Betula* species); Cedar (*Cedurus* species);

Ash (*Fraxinus* species); Larch (*Larix* species); *Eucalyptus* species; Bamboo (*Bambuseae* species) and Poplars (*Populus* species).

Plants Grown for Conversion to Energy, Biofuels or Industrial Products by Extractive, Biological, Physical or Biochemical Treatment Oil-producing plants such as oil palm, jatropha, soybean, cotton, linseed; Latex-producing plants such as the Para Rubber tree, *Hevea brasiliensis* and the Panama Rubber Tree *Castilla elastica*; plants used as direct or indirect feedstocks for the production of biofuels i.e., after chemical, physical (e.g., thermal or catalytic) or biochemical (e.g., enzymatic pre-treatment) or biological (e.g., microbial fermentation) transformation during the production of biofuels, industrial solvents or chemical products e.g., ethanol or butanol, propane dials, or other fuel or industrial material including sugar crops (e.g., beet, sugar cane), starch producing crops (e.g., C3 and C4 cereal crops and tuberous crops), cellulosic crops such as forest trees (e.g., Pines, Eucalypts) and Graminaceous and Poaceous plants such as bamboo, switch grass, miscanthus; crops used in energy, biofuel or industrial chemical production via gasification and/or microbial or catalytic conversion of the gas to biofuels or other industrial raw materials such as solvents or plastics, with or without the production of biochar (e.g., biomass crops such as coniferous, eucalypt, tropical or broadleaf forest trees, graminaceous and poaceous crops such as bamboo, switch grass, miscanthus, sugar cane, or hemp or softwoods such as poplars, willows; and, biomass crops used in the production of biochar;

Crops Producing Natural Products Useful for the Pharmaceutical, Agricultural Nutraceutical and Cosmeceutical Industries Crops producing pharmaceutical precursors or compounds or nutraceutical and cosmeceutical compounds and materials for example, star anise (shikimic acid), Japanese knotweed (resveratrol), kiwifruit (soluble fiber, proteolytic enzymes);

Floricultural, Ornamental and Amenity Plants Grown for their Aesthetic or Environmental Properties Flowers such as roses, tulips, chrysanthemums;

Ornamental shrubs such as Buxus, Hebe, Rosa, Rhododendron, Hedera

Amenity plants such as Platanus, Choisya, Escallonia, Euphorbia, Carex

Mosses such as sphagnum moss

Plants Grown for Bioremediation

In certain aspects, the microbes of the present disclosure are applied to hybrid plants to increase beneficial traits of said hybrids. In other aspects, the microbes of the present disclosure are applied to genetically modified plants to increase beneficial traits of said GM plants. The microbes taught herein are able to be applied to hybrids and GM plants and thus maximize the elite genetics and trait technologies of these plants.

It should be appreciated that a plant may be provided in the form of a seed, seedling, cutting, propagule, or any other plant material or tissue capable of growing. In one embodiment the seed may be surface-sterilised with a material such as sodium hypochlorite or mercuric chloride to remove surface-contaminating microorganisms. In one embodiment, the propagule is grown in axenic culture before being placed in the plant growth medium, for example as sterile plantlets in tissue culture.

Methods of Application

The microorganisms may be applied to a plant, seedling, cutting, propagule, or the like and/or the growth medium containing said plant, using any appropriate technique known in the art.

However, by way of example, an isolated microbe, consortia, or composition comprising the same, and/or a composition produced therefrom, may be applied to a plant, seedling, cutting, propagule, or the like, by spraying, coating, dusting, or any other method known in the art.

In another embodiment, the isolated microbe, consortia, or composition comprising the same may be applied directly to a plant seed prior to sowing.

In another embodiment, the isolated microbe, consortia, or composition comprising the same may applied directly to a plant seed, as a seed coating.

In one embodiment of the present disclosure, the isolated microbe, consortia, or composition comprising the same is supplied in the form of granules, or plug, or soil drench that is applied to the plant growth media.

In other embodiments, the isolated microbe, consortia, or composition comprising the same are supplied in the form of a foliar application, such as a foliar spray or liquid composition. The foliar spray or liquid application may be applied to a growing plant or to a growth media, e.g., soil.

In some embodiments, the isolated microbe, consortia, or composition comprising the same are supplied in a form selected from: a soil drench, a foliar spray, a dip treatment, an in furrow treatment, a soil amendment, granules, a broadcast treatment, a post-harvest disease control treatment, or a seed treatment. In some embodiments, the agricultural compositions may be applied alone in or in rotation spray programs.

In some embodiments, the isolated microbe, consortia, or composition comprising the same may be compatible with tank mixing. In some embodiments, the agricultural compositions may be compatible with tank mixing with other agricultural products. In some embodiments, the agricultural compositions may be compatible with equipment used for grould, aerial, and irrigation applications.

In another embodiment, the isolated microbe, consortia, or composition comprising the same may be formulated into granules and applied alongside seeds during planting. Or the granules may be applied after planting. Or the granules may be applied before planting.

In some embodiments, the isolated microbe, consortia, or composition comprising the same are administered to a plant or growth media as a topical application and/or drench application to improve crop growth, yield, and quality. The topical application may be via utilization of a dry mix or powder or dusting composition or may be a liquid based formulation.

In embodiments, the isolated microbe, consortia, or composition comprising the same can be formulated as: (1) solutions; (2) wettable powders; (3) dusting powders; (4) soluble powders; (5) emulsions or suspension concentrates; (6) seed dressings or coatings, (7) tablets; (8) water-dispersible granules; (9) water soluble granules (slow or fast release); (10) microencapsulated granules or suspensions; (11) as irrigation components, and (12) a component of fertilizers, pesticides, and other compatible amendments, among others. In in certain aspects, the compositions may be diluted in an aqueous medium prior to conventional spray application. The compositions of the present disclosure can be applied to the soil, plant, seed, rhizosphere, rhizosheath, or other area to which it would be beneficial to apply the microbial compositions. Further still, ballistic methods can be utilized as a means for introducing endophytic microbes.

In aspects, the compositions are applied to the foliage of plants. The compositions may be applied to the foliage of plants in the form of an emulsion or suspension concentrate, liquid solution, or foliar spray. The application of the compositions may occur in a laboratory, growth chamber, greenhouse, or in the field.

In another embodiment, microorganisms may be inoculated into a plant by cutting the roots or stems and exposing the plant surface to the microorganisms by spraying, dipping, or otherwise applying a liquid microbial suspension, or gel, or powder.

In another embodiment, the microorganisms may be injected directly into foliar or root tissue, or otherwise inoculated directly into or onto a foliar or root cut, or else into an excised embryo, or radicle, or coleoptile. These inoculated plants may then be further exposed to a growth media containing further microorganisms; however, this is not necessary.

In other embodiments, particularly where the microorganisms are unculturable, the microorganisms may be transferred to a plant by any one or a combination of grafting, insertion of explants, aspiration, electroporation, wounding, root pruning, induction of stomatal opening, or any physical, chemical or biological treatment that provides the opportunity for microbes to enter plant cells or the intercellular space. Persons of skill in the art may readily appreciate a number of alternative techniques that may be used.

In one embodiment, the microorganisms infiltrate parts of the plant such as the roots, stems, leaves and/or reproductive plant parts (become endophytic), and/or grow upon the surface of roots, stems, leaves and/or reproductive plant parts (become epiphytic) and/or grow in the plant rhizosphere. In one embodiment, the microorganisms form a symbiotic relationship with the plant.

Aspects

Some aspects of the disclosure include, but are not limited to:

Aspect 1: An isolated bacterial strain selected from the group consisting of: *Bacillus velezensis* deposited as NRRL Accession No. B-67810 (Strain ID: BEC-80, SEQ ID NO: 1); *Bacillus methylotrophicus* deposited as NRRL Accession No. B-67812 (Strain ID: BCP-60, SEQ ID NO: 2); *Bacillus amyloliquefaciens* deposited as NRRL Accession No. B-67815 (Strain ID: BCP-69, SEQ ID NO: 3); *Bacillus amyloliquefaciens* deposited as NRRL Accession No. B-67947 (Strain ID: BCP-77A, SEQ ID NO: 4); *Bacillus amyloliquefaciens* deposited as NRRL Accession No. B-67949 (Strain ID: BCP-77B, SEQ ID NO: 5); *Paenibacillus alginolyticus* deposited as NRRL Accession No. B-67813 (Strain ID: BCP-68A, SEQ ID NO: 6); *Paenibacillus alginolyticus* (Strain ID: BCP-68B, SEQ ID NO: 7); *Paenibacillus alginolyticus* (Strain ID: BCP-68C, SEQ ID NO: 8); *Paenibacillus alginolyticus* deposited as NRRL Accession No. B-67811 (Strain ID: BCP-68D, SEQ ID NO:); *Orbilia auricolor/Arthrobotrys oligospora* deposited as NRRL Accession No. 67879 (Strain ID: BCP-93, SEQ ID NO: 10); *Bacillus pumilus* deposited as NRRL Accession No. B-67878 (Strain ID: BCP-89B, SEQ ID NO: 11); and *Lysinibacillus fusiformis* deposited as NRRL Accession No. B-67871 (Strain ID: BCP-91, SEQ ID NO: 12), or an isolated bacterial strain having substantially similar morphological and physiological characteristics, substantially similar genetic characteristics, progeny, mutants, or genetically edited, altered, or modified variants thereof.

Aspect 2: The isolated bacterial strain of Aspect 1, wherein the isolated bacterial strain has substantially similar morphological and physiological characteristics to a strain selected from the group consisting of: *Bacillus velezensis* deposited as NRRL Accession No. B-67810 (Strain ID: BEC-80, SEQ ID NO: 1); *Bacillus methylotrophicus* deposited as NRRL Accession No. B-67812 (Strain ID: BCP-60, SEQ ID NO: 2); *Bacillus amyloliquefaciens* deposited as NRRL Accession No. B-67815 (Strain ID: BCP-69, SEQ ID NO: 3); *Bacillus amyloliquefaciens* deposited as NRRL Accession No. B-67947 (Strain ID: BCP-77A, SEQ ID NO: 4); *Bacillus amyloliquefaciens* deposited as NRRL Accession No. B-67949 (Strain ID: BCP-77B, SEQ ID NO: 5); *Paenibacillus alginolyticus* deposited as NRRL Accession No. B-67813 (Strain ID: BCP-68A, SEQ ID NO: 6); *Paenibacillus alginolyticus* (Strain ID: BCP-68B, SEQ ID NO: 7); *Paenibacillus alginolyticus* (Strain ID: BCP-68C, SEQ ID NO: 8); *Paenibacillus alginolyticus* deposited as NRRL Accession No. B-67811 (Strain ID: BCP-68D, SEQ ID NO:); *Orbilia auricolor/Arthrobotrys oligospora* deposited as NRRL Accession No. 67879 (Strain ID: BCP-93, SEQ ID NO: 10); *Bacillus pumilus* deposited as NRRL Accession No. B-67878 (Strain ID: BCP-89B, SEQ ID NO: 11); and *Lysinibacillus fusiformis* deposited as NRRL Accession No. B-67871 (Strain ID: BCP-91, SEQ ID NO: 12), or an isolated bacterial strain having substantially similar morphological and physiological characteristics, substantially similar genetic characteristics, progeny, mutants, or genetically edited, altered, or modified variants thereof.

Aspect 3: The isolated bacterial strain of Aspect 1, wherein the isolated bacterial strain has substantially similar genetic characteristics to a strain selected from the group consisting of: *Bacillus velezensis* deposited as NRRL Accession No. B-67810 (Strain ID: BEC-80, SEQ ID NO: 1); *Bacillus methylotrophicus* deposited as NRRL Accession No. B-67812 (Strain ID: BCP-60, SEQ ID NO: 2); *Bacillus amyloliquefaciens* deposited as NRRL Accession No. B-67815 (Strain ID: BCP-69, SEQ ID NO: 3); *Bacillus amyloliquefaciens* deposited as NRRL Accession No. B-67947 (Strain ID: BCP-77A, SEQ ID NO: 4); *Bacillus amyloliquefaciens* deposited as NRRL Accession No. B-67949 (Strain ID: BCP-77B, SEQ ID NO: 5); *Paenibacillus alginolyticus* deposited as NRRL Accession No. B-67813 (Strain ID: BCP-68A, SEQ ID NO: 6); *Paenibacillus alginolyticus* (Strain ID: BCP-68B, SEQ ID NO: 7); *Paenibacillus alginolyticus* (Strain ID: BCP-68C, SEQ ID NO: 8); *Paenibacillus alginolyticus* deposited as NRRL Accession No. B-67811 (Strain ID: BCP-68D, SEQ ID NO:); *Orbilia auricolor/Arthrobotrys oligospora* deposited as NRRL Accession No. 67879 (Strain ID: BCP-93, SEQ ID NO: 10); *Bacillus pumilus* deposited as NRRL Accession No. B-67878 (Strain ID: BCP-89B, SEQ ID NO: 11); and *Lysinibacillus fusiformis* deposited as NRRL Accession No. B-67871 (Strain ID: BCP-91, SEQ ID NO: 12), or an isolated bacterial strain having substantially similar morphological and physiological characteristics, substantially similar genetic characteristics, progeny, mutants, or genetically edited, altered, or modified variants thereof.

Aspect 4: The isolated bacterial strain of Aspect 1, wherein the isolated bacterial strain is a progeny of a strain selected from the group consisting of: *Bacillus velezensis* deposited as NRRL Accession No. B-67810 (Strain ID: BEC-80, SEQ ID NO: 1); *Bacillus methylotrophicus* deposited as NRRL Accession No. B-67812 (Strain ID: BCP-60, SEQ ID NO: 2); *Bacillus amyloliquefaciens* deposited as NRRL Accession No. B-67815 (Strain ID: BCP-69, SEQ ID NO: 3); *Bacillus amyloliquefaciens* deposited as NRRL Accession No. B-67947 (Strain ID: BCP-77A, SEQ ID NO: 4); *Bacillus amyloliquefaciens* deposited as NRRL Accession No. B-67949 (Strain ID: BCP-77B, SEQ ID NO: 5);

*Paenibacillus alginolyticus* deposited as NRRL Accession No. B-67813 (Strain ID: BCP-68A, SEQ ID NO: 6); *Paenibacillus alginolyticus* (Strain ID: BCP-68B, SEQ ID NO: 7); *Paenibacillus alginolyticus* (Strain ID: BCP-68C, SEQ ID NO: 8); *Paenibacillus alginolyticus* deposited as NRRL Accession No. B-67811 (Strain ID: BCP-68D, SEQ ID NO:); *Orbilia auricolor/Arthrobotrys oligospora* deposited as NRRL Accession No. 67879 (Strain ID: BCP-93, SEQ ID NO: 10); *Bacillus pumilus* deposited as NRRL Accession No. B-67878 (Strain ID: BCP-89B, SEQ ID NO: 11); and *Lysinibacillus fusiformis* deposited as NRRL Accession No. B-67871 (Strain ID: BCP-91, SEQ ID NO: 12), or an isolated bacterial strain having substantially similar morphological and physiological characteristics, substantially similar genetic characteristics, progeny, mutants, or genetically edited, altered, or modified variants thereof.

Aspect 5: The isolated bacterial strain of Aspect 1, wherein the isolated bacterial strain is a mutant of a strain selected from the group consisting of: *Bacillus velezensis* deposited as NRRL Accession No. B-67810 (Strain ID: BEC-80, SEQ ID NO: 1); *Bacillus methylotrophicus* deposited as NRRL Accession No. B-67812 (Strain ID: BCP-60, SEQ ID NO: 2); *Bacillus amyloliquefaciens* deposited as NRRL Accession No. B-67815 (Strain ID: BCP-69, SEQ ID NO: 3); *Bacillus amyloliquefaciens* deposited as NRRL Accession No. B-67947 (Strain ID: BCP-77A, SEQ ID NO: 4); *Bacillus amyloliquefaciens* deposited as NRRL Accession No. B-67949 (Strain ID: BCP-77B, SEQ ID NO: 5); *Paenibacillus alginolyticus* deposited as NRRL Accession No. B-67813 (Strain ID: BCP-68A, SEQ ID NO: 6); *Paenibacillus alginolyticus* (Strain ID: BCP-68B, SEQ ID NO: 7); *Paenibacillus alginolyticus* (Strain ID: BCP-68C, SEQ ID NO: 8); *Paenibacillus alginolyticus* deposited as NRRL Accession No. B-67811 (Strain ID: BCP-68D, SEQ ID NO:); *Orbilia auricolor/Arthrobotrys oligospora* deposited as NRRL Accession No. 67879 (Strain ID: BCP-93, SEQ ID NO: 10); *Bacillus pumilus* deposited as NRRL Accession No. B-67878 (Strain ID: BCP-89B, SEQ ID NO: 11); and *Lysinibacillus fusiformis* deposited as NRRL Accession No. B-67871 (Strain ID: BCP-91, SEQ ID NO: 12), or an isolated bacterial strain having substantially similar morphological and physiological characteristics, substantially similar genetic characteristics, progeny, mutants, or genetically edited, altered, or modified variants thereof.

Aspect 6: The isolated bacterial strain of Aspect 1, wherein the isolated bacterial strain is a genetically edited, altered, or modified variant of a strain selected from the group consisting of: *Bacillus velezensis* deposited as NRRL Accession No. B-67810 (Strain ID: BEC-80, SEQ ID NO: 1); *Bacillus methylotrophicus* deposited as NRRL Accession No. B-67812 (Strain ID: BCP-60, SEQ ID NO: 2); *Bacillus amyloliquefaciens* deposited as NRRL Accession No. B-67815 (Strain ID: BCP-69, SEQ ID NO: 3); *Bacillus amyloliquefaciens* deposited as NRRL Accession No. B-67947 (Strain ID: BCP-77A, SEQ ID NO: 4); *Bacillus amyloliquefaciens* deposited as NRRL Accession No. B-67949 (Strain ID: BCP-77B, SEQ ID NO: 5); *Paenibacillus alginolyticus* deposited as NRRL Accession No. B-67813 (Strain ID: BCP-68A, SEQ ID NO: 6); *Paenibacillus alginolyticus* (Strain ID: BCP-68B, SEQ ID NO: 7); *Paenibacillus alginolyticus* (Strain ID: BCP-68C, SEQ ID NO: 8); *Paenibacillus alginolyticus* deposited as NRRL Accession No. B-67811 (Strain ID: BCP-68D, SEQ ID NO:); *Orbilia auricolor/Arthrobotrys oligospora* deposited as NRRL Accession No. 67879 (Strain ID: BCP-93, SEQ ID NO: 10); *Bacillus pumilus* deposited as NRRL Accession No. B-67878 (Strain ID: BCP-89B, SEQ ID NO: 11); and *Lysinibacillus fusiformis* deposited as NRRL Accession No. B-67871 (Strain ID: BCP-91, SEQ ID NO: 12), or an isolated bacterial strain having substantially similar morphological and physiological characteristics, substantially similar genetic characteristics, progeny, mutants, or genetically edited, altered, or modified variants thereof.

Aspect 7: *Bacillus velezensis* deposited as NRRL Accession No. B-67810 (Strain ID: BEC-80, SEQ ID NO: 1); *Bacillus methylotrophicus* deposited as NRRL Accession No. B-67812 (Strain ID: BCP-60, SEQ ID NO: 2); *Bacillus amyloliquefaciens* deposited as NRRL Accession No. B-67815 (Strain ID: BCP-69, SEQ ID NO: 3); *Bacillus amyloliquefaciens* deposited as NRRL Accession No. B-67947 (Strain ID: BCP-77A, SEQ ID NO: 4); *Bacillus amyloliquefaciens* deposited as NRRL Accession No. B-67949 (Strain ID: BCP-77B, SEQ ID NO: 5); *Paenibacillus alginolyticus* deposited as NRRL Accession No. B-67813 (Strain ID: BCP-68A, SEQ ID NO: 6); *Paenibacillus alginolyticus* (Strain ID: BCP-68B, SEQ ID NO: 7); *Paenibacillus alginolyticus* (Strain ID: BCP-68C, SEQ ID NO: 8); *Paenibacillus alginolyticus* deposited as NRRL Accession No. B-67811 (Strain ID: BCP-68D, SEQ ID NO:); *Orbilia auricolor/Arthrobotrys oligospora* deposited as NRRL Accession No. 67879 (Strain ID: BCP-93, SEQ ID NO: 10); *Bacillus pumilus* deposited as NRRL Accession No. B-67878 (Strain ID: BCP-89B, SEQ ID NO: 11); and *Lysinibacillus fusiformis* deposited as NRRL Accession No. B-67871 (Strain ID: BCP-91, SEQ ID NO: 12), or an isolated bacterial strain having substantially similar morphological and physiological characteristics, substantially similar genetic characteristics, progeny, mutants, or genetically edited, altered, or modified variants thereof.

Aspect 8: An isolated bacterial strain comprising a polynucleotide sequence sharing at least 97% sequence identity with any one of SEQ ID NOs: 1-12.

Aspect 9: A substantially pure culture of an isolated bacterial strain according to any one of Aspects 1-8.

Aspect 10: A cell-free or inactivated preparation of an isolated bacterial strain according to any one of Aspects 1-8.

Aspect 11: A metabolite produced by an isolated bacterial strain according to any one of Aspects 1-8.

Aspect 12: An agricultural composition, comprising: the isolated bacterial strain of any one of Aspects 1-8; and an agriculturally acceptable carrier.

Aspect 13: The agricultural composition of Aspect 12, wherein the isolated bacterial strain is present in the composition at a concentration of $1\times10^2$ to $1\times10^{12}$ bacterial cells per gram.

Aspect 14: The agricultural composition of Aspect 12 or 13, wherein the agricultural composition is formulated as a seed coating, a foliar spray, a soil drench, a dip treatment, an in furrow treatment, a soil amendment, granules, a broadcast treatment, or a post-harvest disease control treatment.

Aspect 15: A method of imparting at least one beneficial trait upon a plant species, comprising: applying the isolated bacterial strain of any one of Aspects 1-8 to the plant species, or to a growth medium in which the plant species is located.

Aspect 16: A method of imparting at least one beneficial trait upon a plant species, comprising: applying the agricultural composition of any one of Aspects 12-14 to the plant species, or to a growth medium in which the plant species is located.

Aspect 17: A microbial consortium, comprising at least two microbes selected from the groups consisting of: A) *Bacillus tequilensis, Bacillus methylotrophicus, Bacillus* amyloliquefaciens, Paenibacillus alginolyticus, Orbilia auricolor/*Arthrobotrys oligospora, Bacillus pumilus,* and *Lysini-* bacillus fusiformis; and B) *Arthrobacter cupressi, Arthrobacter mysorens, Arthrobacter nicotinovorans, Arthrobacter pascens, Bacillus megaterium, Bacillus subtilis, Bacillus thuringiensis, Bacillus velezensis, Brevibacterium frigoritolerans, Herbaspirillum chlorophenolicum, Kosakonia radicincitans, Lysinibacillus fusiformis, Massilia kyonggiensis, Massilia niastensis, Novosphingobium sediminicola, Paenibacillus amylolyticus, Paenibacillus glycanilyticus, Paenibacillus polymyxa, Pseudomonas fluorescens, Pseudomonas jinjuensis, Pseudomonas oryzihabitans, Pseudomonas putida, Rahnella aquatilis,* and *Tumebacillus permanentifrigoris*; wherein at least one microbe is selected from group A).

Aspect 18: The microbial consortium of Aspect 17, wherein at least one of the microbes is characterized as having substantially similar morphological and physiological characteristics to a microbe selected from group A).

Aspect 19: The microbial consortium of Aspect 17, wherein at least one of the microbes is characterized as having substantially similar genetic characteristics to a microbe selected from group A).

Aspect 20: The microbial consortium of Aspect 17, wherein the at least one of the microbes is characterized as a progeny of a microbe selected from group A).

Aspect 21: The microbial consortium of Aspect 17, wherein at least one of the microbes is characterized as a mutant of a microbe selected from group A).

Aspect 22: The microbial consortium of Aspect 17, wherein at least one of the microbes is characterized as a genetically edited, altered, or modified variant of a microbe selected from group A).

Aspect 23: A substantially pure culture of the microbial consortium of any one of Aspects 17-22.

Aspect 24: A cell-free of inactivated preparation of the microbial consortium of any one of Aspects 17-22.

Aspect 25: A metabolite produced by the microbial consortium of any one of Aspects 17-22.

Aspect 26: An agricultural composition, comprising: the microbial consortium of any one of Aspects 17-22; and an agriculturally acceptable carrier.

Aspect 27: The agricultural composition of Aspect 26, wherein the microbial consortium is present in the composition at $1\times10^2$ to $1\times10^{12}$ bacterial cells per gram.

Aspect 28: The agricultural composition of Aspect 26 or 27, wherein the agricultural composition is formulated as a seed coating, a foliar spray, a soil drench, a dip treatment, an in furrow treatment, a soil amendment, granules, a broadcast treatment, or a post-harvest disease control treatment.

Aspect 29: A method of imparting at least one beneficial trait upon a plant species, comprising: applying the microbial consortium of any one of Aspects 17-22 to the plant species, or to a growth medium in which the plant species is located.

Aspect 30: A method of imparting at least one beneficial trait upon a plant species, comprising: applying the agricultural composition of any one of Aspects 26 or 27 to the plant species, or to a growth medium in which the plant species is located.

Aspect 31: A microbial consortium, comprising at least two isolated bacterial strains selected from the groups consisting of: *Bacillus velezensis* deposited as NRRL Accession No. B-67810 (Strain ID: BEC-80, SEQ ID NO: 1); *Bacillus methylotrophicus* deposited as NRRL Accession No. B-67812 (Strain ID: BCP-60, SEQ ID NO: 2); *Bacillus amyloliquefaciens* deposited as NRRL Accession No. B-67815 (Strain ID: BCP-69, SEQ ID NO: 3); *Bacillus amyloliquefaciens* deposited as NRRL Accession No. B-67947 (Strain ID: BCP-77A, SEQ ID NO: 4); *Bacillus amyloliquefaciens* deposited as NRRL Accession No. B-67949 (Strain ID: BCP-77B, SEQ ID NO: 5); *Paenibacillus alginolyticus* deposited as NRRL Accession No. B-67813 (Strain ID: BCP-68A, SEQ ID NO: 6); *Paenibacillus alginolyticus* (Strain ID: BCP-68B, SEQ ID NO: 7); *Paenibacillus alginolyticus* (Strain ID: BCP-68C, SEQ ID NO: 8); *Paenibacillus alginolyticus* deposited as NRRL Accession No. B-67811 (Strain ID: BCP-68D, SEQ ID NO:); *Orbilia auricolor/Arthrobotrys oligospora* deposited as NRRL Accession No. 67879 (Strain ID: BCP-93, SEQ ID NO: 10); *Bacillus pumilus* deposited as NRRL Accession No. B-67878 (Strain ID: BCP-89B, SEQ ID NO: 11); and *Lysinibacillus fusiformis* deposited as NRRL Accession No. B-67871 (Strain ID: BCP-91, SEQ ID NO: 12), or an isolated bacterial strain having substantially similar morphological and physiological characteristics, substantially similar genetic characteristics, progeny, mutants, or genetically edited, altered, or modified variants thereof, and combinations thereof, or an isolated bacterial strain having substantially similar morphological and physiological characteristics, substantially similar genetic characteristics, progeny, mutants, or genetically edited, altered, or modified variants thereof; and *Arthrobacter cupressi* deposited as NRRL Accession No. B-67183 (SEQ ID NO: 23); *Arthrobacter cupressi* deposited as NRRL Accession No. B-67184 (SEQ ID NO: 22), *Arthrobacter mysorens* (SEQ ID NO: 24), *Arthrobacter nicotinovorans* deposited as NRRL Accession No. B-67289 (SEQ ID NO: 25), *Arthrobacter pascens* (SEQ ID NO: 26), *Bacillus megaterium* deposited as NRRL Accession No. B-67370 (SEQ ID NO: 27), *Bacillus megaterium* (SEQ ID NO: 28), *Bacillus megaterium* (SEQ ID NO: 29), *Bacillus subtilis* (SEQ ID NO: 30), *Bacillus subtilis* (SEQ ID NO: 31), *Bacillus subtilis* (SEQ ID NO: 32), *Bacillus thuringiensis* (SEQ ID NO: 33), *Bacillus velezensis* deposited as NRRL Accession No. B-50614 (SEQ ID NO: 34), *Brevibacterium frigoritolerans* deposited as NRRL Accession No. B-67360 (SEQ ID NO: 35), *Herbaspirillum chlorophenolicum* deposited as NRRL Accession No. B-67236 (SEQ ID NO: 36), *Herbaspirillum chlorophenolicum* deposited as NRRL Accession No. B-67197 (SEQ ID NO: 37), *Kosakonia radicincitans* deposited as NRRL Accession No. B-67171 (SEQ ID NO: 38), *Kosakonia radicincitans* deposited as NRRL Accession No. B-67946 (SEQ ID NO: 39), *Lysinibacillus fusiformis* (SEQ ID NO: 40), *Massilia kyonggiensis* deposited as NRRL Accession No. B-67198 (SEQ ID NO: 41), *Massilia niastensis* deposited as NRRL Accession No. B-67235 (SEQ ID NO: 43), *Massilia niastensis* deposited as NRRL Accession No. B-67199 (SEQ ID NO: 44), *Massilia niastensis* (SEQ ID NO: 42), *Novosphingobium sediminicola* deposited as NRRL Accession No. B-67945 (SEQ ID NO: 45), *Paenibacillus amylolyticus* (SEQ ID NO: 46), *Paenibacillus glycanilyticus* deposited as NRRL Accession No. B-67204 (SEQ ID NO: 47), *Paenibacillus polymyxa* (SEQ ID NO: 48), *Pseudomonas fluorescens* (SEQ ID NO: 49), *Pseudomonas fluorescens* (SEQ ID NO: 50), *Pseudomonas fluorescens* (SEQ ID NO: 51), *Pseudomonas fluorescens* (SEQ ID NO: 52), *Pseudomonas fluorescens* (SEQ ID NO: 53), *Pseudomonas jinjuensis* deposited as NRRL Accession No. B-67207 (SEQ ID NO: 54), *Pseudomonas oryzihabitans* deposited as NRRL Accession No. B-67225 (SEQ ID NO: 55), *Pseudomonas oryzihabitans* (SEQ ID NO: 56), *Pseudomonas oryzihabitans* (SEQ ID NO: 57), *Pseudomonas oryzihabitans* (SEQ ID NO: 58), *Pseudomonas putida* (SEQ ID NO: 59), *Pseudomonas putida* (SEQ ID NO: 60), *Pseudomonas putida* (SEQ ID NO: 61), *Pseudomonas putida* (SEQ ID NO: 62), *Pseudomonas putida* (SEQ ID NO: 63), *Pseudomonas putida* (SEQ ID NO: 64), *Pseudomonas putida* (SEQ ID NO: 65), *Pseudomonas putida* (SEQ ID NO: 66), *Rahnella aquatilis* (SEQ ID NO: 67), *Tumebacillus permanentifrigoris* deposited as NRRL Accession No. B-67301 (SEQ ID NO: 68), and *Tumebacillus permanentifrigoris* deposited as NRRL Accession No. B-67302 (SEQ ID NO: 69) and combinations thereof, or an isolated bacterial strain having substantially similar morphological and physiological characteristics, substantially similar genetic characteristics, progeny, mutants, or genetically edited, altered, or modified variants thereof; wherein at least one isolated bacterial strain is selected from Group A).

Aspect 32: The microbial consortium of Aspect 32, wherein the microbial consortium comprises *Paenibacillus alginolyticus* deposited as NRRL Accession No. NRRL B-67813 (Strain ID: BCP-68A, SEQ ID NO: 6), *Paenibacillus alginolyticus* (Strain ID: BCP-68B, SEQ ID NO: 7), *Paenibacillus alginolyticus* (Strain ID: BCP-68C, SEQ ID NO: 8), and *Paenibacillus alginolyticus* deposited as NRRL Accession No. B-67811 (Strain ID: BCP-68D, SEQ ID NO: 9).

Aspect 33: The microbial consortium of Aspect 32, wherein the microbial consortium comprises *Bacillus amyloliquefaciens* deposited as NRRL Accession No. B-67947 (Strain ID: BCP-77A, SEQ ID NO: 4) and *Bacillus amyloliquefaciens* deposited as NRRL Accession No. B-67949 (Strain ID: 77-B, SEQ ID NO: 5).

Aspect 34: The microbial consortium of Aspect 32, wherein the microbial consortium comprises *Bacillus pumilus* deposited as NRRL Accession No. B-67878 (Strain ID: BCP-89B, SEQ ID NO: 11) and *Bacillus velezensis* deposited as NRRL Accession No. B-50614 (SEQ ID NO: 34).

Aspect 35: The microbial consortium of Aspect 32, wherein at least one of the isolated bacterial strains is characterized as having substantially similar morphological and physiological characteristics to an isolated bacterial strain selected from group A).

Aspect 36: The microbial consortium of Aspect 32, wherein at least one of the isolated bacterial strains is characterized as having substantially similar genetic characteristics to an isolated bacterial strain selected from group A).

Aspect 37: The microbial consortium of Aspect 32, wherein at least one of the isolated bacterial strains is characterized as a progeny of an isolated bacterial strain selected from group A).

Aspect 38: The microbial consortium of Aspect 32, wherein at least one of the isolated bacterial strains is characterized as a mutant of an isolated bacterial strain selected group A).

Aspect 39: The microbial consortium of Aspect 32, wherein at least one of the isolated bacterial strains is characterized as a genetically edited, altered, or modified variant of an isolated bacterial strain selected from group A).

Aspect 40: A substantially pure culture of the microbial consortium of any one of Aspects 32-39.

Aspect 41: A cell-free of inactivated preparation of the microbial consortium of any one of Aspects 32-39.

Aspect 42: A metabolite produced by the microbial consortium of any one of Aspects 32-39.

Aspect 43: An agricultural composition, comprising: the microbial consortium of any one of Aspects 32-39; and an agriculturally acceptable carrier.

Aspect 44: The agricultural composition of Aspect 43, wherein the microbial consortium is present in the composition at $1\times10^2$ to $1\times10^{12}$ bacterial cells per gram.

Aspect 45: The agricultural composition of Aspect 43 or 44, wherein the agricultural composition is formulated as a seed coating, a foliar spray, a soil drench, a dip treatment, an in furrow treatment, a soil amendment, granules, a broadcast treatment, or a post-harvest disease control treatment.

Aspect 46: A method of imparting at least one beneficial trait upon a plant species, comprising: applying the microbial consortium of any one of Aspects 32-39 to the plant species, or to a growth medium in which the plant species is located.

Aspect 47: A method of imparting at least one beneficial trait upon a plant species, comprising: applying the agricultural composition of any one of Aspects 43-45 to the plant species, or to a growth medium in which the plant species is located.

Aspect 48: A method of imparting at least one beneficial trait upon a plant species, comprising: applying at least one isolated bacterial species to the plant species, or to a growth medium in which the plant species is located; wherein the at least one isolated bacterial species is selected from the group consisting of *Bacillus tequilensis, Bacillus methylotrophicus, Bacillus amyloliquefaciens, Paenibacillus alginolyticus, Orbilia auricolor/Arthrobotrys oligospora, Bacillus pumilus,* and *Lysinibacillus fusiformis*.

Aspect 49: The method of Aspect 48, wherein the at least one isolated bacterial species is a strain selected from the group consisting: *Bacillus velezensis* deposited as NRRL Accession No. B-67810 (Strain ID: BEC-80, SEQ ID NO: 1); *Bacillus methylotrophicus* deposited as NRRL Accession No. B-67812 (Strain ID: BCP-60, SEQ ID NO: 2); *Bacillus amyloliquefaciens* deposited as NRRL Accession No. B-67815 (Strain ID: BCP-69, SEQ ID NO: 3); *Bacillus amyloliquefaciens* deposited as NRRL Accession No. B-67947 (Strain ID: BCP-77A, SEQ ID NO: 4); *Bacillus amyloliquefaciens* deposited as NRRL Accession No. B-67949 (Strain ID: BCP-77B, SEQ ID NO: 5); *Paenibacillus alginolyticus* deposited as NRRL Accession No. B-67813 (Strain ID: BCP-68A, SEQ ID NO: 6); *Paenibacillus alginolyticus* (Strain ID: BCP-68B, SEQ ID NO: 7); *Paenibacillus alginolyticus* (Strain ID: BCP-68C, SEQ ID NO: 8); *Paenibacillus alginolyticus* deposited as NRRL Accession No. B-67811 (Strain ID: BCP-68D, SEQ ID NO:); *Orbilia auricolor/Arthrobotrys oligospora* deposited as NRRL Accession No. 67879 (Strain ID: BCP-93, SEQ ID NO: 10); *Bacillus pumilus* deposited as NRRL Accession No. B-67878 (Strain ID: BCP-89B, SEQ ID NO: 11); and *Lysinibacillus fusiformis* deposited as NRRL Accession No. B-67871 (Strain ID: BCP-91, SEQ ID NO: 12).

Aspect 50: An isolated bacterial strain selected from Table 1, or an isolated bacterial strain having substantially similar morphological and physiological characteristics, substantially similar genetic characteristics, progeny, mutants, or genetically edited, altered, or modified variants thereof.

Aspect 51: The isolated bacterial species of Aspect 50, wherein the isolated bacterial strain has substantially similar morphological and physiological characteristics to a strain selected from Table 1.

Aspect 52: The isolated bacterial species of Aspect 50, wherein the isolated bacterial strain has substantially similar genetic characteristics to a strain selected from Table 1.

Aspect 53: The isolated bacterial strain of Aspect 50, wherein the isolated bacterial strain is a progeny of a strain selected from Table 1.

Aspect 54: The isolated bacterial strain of Aspect 50, wherein the isolated bacterial strain is a mutant of a strain selected from Table 1.

Aspect 55: The isolated bacterial strain of Aspect 50, wherein the isolated bacterial strain is a genetically edited, altered, or modified variant of a strain selected from Table 1.

Aspect 56: An isolated bacterial strain selected from Table 1.

Aspect 57: A substantially pure culture of the isolated bacterial strain of any one of Aspects 50-56.

Aspect 58: A cell-free or inactivated preparation of an isolated bacterial strain according to any one of Aspects 50-56.

Aspect 59: A metabolite produced by an isolated bacterial strain according to any one of Aspects 50-56.

Aspect 60: An agricultural composition, comprising: the isolated bacterial strain of any one of Aspects 50-56; and an agriculturally acceptable carrier.

Aspect 61: The agricultural composition of Aspect 60, wherein the isolated bacterial strain is present in the composition at a concentration of $1 \times 10^2$ to $1 \times 10^{12}$ bacterial cells per gram.

Aspect 62: The agricultural composition of Aspect 60 or 61, wherein the agricultural composition is formulated as a seed coating, a foliar spray, a soil drench, a dip treatment, an in furrow treatment, a soil amendment, granules, a broadcast treatment, or a post-harvest disease control treatment.

Aspect 63: A method of imparting at least one beneficial trait upon a plant species, comprising: applying the isolated bacterial strain of any one of Aspects 50-56 to the plant species, or to a growth medium in which the plant species is located.

Aspect 64: A method of imparting at least one beneficial trait upon a plant species, comprising: applying the agricultural composition of any one of Aspects 60-62 to the plant species, or to a growth medium in which the plant species is located.

While the invention has been particularly shown and described with reference to a preferred embodiment and various alternate embodiments, it will be understood by persons skilled in the relevant art that various changes in form and details can be made therein without departing from the spirit and scope of the invention. For instance, while the particular examples below may illustrate the methods and embodiments described herein using a specific plant, the principles in these examples may be applied to any plant. Therefore, it will be appreciated that the scope of this invention is encompassed by the embodiments recited herein rather than solely by the specific examples that are exemplified below.

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description are by way of example to illustrate the discoveries provided herein. Furthermore, the foregoing Description and Examples are exemplary of the present invention and not limiting thereof. The scope of the invention is therefore set out in the appended claims.

All cited patents and publications referred to in this application are herein incorporated by reference in their entirety, for all purposes, to the same extent as if each were individually and specifically incorporated by reference.

EXAMPLES

The methods and compositions presented herein—based upon utilizing the disclosed isolated microbes, communities, consortia, and/or compositions comprising and/or produced by microbes or consortia or communities—improve one or more characteristics of plants, for example agricultural crops.

Isolation and Identification of Microbes

Microbes of interest are selected, for example from the AMS process as shown in FIGS. 1-4, or according to any method known in the art.

Isolation of microbes may be performed according to any method known in the art. One exemplary, non-limiting example is given below.

Approximately 4 cm sections from a diversity of plant element sections are prepared and placed in a plastic bag with a zipper enclosure. For example, if corn is the plant and roots are the desired tissue, take sections from the (1) primary roots, (2) seminal roots, (3) crown roots, and (4) brace roots to ensure a diversity of tissue for isolations.

Tissue is then sterilized as follows. Wash the tissue to ensure that it is free of soil in a 50 mL falcon tube with 25 mL of sterile reverse osmosis (RO) water by vortexing. This may take multiple washes and use tweezers to clear roots of dirt. Using tweezers, submerge the root tissue in 70% ethanol in a 50 mL falcon tube for 10 seconds. Immediately take the root system out of the ethanol bath, shake off excess liquid, and submerge it in 1.5% NaOCl in a 50 mL falcon tube for 3 minutes. Move the root system to a sterile 50 ml falcon tube and wash with sterile RO water 6 times by submerging plant material in clean, sterile water 6 times.

Extraction of plant tissue-associated microbes may be performed by culturing, subculturing, and selection of the supernatant liquid from the previous step. Alternatively, move the sterilized and washed tissue to a petri dish and using sterile scissors cut fine pieces. Move approximately 500 µL of this tissue to a sterile 2 ml tube and add 100 µL of media and macerate with a sterile utensil such as tweezers or the back end of an L-spreader. These small pieces of root tissue may be added to just poured (warm, not hot) media to embed in the agar. Look for colonies growing out of the 'cut' ends of the plant material. Add 1 ml of 10 mM sterile potassium phosphate buffer pH 7 per 500 µL of tissue. Mix the solution well. Using 50 ul of this solution in 450 µL of phosphate buffer, create 10×, 100×, and 1000× dilutions by serial dilutions. Spread 100-150 µL of this solution on appropriate isolation plates with a sterile L-spreader and incubate.

Isolation of spore-forming bacteria may be performed as follows. Take an aliquot of the undiluted solution from above and pipette in a sterile Eppendorf tube. Seal the tube and heat in 60° C. water bath for 20 minutes to enrich for spore-forming bacteria. Using 50 ul of this solution in 450 µL of phosphate buffer, create 10× 100×, and 1000× dilutions by serial dilutions. Spread 100-150 µL of this solution on appropriate isolation plates with a sterile L-spreader and incubate.

Sequencing preparation for microbe identification, and long-term storage, may be performed by the following method:

Day 1:

Use a 10 µL sterile tip to transfer a colony from a plate to a flask containing an appropriate liquid growth medium". Place the isolates on a shaker at room temperature and incubate for 2 days.

Day 3:

Tubes may be cloudy after being on the shaker for 2 days. All samples will be analyzed by PCR. Vortex each tube, collect a 50 µL sample from each vortexed tube, and dispense in a 96-well plate. Using a multichannel pipette, dispense 15 μL of the 50 μL samples into a new 96-well plate. The 96-well plate containing 35 μL of each sample will be used for phenotyping, and the 96-well plate containing 15 μL of each sample will be used for PCR analysis. 27F/1492R primers are generally used for 16S PCR analysis, as they yield better results than PB36/38. Appropriate negative controls should be included with the plate and analyzed by PCR. The plate will be analyzed by PCR using an Eppendorf thermocycler. Once the PCR is finished, run a gel using standard gel electrophoresis technique. This is important because most isolates are grown enough where they should ideally be put into long-term storage on day 3. The PCR and gel electrophoresis analysis are used to confirm that the isolates contain bacteria, rather than other microbes. For isolates that do not pass PCR or have clear broth, vortex tubes and use a loop to streak out onto a petri plate. Check after several days to see if anything grows, or if the tube is contaminated. For isolates that pass PCR, dispense 600 ul of 50% glycerol into a 2 ml screw cap tubes and add 1200 μL of the bacterial culture, such that the broth is stored in 20% glycerol. Store the glycerol stock at −80° C. and record an image of the gel of the PCR samples.

Day 4 On:

Check the petri plates of the streaked isolates that failed PCR for growth. (During this time, the 2 ml broth tubes will remain on the shaker.) Once there is growth on the plate and the colonies appear to have been successfully isolated, dispense 600 ul of the broth-glycerol mixture in the small tube, and put both tubes in their respective −80 boxes. It is possible for isolates to fail the PCR check because of any of the following reasons: the primers may not work on all bacteria, the isolate is actually a fungus, the isolate is very adherent and therefore does not homogenize in the broth, the isolate produces too much EPS therefore needs dilution prior to PCR set-up, or the isolate is a slow grower. Over the next few days, continue checking the plate to confirm that only a single bacterial species was isolated. If you contamination is observed, prepare a new isolate. Viability of the prepared glycerol stocks should be verified.

Formulation of Microbes

Microbes identified according to the previous examples may be formulated with additional components for application via methods such as, but not be limited to: seed treatment, root wash, seedling soak, foliar application, soil inocula, in-furrow application, sidedress application, soil pre-treatment, wound inoculation, drip tape irrigation, vector-mediation via a pollinator, injection, osmopriming, hydroponics, aquaponics, aeroponics. The formulation comprising the microbes are prepared for agricultural application as a liquid, a solid, or a gas formulation. Application to the plant is achieved, for example, as a powder for surface deposition onto plant leaves, as a spray to the whole plant or selected plant element, as part of a drip to the soil or the roots, or as a coating onto the plant element prior to planting.

Such examples are meant to be illustrative and not limiting to the scope of the invention.

Media components for an exemplary microbe preparation are shown below in Table 3. Add all contents with 50% of the final volume of water needed, and stir the solution at an elevated temperature until dissolved. After all contents have been dissolved, use sterile RO water to bring the solution to the final desired volume. Field trial preparations are typically performed using the 4× formulation.

TABLE 3

Exemplary media components and concentrations for microbe formulation

| | 0.9× (only ME) 1 ml | fill vol. below | 1.1× (only ME) 30 ml | fill vol. below 30 | 2× 1 ml | fill vol. below | 4× 1 ml | fill vol. below 10 |
|---|---|---|---|---|---|---|---|---|
| Xanthan Gum (mg) | 1.8 | 0 | 2.2 | 66 | 4 | 0 | 8 | 80 |
| Trehalose (mg) | 45.3 | 0 | 55 | 1650 | 100 | 0 | 200 | 2000 |
| Isomalt (mg) | 22.65 | 0 | 27.5 | 825 | 50 | 0 | 100 | 1000 |

The procedure to mix TIX formulation is as follows: Measure all dry ingredients into a 50 ml tube. Vortex the ingredients well to ensure xanthan gum is "separated" through the other carbon sources. Add about half of total sterile RO water to the mix, vortex. Use the long end of an L-spreader to break up chunks as much as you can. Heat some sterile RO water in the microwave to warm water bath temperature (45-50° C.). Add the remaining sterile RO water to the mix, vortex. Repeat step 4 and vortex as needed until you have a clear solution with no lumps. Spin down the bubbles created in the process of mixing by using a centrifuge for 5-10 seconds on "fast spin". Remember to have a balance to counter the formulation (TIX) tube. Allow formulation to cool to room temperature. 1. Mix in the microbial consortia. Vortex to ensure homogeneity. It is ideal to add microbes at a concentration of 10^9 CFU/ml to the formulation.

Apply the formulation to the plant or plant element for testing in field trial.

Application of Microbes to Plant Elements and Cultivation Thereof

A microbial composition (comprising one or more isolated microbes of a single strain, a consortium, a community, a combination, or any combination of the preceding) is prepared according to the previous Examples. The microbial composition comprises one or more microbes from Table 1 or Table 1A, optionally in combination with one or more additional microbes disclosed herein.

Microbial Compositions for Application

In some methods, the microbial composition is dried and applied directly to a plant element.

In some methods, the microbial composition is suspended in a liquid formulation for application to a plant element.

In some methods, the microbial composition is combined with an other composition, such as but not limited to: a carrier, a wetting agent, a stabilizer, a salt. In some methods, the other composition comprises a molecule that introduces additional agriculturally-beneficial outcomes to the plant to which the microbial composition is applied. The other composition includes, for example but not limited to: an herbicide, a fungicide, a bactericide, a pesticide, an insecticide, a nematicide, a biostimulant.

Application Types

The microbial composition is applied to a plant element, at a time during development appropriate to the desired outcome, for example: in a formulation of a pre-planting soil drench/in-furrow application; as a seed or other reproductive element treatment; as a post-planting reproductive element application; as an in-furrow, drip, or drench application after planting; as a direct application to a plant element (e.g., root, leaf, stem); as an application to a harvested plant element (e.g., a fruit or a grain). Combinations of application types are also tested.

Application Methods

The microbial composition is applied to (inoculating) a plant or plant element or plant product (pre-planting, post planting, pre-harvest, or post-harvest). This can be accomplished, for example, by applying the agricultural composition to a hopper or spreader or tank, which contains the microbial composition and which is configured to broadcast the same.

A seed coating of the microbial composition is applied to one or more seeds of a crop plant. Upon applying the isolated microbe as a seed coating, the seed is planted and cultivated according to practices established for that crop.

Alternatively, the microbial composition is applied to the soil for the benefit of a plant existing in that soil. Methods of soil application include in-furrow treatment, drench, and drip applications.

Alternatively, the microbial composition is applied to the surface of a plant or plant part after germination.

Alternatively, the microbial composition is applied to material obtained from the plant after harvest.

A control plot of plants, which did not have the isolated microbe applied, are also planted. Plants associated with the microbial composition exhibit improved characteristics of interest.

Application methods may be performed according to any protocol known in the art.

Plant elements, plants, or growth medium (e.g., soil) may further be inoculated with a disease or pest, according to the purpose of the test.

An exemplary, non-limiting protocol for drenching tomato plants is given below:

1. Ten days after planting carefully separate plants out into 6 reps for each treatment. Plants are delicate and leaves can tear easily. Ensure that the size and overall appearance of plants is as uniform as possible (The purpose of thinning is continuing with an homogenous plant population). Transplant if there are not enough plants per reps. See step 3 for guidelines on transplanting.
2. Begin thinning pots down to one plant per pot. Remove the smaller plant, one that is unhealthy or deformed in some way. If there are 2 or more healthy plants per pot, the extras can be transplanted into another pot. Use leftover soil prepped from initial planting or from pots where seeds did not germinate.
3. To transplant: If some pots didn't germinate, they can be filled with a plant from another container. To do this simply scoop out the extra plant (trying to scoop out as much root mass as possible without disturbing the other plant) with a scoopula and place into a hole made in the empty pot. Firm the soil around the plant with slight finger pressure.
4. Space out the pots into 6 pot lines (1 line of pots per treatment), will take 4 RL98 trays. Once done, have a look at all the treatments and consider making some pot switches to ensure some treatments don't have all large plants and others have all large plants.
5. Change gloves if necessary. Label each pot with your pre-prepared Avery Labels. Treatments should be labeled into rows of 6 replicates i.e., 1-1, 1-2, 1-3 to 1-6, etc. Makes it easier to find all replicates for each treatment
6. Two weeks after planting (roughly 4 days after thinning and labeling), obtain treatments from the Microbiology team; set on the table with trays of prepped plants. Gather combitips, repeater, and RO water. (note: Plants should be watered lightly the day of treatment)
7. Mix microbial solution by inverting tube/container (microbial treatment) 2-3 times or give a light shake. Set combitip to dispense 2 ml. Collect treatment fluid into combitip, dispense first step back into the tube. Ensure the treatment you have corresponds to the row of plants to be treated. Once confirmed, gently dispense 2 ml of treatment onto the surface soil of each pot, close to the stem but avoid direct contact with the stem and leaves.
8. Dispose of combitip and repeat step 6 for all treatments. For the inoculated control (IC or InoCon) and untreated control (UTC), apply RO water in place of a treatment. Once all treatments have been applied, place plants back into growth chamber for (optional inoculation), growth, evaluation.

Visualization of Microbes Associated with Plant Elements

Individual microbes can be tagged with a fluorescent protein according to methods known in the art. Microscopic image analysis demonstrated that the microbes disclosed herein were found associated with various plant tissues, as demonstrated, for example, in FIGS. 5, 10, 14, 15, 16, and 17.

Improvement of Crop Yield During Normal and Stressed Conditions

Plant/crop yield increases are realized without the need for addition of chemical fertilizer, in some aspects by virtue of association of a plant with one or more microbes disclosed herein. In some aspects, the microbe acts as a "biostimulant", that is, an agent that promotes the health, growth, vigor, and/or production ("yield") of the plant.

In some aspects, "yield" can be determined by, for example but not limited to: the biomass of one or more crop products, seed size, seed weight, leaf composition, fiber production.

In some aspects, the yield increase is statistically significant. In other aspects, the biomass increase is not statistically significant, but is still quantifiable and relevant for crop improvement. Other parameters relating to yield may be improved by the addition of the microbes disclosed herein, for example but not limited to: plant vigor, NDVI score, photosynthetic capability, nutrient utilization, stress tolerance. In some cases, the microbe stimulates plant health, which may further improve crop yield. Yield parity under microbial and control conditions is one desirable outcome, when other parameters are improved.

Improvements of plant health or yield can be under relatively stress-free conditions. In other cases, improvement can be in plants grown under any number of abiotic or biotic stresses, including drought stress, salt stress, heat stress, cold stress, low nutrient stress, nematode stress, insect herbivory stress, fungal pathogen stress, complex pathogen stress, or viral pathogen stress.

It is expected that the plants grown from the seeds treated with the agricultural composition will exhibit a quantifiably higher yield and/or plants with improved health and/or plants with improved stress tolerance than the control plants.

The yield from the treated plants is about 1-10% higher, 10-20% higher, 20-30% higher, 30-40% higher, 40-50% higher, 50-60% higher, 60-70% higher, 70-80% higher, 80-90% higher, or more. The biomass from the treated plants equates to about a 1 bushel per acre increase over the controls, or a 2 bushel per acre increase, or a 3 bushel per acre increase, or a 4 bushel per acre increase, or a 5 bushel per acre increase, or more. In some cases, yield improves under normal or typical conditions with no biotic or abiotic stressor(s). In some cases, yield is normal under conditions of biotic and/or abiotic stress. In some cases, yield increases under conditions of biotic and/or abiotic stress.

The microbes described herein improve the health and/or yield of various crop plants, including those described below. Yield of a particular harvested material and/or plant health is improved under normal conditions, as well as under conditions of abiotic stress (e.g., drought, application of herbicide, application of pesticide, reduction or elimination of applied nutrients such as Nitrogen, Phosphorous, Potassium), or biotic stress (e.g., presence of insects, larvae, nematodes, fungal diseases, bacterial diseases, viral diseases).

Figure 18B:
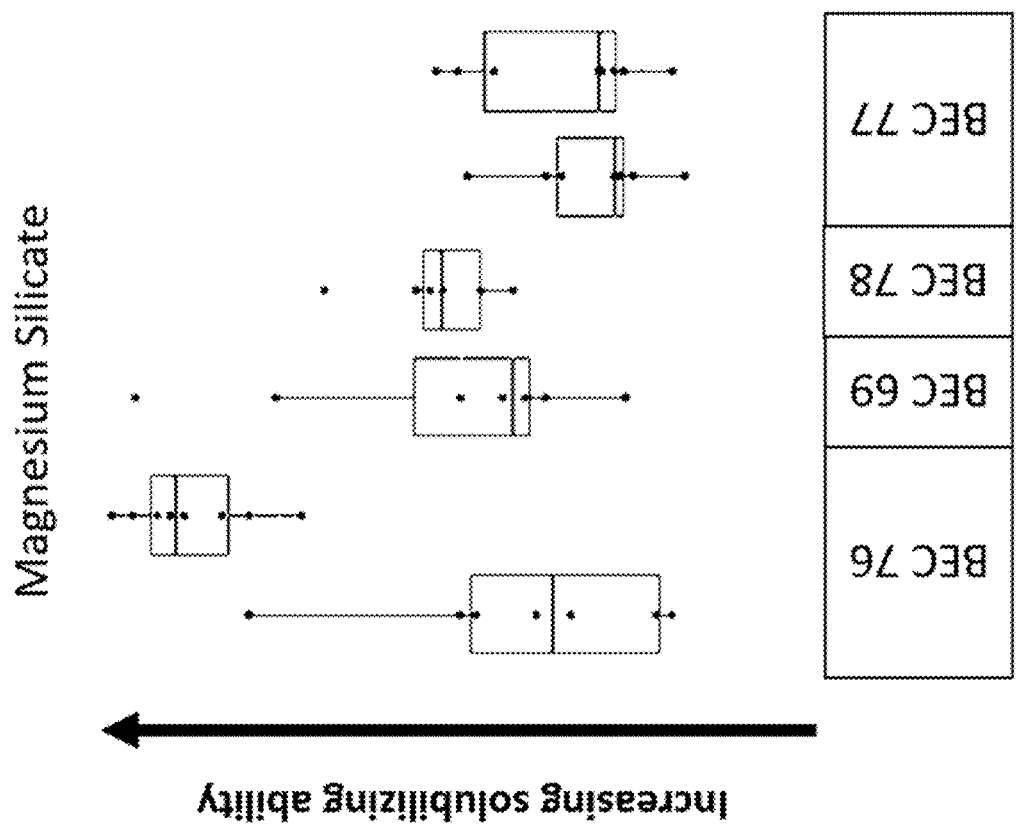
FIG. 18B shows improved magnesium silicate solubilizing activities for some of the biostimulant microbes disclosed herein.
Figure 18A:
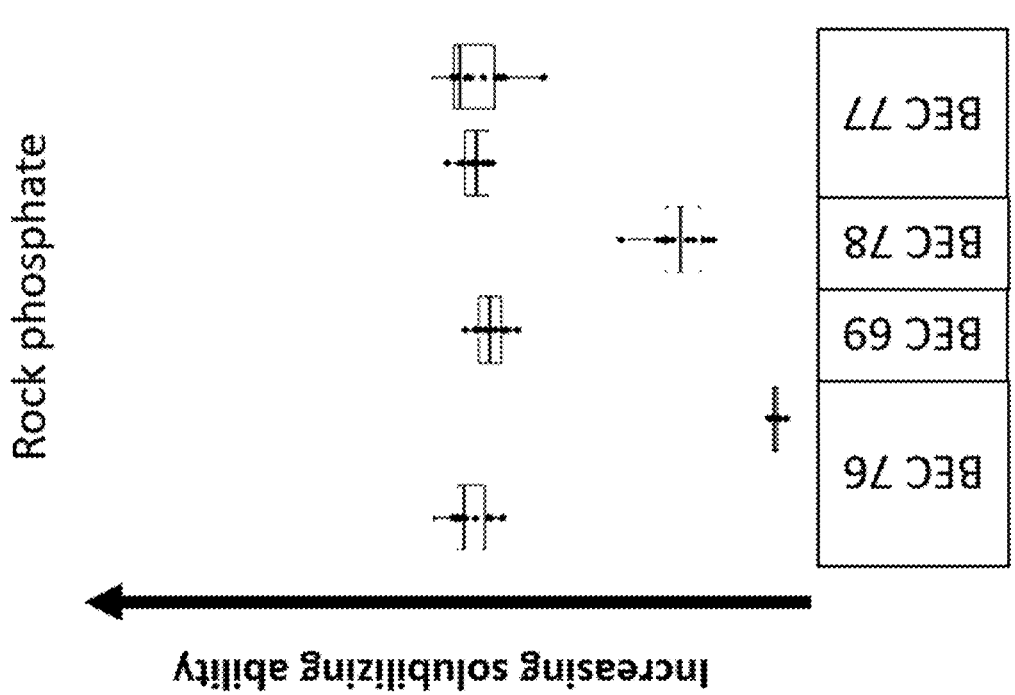
FIG. 18A shows improved rock phosphate solubilizing activities for some of the biostimulant microbes disclosed herein.

FIGS. 18A and 18B show improved rock phosophate and magnesium silicate solubilizing activities (respectively) for some of the biostimulant microbes disclosed herein.

Microbes that impart improved yield, biomass, and/or biostimulant activity to crop plants include those represented by: SEQ ID NOs: 3-9 and 14-21.

*Bacillus amyloliquefaciens* BEC69

When added to a crop plant, *B. amyloliquefaciens* improved crop yield across several different species of plant. Phylogenetic analysis of whole genome sequences reveals BEC69 as distinct from other *B. amyloliquefaciens* microbes, including commercial products on the market. BEC69 improves nutrient availability (Phytase, Iron scavenging, Cellulase, chitinase, Nitrate assimilation and Ammonia release, chitinase) as shown in Table 4a, and improves rhizosphere competence with biofilm capabilities, when applied at a rate of 2-4 quarts/acre as a suspension concentrate. Microbial genotype analyses of other strains can be performed using similar methods.

TABLE 4a

Microbial genotype analysis of BEC69

| Area of interest | BEC 69 |
| --- | --- |
| ACC Deaminase | − |
| Exopolysaccharides | + |
| Volatiles | − |
| Exoenzymes | + |
| Chitinase | + |
| Siderophores | + |
| Nitrate transport | + |
| Nitrogen fixation | − |
| Phosphate sol. | − |
| Motility | + |
| Chemotaxis | − |
| Reistance to Surfactin | − |
| Suraface adhesion | − |
| Biofilm | + |

Figure 13:
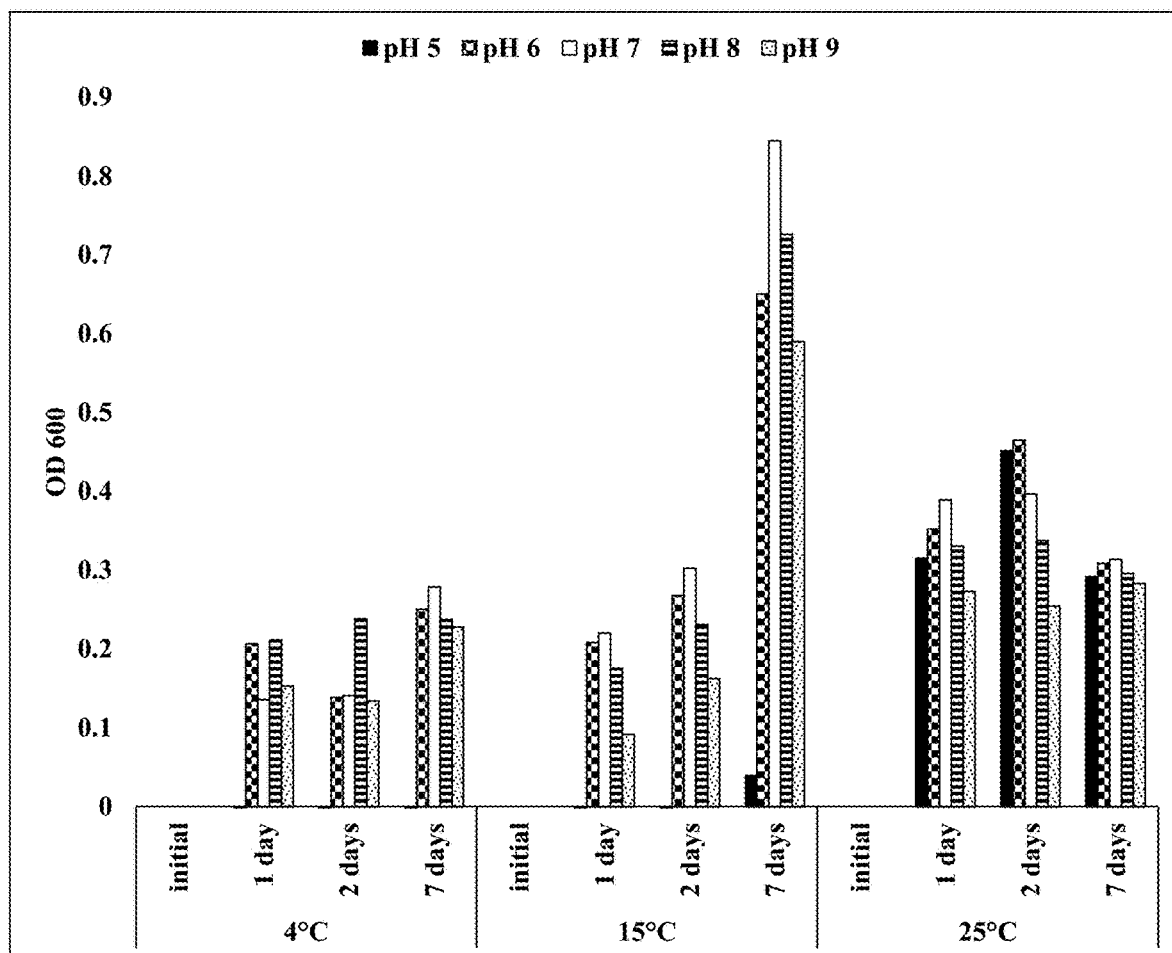
FIG. 13 shows growth of *B. amyloliquefaciens* BEC69 across a broad range of temperatures and pH conditions.
Figure 14:
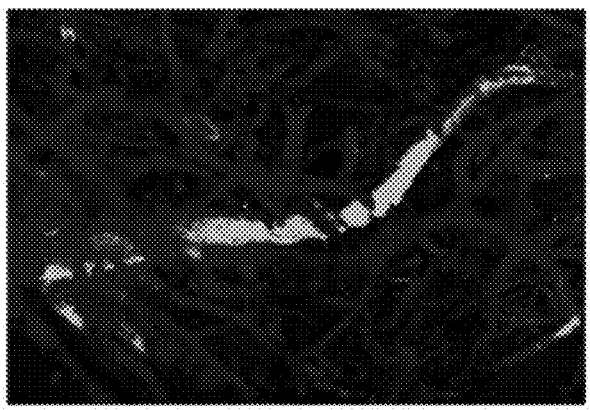
FIG. 14 shows plant element colonization of *B. amyloliquefaciens* BEC69 in tomato, soy, wheat, and corn (fluorescent-tagged microbes).
Figure 14:
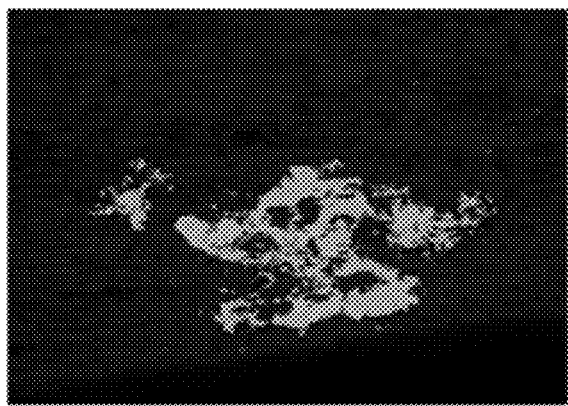
Figure 14:
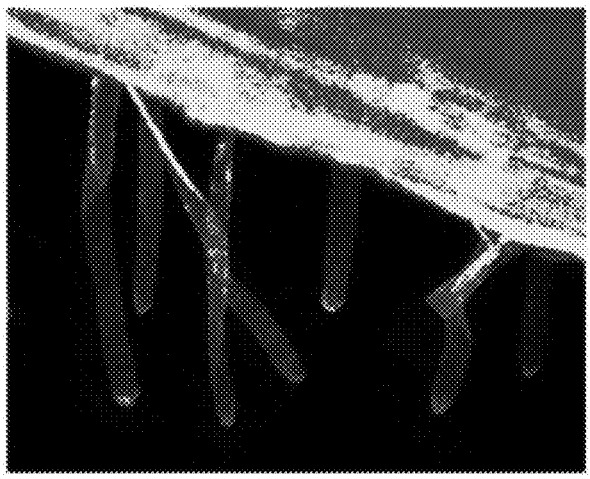
Figure 14:

*B. amyloliquefaciens* BEC69 grows robustly across a broad range of temperatures and pH conditions (FIG. 13). Plant element colonization was confirmed in tomato, soy, wheat, and corn with microscopic detection of fluorescent-tagged proteins (FIG. 14).

In greenhouse trials, BEC69 promoted increases in soybean and sorghum shoot biomass. When analyzing the NDVI (Normalized Difference Vegetation Index—an agricultural standard for measuring the health and vigor of crops) for various crops, BEC69 provided a positive impact for 46% of all row crop evaluations; BEC69 improved NUE ratings 63% of the time for all row crop Nitrogen Use Efficiency evaluations; BEC69 improved the NDVI rating of wheat in 100% of the trials.

Greenhouse evaluations also showed that seed treatment with BEC69 increased NDVI and greenness, two indices associated with plant health in 100% of evaluations on wheat grown under nitrogen limitation. A 10% increase in leaf area was seen in 75% of evaluations on corn and sorghum across diverse assays.

Tomato field trials were conducted in multiple locations using standard agronomic practice. BEC69 was applied as a drench up to 3 times during the course of tomato field trial. Final yield was collected at the end at the typical time of harvest. There was little to no disease pressure for any of these trials. BEC69 provided a 16% harvested yield increase over the control across multiple trial locations and years.

Fruit and vegetable field trials were conducted using standard agronomic practice. BEC69 was applied as a drench up to 3 times during fruit and vegetable field trials (broccoli, cucumber, snap beans, pepper, potato). Final yield was collected at the end at the typical time of harvest. BEC69 performed superior or similar to a commercially-available biostimulant in fruit and vegetable biostimulant field trials.

A summary of BEC69 results in some vegetable crops is given in Table 4b.

TABLE 4b

BEC69 improves yield in vegetable crops

| Pepper | Potato | Snap beans | Tomato | Zucchini | Total |
| --- | --- | --- | --- | --- | --- |
| 11% | −4% | 11% | 5% | 4% | 6% |

Soybean field trials at high-yielding locations across the US Midwest using standard agronomic practice. BEC69 was applied as a seed treatment on top of existing seed chemistry for soybean. Final yield was collected at the end at the typical time of harvest. BEC69 provided a 2.64 bu/ac yield increase over the control across multiple trial locations and years.

Spring wheat microplot field trials were planted in two locations using standard agronomic practices. BEC69 was applied as a seed treatment on top of existing seed chemistry for wheat. Final yield was collected at the end at the typical time of harvest. BEC69 provided an average of 3.1% bu/ac yield increase over the control across multiple microplot trials. Winter wheat trials showed a similar biostimulant effect.

A summary of some of the Greenhouse and Field Trial results for BEC69 is given in Tables 5a (fruit and vegetable) and 5b (row crops).

TABLE 5a

Presence (+) or non-detection (nd) of biostimulant activity of *B. amyloliquefaciens* BEC69 in in planta studies for selected fruit and vegetable crops

| Greenhouse | | | | Field trial | | | | | |
|---|---|---|---|---|---|---|---|---|---|
| Tomato | Lettuce | Pea | Pepper | Tomato | Lettuce | Snap beans | Pepper | Potato | Broccoli |
| + | + | + | nd | + | + | + | + | nd | + |

TABLE 5b

Presence (+) or non-detection (nd) of biostimulant activity of *B. amyloliquefaciens* BEC69 in in planta studies for selected row crops

| Greenhouse | | | | | | Field trial | | |
|---|---|---|---|---|---|---|---|---|
| Canola | Corn | Cotton | Sorghum | Soy | wheat | Corn | Soy | wheat |
| nd | nd | + | nd | nd | + | nd | + | + |

*Bacillus tequilensis* BEC78

When added to a crop plant, *B. tequilensis* improved crop yield across several different species of plant.

A summary of BEC78 results in some vegetable crops is given in Table 6.

TABLE 6

BEC78 improves yield in vegetable crops

| Pepper | Potato | Snap beans | Tomato | Zucchini | Total |
|---|---|---|---|---|---|
| 16% | −4% | 15% | 3% | −12% | 1% |

*Bacillus amyloliquefaciens* BEC69+*Bacillus tequilensis* BEC78

Stacking microbes can produce synergistic or other positive effects, apart from what any one or more of the components contributes individually. When added to a crop plant, the combination of microbes *Bacillus amyloliquefaciens* BEC69+*Bacillus tequilensis* BEC78 improved crop yield across several different species of plant.

Figure 17:
FIG. 17 shows that BEC68 and BEC78 co-colonize plant roots (fluorescent-tagged microbes).

Fluroescent-tagged microbes show that BEC68 and BEC78 co-colonize plant roots (FIG. 17).

The seed treatment of the BEC69+BEC78 combination provided equal or improved performance as compared to seed treatment with each of the individual strains alone, as shown in Table 7 for 12 different soybean field trials on soybeans on top of one commercially-available seed treatment.

TABLE 7

Synergistic effects of BEC69 + BEC78 in soybean field trials

| Trial # | Increase (bu/ac) over BEC69 single | Increase (bu/ac) over BEC78 single | Stack performance vs singles |
|---|---|---|---|
| 1 | 1.9 | 3.4 | improved |
| 2 | 1.8 | 3.5 | improved |
| 3 | 0.8 | 4.5 | improved |
| 4 | −1.1 | −0.4 | equal |
| 5 | −7.5 | −2.2 | poor |
| 6 | 3.4 | 3.9 | improved |
| 7 | 2.2 | 0.9 | improved |
| 8 | 2.6 | −0.2 | improved |
| 9 | −1.2 | 1.3 | equal |
| 10 | 0.6 | −0.8 | equal |
| 11 | 0.6 | −1.5 | equal |
| 12 | −1.4 | 1.3 | equal |

On another soybean variety with a different commercially-available seed treatment, individual microbes did not statistically raise final yield (in some cases may have had a marginal drag); however, the stack of BEC69+BEC78 outperformed either of the single microbe treatments, with an average positive yield change vs untreated. This trend of providing a yield increase was also seen at sites with average lower yields.

A summary of the stacked combination results in some vegetable crops is given in Table 8.

TABLE 8

BEC69 + BEC78 improves yield in vegetable crops

| Pepper | Potato | Snap beans | Tomato | Zucchini | Total |
|---|---|---|---|---|---|
| 12% | −3% | 26% | 8% | 9% | 9% |

*Bacillus amyloliquefaciens* BEC77

When added to a crop plant, *B. amyloliquefaciens* improved crop yield across several different species of plant. Two different strains of *B. amyloliquefaciens*, represented by SEQ ID NOs. 4 and 5, comprise BEC77. Phylogenetic analysis of whole genome sequences reveals BEC77 as comprising strains distinct from other *B. amyloliquefaciens* microbes, including commercial products on the market.

Increased yield was observed in 5 out of 6 tomato field trials across multiple years, and increased yield observed in numerous fruit and vegetable and row crop field trials, when applied at a rate of 2-4 quarts/acre as a seed treatment of suspension concentrate.

Microbe phenotyping revealed solubilization of Phosphate and Zinc.

Figure 16:
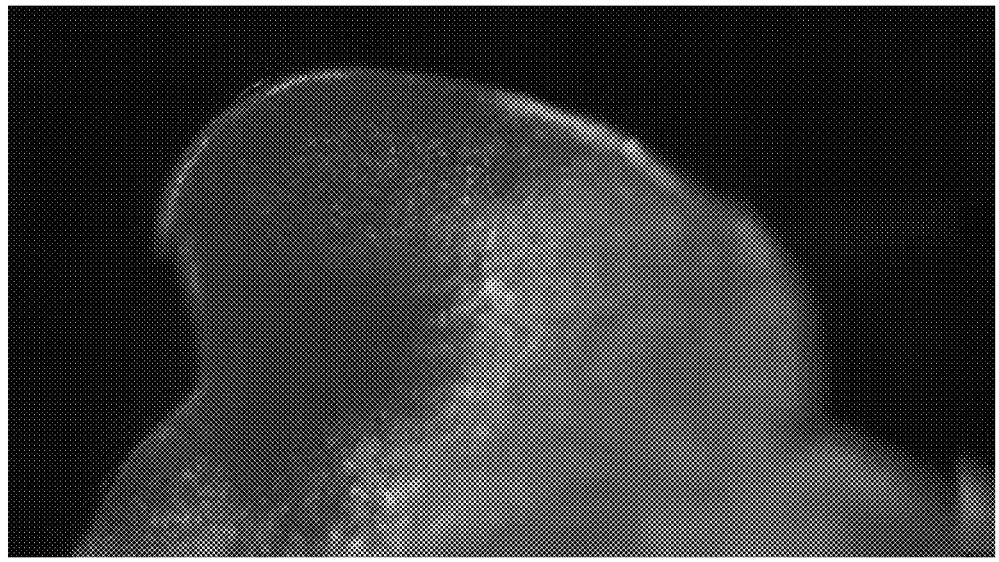
FIG. 16 shows that BEC77 colonizes in above ground and below ground plant surfaces (cauliflower phyllosphere and cauliflower rhizosphere) (fluorescent-tagged microbes).
Figure 16:
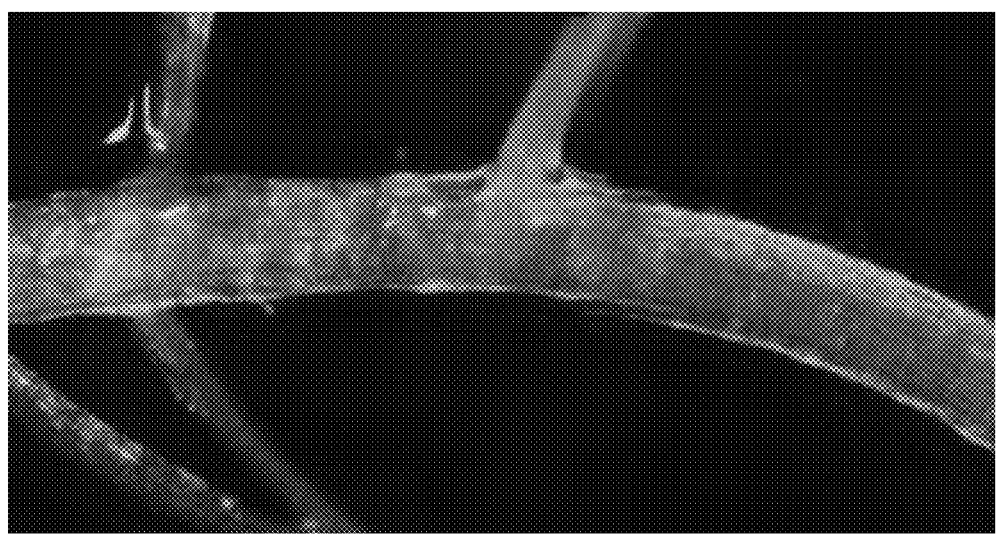

As shown in FIG. 16, fluorescent-tagged BEC77 showed colonization in both above ground and below ground plant surfaces (cauliflower phyllosphere and cauliflower rhizosphere).

Tomato field trials were conducted in multiple locations using standard agronomic practice. BEC77 was applied as a drench up to 3 times during the course of the field trial. Final yield was determined at the end at the typical time of harvest. There was little to no disease pressure for any of these trials. BEC77 provided a 12.5% harvested yield increase over the control across multiple trial locations and years.

Yield increases of water control were seen in field trials of cucumber, potato, and tomato.

Yield increases of around 1 bushel/acre were seen in wheat microplot trials.

A summary of some of the Greenhouse and Field Trial results for BEC77 is given in Tables 9a (fruit and vegetable) and 9b (row crops):

TABLE 9a

Presence (+) or non-detection (nd)
of biostimulant activity of *B. amyloliquefaciens*
BEC77 in in planta studies for selected fruit and vegetable crops

| Greenhouse | | | | Field trial | | | |
|---|---|---|---|---|---|---|---|
| Tomato | Lettuce | Pea | Pepper | Tomato | Lettuce | Snap beans | Potato |
| + | + | + | + | + | + | nd | + |

TABLE 9b

Presence (+) or non-detection (nd) of biostimulant activity
of *B. amyloliquefaciens* BEC77 in
in planta studies for selected row crops

| Greenhouse | | | | | | Field trial |
|---|---|---|---|---|---|---|
| Canola | Corn | Cotton | Sorghum | Soy | wheat | wheat |
| + | nd | + | nd | + | nd | + |

A summary of BEC77 results in some vegetable crops is given in Table 10.

TABLE 10

BEC77 improves yield in vegetable crops

| Pepper | Potato | Snap beans | Tomato | Zucchini | Total |
|---|---|---|---|---|---|
| 18% | −5% | 42% | 4% | 2% | 7% |

*Paenibacillus alginolyticus* BEC68

When added to a crop plant, *P. alginolyticus* improved crop yield across several different species of plant. Four different endospore-forming strains isolated from tomato plants of *P. alginolyticus*, represented by SEQ ID NOs. 6-9, comprise BEC68. Strong PGP was shown in greenhouse evaluation on Corn, Sorghum, Wheat and yield enhancements observed in Corn field trials. Microbe phenotyping revealed the production of indole-3-acetic acid (IAA) and ACC deaminase.

Figure 15:
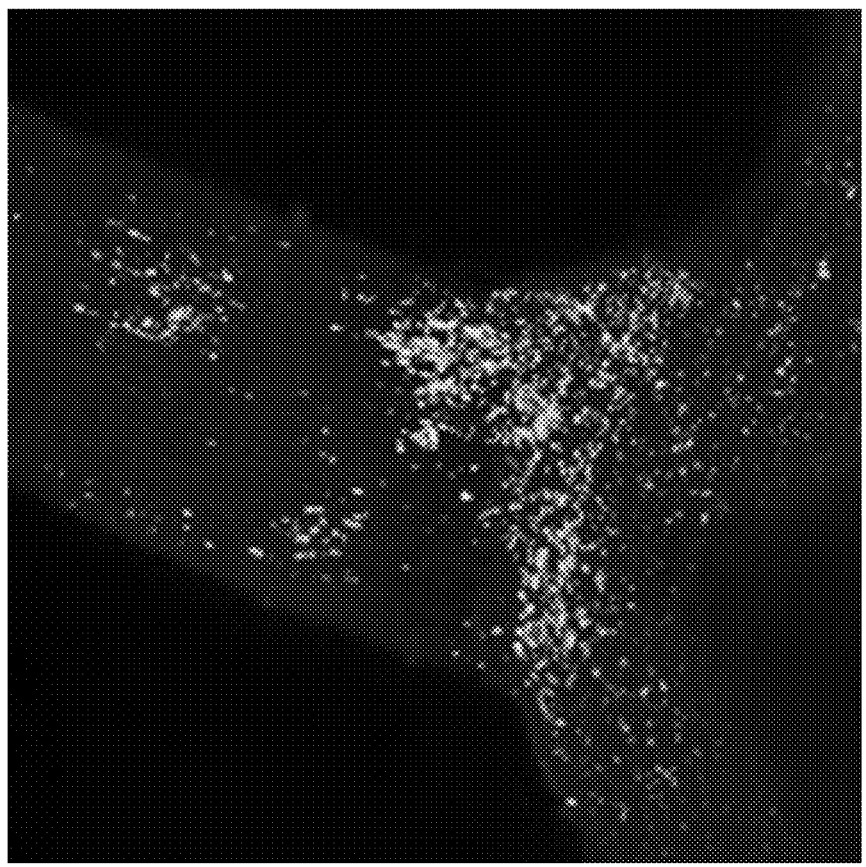
FIG. 15 shows plant element colonization of *Paenibacillus alginolyticus* BEC68 in corn rhizosphere tissue (fluorescent-tagged microbes).

As shown in FIG. 15, fluorescent-tagged BEC68 microbes colonized the corn rhizosphere.

Table 11 shows the genomic profile and in vitro characteristics of BEC68.

TABLE 11

Microbial genotype analysis of BEC68

| | Genomic profile | | | | in vitro microbe phenotype | | | | | | | | |
|---|---|---|---|---|---|---|---|---|---|---|---|---|---|
| | Root colonization | Cold tolerance | Heat tolerance | Nutirent acquisition | IAA | P | Zn | Iron | Chitin | IAA | Urease | Temp assessment | pH assessment |
| BEC68A | +++ | +++ | ++ | ++ | ++ | | ++ | | ++ | ++ | + | mild/warm | broad |
| BEC68B | +++ | +++ | ++ | ++ | ++ | + | | | | ++ | | warm | broad |
| BEC68C | +++ | +++ | ++ | ++ | ++ | ++ | + | + | | ++ | + | mild/warm | broad |
| BEC68D | ++ | +++ | + | +++ | + | | ++ | | ++ | ++ | + | mild/warm | broad |

In greenhouse evaluations, seed treatment with BEC68 resulted in an 11% increase in shoot biomass and 12% increase of leaf area and evidence of increased chlorophyll content in 70% of evaluations across three crops and assay types.

High yielding locations were chosen for corn field trials in non-acidic soil types using standard agronomic practices. BEC68 was applied as a seed treatment over existing chemistry. Final yield was collected at the end at the typical time of harvest. BEC68 provided a 10.6 bushel/acre increase over the control (85% consistency) across multiple trial locations in soils with a pH above 6.1.

High yielding locations were chosen for corn field trials (all soil types) using standard agronomic practices. BEC68 was applied as a seed treatment over existing chemistry. Final yield was collected at the end at the typical time of harvest. BEC68 provided a 3.6 bushel/acre increase over the control (70% consistency) across all soil types.

Additional corn field trials were conducted in the Midwest region of the United States in 2018. Tables 12a and 12b shows that all locations showed an average improvement for yield as measured in bushels/acre.

TABLE 12a

Summary of 2018 corn field trials
(10 locations, 20 trials)

| Yield Level bu/ac | Number of trials | Yield increase bu/ac | Win rate |
|---|---|---|---|
| Low ≤180 bu/ac | 5 | 4.3 | 60% |
| Medium 181-220 bu/ac | 3 | 4.7 | 100% |
| High >220 bu/ac | 12 | 2.9 | 58% |
| All trials | 20 | 3.5 | 65% | p = 0.09

TABLE 12b

Summary of 2019 corn field trials
(50 locations, 70 trials planted, 58 harvested)

| Yield Level bu/ac | Number of trials | Yield increase bu/ac | Win rate |
|---|---|---|---|
| Low ≤180 bu/ac | 14 | 2.49 | 71% |
| Medium 181-220 bu/ac | 25 | 4.02 | 72% |
| High >220 bu/ac | 19 | 1.06 | 63% |
| All trials | 58 | 2.39 | 69% | p = 0.01 (41 trials), p = 0.09 (17 trials)

Wheat field trials across 20 trials in 10 locations over 2 years demonstrated an average yield gain of 1.3 to over 3.0 bushels/acre, for wheat plants that were treated with BEC68.

*Talaromyces pinophilus* BEC101

When added to a crop plant, T *pinophilus* improved crop yield and nitrogen use efficiency in wheat. BEC101 is a robust fungal strain producing high amounts of spores during growth. BEC101 is an aggressive root colonizer (in addition to other plant tissues) on multiple wheat, cotton, and sorghum plants, with broad capabilities in nitrogen use and conversion (ACC, urea, nitrate, ammonium), phosphate solubilization, and PGP. Phosphate solubilization for BEC101 was nearly 400 mg/L for BEC101, as compared to less than 100 for *Penicillium* sp., *Trichoderma* sp., and a commercially-available biostimulant.

Nitrogen utilization and conversion profiles for BEC101 are shown in Table 13.

TABLE 13

NUE and conversion profile for BEC101

| Ammonium | Urea | ACC* | Plant-based protein |
|---|---|---|---|
| + | − | ++ | +++ |

*reduction in ethylene linked to increased root biomass

Across 20 different spring wheat field trials, BEC101 provided average yield gain of 1.6 bu/acre under optimal and reduced nitrogen fertilization conditions.

*Microbacterium arabinogalactanolyticum* BEC102

When added to a crop plant, M *arabinogalactanolyticum* improved crop yield and nitrogen use efficiency in wheat. BEC102 is a single Gram positive bacterial strain for use in wheat seed treatments, demonstrating broad activities in nitrogen use/conversion and PGP. Field trials were run using standard seed treatment chemistry.

Nitrogen utilization and conversion profiles for BEC102 are shown in Table 14.

TABLE 14

NUE and conversion profile for BEC102

| Ammonium | Urea | Nitrates | Plant amino acids |
|---|---|---|---|
| +++ | + | + | ++ |

As shown in Table 15, BEC102 improved plant growth promotion properties.

TABLE 15

NUE and conversion profile for BEC102

| Phosphate solubilization | Zinc solubilization | IAA production | Acetoin synthesis genes |
|---|---|---|---|
| + | +++ | ++ | + |

Figure 19:
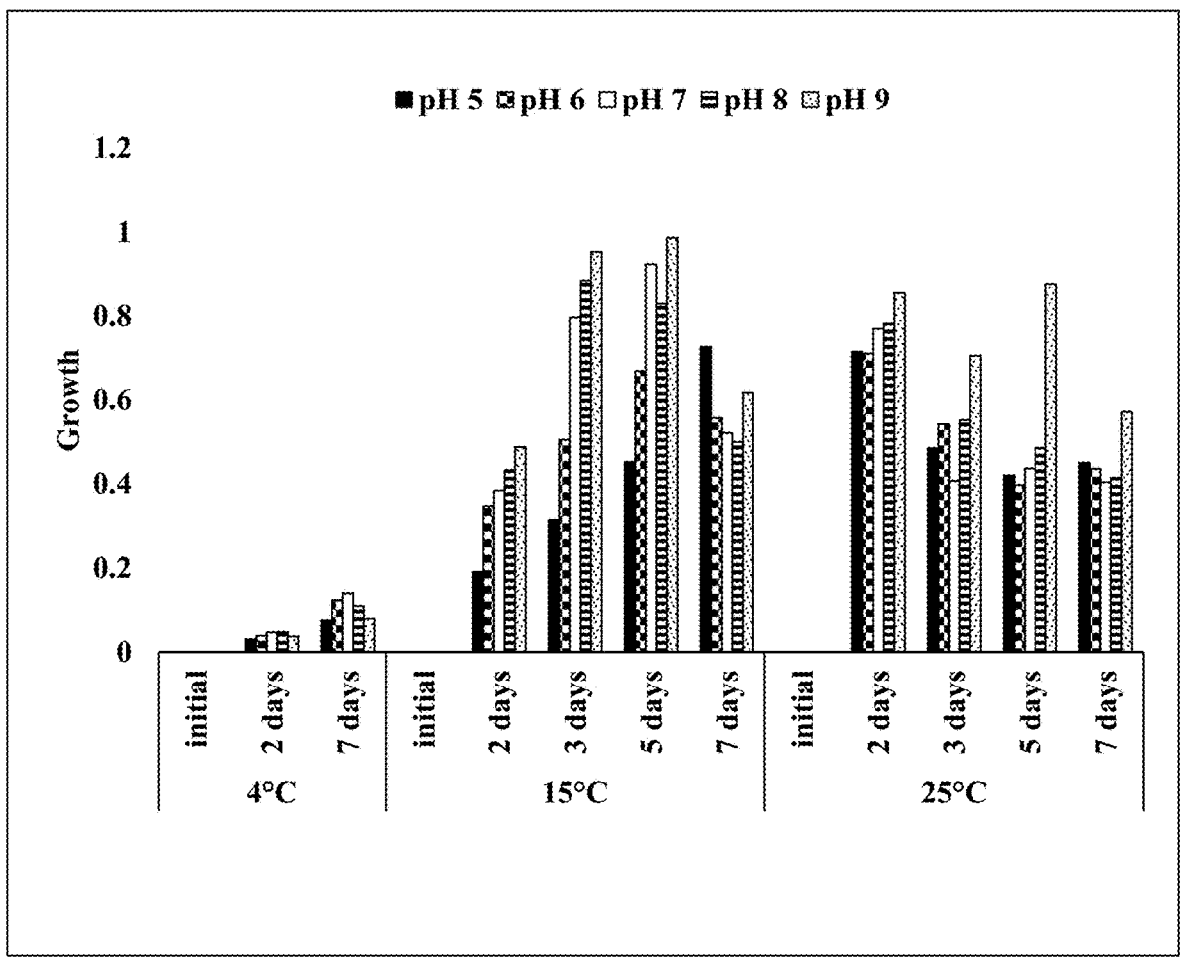
FIG. 19 shows the growth of *Microbacterium arabinogalactanolyticum* BEC102 across a broad range of temperatures and pH conditions.

BEC102 also had a robust growth profile across a wide rage of pH and temperatures (FIG. 19).

Across 20 different spring wheat field trials, BEC102 provided average yield gain of 2.2 bu/acre under optimal and reduced nitrogen fertilization conditions.

*Bacillus megaterium* BEC71

When added to a crop plant, B. *megaterium* improved crop yield in corn. BEC71 is a root colonizer with positive impacts for ACC, organic phosphorous, and siderophore.

Corn field trials with seeds treated with BEC71 demonstrated an average grain yield increase of +3.1 bushel/acre.

A summary of BEC71 results in some vegetable crops is given in Table 16.

TABLE 16

BEC71 improves yield in vegetable crops

| Pepper | Potato | Snap beans | Tomato | Zucchini | Total |
|---|---|---|---|---|---|
| 14% | 1% | 25% | 4% | 7% | 7% |

*Paenibacillus taichungensis* BEC110

When added to a crop plant, *P. taichungensis* improved crop yield across several different species of plant.

A summary of BEC110 results in some vegetable crops is given in Table 17.

TABLE 17

BEC110 improves yield in vegetable crops

| Pepper | Potato | Snap beans | Tomato | Zucchini | Total |
|---|---|---|---|---|---|
| 11% | −8% | 44% | 7% | −3% | 5% |

*Paenibacillus ehimensis* BEC120

When added to a crop plant, *P. ehimensis* improved crop yield across several different species of plant.

A summary of BEC120 results in some vegetable crops is given in Table 18.

TABLE 18

BEC120 improves yield in vegetable crops

| Pepper | Potato | Snap beans | Tomato | Zucchini | Total |
|---|---|---|---|---|---|
| 6% | −4% | −14% | 1% | 12% | 6% |

*Paenibacillus illinoisensis* BEC108

When added to a crop plant, *P. illinoisensis* improved crop yield across several different species of plant.

A summary of BEC108 results in some vegetable crops is given in Table 19.

TABLE 19

BEC108 improves yield in vegetable crops

| Pepper | Potato | Snap beans | Tomato | Zucchini | Total |
|---|---|---|---|---|---|
| 15% | −4% | 14% | 3% | −5% | 3% |

Improvement of Crop Pest Resistance

The microbes described herein benefitted crop plants via application methods such as, but not limited to: seed treatment, drench, as well as other application methods; those plants were compared to control plants not associated with the microbes. A wide variety of crops (tomato, carrot, cotton, cucumber, strawberry, corn, soybean, wheat, peanut, potato) were planted and cultivated according to standard agronomic practices. Exemplary conditions and microbe application rates are described above. Percent yield and pest reduction measurements were recorded, under conditions in growth chamber, greenhouse, and field trials. Improvements were seen with the microbes described below, at levels comparable or better than a comparator commercial bionematicide in greenhouse trials.

Pests included: Root Knot Nematode (RKN), Soybean Cyst Nematode (SCN), Root Lesion Nematode (RLN), Stubby Root Nematode (SRN), Sting Nematode (SN), Cereal Cyst Nematode (CCN).

Six maize field trials were conducted using seeds treated with microbes prior to planting. Four trials comprised SRN as the most abundant nematode, and two trials comprised RKN as the most abundant nematode. Five trials had high pest pressure (counts between 200-800) and one trial had low pest pressure (counts <200).

Ten soybean field trials were conducted using seeds treated with microbes prior to planting. Nine trials comprised SCN as the most abundant nematode, and one trial comprised RKN as the most abundant nematode. Five trials had high pest pressure (counts between 200-800600-16000) and one trial had low pest pressure (counts <80). Three trials with zero final nematode counts were removed from analysis.

Some tomato field trials were conducted using soil drench of microbes onto the plants with treatment at transplant, one, and two weeks after transplant, at an application rate of 4-8 quarts per acre. Other tomato field trials were conducted using soil drench of microbes at transplant, one, and two weeks after transplant, at an application rate of 4 and 8 quarts per acre.

Carrot field trials were conducted using soil drench of microbes with treatment at transplant, one, and two weeks after transplant, at an application rate of 4 quarts per acre.

Cotton field trials were conducted using in-furrow microbial treatments as well as at planting and Day 14 post-planting, at an application rate of 6-8 quarts/acre. Nematode pressures included natural infestation of primarily SRN and low levels of RKN.

Figure 12A:
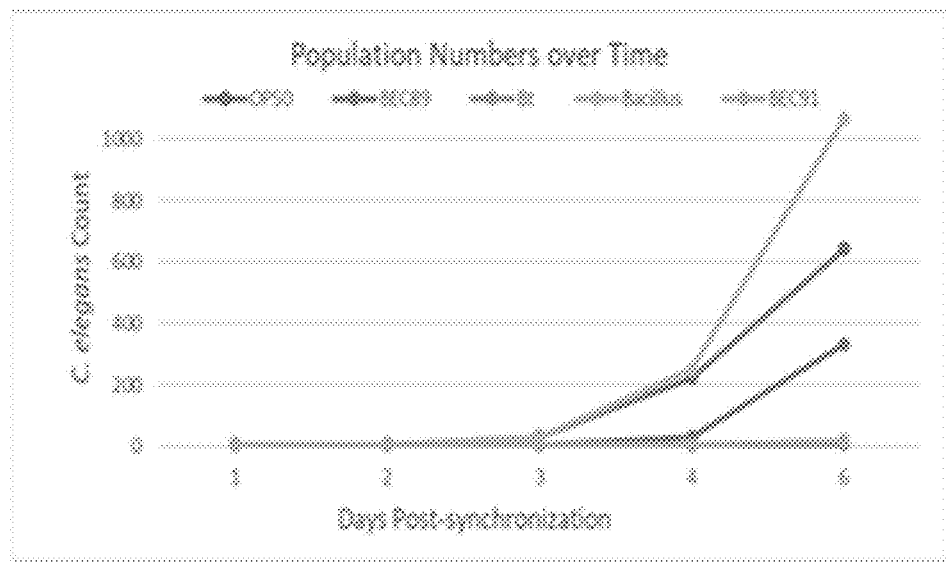
FIG. 12A shows *C. elegans* development population counts over time. OP50 bacterial (−) control, Bt (+) control, *Bacillus* (−) control.
Figure 12B:
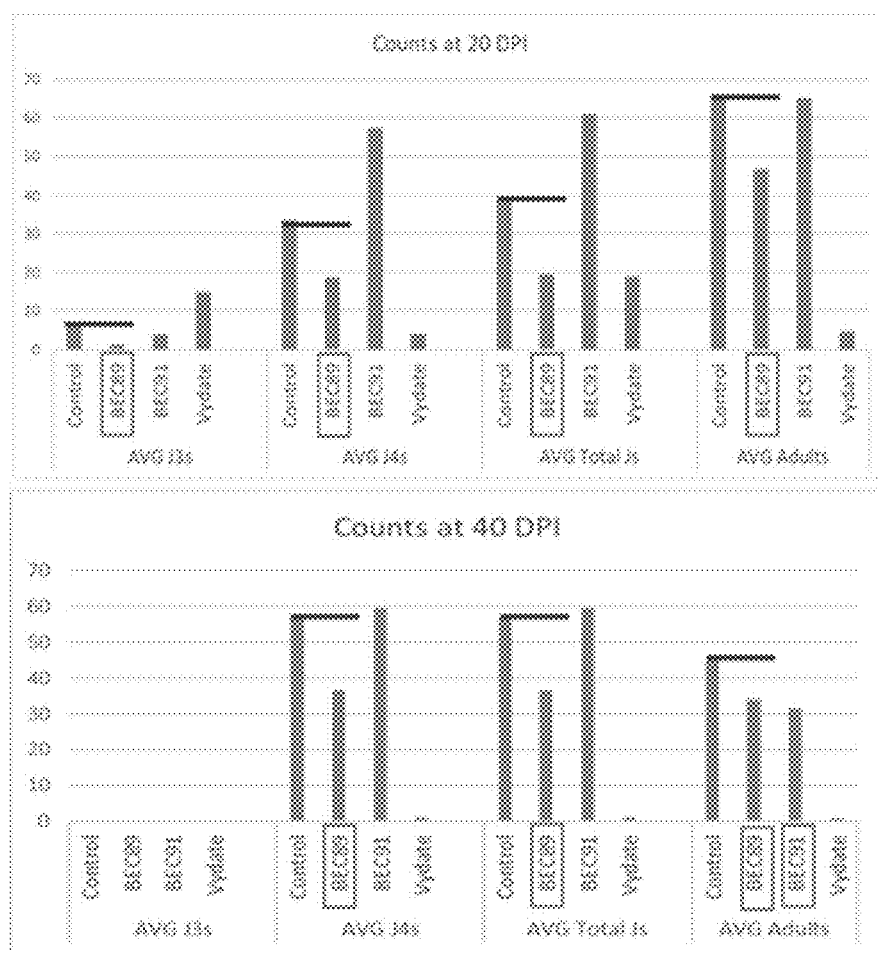
FIG. 12B shows in planta mode of action testing (Tomato). Root knot nematode infective juveniles and adult counts in tomato roots, at different stages after inoculation.

In planta modes of action studies were conducted, to determine if microbial formulations affect infectivity, and nematode development. Tomato plants were grown and treated with microbials and J2s (Infective juveniles). Tomato roots were assessed at different time points throughout the experiment, and number of nematodes and developmental stages were counted in the roots at each time point. FIG. 12B: In planta mode of action testing (Tomato). Root knot nematode infective juveniles and adult counts in tomato roots, at different stages after inoculation.

In other studies, synchronized *C. elegans* were placed on artificial media inoculated with test microbes. Worms' development and numbers were monitored through their life cycle. *C. elegans* mode of action studies were conducted in 8 replicates with 1-3 L1s inoculated in each well of the assay. A control microbe of an ineffective *Bacillus* species and a positive control of a nematicide reference strain of *B. thuringiensis* were tested alongside each treatment. Results were assessed at 3 days post-synchronization. FIG. 12A: *C. elegans* development population counts over time. OP50 bacterial (−) control, Bt (+) control, *Bacillus* (−) control.

Microbes that impart nematode stress tolerance to plants include those represented by: SEQ ID NOs: 10-12.

*Orbilia auricolor/Arthrobotrys oligospora* BEC93

TABLE 20A

Percent Nematode reduction relative to control (Nem Red % IOC) and Percent Yield improvement over control (% IOC) for crops treated with BEC93, in the Field

| Crop | Nematode | Nem Red % IOC | Change in Yield % IOC |
|---|---|---|---|
| Tomato - spring | RKN | 5% | 14% |
| Carrot - spring | Lesion | −34.20% | 14.08% |
| Cotton - spring | Stubby | −73% | 30% |
| Tomato - fall | RKN | −26.16% | 10% |
| Cucumber - fall | RKN | 103.70% | −1.13% |

TABLE 20A-continued

Percent Nematode reduction relative to control (Nem Red % IOC) and Percent Yield improvement over control (% IOC) for crops treated with BEC93, in the Field

| Crop | Nematode | Nem Red % IOC | Change in Yield % IOC |
|---|---|---|---|
| Strawberry - fall | Sting | −0.07% | 24.92% |
| Soy | SCN | n/a | 2.99% |
| Wheat | CCN | −58.89% | 68.83% |

TABLE 20B

Percent Nematode reduction relative to control (Nem Red % IOC) on tomatoes treated with BEC93, in the Greenhouse

| Treatment | Nematode Reduction |
|---|---|
| BEC93 | −66.03% |
| Commercial product | −20.64% |

TABLE 20C

Percent Nematode reduction relative to control (Nem Red % IOC) for crops treated with BEC93, in the Growth Chamber

| Tomato IOC % | Tomato IOC % | Cucumber % IOC | Dose Response Tomato | Wins % | Avg reduction | Nematode reduction |
|---|---|---|---|---|---|---|
| −11% | −6% | −55% | −43% | 100% | −29% | −29% |

BEC93 improved yield versus control treatment in 7 out of 8 trials under nematode pressure. While nematode reduction was not always seen (due to hypothesized mode of action) plant health and yield were improved.

*Lysinibacillus fusiformis* BEC91

TABLE 21A

Percent Nematode reduction relative to control (Nem Red % IOC) and Percent Yield improvement over control (% IOC) for crops treated with BEC91, in the Field

| Crop | Nematode | Nem Red % IOC | Change in Yield % IOC |
|---|---|---|---|
| Tomato - spring | RKN | −4% | 9% |
| Carrot - spring | Lesion | −13.66% | 20.11% |
| Cotton - spring | Stubby | 3% | 26.00% |
| Tomato - fall | RKN | −22.55% | 12.90% |
| Cucumber - fall | RKN | −18.70% | −1.33% |
| Strawberry - fall | Sting | −21.79% | 12.78% |
| Corn | SRN | −44.25% | 0.57% |
| Soy | SCN | n/a | 2.14% |
| Wheat | CCN | −54.0d2% | 73.31% |
| Cotton | RKN | −77.10% | 3.34% |

TABLE 21B

Percent Nematode reduction relative to control (Nem Red % IOC) for tomatoes treated with BEC91, in the Greenhouse

| Treatment | Nematode Reduction |
|---|---|
| BEC91 | −74.22% |
| Commercial product | −20.64% |

TABLE 21C

Percent Nematode reduction relative to control (Nem Red % IOC) for crops treated with BEC91, in the Growth Chamber

| Tomato IOC % | Tomato IOC % | Cucumber % IOC | Dose Response Tomato | Wins % | Avg reduction | Nematode reduction |
|---|---|---|---|---|---|---|
| −24% | 8% | −88% | −51% | 75% | −54% | −40.83 |

At 3 days post-synchronization no adults were detected for the positive control Bt, and BEC91, while adults and eggs were already present in the negative control treatments, demonstrating that BEC91 affects nematode development and reproduction. At 4 and 6 days post-synchronization, BEC91 continued to demonstrate nematicidal activity, with very few *C. elegans* numbers detected. In tomato plant roots, BEC91 was effective at reducing amounts of total adult root knot nematods at late stages of infection, also, indicative of an effect on development.

In-planta modes of action studies demonstrated fewer total adults at 40 Days Post Infection (DPI), but no improvement in juveniles at either 20 or 40 DPI or of adults at 20 DPI.

*Bacillus velenzensis* BEC89A (BEC89Single)

TABLE 22

Percent improvement over control (% IOC) in Yield and Reduction in Nematode numbers relative to control (NEM Red % IOC) for crops treated with BEC89 Single

| Crop | Yield % IOC | Nematode reduction % IOC |
|---|---|---|
| Wheat | 66.2 | −59.3 |
| Corn | 4.6 | −21.9 |
| Cotton | −1.4 | −49.96 |
| Peanuts | 13.6 | −32.8 |
| Strawberries | 36.3 | −9.7 |
| Cucumbers | 4.2 | −0.6 |

At 3 days post-synchronization no adults were detected for the positive control Bt, and BEC89 while adults and eggs were already present in the negative control treatments, demonstrating that BEC89 is effective for nematode control. At 4 and 6 days post-synchronization, BEC89 continued to demonstrate nematicidal activity, with very few *C. elegans* numbers detected at 4 days and a significant reduction from negative control at 6 days post synchronization. Treatment of tomato plant roots with BEC89 was effective at reducing amounts of Juveniles and Adult root knot nematodes at 20 and 40 days post inoculation.

*Bacillus velenzensis* BEC89A in Combination with *Bacillus pumilus* BEC89B (BEC89Double)

TABLE 23

Percent improvement over control (% IOC) in Yield and Reduction in Nematode numbers relative to control (NEM Red % IOC) for crops treated with BEC89 Double

| Crop | Yield % IOC | Nematode reduction % IOC |
|---|---|---|
| Wheat | 62.1 | 49.6 |
| Corn | 1.4 | −23.7 |
| Cotton | 4.27 | 45.9 |
| Peanuts | 40 | −24.2 |
| Strawberries | 14.62 | −27 |
| Cucumbers | 0.1 | −32.4 |

In-planta modes of action studies demonstrated fewer total juveniles at 20 Days Post Infection (DPI), and fewer total nematodes at 20 and 40 DPI.

Improvement of Crop Disease Resistance

Seeds treated with the microbes described herein, as well as control seeds not treated with the microbes, from a wide variety of crops were planted and cultivated according to standard agronomic practices. Exemplary conditions and microbe application rates are given below. Percent yield and disease reduction measurements were recorded, under conditions in growth chamber, greenhouse, and field trials. Improvements were seen with the microbes described below, at levels comparable or better than a comparator commercial biofungicide.

Diseases included both plant pathogens and soil diseases: *Verticillium dahliae*, *Fusarium oxysporum*, *Macrophomina phaseolina*, *Botrytis cinerea*, *Xanthomonas Pseudomonas*, *Erwinia*, *Clavibacter*, *Agrobacterium*, *Fusarium*, *Pythium*, *Verticillium*, *Rhizoctonia*.

Results demonstrate opportunity for residue and resistance management while maintaining best efficacy.

Microbes that impart fungal stress tolerance to plants include those represented by: SEQ ID NOs: 1, 2, and 13.

*Bacillus tequilensis* BEC80

BEC80 demonstrated strong field performance on soil and foliar disease control, growth & yield enhancement on fruit and vegetable crops, and outstanding activity against *Pythium*, especially metalaxyl-resistant *Pythium*, with a different metabolite profile from other *Bacillus* biofungicides. Exemplary diseases that were controlled included Powdery mildew, *Botrytis* gray mold, apple scab, pear scab, *Fusarium*, *Verticillium*, *Rhizoctonia*, *Sclerotinia*, *Pythium*.

Suspension concentrates of BEC80 were prepared for application rates of 2-4 quarts/acre for soil inoculation and/or foliar treatment of target crop plants.

Figure 6:
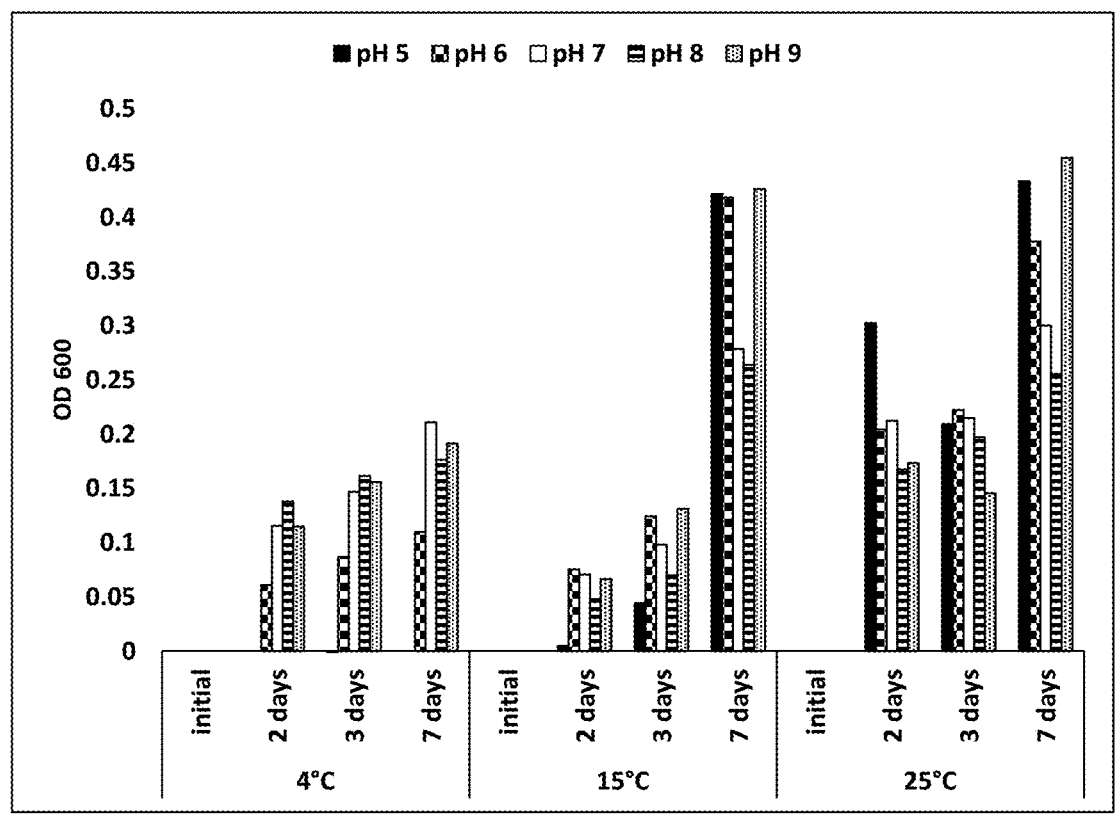
FIG. 6 shows the activity profiles of *B. velezensis* BEC80 across a range of temperatures and pH at 0, 2, 3, and 7 days.

GFP-tagged BEC80 demonstrated strong root colonization (FIG. 5) and had a robust growth profile across a wide rage of pH and temperatures (FIG. 6).

Genomic analysis of bioactive metabolites demonstrated antibacterial, anti-fungal, siderophore, and phosphate-limiting survival activities, as shown in Table 24.

TABLE 24

Analysis of Bioactive Metabolites and Activities of BEC80

| Metabolite | Biosynthetic gene/genes detected | Result |
|---|---|---|
| Bacillaene | Antibacterial | + |
| Difficidin | Antibacterial | + |
| Haloduracin/Mersacidin | Antibacterial (gram+) | − |

TABLE 24-continued

Analysis of Bioactive Metabolites and Activities of BEC80

| Metabolite | Biosynthetic gene/genes detected | Result |
|---|---|---|
| MacroLactin | Antibacterial | + |
| Paenibacterin | Antibacterial | − |
| Plantathiazolicin | Antibacterial (gram+) | + |
| Sporulation_killing_factor_skfA | Antibacterial | − |
| Subtilin | Antibacterial (gram+) | − |
| Subtilosin_A | Antibacterial (gram+) | − |
| Tyrocidine | Antibacterial | − |
| Surfactin | Antifungal, Antibacterial | + |
| Locillomycin | Antifungal, Antibacterial | − |
| Basiliskamides | Antifungal | − |
| Fengycin/Plipastatin | Antifungal | + |
| Bacilysin | Antifungal, Antibacterial | + |
| Iturin A* | Antifungal | + |
| Bacillomycin (Iturin) | Antifungal | + |
| Mycosubtilin (Iturin) | Antifungal | − |
| Paenilarvins (Iturin) | Antifungal | − |
| Bacillibactin | Siderophore (iron-binding) | + |
| Petrobactin | Siderophore (iron-binding) | − |
| Teichuronic acid | Survival in phosphate-limiting conditions | + |

Figure 7:
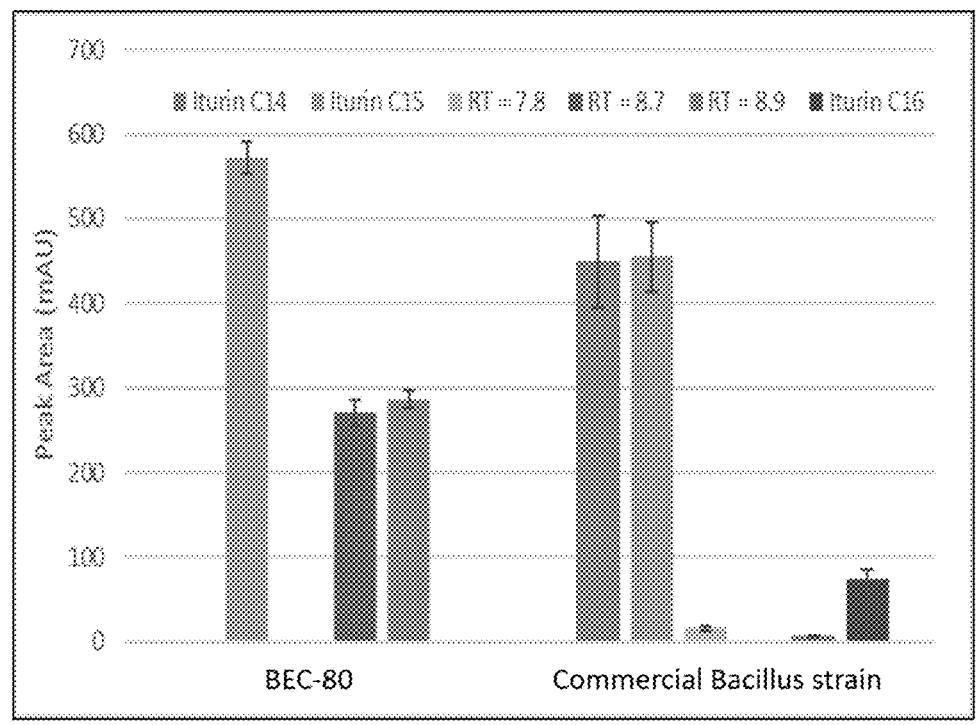
FIG. 7 shows the relative production of iturins for *B. velezensis* BEC80 and a reference *Bacillus* strain.
Figure 8:
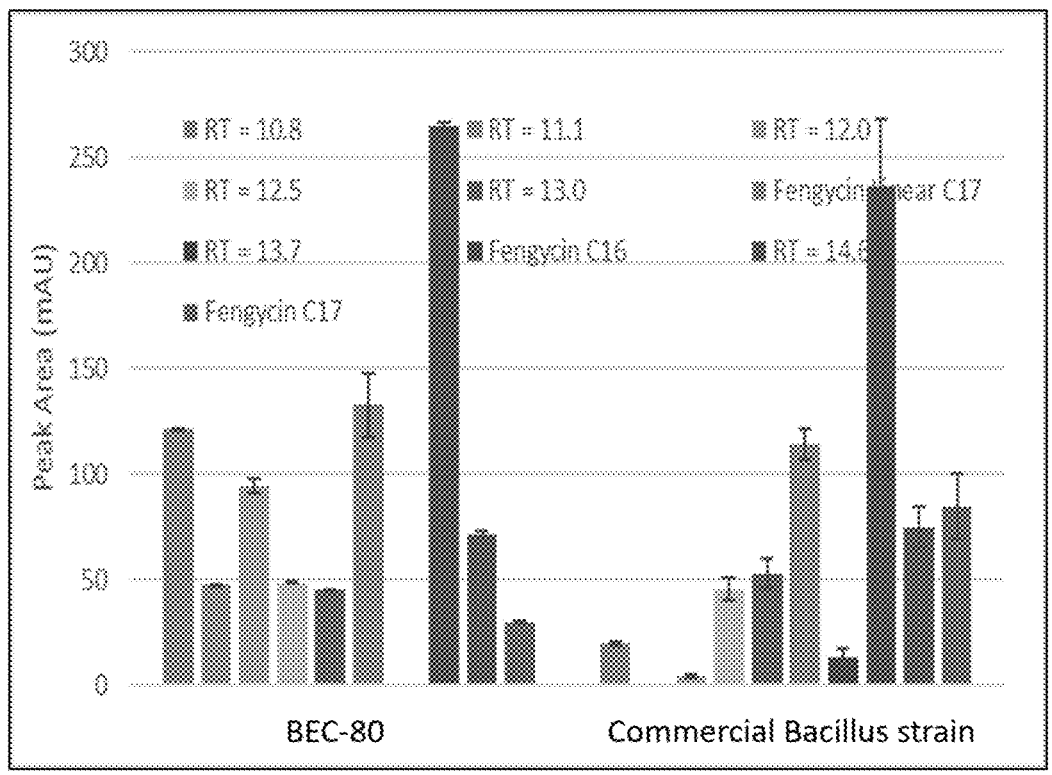
FIG. 8 shows the relative production of fengycins for *B. velezensis* BEC80 and a reference *Bacillus* strain.
Figure 9:
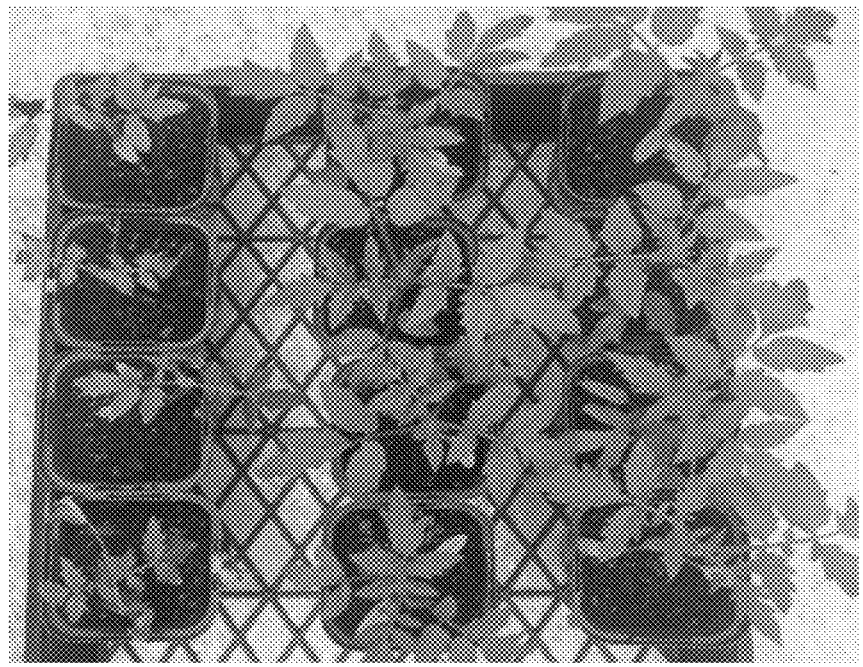
FIG. 9 shows a photograph of in planta biostimulant activity for *B. methylotrophicus* BEC60.
Figure 10:
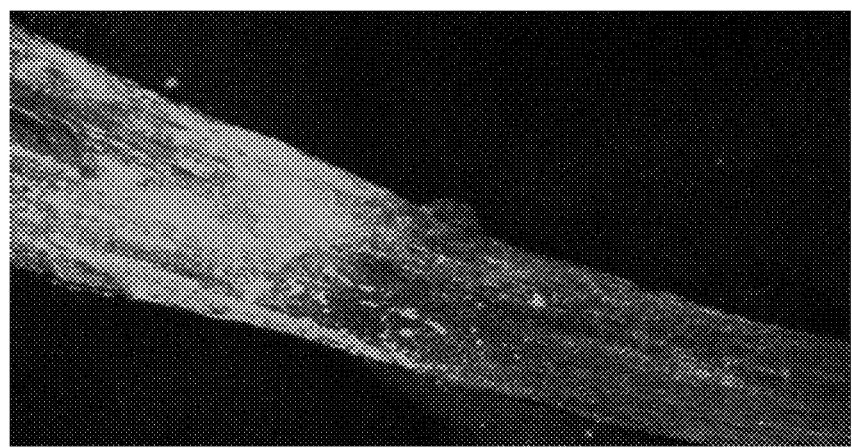
FIG. 10 shows that *B. methylotrophicus* BEC60 colonizes roots (fluorescent-tagged microbes on wheat roots).
Figure 11:
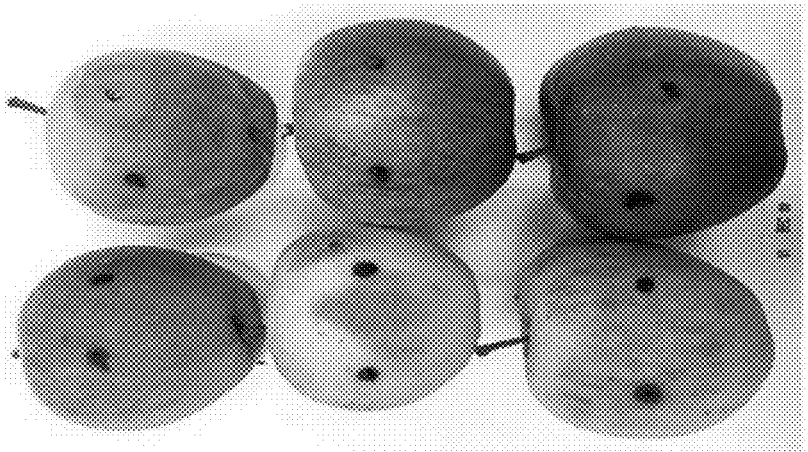
FIG. 11 shows post-harvest apples with no treatment, 100 ppm of a commercially-available treatment, and treatment with *B. velezensis* BEC80.
Figure 11:
Figure 11:
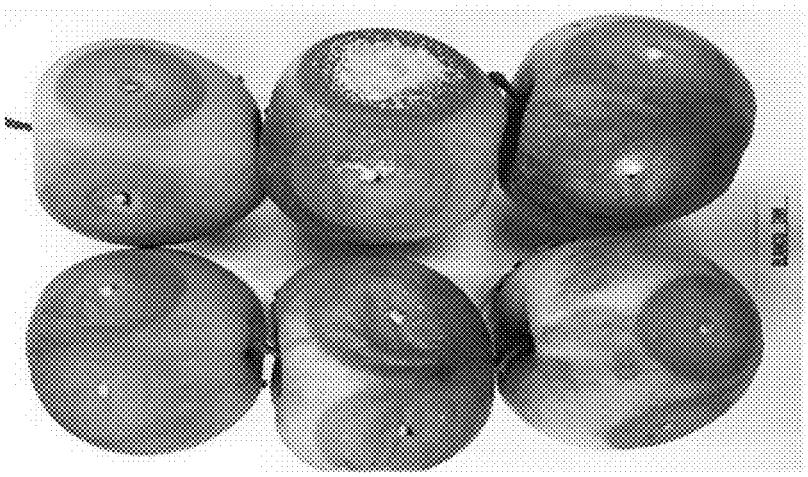

BEC80 produced unique lipopeptides, that is different than those of commercially-available *Bacillus* strains, which may be the mode of action for superior *Pythium* control. Results are shown in FIGS. 7-8.

BEC80 conferred broad-spectrum activity against plant pathogens in in vitro bioassays, with results better than the control microbe against *Verticillium dahliae*, *Fusarium oxysporum*, *Macrophomina phaseolina*, *Botrytis cinerea*, *Xanthomonas Pseudomonas*, *Erwinia*, *Clavibacter*, and *Agrobacterium*.

BEC80 conferred broad-spectrum activity, with results better than the control microbe against soil pathogens such as *Fusarium*, *Pythium* and *Rhizoctonia* for tomato and *Verticillium* for lettuce.

BEC80 demonstrated superior in vitro activity versus *Pythium* and *Fusarium*.

TABLE 25A

Pythium and Fusarium activity for various B. tequilensis BEC80 treatments

| Treatments | Pythium activity (0-4) | Fusarium activity (0-5) |
|---|---|---|
| Unmodified Supernatant | 4 | 4 |
| Heated Supernatant (80 C., 20 min) | 4 | 4 |
| Autoclaved Supernatant | 4 | 3 |
| Proteinase K Protease (Heated for enzyme inactivation) | 4 | 3 |
| Trypsin Protease (Heated for enzyme inactivation) | 4 | 4 |
| Pronase Protease (Heated for enzyme inactivation) | 4 | 3 |
| Glucosidase (Heated for enzyme inactivation) | 4 | 3 |
| Lipase (Heated for enzyme inactivation) | 4 | 4 |

TABLE 25B

Pythium and Fusarium activity for B. tequilensis BEC80 treatments as compared to two different commercially-available products Hyphae diameter is after 3 days of growth on PDA with treatment in the media.

| Treatments | Pythium hyphae diameter (cm) | Fusarium activity (0-5) |
|---|---|---|
| BEC80 | 0 | 4 |
| Commercial Product 1 | 4.5 | 1 |
| Commercial Product 2 | 4.5 | 2 |

Millet bioassay with Metalyxyl-resistant *Pythium* showed that BEC80 showed superior plant emergence frequencies than a commercially-available biological control agent.

Field efficacy of BEC80 was demonstrated for soil diseases across multiple years of field trials, with comparable performance in disease suppression and crop yield to a commercially-available biological control agent, for lettuce (*Verticillium, S. minor, S. sclerotoiorum*), tomato (*Fusarium, Rhizoctonia*), Cucumber (*P. capisici*).

Foliar apple scab trials (application rate of 4 quarts/acre, at an application frequency of 1 application per week for 12 weeks) demonstrated BEC80 reduced apple scab disease severity throughout the trial, with a final disease severity (% area) index of approximately 14% as compared to the untreated control of nearly 40%.

Reductions in disease severity (% infestation) were seen for foliar squash powdery mildew at one location, with weekly applications of 4 quarts/acre of squash plants over 6 weeks. BEC80 showed a final % infestation rate of approximately 55%, as compared to a control treatment (water only) of over 90%. BEC80 in combination with a commercially-available biocontrol agent reduced infestation further, to around 20%. Trials at a second location of foliar applications of microbe at 2 or 4 quarts/acre for weekly applications over 6 weeks showed that powdery mildew disease severity (score 0-100) was nearly 80 for an untreated control and approximately 20 and 8 for *B. tequilensis* (at 2 q/A and 4 q/A, respectively) at the 6 week mark.

Reductions in disease severity were seen for Citrus Canker trials, with weekly application rates over 12 weeks of *B. tequilensis* alone and in combination with a commercial disease chemistry product, at foliar application rates of 4 quarts/acre. Disease severity index (0-100) was reduced to 20 for *B. tequilensis* as compared to around 23 for the untreated control. Reduction to approximately 8 was seen at 12 weeks for *B. tequilensis* in combination with a commercially-available chemistry, and performed better than the chemistry alone.

Reductions in disease severity were seen with BEC80 on citrus crops for Greasy Spot disease, at foliar application with 12 weekly applications of BEC80 alone and in combination with a commercial disease chemistry product, at foliar application rates of 4 quarts/acre. Disease severity index (0-100) was reduced to around 20 for *B. tequilensis* as compared to around 23 for the untreated control. Reduction to approximately 14 was seen at 12 weeks for BEC80 in combination with a commercially-available chemistry, and performed better than the chemistry alone (which was provided at 4 quarts/acre).

Reductions in disease severity were seen with BEC80 on strawberry crops for Powdery Mildew disease, at foliar application with 6 weekly applications of BEC80 at foliar application rates of 2 or 4 quarts/acre. Disease severity index (0-100) was reduced to around 8 for *B. tequilensis* at 4 q/A as compared to around 12 for the untreated control and 9 for the commercially-available chemistry; BEC80 at 2 q/A as compared to around 12 for the untreated control and 9 for the commercially-available chemistry.

BEC80 also demonstrated excellent control of post-harvest pathogens on fruit (FIG. 11), comparable to synthetic chemistry.

*Bacillus methylotrophicus* BEC60

*B. methylotrophicus* demonstrated strong field performance on soil and foliar disease control, growth & yield enhancement, and is a prolific bioactive metabolite producer and robust root colonizer on many crops.

Exemplary diseases that were controlled included Powdery mildew, *Botrytis* gray mold, apple scab, pear scab, *Fusarium, Verticillium, Rhizoctonia, Sclerotinia.*

Suspension concentrates of *B. methylotrophicus* were prepared for application rates of 2-4 quarts/acre for soil inoculation and/or foliar treatment of target crop plants.

GFP-tagged *B. methylotrophicus* demonstrated strong root colonization (FIG. 10).

Genomic analysis of bioactive metabolites demonstrated antibacterial, anti-fungal, siderophore, and phosphate-limiting survival activities.

TABLE 26

Analysis of Bioactive Metabolites and Activities of BEC60

| Metabolite | Biosynthetic gene/genes detected | Result |
|---|---|---|
| Bacillaene | Antibacterial | + |
| Difficidin | Antibacterial | + |
| Haloduracin | Antibacterial (gram+) | + |
| Macrolactin | Antibacterial | + |
| Plantathiazolicin | Antibacterial (gram+) | + |
| Surfactin | Antifungal, Antibacterial | + |
| Locillomycin | Antifungal, Antibacterial | + |
| Fengycin/Plipastatin | Antifungal | + |
| Bacilysin | Antifungal, Antibacterial | + |
| Iturin A | Antifungal | + |
| Bacillibactin | Siderophore | + |
| Teichuronic acid | Survival in P limitation | + |

*B. methylotrophicus* conferred broad-spectrum activity against plant pathogens in in vitro bioassays, with results better than the control microbe against *Verticillium dahliae, Fusarium oxysporum, Macrophomina phaseolina, Botrytis cinerea, Xanthomonas Pseudomonas.*

*B. methylotrophicus* conferred broad-spectrum activity, with results better than the control microbe against soil pathogens such as *Fusarium* and *Pythium* for tomato, and better than an untreated control for *Rhizoctonia* for tomato and *Verticillium* for lettuce. Exemplary plant data is shown in the photograph of FIG. 9.

Reductions in disease severity were seen with *B. methylotrophicus* on tomato crops for *Fusarium* Wilt disease (experiencing a high disease pressure), at foliar application with 5 weekly applications of *B. methylotrophicus* alone and in combination with a commercial disease chemistry product, at foliar application rates of 4 quarts/acre. Disease severity index (0-10) was reduced to near zero for *B. methylotrophicus*, which was better than both the untreated control as well as two different commercially-available chemistries.

Reductions in disease severity were seen with *B. methylotrophicus* on tomato crops for Bacterial Leaf Spot disease (experiencing a high disease pressure), at foliar application with 4 weekly applications of *B. methylotrophicus* alone and in combination with a commercial disease chemistry product. Disease severity index (0-100) was reduced to near less than 10 for *B. methylotrophicus*, which was better than both the untreated control as well as a commercially-available control product. Yield improvement was also seen when tomato crops were treated both with *B. methylotrophicus* by itself, and also when in combination with a commercially-available control product.

Reductions in disease severity were seen with *B. methylotrophicus* on pear crops for Pear Scab disease (experiencing a high disease pressure), at foliar application with 4 weekly applications of *B. methylotrophicus*. Disease severity index (0-10) was reduced to approximately 3 for *B. methylotrophicus*, which was better than the untreated control (around 6) and just one point higher than a commercially-available synthetic chemistry product.

Reductions in other types of foliar diseases were seen for strawberry crop *Botrytis* infection, strawberry Powdery Mildew infection, squash Powdery Mildew infection, and cucumber Powdery Mildew infection; all at levels at least 20% below that of the untreated plants, and levels bettor or equivalent to commercially-available treatments.

Foliar apple scab trials (application rate of 4 quarts/acre, at an application frequency of 1 application per week for 3 weeks) demonstrated *B. methylotrophicus* reduced apple scab disease severity throughout the trial, with a final disease severity (% infestation) of approximately 4% as compared to the untreated control of approximately 13%. Treated plants showed equivalent response to a commercially-available control product.

Reductions in disease severity were seen with *B. methylotrophicus* on cucumber plants for Powdery Mildew disease, at foliar application with 6 weekly applications of *B. methylotrophicus* alone and in combination with a commercial disease control product. Disease severity index (0-100% infestation) was reduced to approximately 7% for *B. methylotrophicus*, which was better than the inoculated untreated control (around 26%), and nearly equivalent to different commercially-available product.

Reductions in disease severity were seen with *B. methylotrophicus* on strawberry crops for *Botrytis* disease, at foliar application with 6 weekly applications of *B. methylotrophicus* alone and in combination with a commercial disease control product, at foliar application rates of 4 quarts/acre. Disease severity index (0-100% rot) was reduced to approximately 35% for *B. methylotrophicus*, which was better than both the inoculated untreated control (around 65%) as well as a different commercially-available product (around 40%). Combinations of *B. methylotrophicus* with three applications of a commercially-available chemistry provided *Botrytis* control equivalent to six applications of the chemistry alone. *B. methylotrophicus* also improved total yield of treated strawberry crops.

Reductions in disease severity (% infestation) were seen for foliar squash powdery mildew at one location, with weekly applications of 4 quarts/acre of squash plants over 6 weeks. *B. methylotrophicus* showed a final % infestation rate of approximately 40%, as compared to a control treatment (water only) of over 90%. *B. methylotrophicus* also performed better than two different commercially-available control products, both alone and in combination, to around 20%. Trials at a second location of foliar applications of microbe at 2 or 4 quarts/acre for weekly applications over 6 weeks showed that powdery mildew disease severity (score 0-100) was nearly 80 for an untreated control and approximately 25 for *B. methylotrophicus* (at both 2 q/A and 4 q/A) at the 6 week mark.

Reductions in disease severity were seen for Citrus Canker trials, with weekly application rates over 12 weeks of *B. methylotrophicus* alone and in combination with a commercial disease chemistry product, at foliar application rates of 4 quarts/acre. Disease severity index (0-100) was reduced to 20 for *B. methylotrophicus* as compared to around 23 for the untreated control. Reduction to approximately 8 was seen at 12 weeks for *B. methylotrophicus* in combination with a commercially-available chemistry, and performed better than the chemistry alone.

Reductions in disease severity were seen with *B. methylotrophicus* on citrus crops for Greasy Spot disease, at foliar application with 12 weekly applications of *B. methylotrophicus* alone and in combination with a commercial disease chemistry product, at foliar application rates of 4 quarts/acre. Disease severity index (0-100) was reduced to around 20 for *B. methylotrophicus* treated plants, as compared to around 23 for the untreated control. Reduction to approximately 12 was seen at 12 weeks for *B. methylotrophicus* in combination with a commercially-available chemistry, and performed better than the chemistry alone (which was provided at 4 quarts/acre).

Reductions in disease severity were seen with *B. methylotrophicus* on strawberry crops for Powdery Mildew disease, at foliar application with 6 weekly applications of *B. methylotrophicus* at foliar application rates of 2 or 4 quarts/acre. Disease severity index (0-100) was reduced to around 6 for *B. methylotrophicus* at 4 q/A as compared to around 12 for the untreated control and 9 for a commercially-available chemistry and 3 for another commercially-available chemistry.

TABLE 26

*Pythium* and *Fusarium* activity for various *B. tequilensis* BEC60 treatments

| Treatments | Pythium activity (0-4) | Fusarium activity (0-5) |
|---|---|---|
| Unmodified Supernatant | 1 | 4 |
| Heated Supernatant (80 C., 20 min) | 0 | 4 |
| Autoclaved Supernatant | 1 | 4 |
| Proteinase K Protease (Heated for enzyme inactivation) | 1 | 4 |
| Trypsin Protease (Heated for enzyme inactivation) | 0 | 4 |
| Pronase Protease (Heated for enzyme inactivation) | 0 | 4 |
| Glucosidase (Heated for enzyme inactivation) | 0 | 4 |
| Lipase (Heated for enzyme inactivation) | 0 | 4 |

*Bacillus methylotrophicus* BEC56

*B. methylotrophicus* BEC59 increased total yield in strawberry trials with *botrytis* infection, when applied at rates of 2 qt/Ac and 4 qt/Ac, by up to 2.25 kg/Ac harvested strawberries (as compared to a water control) for the 2 qt/Ac application. BEC59 out-performed two different commercially-available products.

BEC59 also showed strong reduction in apple scab disease severity, performing slightly better than a commercially-available product, reducing % infestation from approximately 13% (water control) to approximately 2%.

BEC56 showed reduction in disease severity for cucumber powdery mildew, reducing disease from over 25% to approximately 17%.

SEQUENCE LISTING

<160> NUMBER OF SEQ ID NOS: 21

<210> SEQ ID NO 1
<211> LENGTH: 902
<212> TYPE: DNA
<213> ORGANISM: Bacillus tequilensis

<400> SEQUENCE: 1

| | | | | | |
|---|---|---|---|---|---|
| taaaggttac | ctcaccgact | tcgggtgtta | caaactctcg | tggtgtgacg | ggcggtgtgt | 60 |
| acaaggcccg | ggaacgtatt | caccgcggca | tgctgatccg | cgattactag | cgattccagc | 120 |
| ttcacgcagt | cgagttgcag | actgcgatcc | gaactgagaa | cagatttgtg | ggattggctt | 180 |
| aacctcgcgg | tttcgctgcc | ctttgttctg | tccattgtag | cacgtgtgta | gcccaggtca | 240 |
| taagggcat | gatgatttga | cgtcatcccc | accttcctcc | ggtttgtcac | cggcagtcac | 300 |
| cttagagtgc | ccaactgaat | gctggcaact | aagatcaagg | gttgcgctcg | ttgcgggact | 360 |
| taacccaaca | tctcacgaca | cgagctgacg | acaaccatgc | accacctgtc | actctgcccc | 420 |
| cgaaggggac | gtcctatctc | taggattgtc | agaggatgtc | aagacctggt | aaggttcttc | 480 |
| gcgttgcttc | gaattaaacc | acatgctcca | ccgcttgtgc | gggcccccgt | caattccttt | 540 |
| gagtttcagt | cttgcgaccg | tactccccag | gcggagtgct | taatgcgtta | gctgcagcac | 600 |
| taagggcgg | aaacccccta | acacttagca | ctcatcgttt | acggcgtgga | ctaccagggt | 660 |
| atctaatcct | gttcgctccc | cacgctttcg | ctcctcagcg | tcagttacag | accagagagt | 720 |
| cgccttcgcc | actggtgttc | ctccacatct | ctacgcattt | caccgctaca | cgtggaattc | 780 |
| cactctcctc | ttctgcactc | aagttcccca | gtttccaatg | accctccccg | gttgagccgg | 840 |
| gggctttcac | atcagactta | agaaaccgcc | tgcgagccct | ttacgcccaa | taattccgga | 900 |
| ca | | | | | | 902 |

<210> SEQ ID NO 2
<211> LENGTH: 1374
<212> TYPE: DNA
<213> ORGANISM: Bacillus methylotrophicus

<400> SEQUENCE: 2

| | | | | | |
|---|---|---|---|---|---|
| cagatgggag | cttgctccct | gatgttagcg | gcggacgggt | gagtaacacg | tgggtaacct | 60 |
| gcctgtaaga | ctgggataac | tccgggaaac | cggggctaat | accggatgct | tgtttgaacc | 120 |
| gcatggttca | gacataaaag | gtggcttcgg | ctaccactta | cagatggacc | cgcggcgcat | 180 |
| tagctagttg | gtgaggtaac | ggctcaccaa | ggcgacgatg | cgtagccgac | ctgagagggt | 240 |
| gatcggccac | actgggactg | agacacggcc | cagactccta | cgggaggcag | cagtagggaa | 300 |
| tcttccgcaa | tggacgaaag | tctgacggag | caacgccgcg | tgagtgatga | aggttttcgg | 360 |
| atcgtaaagc | tctgttgtta | gggaagaaca | agtgccgttc | aaatagggcg | gcaccttgac | 420 |
| ggtacctaac | cagaaagcca | cggctaacta | cgtgccagca | gccgcggtaa | tacgtaggtg | 480 |
| gcaagcgttg | tccggaatta | ttgggcgtaa | agggctcgca | ggcggtttct | taagtctgat | 540 |
| gtgaaagccc | ccggctcaac | cggggagggt | cattggaaac | tggggaactt | gagtgcagaa | 600 |
| gaggagagtg | gaattccacg | tgtagcggtg | aaatgcgtag | agatgtggag | gaacaccagt | 660 |
| ggcgaaggcg | actctctggt | ctgtaactga | cgctgaggag | cgaaagcgtg | gggagcgaac | 720 |
| aggattagat | accctggtag | tccacgccgt | aaacgatgag | tgctaagtgt | taggggggttt | 780 |
| ccgcccctta | gtgctgcagc | taacgcatta | agcactccgc | ctggggagta | cggtcgcaag | 840 |
| actgaaactc | aaaggaattg | acgggggccc | gcacaagcgg | tggagcatgt | ggtttaattc | 900 |

| gaagcaacgc gaagaacctt accaggtctt gacatcctct gacaatccta gagataggac | 960 |
| gtccccttcg ggggcagagt gacaggtggt gcatggttgt cgtcagctcg tgtcgtgaga | 1020 |
| tgttgggtta agtcccgcaa cgagcgcaac ccttgatctt agttgccagc attcagttgg | 1080 |
| gcactctaag gtgactgccg gtgacaaacc ggaggaaggt ggggatgacg tcaaatcatc | 1140 |
| atgcccctta tgacctgggc tacacacgtg ctacaatgga cagaacaaag ggcagcgaaa | 1200 |
| ccgcgaggtt aagccaatcc cacaaatctg ttctcagttc ggatcgcagt ctgcaactcg | 1260 |
| actgcgtgaa gctggaatcg ctagtaatcg cggatcagca tgccgcggtg aatacgttcc | 1320 |
| cgggccttgt acacaccgcc cgtcacacca cgagagtttg taacacccga agtc | 1374 |

<210> SEQ ID NO 3
<211> LENGTH: 1374
<212> TYPE: DNA
<213> ORGANISM: Bacillus amyloliquefaciens

<400> SEQUENCE: 3

| cagatgggag cttgctccct gatgttagcg gcggacgggt gagtaacacg tgggtaacct | 60 |
| gcctgtaaga ctgggataac tccgggaaac cggggctaat accggatgct tgtttgaacc | 120 |
| gcatggttca gacataaaag gtggcttcgg ctaccactta cagatggacc cgcggcgcat | 180 |
| tagctagttg gtgaggtaac ggctcaccaa ggcgacgatg cgtagccgac ctgagagggt | 240 |
| gatcggccac actgggactg agacacggcc cagactccta cgggaggcag cagtagggaa | 300 |
| tcttccgcaa tggacgaaag tctgacggag caacgccgcg tgagtgatga aggttttcgg | 360 |
| atcgtaaagc tctgttgtta gggaagaaca agtgccgttc aaatagggcg gcaccttgac | 420 |
| ggtacctaac cagaaagcca cggctaacta cgtgccagca gccgcggtaa tacgtaggtg | 480 |
| gcaagcgttg tccggaatta ttgggcgtaa agggctcgca ggcggtttct taagtctgat | 540 |
| gtgaaagccc ccggctcaac cggggagggt cattggaaac tggggaactt gagtgcagaa | 600 |
| gaggagagtg gaattccacg tgtagcggtg aaatgcgtag agatgtggag gaacaccagt | 660 |
| ggcgaaggcg actctctggt ctgtaactga cgctgaggag cgaaagcgtg gggagcgaac | 720 |
| aggattagat accctggtag tccacgccgt aaacgatgag tgctaagtgt tagggggttt | 780 |
| ccgcccctta gtgctgcagc taacgcatta agcactccgc ctggggagta cggtcgcaag | 840 |
| actgaaactc aaaggaattg acgggggccc gcacaagcgg tggagcatgt ggtttaattc | 900 |
| gaagcaacgc gaagaacctt accaggtctt gacatcctct gacaatccta gagataggac | 960 |
| gtccccttcg ggggcagagt gacaggtggt gcatggttgt cgtcagctcg tgtcgtgaga | 1020 |
| tgttgggtta agtcccgcaa cgagcgcaac ccttgatctt agttgccagc attcagttgg | 1080 |
| gcactctaag gtgactgccg gtgacaaacc ggaggaaggt ggggatgacg tcaaatcatc | 1140 |
| atgcccctta tgacctgggc tacacacgtg ctacaatgga cagaacaaag ggcagcgaaa | 1200 |
| ccgcgaggtt aagccaatcc cacaaatctg ttctcagttc ggatcgcagt ctgcaactcg | 1260 |
| actgcgtgaa gctggaatcg ctagtaatcg cggatcagca tgccgcggtg aatacgttcc | 1320 |
| cgggccttgt acacaccgcc cgtcacacca cgagagtttg taacacccga agtc | 1374 |

<210> SEQ ID NO 4
<211> LENGTH: 1388
<212> TYPE: DNA
<213> ORGANISM: Bacillus amyloliquefaciens

<400> SEQUENCE: 4

```
gacttcgggt gttacaaact ctcgtggtgt gacgggcggt gtgtacaagg cccgggaacg      60
tattcaccgc ggcatgctga tccgcgatta ctagcgattc cagcttcacg cagtcgagtt     120
gcagactgcg atccgaactg agaacagatt tgtgggattg gcttaacctc gcggtttcgc     180
tgcccttttgt tctgtccatt gtagcacgtg tgtagcccag gtcataaggg gcatgatgat    240
ttgacgtcat ccccaccttc ctccggtttg tcaccggcag tcaccttaga gtgcccaact    300
gaatgctggc aactaagatc aagggttgcg ctcgttgcgg gacttaaccc aacatctcac    360
gacacgagct gacgacaacc atgcaccacc tgtcactctg ccccgaagg ggacgtccta     420
tctctaggat tgtcagagga tgtcaagacc tggtaaggtt cttcgcgttg cttcgaatta    480
aaccacatgc tccaccgctt gtgcgggccc ccgtcaattc ctttgagttt cagtcttgcg    540
accgtactcc ccaggcggag tgcttaatgc gttagctgca gcactaaggg gcggaaaccc    600
cctaacactt agcactcatc gtttacggcg tggactacca gggtatctaa tcctgttcgc    660
tccccacgct ttcgctcctc agcgtcagtt acagaccaga gagtcgcctt cgccactggt    720
gttcctccac atctctacgc atttcaccgc tacacgtgga attccactct cctcttctgc    780
actcaagttc cccagtttcc aatgaccctc cccggttgag ccggggcctt cacatcaga    840
cttaagaaac cgcctgcgag ccctttacgc ccaataattc cggacaacgc ttgccaccta    900
cgtattaccg cggctgctgg cacgtagtta gccgtggctt tctggttagg taccgtcaag    960
gtgccgccct atttgaacgg cacttgttct tccctaacaa cagagcttta cgatccgaaa   1020
accttcatca ctcacgcggc gttgctccgt cagactttcg tccattgcgg aagattccct   1080
actgctgcct cccgtaggag tctgggccgt gtctcagtcc cagtgtggcc gatcaccctc   1140
tcaggtcggc tacgcatcgt tgccttggtg agccgttacc tcaccaacta gctaatgcgc   1200
cgcgggtcca tctgtaagtg gtagccgaag ccaccttta tgtctgaacc atgcggttca    1260
aacaaccatc cggtattagc cccggtttcc cggagttatc ccagtcttac aggcaggtta    1320
cccacgtgtt actcacccgt ccgccgctaa catcagggag caagctccca tctgtccgct   1380
cgactgca                                                             1388
```

<210> SEQ ID NO 5
<211> LENGTH: 1388
<212> TYPE: DNA
<213> ORGANISM: Bacillus amyloliquefaciens

<400> SEQUENCE: 5

```
gacttcgggt gttacaaact ctcgtggtgt gacgggcggt gtgtacaagg cccgggaacg      60
tattcaccgc ggcatgctga tccgcgatta ctagcgattc cagcttcacg cagtcgagtt     120
gcagactgcg atccgaactg agaacagatt tgtgggattg gcttaacctc gcggtttcgc     180
tgcccttttgt tctgtccatt gtagcacgtg tgtagcccag gtcataaggg gcatgatgat    240
ttgacgtcat ccccaccttc ctccggtttg tcaccggcag tcaccttaga gtgcccaact    300
gaatgctggc aactaagatc aagggttgcg ctcgttgcgg gacttaaccc aacatctcac    360
gacacgagct gacgacaacc atgcaccacc tgtcactctg ccccgaagg ggacgtccta     420
tctctaggat tgtcagagga tgtcaagacc tggtaaggtt cttcgcgttg cttcgaatta    480
aaccacatgc tccaccgctt gtgcgggccc ccgtcaattc ctttgagttt cagtcttgcg    540
accgtactcc ccaggcggag tgcttaatgc gttagctgca gcactaaggg gcggaaaccc    600
cctaacactt agcactcatc gtttacggcg tggactacca gggtatctaa tcctgttcgc    660
tccccacgct ttcgctcctc agcgtcagtt acagaccaga gagtcgcctt cgccactggt    720
```

```
gttcctccac atctctacgc atttcaccgc tacacgtgga attccactct cctcttctgc    780
actcaagttc cccagtttcc aatgaccctc cccggttgag ccgggggctt tcacatcaga    840
cttaagaaac cgcctgcgag ccctttacgc ccaataattc cggacaacgc ttgccaccta    900
cgtattaccg cggctgctgg cacgtagtta gccgtggctt tctggttagg taccgtcaag    960
gtgccgccct atttgaacgg cacttgttct tccctaacaa cagagcttta cgatccgaaa   1020
accttcatca ctcacgcggc gttgctccgt cagactttcg tccattgcgg aagattccct   1080
actgctgcct cccgtaggag tctgggccgt gtctcagtcc cagtgtggcc gatcaccctc   1140
tcaggtcggc tacgcatcgt tgccttggtg agccgttacc tcaccaacta gctaatgcgc   1200
cgcgggtcca tctgtaagtg gtagccgaag ccacctttta tgtctgaacc atgcggttca   1260
aacaaccatc cggtattagc cccggtttcc cggagttatc ccagtcttac aggcaggtta   1320
cccacgtgtt actcacccgt ccgccgctaa catcagggag caagctccca tctgtccgct   1380
cgactgca                                                            1388
```

<210> SEQ ID NO 6
<211> LENGTH: 1365
<212> TYPE: DNA
<213> ORGANISM: Paenibacillus alginolyticus

<400> SEQUENCE: 6

```
gcgggttacc cacaccgact tcgggtgttg taaactctcg tggtgtgacg ggcggtgtgt     60
acaagacccg ggaacgtatt caccgcggca tgctgatccg cgattactag caattccgac    120
ttcatgcagg cgagttgcag cctgcaatcc gaactgagat cggcttataa ggattcgctc    180
cacctcgcgg cttcgcttcc cgttgtaccg accattgtag tacgtgtgta gcccaggtca    240
taaggggcat gatgatttga cgtcatcccc accttcctcc ggtttgtcac cggcagtcat    300
cttagagtgc ccacccgaag tgctggcaac taagatcaag ggttgcgctc gttgcgggac    360
ttaacccaac atctcacgac acgagctgac gacaaccatg caccacctgt ctcggctgct    420
ccgaagaggg gcactatctc tagtgcttac accgggatgt caagacctgg taaggttctt    480
cgcgttgctt cgaattaaac cacatactcc actgcttgtg cgggtccccg tcaattcctt    540
tgagtttcac tcttgcgagc gtactcccca ggcggcatac ttactgtgtt aacttcggca    600
ccgagaaatc gaatccccga cacctagtat gcatcgttta cggcgtggac taccagggta    660
tctaatcctg tttgctcccc acgctttcgc gcctcagcgt cagttatagg ccagaaagtc    720
gccttcgcca ctggtgttcc tccacatctc tacgcatttc accgctacac gtggaattcc    780
actttcctct cctacactca agtcaaccag ttttggatgc gaaccggggt tgagccccgg    840
gcttaaacac ccaacttaat taaccgcctg cgcgcgcttt acgcccaata attccggaca    900
acgcttgccc cctacgtatt accgcggctg ctggcacgta gttagccggg ctttcttct    960 cctataccgt cacacacaag gcagttactc ctcatgctgt tcgtctaggg caacagagct   1020
ttacgatccg aaaaccttca tcactcacgc ggcgttgctc cgtcagactt cgtccattg   1080 cggaagattc cctactgctg cctcccgtag gagtctgggc cgtgtctcag tcccagtgtg   1140
gccgttcacc ctctcaggtc ggctacgcat cgtcgccttg gtgagccgtt accccaccaa   1200
ctagctaatg cgccgcaggc ccatctatca gccacagatt gctccgtgtt tcataattct   1260
ctcatgcgag aaaaccagtt atccggtctt agctatcgtt tccgatagtt atcccgatct   1320
gataggcagg ttacctacgt gttactcacc cgtccgccgc taagc                   1365
```

<210> SEQ ID NO 7
<211> LENGTH: 1388
<212> TYPE: DNA
<213> ORGANISM: Paenibacillus alginolyticus

<400> SEQUENCE: 7

| | | | | | |
|---|---|---|---|---|---|
| ctcccttgcg | ggttacccca | ccgacttcgg | gtgttgtaaa | ctctcgtggt | gtgacgggcg | 60 |
| gtgtgtacaa | gacccgggaa | cgtattcacc | gcggcatgct | gatccgcgat | tactagcaat | 120 |
| tccgacttca | tgcaggcgag | ttgcagcctg | caatccgaac | tgagatcggc | ttataaggat | 180 |
| tcgctccacc | tcgcggcttc | gcttcccgtt | gtaccgacca | ttgtagtacg | tgtgtagccc | 240 |
| aggtcataag | gggcatgatg | atttgacgtc | atccccacct | tcctccggtt | tgtcaccggc | 300 |
| agtcatctta | gagtgcccac | ccgaagtgct | ggcaactaag | atcaagggtt | gcgctcgttg | 360 |
| cgggacttaa | cccaacatct | cacgacacga | gctgacgaca | accatgcacc | acctgtctcc | 420 |
| tatgctccga | gagggcccc | tatctctagg | ggttacatcg | ggatgtcaag | acctggtaag | 480 |
| gttcttcgcg | ttgcttcgaa | ttaaaccaca | tactccactg | cttgtgcggg | tccccgtcaa | 540 |
| ttcctttgag | tttcactctt | gcgagcgtac | tccccaggcg | gcatacttac | tgtgttaact | 600 |
| tcggcaccga | gaaatcgaat | ccccgacacc | tagtatgcat | cgtttacggc | gtggactacc | 660 |
| agggtatcta | atcctgtttg | ctccccacgc | tttcgcgcct | cagcgtcagt | tataggccag | 720 |
| aaagtcgcct | tcgccactgg | tgttcctcca | catctctacg | catttcaccg | ctacacgtgg | 780 |
| aattccactt | tcctctccta | cactcaagtc | aaccagtttt | ggatgcgaac | cggggttgag | 840 |
| ccccgggctt | aaacacccaa | cttaattaac | cgcctgcgcg | cgcttacgc | ccaataattc | 900 |
| cggacaacgc | ttgccccta | cgtattaccg | cggctgctgg | cacgtagtta | gccggggctt | 960 |
| tcttctccta | taccgtcaca | cacaaggcag | ttactcctca | tgctgttcgt | ctagggcaac | 1020 |
| agagctttac | gatccgaaaa | ccttcatcac | tcacgcggcg | ttgctccgtc | agacttgcgt | 1080 |
| ccattgcgga | agattcccta | ctgctgcctc | ccgtaggagt | ctgggccgtg | tctcagtccc | 1140 |
| agtgtggccg | ttcaccctct | caggtcggct | acgcatcgtc | gccttggtga | gccgttaccc | 1200 |
| caccaactag | ctaatgcgcc | gcaggcccat | ctatcagcca | cagattgctc | cgtgtttcat | 1260 |
| aattctctca | tgcgagaaaa | ccagttatcc | ggtcttagct | atcgtttccg | atagttatcc | 1320 |
| cgatctgata | ggcaggttac | ctacgtgtta | ctcacccgtc | cgccgctaag | cattccccga | 1380 |
| aggaaata | | | | | 1388 |

<210> SEQ ID NO 8
<211> LENGTH: 1357
<212> TYPE: DNA
<213> ORGANISM: Paenibacillus alginolyticus

<400> SEQUENCE: 8

| | | | | | |
|---|---|---|---|---|---|
| ttgcgggtta | ccccaccgac | ttcgggtgtt | gtaaactctc | gtggtgtgac | gggcggtgtg | 60 |
| tacaagaccc | gggaacgtat | tcaccgcggc | atgctgatcc | gcgattacta | gcaattccga | 120 |
| cttcatgcag | gcgagttgca | gcctgcaatc | cgaactgaga | tcggcttata | aggattcgct | 180 |
| ccacctcgcg | gcttcgcttc | cgttgtacc | gaccattgta | gtacgtgtgt | agcccaggtc | 240 |
| ataaggggca | tgatgatttg | acgtcatccc | caccttcctc | cggtttgtca | ccggcagtca | 300 |
| tcttagagtg | cccaccccgaa | gtgctggcaa | ctaagatcaa | gggttgcgct | cgttgcggga | 360 |
| cttaacccaa | catctcacga | cacgagctga | cgacaaccat | gcaccacctg | tctcgggtgc | 420 |
| tccgaagagg | ggcactatct | ctagggctta | cacagggatg | tcaagacctg | gtaaggttct | 480 |

```
tcgcgttgct tcgaattaaa ccacatactc cactgcttgt gcgggtcccc gtcaattcct    540
ttgagtttca ctcttgcgag cgtactcccc aggcggcata cttactgtgt taacttcggc    600
accgagaaat cgaatcccg acacctagta tgcatcgttt acggcgtgga ctaccagggt     660
atctaatcct gtttgctccc cacgctttcg cgcctcagcg tcagttatag ccagaaagt     720 cgccttcgcc actggtgttc ctccacatct ctacgcattt caccgctaca cgtggaattc    780
cactttcctc tcctacactc aagtcaacca gttttggatg cgaaccgggg ttgagccccg    840
ggcttaaaca cccaacttaa ttaaccgcct gcgcgcgctt tacgcccaat aattccggac    900
aacgcttgcc ccctacgtat taccgcggct gctggcacgt agttagccgg ggctttcttc    960
tcctataccg tcacacacaa ggcagttact cctcatgctg ttcgtctagg caacagagc    1020 tttacgatcc gaaaaccttc atcactcacg cggcgttgct ccgtcagact tgcgtccatt   1080
gcggaagatt ccctactgct gcctcccgta ggagtctggg ccgtgtctca gtcccagtgt   1140
ggccgttcac cctctcaggt cggctacgca tcgtcgcctt ggtgagccgt taccccacca   1200
actagctaat gcgccgcagg cccatctatc agccacagat tgctccgtgt ttcataattc   1260
tctcatgcga gaaaaccagt tatccggtct tagctatcgt ttccgatagt tatcccgatc   1320
tgataggcag gttacctacg tgttactcac ccgtccg                            1357
```

<210> SEQ ID NO 9
<211> LENGTH: 1396
<212> TYPE: DNA
<213> ORGANISM: Paenibacillus alginolyticus
<220> FEATURE:
<221> NAME/KEY: misc_feature
<222> LOCATION: (1379)..(1396)
<223> OTHER INFORMATION: n is a, c, g, or t

<400> SEQUENCE: 9

```
cttagcggcg gacgggtgag taacacgtag gtaacctgcc tatcagatcg ggataactat     60
cggaaacgat agctaagacc ggataactgg ttttctcgca tgagagaatt atgaaacacg    120
gagcaatctg tggctgatag atgggcctgc ggcgcattag ctagttggtg gggtaacggc    180
tcaccaaggc gacgatgcgt agccgacctg agagggtgaa cggccacact gggactgaga    240
cacggcccag actcctacgg gaggcagcag tagggaatct tccgcaatgg acgcaagtct    300
gacggagcaa cgccgcgtga gtgatgaagg ttttcggatc gtaaagctct gttgccctag    360
acgaacagca tgaggagtaa ctgccttgtg tgtgacggta taggagaaga agcccccggc    420
taactacgtg ccagcagccg cggtaatacg taggggggcaa gcgttgtccg gaattattgg    480
gcgtaaagcg cgcgcaggcg gttaattaag ttgggtgttt aagcccgggg ctcaaccccg    540
gttcgcatcc aaaactggtt gacttgagtg taggagagga agtggaatt ccacgtgtag    600 cggtgaaatg cgtagagatg tggaggaaca ccagtggcga aggcgacttt ctggcctata    660
actgacgctg aggcgcgaaa gcgtggggag caaacaggat tagataccct ggtagtccac    720
gccgtaaacg atgcatacta ggtgtcgggg attcgatttc tcggtgccga agttaacaca    780
gtaagtatgc cgcctgggga gtacgctcgc aagagtgaaa ctcaaaggaa ttgacgggga    840
cccgcacaag cagtggagta tgtggtttaa ttcgaagcaa cgcgaagaac cttaccaggt    900
cttgacatcc cgatgtaacc cctagagata ggcgccctct tcggagcatc cgagacaggt    960
ggtgcatggt tgtcgtcagc tcgtgtcgtg agatgttggg ttaagtcccg caacgagcgc   1020 aaccccttgat cttagttgcc agcacttcgg gtgggcactc taagatgact gccggtgaca   1080
```

| | |
|---|---|
| aaccggagga aggtggggat gacgtcaaat catcatgccc cttatgacct gggctacaca | 1140 |
| cgtactacaa tggtcggtac aacgggaagc gaagccgcga ggtggagcga atccttataa | 1200 |
| gccgatctca gttcggattg caggctgcaa ctcgcctgca tgaagtcgga attgctagta | 1260 |
| atcgcggatc agcatgccgc ggtgaatacg ttcccgggtc ttgtacacac cgcccgtcac | 1320 |
| accacgagag tttacaacac ccgaagtcgg tggggtaacc gcaagggag ccagccgcnn | 1380 |
| nnnnnnnnnn nnnnn | 1396 |

```
<210> SEQ ID NO 10
<211> LENGTH: 525
<212> TYPE: DNA
<213> ORGANISM: Unknown
<220> FEATURE:
<223> OTHER INFORMATION: Orbilia auricolor/Arthrobotrys oligospora

<400> SEQUENCE: 10
```

| | |
|---|---|
| gggtaggttt tgttcaggcc gtacctgttc aactttcacct tgaacaagca gtgttttttac | 60 |
| tatgttctgg tttgggctga acggccagca gagcttacaa ctttgaaacc ggctcggttc | 120 |
| tcaccggagc aggttcatga ccagcagtca agctgagggt tgtaatgacg ctcaaacaga | 180 |
| catgcccaaa ggaataccaa tgggcgcaat gtgcgttcaa agactcgatg attcactgaa | 240 |
| ttctgcaatt cacattaact atcgcgtttc gctgcgttct tcatcgatgg gggaaccaag | 300 |
| agatccgttg ttgaaagttt tgattttcat tcgaaaattt ggttatcaga caatgttttg | 360 |
| acaacaggtt ttgaaggttg gtgctagcgg caggctgaca ggcggtgaag cccagctgcc | 420 |
| gaagcgaaaa ggttttttgg ttcacaaagg gtagaccagt cagcgacccg agggccaccg | 480 |
| agcaggtaga aagtgatttc tcactctttg gtaatgatcc ttccg | 525 |

```
<210> SEQ ID NO 11
<211> LENGTH: 1403
<212> TYPE: DNA
<213> ORGANISM: Bacillus pumilus

<400> SEQUENCE: 11
```

| | |
|---|---|
| taaaggttac ctcaccgact tcgggtgttg caaactctcg tggtgtgacg ggcggtgtgt | 60 |
| acaaggcccg ggaacgtatt caccgcggca tgctgatccg cgattactag cgattccagc | 120 |
| ttcacgcagt cgagttgcag actgcgatcc gaactgagaa cagatttatg ggattggcta | 180 |
| aaccttgcgg tctcgcagcc ctttgttctg tccattgtag cacgtgtgta gcccaggtca | 240 |
| taagggcat gatgatttga cgtcatcccc accttcctcc ggtttgtcac cggcagtcac | 300 |
| cttagagtgc ccaactaaat gctggcaact aagatcaagg gttgcgctcg ttgcgggact | 360 |
| taacccaaca tctcacgaca cgagctgacg acaaccatgc accacctgtc actctgtccc | 420 |
| cgaagggaaa gccctatctc tagggttgtc agaggatgtc aagacctggt aaggttcttc | 480 |
| gcgttgcttc gaattaaacc acatgctcca ccgcttgtgc gggcccccgt caattccttt | 540 |
| gagtttcagt cttgcgaccg tactccccag gcggagtgct taatgcgtta gctgcagcac | 600 |
| taagggcgg aaacccccta acacttagca ctcatcgttt acggcgtgga ctaccagggt | 660 |
| atctaatcct gttcgctccc cacgctttcg ctcctcagcg tcagttacag accagagagt | 720 |
| cgccttcgcc actggtgttc ctcccacatct ctacgcattt caccgctaca cgtggaattc | 780 |
| cactctcctc ttctgcactc aagtttccca gtttccaatg accctcccg gttgagccgg | 840 |
| gggctttcac atcagactta agaaaccgcc tgcgagccct ttacgcccaa taattccgga | 900 |
| caacgcttgc cacctacgta ttaccgcggc tgctggcacg tagttagccg tggctttctg | 960 |

```
gttaggtacc gtcaaggtgc gagcagttac tctcgcactt gttcttccct aacaacagag    1020
ctttacgatc cgaaaacctt catcactcac gcggcgttgc tccgtcagac tttcgtccat    1080
tgcggaagat ccctactgc tgcctcccgt aggagtctgg gccgtgtctc agtcccagtg    1140
tggccgatca ccctctcagg tcggctacgc atcgtcgcct tggtgagcca ttaccccacc    1200
aactagctaa tgcgccgcgg gtccatctgt aagtgacagc cgaaaccgtc tttcatcctt    1260
gaaccatgcg gttcaaggaa ctatccggta ttagctccgg tttcccggag ttatcccagt    1320
cttacaggca ggttacccac gtgttactca cccgtccgcc gctaacatcc gggagcaagc    1380
tcccttctgt ccgctcgact gca                                             1403

<210> SEQ ID NO 12
<211> LENGTH: 1388
<212> TYPE: DNA
<213> ORGANISM: Lysinibacillus fusiformis
<220> FEATURE:
<221> NAME/KEY: misc_feature
<222> LOCATION: (1388)..(1388)
<223> OTHER INFORMATION: n is a, c, g, or t

<400> SEQUENCE: 12
gagaaggagc ttgctccttc gacgttagcg gcggacgggt gagtaacacg tgggcaacct      60
accttatagt ttgggataac tccgggaaac cggggctaat accgaataat ctgtttcacc     120
tcatggtgaa acactgaaag acggtttcgg ctgtcgctat aggatgggcc cgcggcgcat     180
tagctagttg gtgaggtaac ggctcaccaa ggcgacgatg cgtagccgac ctgagagggt     240
gatcggccac actgggactg agacacggcc cagactccta cgggaggcag cagtagggaa     300
tcttccacaa tgggcgaaag cctgatggag caacgccgcg tgagtgaaga aggatttcgg     360
ttcgtaaaac tctgttgtaa gggaagaaca agtacagtag taactggctg taccttgacg     420
gtaccttatt agaaagccac ggctaactac gtgccagcag ccgcggtaat acgtaggtgg     480
caagcgttgt ccggaattat tgggcgtaaa gcgcgcgcag gtggtttctt aagtctgatg     540
tgaaagccca cggctcaacc gtggagggtc attggaaact gggagacttg agtgcagaag     600
aggatagtgg aattccaagt gtagcggtga atgcgtaga gatttggagg aacaccagtg     660
gcgaaggcga ctatctggtc tgtaactgac actgaggcgc gaaagcgtgg ggagcaaaca     720
ggattagata ccctggtagt ccacgccgta acgatgagt gctaagtgtt aggggggtttc    780 cgccccttag tgctgcagct aacgcattaa gcactccgcc tggggagtac ggtcgcaaga     840
ctgaaactca aaggaattga cggggggcccg cacaagcggt ggagcatgtg gtttaattcg     900
aagcaacgcg aagaacctta ccaggtcttg acatcccgtt gaccactgta gagatatagt     960
ttccccttcg ggggcaacgg tgacaggtgg tgcatggttg tcgtcagctc gtgtcgtgag    1020
atgttgggtt aagtcccgca acgagcgcaa cccttgatct tagttgccat catttagttg    1080
ggcactctaa ggtgactgcc ggtgacaaac cggaggaagg tggggatgac gtcaaatcat    1140
catgcccctt atgacctggg ctacacacgt gctacaatgg acgatacaaa cggttgccaa    1200
ctcgcgagag ggagctaatc cgataaagtc gttctcagtt cggattgtag gctgcaactc    1260
gcctacatga agccggaatc gctagtaatc gcggatcagc atgccgcggt gaatacgttc    1320
ccgggccttg tacacaccgc ccgtcacacc acgagagttt gtaacacccg aagtcggtga    1380 ggtaaccn                                                              1388

<210> SEQ ID NO 13
```

```
<211> LENGTH: 1385
<212> TYPE: DNA
<213> ORGANISM: Bacillus methylotrophicus
<220> FEATURE:
<221> NAME/KEY: misc_feature
<222> LOCATION: (1319)..(1319)
<223> OTHER INFORMATION: n is a, c, g, or t

<400> SEQUENCE: 13
taaaggttac ctcaccgact tcgggtgtta caaactctcg tggtgtgacg ggcggtgtgt      60
acaaggcccg ggaacgtatt caccgcggca tgctgatccg cgattactag cgattccagc     120
ttcacgcagt cgagttgcag actgcgatcc gaactgagaa cagatttgtg ggattggctt     180
aacctcgcgg tttcgctgcc ctttgttctg tccattgtag cacgtgtgta gcccaggtca     240
taagggcat gatgatttga cgtcatcccc accttcctcc ggtttgtcac cggcagtcac      300
cttagagtgc ccaactgaat gctggcaact aagatcaagg gttgcgctcg ttgcgggact     360
taacccaaca tctcacgaca cgagctgacg acaaccatgc accacctgtc actctgcccc     420
cgaaggggac gtcctatctc taggattgtc agaggatgtc aagacctggt aaggttcttc     480
gcgttgcttc gaattaaacc acatgctcca ccgcttgtgc gggcccccgt caattccttt     540
gagtttcagt cttgcgaccg tactccccag gcggagtgct taatgcgtta gctgcagcac     600
taagggcgg aaacccccta acacttagca ctcatcgttt acggcgtgga ctaccagggt      660
atctaatcct gttcgctccc cacgctttcg ctcctcagcg tcagttacag accagagagt     720
cgccttcgcc actggtgttc ctccacatct ctacgcattt caccgctaca cgtggaattc     780
cactctcctc ttctgcactc aagttcccca gtttccaatg accctccccg ttgagccgg     840
gggctttcac atcagactta agaaaccgcc tgcgagccct ttacgcccaa taattccgga     900
caacgcttgc cacctacgta ttaccgcggc tgctggcacg tagttagccg tggctttctg     960
gttaggtacc gtcaaggtgc cgccctattt gaacggcact tgttcttccc taacaacaga   1020
gctttacgat ccgaaaacct tcatcactca cgcggcgttg ctccgtcaga ctttcgtcca   1080
ttgcggaaga ttccctactg ctgcctcccg taggagtctg ggccgtgtct cagtcccagt   1140
gtggccgatc accctctcag gtcggctacg catcgtcgcc ttggtgagcc gttacctcac   1200
caactagcta atgcgccgcg gtccatctg taagtggtag ccgaagccac cttttatgtc    1260
tgaaccatgc ggttcaaaca accatccggt attagcccg gtttcccgga gttatcccng    1320
tcttacaggc aggttaccca cgtgttactc acccgtccgc cgctaacatc agggagcaag   1380
ctccc                                                               1385

<210> SEQ ID NO 14
<211> LENGTH: 1374
<212> TYPE: DNA
<213> ORGANISM: Bacillus amyloliquefaciens

<400> SEQUENCE: 14
cagatgggag cttgctccct gatgttagcg gcggacgggt gagtaacacg tgggtaacct      60
gcctgtaaga ctgggataac tccgggaaac cggggctaat accggatgct tgtttgaacc     120
gcatggttca gacataaaag gtggcttcgg ctaccactta cagatggacc cgcggcgcat     180
tagctagttg gtgaggtaac ggctcaccaa ggcgacgatg cgtagccgac ctgagagggt     240
gatcggccac actgggactg agacacggcc cagactccta cgggaggcag cagtagggaa    300
tcttccgcaa tggacgaaag tctgacggag caacgccgcg tgagtgatga aggttttcgg    360
atcgtaaagc tctgttgtta gggaagaaca agtgccgttc aaatagggcg gcaccttgac    420
```

-continued

```
ggtacctaac cagaaagcca cggctaacta cgtgccagca gccgcggtaa tacgtaggtg    480
gcaagcgttg tccggaatta ttgggcgtaa agggctcgca ggcggtttct taagtctgat    540
gtgaaagccc ccggctcaac cggggagggt cattggaaac tggggaactt gagtgcagaa    600
gaggagagtg gaattccacg tgtagcggtg aaatgcgtag agatgtggag gaacaccagt    660
ggcgaaggcg actctctggt ctgtaactga cgctgaggag cgaaagcgtg gggagcgaac    720
aggattagat accctggtag tccacgccgt aaacgatgag tgctaagtgt taggggggttt    780 ccgccccctta gtgctgcagc taacgcatta agcactccgc ctggggagta cggtcgcaag    840
actgaaactc aaaggaattg acgggggccc gcacaagcgg tggagcatgt ggtttaattc    900
gaagcaacgc gaagaacctt accaggtctt gacatcctct gacaatccta gagataggac    960
gtccccttcg ggggcagagt gacaggtggt gcatggttgt cgtcagctcg tgtcgtgaga    1020
tgttgggtta agtcccgcaa cgagcgcaac ccttgatctt agttgccagc attcagttgg    1080
gcactctaag gtgactgccg gtgacaaacc ggaggaaggt ggggatgacg tcaaatcatc    1140 atgccccctta tgacctgggc tacacacgtg ctacaatgga cagaacaaag ggcagcgaaa    1200
ccgcgaggtt aagccaatcc cacaaatctg ttctcagttc ggatcgcagt ctgcaactcg    1260
actgcgtgaa gctggaatcg ctagtaatcg cggatcagca tgccgcggtg aatacgttcc    1320
cgggccttgt acacaccgcc cgtcacacca cgagagtttg taacacccga agtc          1374
```

<210> SEQ ID NO 15
<211> LENGTH: 960
<212> TYPE: DNA
<213> ORGANISM: Bacillus tequilensis
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (898)..(898)
<223> OTHER INFORMATION: n is a, c, g, or t
<220> FEATURE:
<221> NAME/KEY: misc_feature
<222> LOCATION: (944)..(945)
<223> OTHER INFORMATION: n is a, c, g, or t
<220> FEATURE:
<221> NAME/KEY: misc_feature
<222> LOCATION: (947)..(950)
<223> OTHER INFORMATION: n is a, c, g, or t

<400> SEQUENCE: 15

```
ggttacctca ccgacttcgg gtgttacaaa ctctcgtggt gtgacgggcg gtgtgtacaa     60
ggcccgggaa cgtattcacc gcggcatgct gatccgcgat tactagcgat tccagcttca    120
cgcagtcgag ttgcagactg cgatccgaac tgagaacaga tttgtgggat tggcttaacc    180
tcgcggtttc gctgccctttt gttctgtcca ttgtagcacg tgtgtagccc aggtcataag    240
gggcatgatg atttgacgtc atccccacct tcctccggtt tgtcaccggc agtcacctta    300
```

```
gagtgcccaa ctgaatgctg caactaaga tcaagggttg cgctcgttgc gggacttaac      360
ccaacatctc acgacacgag ctgacgacaa ccatgcacca cctgtcactc tgccccgaa      420 ggggacgtcc tatctctagg attgtcagag gatgtcaaga cctggtaagg ttcttcgcgt      480
tgcttcgaat taaaccacat gctccaccgc ttgtgcgggc ccccgtcaat tcctttgagt      540
ttcagtcttg cgaccgtact ccccaggcgg agtgcttaat gcgttagctg cagcactaag      600
gggcggaaac cccctaacac ttagcactca tcgtttacgg cgtggactac cagggtatct      660
aatcctgttc gctccccacg ctttcgctcc tcagcgtcag ttacagacca gagagtcgcc      720
ttcgccactg gtgttcctcc acatctctac gcanttcacc gctacacgtg gaattccact      780
ctcctcttnc tgcactcaag ttccccagtt tccaatgacc ctccccggtt gagccggggg      840
ctttcacatc agacttaana aaccgcctgc gagcccttta cncccaataa ttccgganaa      900
cgctggccac ctacgtatta ccgcggctgc tggcacgtag tttnncnnnn cctttctggt      960
```

<210> SEQ ID NO 16
<211> LENGTH: 903
<212> TYPE: DNA
<213> ORGANISM: Bacillus megaterium
<220> FEATURE:
<221> NAME/KEY: misc_feature
<222> LOCATION: (659)..(660)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t
<220> FEATURE:
<221> NAME/KEY: misc_feature
<222> LOCATION: (686)..(686)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (737)..(737)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t
<220> FEATURE:
<221> NAME/KEY: misc_feature
<222> LOCATION: (805)..(807)
<223> OTHER INFORMATION: n is a, c, g, or t
<220> FEATURE:
<221> NAME/KEY: misc_feature
<222> LOCATION: (811)..(811)
<223> OTHER INFORMATION: n is a, c, g, or t
<220> FEATURE:
<221> NAME/KEY: misc_feature
<222> LOCATION: (814)..(817)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t -continued

```
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (827)..(828)
<223> OTHER INFORMATION: n is a, c, g, or t
<220> FEATURE:
<221> NAME/KEY: misc_feature
<222> LOCATION: (833)..(833)
<223> OTHER INFORMATION: n is a, c, g, or t
<220> FEATURE:
<221> NAME/KEY: misc_feature
<222> LOCATION: (837)..(838)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (842)..(842)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (851)..(851)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (856)..(857)
<223> OTHER INFORMATION: n is a, c, g, or t
<220> FEATURE:
<221> NAME/KEY: misc_feature
<222> LOCATION: (860)..(860)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (870)..(873)
<223> OTHER INFORMATION: n is a, c, g, or t
<220> FEATURE:
<221> NAME/KEY: misc_feature
<222> LOCATION: (875)..(875)
<223> OTHER INFORMATION: n is a, c, g, or t
<220> FEATURE:
<221> NAME/KEY: misc_feature
<222> LOCATION: (878)..(878)
<223> OTHER INFORMATION: n is a, c, g, or t
<220> FEATURE:
<221> NAME/KEY: misc_feature
<222> LOCATION: (880)..(880)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (887)..(887)
<223> OTHER INFORMATION: n is a, c, g, or t
<220> FEATURE:
<221> NAME/KEY: misc_feature
<222> LOCATION: (889)..(889)
```

```
<223> OTHER INFORMATION: n is a, c, g, or t
<220> FEATURE:
<221> NAME/KEY: misc_feature
<222> LOCATION: (891)..(892)
<223> OTHER INFORMATION: n is a, c, g, or t
<220> FEATURE:
<221> NAME/KEY: misc_feature
<222> LOCATION: (895)..(898)
<223> OTHER INFORMATION: n is a, c, g, or t
<220> FEATURE:
<221> NAME/KEY: misc_feature
<222> LOCATION: (902)..(903)
<223> OTHER INFORMATION: n is a, c, g, or t

<400> SEQUENCE: 16
tggtgtgacg ggcggtgtgt acaaggcccg ggaacgtatt caccgcggca tgctgatccg     60
cgattactag cgattccagc ttcatgtagg cgagttgcag cctacaatcc gaactgagaa    120
tggttttatg ggattggctt gacctcgcgg tcttgcagcc ctttgtacca tccattgtag    180
cacgtgtgta gcccaggtca taaggggcat gatgatttga cgtcatcccc accttcctcc    240
ggtttgtcac cggcagtcac cttagagtgc ccaactaaat gctggcaact aagatcaagg    300
gttgcgctcg ttgcgggact taacccaaca tctcacgaca cgagctgacg acaaccatgc    360
accacctgtc actctgtccc ccgaagggga acgctctatc tctagagttg tcagaggatg    420
tcaagacctg gtaaggttct tcgcgttgct tcgaattaaa ccacatgctc caccgcttgt    480 gcgggcccc  gtcaattcct ttgagtttca gtcttgcgac cgtactcccc aggcggagtg    540
cttaatgcgt tagctgcagc actaagggc  ggaaaccctc taacacttag cactcatcgt    600
ttacggcgtg gactaccagg gtatctaatc ctgtttgctc cccacgcttt cgcgcctcnn    660
gtcagttaca gaccaaaaag ccnccntcgc cactggtgtt cntccncatc tctacgcatt    720
tcaccgctac acgtggnaat tccgcttttc tcttctgcac tcaagttccc cagttttccan    780 tgaccctnca cggtnagccg tgggnnnttc ncannnnant taanaanncg ccngcgnncn    840
cntttacncc natnannccn ganaacgctn nnnanccnan gnantancng nnggnnnntg    900 gnn                                                                   903

<210> SEQ ID NO 17
<211> LENGTH: 1363
<212> TYPE: DNA
<213> ORGANISM: Paenibacillus taichungensis

<400> SEQUENCE: 17
gtgagtaaca cgtaggcaac ctgccctcaa gtttgggaca actaccggaa acggtagcta     60
ataccgaata gttgttttct tctcctgaag agaactggaa agacggagca atctgtcact    120
tggggatggg cctgcggcgc attagctagt tggtggggta acggctcacc aaggcgacga    180
tgcgtagccg acctgagagg gtgatcggcc acactgggac tgagacacgg cccagactcc    240
tacgggaggc agcagtaggg aatcttccgc aatgggcgaa agcctgacgg agcaatgccg    300
cgtgagtgat gaaggttttc ggatcgtaaa gctctgttgc cagggaagaa cgcttgggag    360
agtaactgct ctcaaggtga cggtacctga aagaaagcc  ccggctaact acgtgccagc    420
agccgcggta atacgtaggg ggcaagcgtt gtccggaatt attgggcgta aagcgcgcgc    480
aggcggtcat ttaagtctgg tgtttaatcc cggggctcaa ccccggatcg cactggaaac    540
tgggtgactt gagtgcagaa gaggagagtg gaattccacg tgtagcggtg aaatgcgtag    600
atatgtggag gaacaccagt ggcgaaggcg actctctggg ctgtaactga cgctgaggcg    660
cgaaagcgtg gggagcaaac aggattagat accctggtag tccacgccgt aaacgatgag    720
```

```
tgctaggtgt tagggtttc gatacccttg gtgccgaagt taacacatta agcactccgc    780
ctggggagta cggtcgcaag actgaaactc aaaggaattg acggggaccc gcacaagcag    840
tggagtatgt ggtttaattc gaagcaacgc gaagaacctt accaggtctt gacatccctc    900
tgatcggtac agagatgtat ctttccttcg gacagagga gacaggtggt gcatggttgt    960
cgtcagctcg tgtcgtgaga tgttgggtta agtcccgcaa cgagcgcaac ccttgatctt   1020
agttgccagc atttcggatg ggcactctaa ggtgactgcc ggtgacaaac cggaggaagg   1080
tggggatgac gtcaaatcat catgcccctt atgacctggg ctacacacgt actacaatgg   1140
ccggtacaac gggctgtgaa gccgcgaggt ggaacgaatc ctaaaaagcc ggtctcagtt   1200
cggattgcag gctgcaactc gcctgcatga agtcggaatt gctagtaatc gcggatcagc   1260
atgccgcggt gaatacgttc ccgggtcttg tacacaccgc ccgtcacacc acgagagttt   1320
ataacacccg aagtcggtgg ggtaaccgca aggagccagc cgc                    1363
```

<210> SEQ ID NO 18
<211> LENGTH: 1363
<212> TYPE: DNA
<213> ORGANISM: Paenibacillus ehimensis
<220> FEATURE:
<221> NAME/KEY: misc_feature
<222> LOCATION: (72)..(73)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (195)..(196)
<223> OTHER INFORMATION: n is a, c, g, or t
<220> FEATURE:
<221> NAME/KEY: misc_feature
<222> LOCATION: (231)..(232)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (417)..(418)
<223> OTHER INFORMATION: n is a, c, g, or t
<220> FEATURE:
<221> NAME/KEY: misc_feature
<222> LOCATION: (456)..(457)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t

<400> SEQUENCE: 18

```
acttcgggtg ttgtaaactc tcgtggtgtg acgggcggtg tgtacaagac ccgggaacgt     60
attcaccgcg gnntgctgat ccgcgattac tagcaattcc gacttcatgc aggcgagttg    120
cagcntgcaa tccgaactga gaccggcttc taaagattcg ctccatctcg cgacttcnct    180
tcccgttgta ccggnnattg tagtacgtgt gtagcccagg tcataagggg nntgatgatt    240
tgacgtcatc cccaccttcc tccggtttgt caccggcagt catcctagag tgcccgcctt    300
tacgcgctgg caactagcat caagggttgc gctcgttgcg ggacttaacc caacatctca    360
```

```
cgacacgagc tgacgacanc catgcaccac ctgtctcctc tgtcccgaag gcctacnnta      420
tctctaacgt attcagaggg atgtcaagac ctggtnnggt tcttcgcgtt gcttcgaatt      480
aaaccacata ctccactgct tgtgcgggtc cccgtcaatt cctttgagtt tcactcttgc      540
gagcgtactc cccaggcgga gtgcttactg tgtttacttc ggcaccgagg gtatcgaaac      600
ccccaacacc tagcactcat cgtttacggc gtggactacc agggtatcta atcctgtttg      660
ctccccacgc tttcgcgcct cagcgtcagt tacaggccag aaagccgcct tcgccactgg      720
tgttcctcca catctctacg catttcaccg ctacacgtgg aattccgctt tcctctcctg      780
cactcaagcc gtccagtttc aatgcgaac cggggttgag cccgggctt aaacatcaga       840 cttaaacagc cgcctgcgcg cgctttacgc ccaataattc cggacaacgc ttgncccct      900 acgtattacc gcggctgctg gcacgtagtt agccggggct ttcttctcct ataccgtcac      960
acgaagagca gttactctcc tcgctgttcg tctagggcaa cagagcttta cgatccgaaa     1020
accttcatca ctcacgcggc gttgctccgt cagacttgcg tccattgcgg aagattccct     1080
actgctgcct cccgtaggag tctgggccgt gtctcagtcc cagtgtggcc gatcaccctc     1140
tcaggtcggc tacgcatcgt cgcctaggtg agccgttacc ccacctacta gctaatgcgc     1200
cgcaggccca tctgtaagcc acaggttgcc ccgtgtttct tgattccctc atgcgagaaa     1260
accacttatc cggtcttagc taccgttcc ggtagttatc ccgatcttac aggcaggttg     1320
cctacgtgtt actcacccgt ccgccgctaa ccatccccga agg                       1363
```

<210> SEQ ID NO 19
<211> LENGTH: 1422
<212> TYPE: DNA
<213> ORGANISM: Paenibacillus illinoisensis
<220> FEATURE:
<221> NAME/KEY: misc_feature
<222> LOCATION: (27)..(27)
<223> OTHER INFORMATION: n is a, c, g, or t

<400> SEQUENCE: 19

```
cggcggctgg ctccttgcgg ttacccnacc gacttcgggt gttataaact ctcgtggtgt       60
gacgggcggt gtgtacaaga cccgggaacg tattcaccgc ggcatgctga tccgcgatta      120
ctagcaattc cgacttcatg caggcgagtt gcagcctgca atccgaactg agaccggctt      180
tttaggattc gttccacctc gcggcttcac agcccgttgt accggccatt gtagtacgtg      240
tgtagcccag gtcataaggg gcatgatgat ttgacgtcat ccccaccttc ctccggtttg      300
tcaccggcag tcaccttaga gtgcccaccc gaagtgctgg caactaagat caagggttgc      360
gctcgttgcg ggacttaacc caacatctca cgacacgagc tgacgacaac catgcaccac      420
ctgtctcctc tgtcccgaag gaaagcccta tctctaggac ggtcagaggg atgtcaagac      480
ctggtaaggt tcttcgcgtt gcttcgaatt aaaccacata ctccactgct tgtgcgggtc      540
cccgtcaatt cctttgagtt tcagtcttgc gaccgtactc cccaggcgga atgcttaatg      600
tgttaacttc ggcaccaagg gtatcgaaac ccctaacacc tagcattcat cgtttacggc      660
gtggactacc agggtatcta atcctgtttg ctccccacgc tttcgcgcct cagcgtcagt      720
tacagcccag agagtcgcct tcgccactgg tgttcctcca catctctacg catttcaccg      780
ctacacgtgg aattccactc tcctcttctg cactcaagtc atccagtttc agtgcgatc      840 cggggttgag cccgggatt aaacaccaga cttaaatgac cgcctgcgcg cgctttacgc      900
ccaataattc cggacaacgc ttgccccta cgtattaccg cggctgctgg cacgtagtta      960 gccgggggctt tcttctcagg taccgtcact ccttgagcag ttactctcaa ggacgttctt    1020
```

```
ccctggcaac agagctttac gatccgaaaa ccttcatcac tcacgcggca ttgctccgtc   1080
aggctttcgc ccattgcgga agattcccta ctgctgcctc ccgtaggagt ctgggccgtg   1140
tctcagtccc agtgtggccg atcaccctct caggtcggct acgcatcgtc gccttggtga   1200
gccgttacct caccaactag ctaatgcgcc gcaggcccat cctcaagtga cagattgctc   1260
cgtctttcca gcttccttca ggcgaaggaa gcaagtattc ggtattagct accgtttccg   1320
gtagttgtcc caagcttgag ggcaggttgc ctacgtgtta ctcacccgtc cgccgctaac   1380
catcagagaa gcaagcttct cttcaagtcc gctcgacttg ca                      1422
```

<210> SEQ ID NO 20
<211> LENGTH: 1167
<212> TYPE: DNA
<213> ORGANISM: Microbacterium arabinogalactanolyticum
<220> FEATURE:
<221> NAME/KEY: misc_feature
<222> LOCATION: (899)..(899)
<223> OTHER INFORMATION: n is a, c, g, or t
<220> FEATURE:
<221> NAME/KEY: misc_feature
<222> LOCATION: (1052)..(1053)
<223> OTHER INFORMATION: n is a, c, g, or t
<220> FEATURE:
<221> NAME/KEY: misc_feature
<222> LOCATION: (1067)..(1067)
<223> OTHER INFORMATION: n is a, c, g, or t
<220> FEATURE:
<221> NAME/KEY: misc_feature
<222> LOCATION: (1104)..(1105)
<223> OTHER INFORMATION: n is a, c, g, or t
<220> FEATURE:
<221> NAME/KEY: misc_feature
<222> LOCATION: (1114)..(1115)
<223> OTHER INFORMATION: n is a, c, g, or t
<220> FEATURE:
<221> NAME/KEY: misc_feature
<222> LOCATION: (1121)..(1121)
<223> OTHER INFORMATION: n is a, c, g, or t
<220> FEATURE:
<221> NAME/KEY: misc_feature
<222> LOCATION: (1123)..(1124)
<223> OTHER INFORMATION: n is a, c, g, or t
<220> FEATURE:
<221> NAME/KEY: misc_feature
<222> LOCATION: (1127)..(1128)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1133)..(1133)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t
<220> FEATURE:
<221> NAME/KEY: misc_feature
<222> LOCATION: (1140)..(1142)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1150)..(1150)

```
<223> OTHER INFORMATION: n is a, c, g, or t
<220> FEATURE:
<221> NAME/KEY: misc_feature
<222> LOCATION: (1152)..(1156)
<223> OTHER INFORMATION: n is a, c, g, or t
<220> FEATURE:
<221> NAME/KEY: misc_feature
<222> LOCATION: (1158)..(1159)
<223> OTHER INFORMATION: n is a, c, g, or t
<220> FEATURE:
<221> NAME/KEY: misc_feature
<222> LOCATION: (1161)..(1162)
<223> OTHER INFORMATION: n is a, c, g, or t
<220> FEATURE:
<221> NAME/KEY: misc_feature
<222> LOCATION: (1165)..(1165)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t

<400> SEQUENCE: 20
caagggttag gccaccggct tcaggtgtta ccgactttca tgacttgacg ggcggtgtgt      60
acaagacccg ggaacgtatt caccgcagcg ttgctgatct gcgattacta gcgactccga     120
cttcatgagg tcgagttgca gcctcaatc cgaactggga ccggcttttt gggattcgct      180
ccaccttacg gtatcgcagc ccattgtacc ggccattgta gcatgcgtga agcccaagac     240
ataaggggca tgatgatttg acgtcatccc caccttcctc cgagttgacc ccggcagtat     300
cccatgagtt cccaccatta cgtgctggca acatagaacg agggttgcgc tcgttgcggg     360
acttaaccca acatctcacg acacgagctg acgacaacca tgcaccacct gttcacgagt     420
gtccaaagag ttgaccattt ctggcccgtt ctcgtgtatg tcaagccttg gtaaggttct     480
tcgcgttgca tcgaattaat ccgcatgctc cgccgcttgt gcgggtcccc gtcaattcct     540
ttgagtttta gccttgcggc cgtactcccc aggcgtggaa cttaatgcgt tagctgcgtc     600
acggaatccg tggaaaggac cccacaacta gttcccaacg tttacggggt ggactaccag     660
ggtatctaag cctgtttgct ccccacccct tcgctcctca gcgtcagtta cggcccagag     720
atctgccttc gccatcggtg ttcctcctga tatctgcgca ttccaccgct acaccaggaa     780
ttccaatctc ccctaccgca ctctagtctg cccgtaccca ctgcaagccc gaagttgagc     840
ctcgggattt cacagcagac gcgacaaacc gcctacgagc tctttacgcc caataattnc     900
cggataacgc ttgcaccta cgtattaccg cggctgctgg cacgtagtta gcccggtgct      960 tttctgcag gtaccgtcac tttcgcttct tccctgctaa aagaggttta caacccgaaa     1020
gccgtcatcc ctcacgcggc gttgctgcat cnncttccgc ccattgngca tattccccac    1080
tgctgcctcc cgtagagtct gggnngtgtc tcanncccag ngnngcnnca ncntcncngn    1140
nntaccgncn annnnngnng nnccntn                                        1167

<210> SEQ ID NO 21
<211> LENGTH: 458
<212> TYPE: DNA
<213> ORGANISM: Talaromyces pinophilus

<400> SEQUENCE: 21
acatggtggt gaccaacccc cgcaggtcct tcccgagcga gtgacagagc cccatacgct      60
cgaggaccag acggacgtcg ccgctgcctt tcgggcaggc cccgggggg accacaccca     120 acacacaagc cgtgcttgag ggcagaaatg acgtcggac aggcatgccc cccggaatgc      180 caggggggcgc aatgtgcgtt caaagattcg atgattcacg gaattctgca attcacatta    240
```

```
cttatcgcat ttcgctgcgt tcttcatcga tgccggaacc aagagatcca ttgttgaaag      300
ttttgacaat tttcacagta ctcagacagc ccatcttcat cagggttcac agagcgcttc      360
ggcgggcgcg ggcccggaga cgtgcgtccc ccggcgacca ggtggcccog gtgggcccgc      420 caaagcaaca ggtgtataga gacaagggtg ggaggttg                              458
```

It is claimed:

1. A synthetic composition, comprising:
   a. a microbe, exudate therefrom, or culture broth therefrom, wherein the microbe is NRRL Deposit No. B-67810; and
   b. at least one heterologous composition selected from the group consisting of: a plant element, a formulation component, an agricultural composition, and any plurality and/or combination of the preceding;
   wherein the microbe is present at a concentration of at least $10^2$ CFU/mL in a liquid formulation, or at least $10^2$ CFU/gram in a non-liquid formulation.

2. The synthetic composition of claim 1, wherein the plant element is a seed.

3. The synthetic composition of claim 2, wherein the seed comprises a transgene.

4. The synthetic composition of claim 1, wherein the plant element is obtained from a plant selected from the group consisting of: maize, soybean, wheat, cotton, cucumber, tomato, pepper, potato, strawberry, orange, lemon, lime, apple, snap beans, zucchini, pea, lettuce, broccoli, celery, cauliflower, sorghum, and canola.

5. The synthetic composition of claim 1, wherein the agricultural composition comprises a growth medium.

6. The synthetic composition of claim 5, wherein the growth medium comprises soil.

7. The synthetic composition of claim 1, further comprising soil, wherein the microbe is heterologously disposed to the soil.

8. A product, comprising:
   the synthetic composition of claim 1, wherein said synthetic composition is substantially confined within an object selected from the group consisting of: a tube, a bottle, a jar, an ampule, a package, a vessel, a bag, a box, a bin, an envelope, a carton, a container, a silo, a shipping container, a truck bed, and a case.

9. The product of claim 8, wherein the synthetic composition is at a temperature below zero degrees Celsius.

* * * * *